(12) United States Patent
Elich et al.

(10) Patent No.: US 7,432,350 B2
(45) Date of Patent: Oct. 7, 2008

US007432350B2

(54) RECOMBINANT BIOTIN CARBOXYLASE DOMAINS FOR IDENTIFICATION OF ACETYLE COA CARBOXYLASE INHIBITORS

(75) Inventors: Tedd E. Elich, Durham, NC (US);
Sandra L. Volrath, Durham, NC (US);
Stephanie C. Weatherly, Durham, NC (US)

(73) Assignee: Cropsolution, Inc., Morrisville, NC (US)

( * ) Notice: Subject to any disclaimer, the term of this patent is extended or adjusted under 35 U.S.C. 154(b) by 498 days.

(21) Appl. No.: 10/633,835

(22) Filed: Aug. 4, 2003

(65) Prior Publication Data

US 2004/0086994 A1 May 6, 2004

Related U.S. Application Data

(60) Provisional application No. 60/401,170, filed on Aug. 5, 2002.

(51) Int. Cl.
*C07K 14/00* (2006.01)
*A61K 38/43* (2006.01)
*C07H 21/04* (2006.01)
*C12N 1/20* (2006.01)
*C12N 9/00* (2006.01)

(52) U.S. Cl. ............... 530/350; 424/94.1; 536/23.7; 536/23.5; 435/2; 435/252.3; 435/320.1; 435/325; 435/183

(58) Field of Classification Search ............ 536/23.2, 536/23.5, 23.7; 530/300, 350; 435/252.3, 435/320.1, 325, 183, 2, 4; 424/94.1
See application file for complete search history.

(56) References Cited

U.S. PATENT DOCUMENTS

| | | | |
|---|---|---|---|
| 5,641,666 A * | 6/1997 | Vahlensieck et al. | ........ 435/183 |
| 5,659,069 A | 8/1997 | Eaton et al. | |
| 5,719,273 A | 2/1998 | Tu et al. | |
| 5,723,289 A | 3/1998 | Eaton et al. | |
| 5,723,592 A | 3/1998 | Eaton et al. | |
| 5,760,266 A | 6/1998 | Eaton et al. | |
| 5,789,160 A | 8/1998 | Eaton et al. | |
| 5,858,660 A | 1/1999 | Eaton et al. | |
| 5,945,527 A | 8/1999 | Tu et al. | |
| 6,030,776 A | 2/2000 | Eaton et al. | |
| 6,048,698 A | 4/2000 | Eaton et al. | |
| 6,153,374 A * | 11/2000 | Vahlensieck et al. | ............ 435/4 |
| 6,399,342 B1 | 6/2002 | Haselkorn | |
| 6,455,688 B1 | 9/2002 | Slabas et al. | |
| 6,514,726 B1 | 2/2003 | Dorr et al. | |
| 6,566,048 B1 | 5/2003 | Dixon et al. | |
| 7,098,032 B2 * | 8/2006 | Trubetskoy et al. | ......... 435/458 |

FOREIGN PATENT DOCUMENTS

WO WO 02/48321 6/2002

OTHER PUBLICATIONS

Levert et al 2000 , Biochemistry, 39 (14), 4122-4128.*
Schulte et al 1997 Proc. Natl. Acad. Sci. USA vol. 94, pp. 3465-3470.*
Grover et al , Biochemistry; 1994; 33(34) pp. 10249-10256.*
Kimura et al , Journal of Bacteriology, 2000, vol. 182 (19). 5462-5469.*
PCT Notification of Transmittal of the International Search Report For International Application No. PCT/US03/24356; mailed Jul. 20, 2005.
Abu-Elheiga et al., Human Acetyl-CoA Carboxylase 2, *The Journal of Biological Chemistry*, vol. 272, No. 16:10669-10677 (1977).
Abu-Elheiga et al., Continuous Fatty Acid Oxidation and Reduced Fat Storage in Mice Lacking Acetyl-CoA Carboxlase 2, *Science*, vol. 291:2613-2616, (Mar. 30, 2001).
Abu-Elheiga et al., Human Acetyl-CoA Carboxylase: Characterization, Molecular Cloning, and Evidence for Two Isoforms, *Proc. Natl. Acad. Sci. USA*, vol. 92:4011-4015 (Apr. 1995).
Al-Feel et al., Cloning of the Yeast FAS3 Gene Primary Structure of Yeast Acetyl-CoA Carboxylase , *Proc. Natl, Acad. USA*, vol. 89:4534-4538 (May 1992).
Bailey et al., The ACC1 Gene, Encoding Acetyl-CoA Carboxylase, is Essential for Growth in *Ustilage maydis*, *Mol. Gen. Genet.* 249:191-201 (1995).
Heike Behrbohm, Acetyl-CoA Carboxylase aus *Ustilago maydis* Reinigung, Charakterisierung under untersuchungen zur Inhibierung durch Soraphen A, *Papierflieger* (1996).
Blanchard et al., Mutations at Four Active Site Residues of Biotin Carboxylase Abolish Substrate-Induced Synergism by Biotin, *Biochemistry*, vol. 38:3393-3400 (1999).
Gregolin et al., Molecular Characteristics of Liver Acetyle CoA Carboxylase, *Proceedings of the National Academy of Sciences*, 56:148-155 (1966).
Egli et al., Purification of Maize Leaf Acetyle CoA Carboxylase, *Maize Genetics Cooperation Newsletter*, vol. 65:95 (1991).
Ha et al., Cloning of Human Acetyl-CoA Carboxylase-β and its Unique Features, *Proc. Natl. Acad. Sci. USA*, vol. 93:11466-11470 (Oct. 1996).
Hargreaves et al., Molecular Genetics and Fungicide Discover—Acetyl-CoA Carboxylase, *Modern Fungicides & Antifungal Compounds II, Intercept Ltd.*, pp. 53-59 (1999).
Kondo et al., Acetyl-CoA Carboxylase from *Escherichia coli*: Gene organization and nucleotide sequence of the biotin carboxylase subunit, *Proc. Natl. Sci. USA*, vol. 88:9730-9733 (Nov. 1991).

(Continued)

*Primary Examiner*—Shanon A. Foley
*Assistant Examiner*—Padma v Baskar
(74) *Attorney, Agent, or Firm*—Myers Bigel Sibley & Sajovec, P.A.

(57) ABSTRACT

A peptide comprising an Acetyl CoA carboxylase (ACCase) having a deleted biotin binding domain, having a deleted carboxy transferase domain, and having a functional biotin carboxylase (BC) domain is described. A nucleic acid that encodes the peptide described above and a recombinant host cell that contains the nucleic acid and expresses the encoded peptide is also described. A method of identifying Acetyl CoA carboxylase inhibitors, fungicides, and herbicides is also described herein.

8 Claims, 21 Drawing Sheets

OTHER PUBLICATIONS

Li et al., The Gene Encoding the Biotin Carboxylase Subunit of *Escherichia coli* Acetyl-CoA Carboxylase, *The Journal of Biological Chemistry*, vol. 267:855-863 (1992).

Michio Matsuhashi, [1] Acetyl-CoA Carboxylase From Yeast, *Methods in Enzymology*, 14:3-8 (1969).

Cronan, J et al. "Multi-subunit acetyl-CoA carboxylases" *Progress in Lipid Research*, 41(5), pp. 407-435, 2002.

Gerth, K et al., The Soraphens: A Family of Novel Antifungal Compounds from *Sorangium Cellulosum* (Myxobacteria). *The Journal of Antibiotics*. 47(1), pp. 23-31, 1994.

Sasaki y. et al., "The Compartmentation of Acetyl-Coenzyme A Carboxylase in Plants" *Plant Physiology*. 108, pp. 445-449, 1995.

Supplementary European Search Report completed on Apr. 19, 2006 for European Application No. 03767154.

Examination Report from corresponding EP Application 03767154 (Jan. 19, 2007).

Elborough et al.; "Isolation of cDNAs from *Brassica napus* encoding the biotin-binding and transcarboxylase domains of acetyl-CoA carboxylase: assignment of the domain structure in a full-length *Arabidopsis thaliana* genomic clone" Biochem. J. (1994) 301, pp. 599-605.

Gornicki et al.; "Plastid-localized acetyl-CoA carboxylase of bread wheat is encoded by a single gene on each of the three ancestral chromosome sets" Proc. Natl. Acad. Sci (1997) 94, pp. 14179-14184.

Podkowinski et al.; "Structure of gene encoding a cytosolic acetyl-CoA carboxylase of hexaploid wheat" Proc. Natl. Acad. Sci. (1996) 93, pp. 1870-1874.

Roesler et al.; "Structure and Expression of an Arabidopsis Acetyl-Coenzyme A Carboxylase Gene" Plant Physiol. (1994) 105, pp. 611-617.

Roessler et al.; "Characteristics of the Gene that Encodes Acetyl-CoA Carboxylase in the Diatom *Cyclotella cryptica*" Annals of the New York Academy of Sciences (1994) 721, pp. 250-256.

* cited by examiner

Figure 1
ACCase: Large, Complex & Labile
*Ustilago maydis* ACCase
- 3 functional domains; 2 enzymatic reactions:
  - BB=biotin binding
  - BC=biotin carboxylase (*site of soraphen inhibition)
  - CT=carboxy transferase
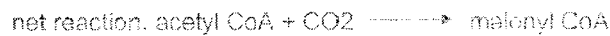
- low abundant and labile protein
Figure 2
Soraphen Binds to and Inhibits recombinant full-length Ustilago ACCase (pCS11 prot

Figure 3 pCS8 Binds Soraphen with Similar Affinity as pCS11 pCS8 $K_D$=1.5nM pCS201 x-axis: $^3$H-soraphen (nM)
y-axis: bound (nM)

Figure 4

Soraphen Binding by a Soluble *Phytopthora infestans* BC domain

- Expressed as N-terminal His-tagged protein
- 54% identical, 67% similar to *Ustilago* BC domain
- Exhibits high-affinity soraphen binding
- Use as additional partition agent to select for broad specificity

*P. infestans* BC domain soraphen binding

Kd = 0.40 nM x-axis: cpm added
y-axis: cpm bound pCS8: Small, Simple & Stable

- N-terminal His-tag to facilitate purification
- high expression in E.coli: 20-50 mg per 1 liter culture
- very stable under laboratory conditions

```
PPPDHKAVSQFIGGNPLETAPASPVADFIRKQGGHSVITKVLI
CNNGIAAVKEIRSIRKWAYETFGDERAIEFTVMATPEDLKVNA
DYIRMADQYVEVPGGSNNNNYANVDLIVDVAERAGVHAVWAGW
GHASENPRLPESLAASKHKIIFIGPPGSAMRSLGDKISSTIVA
QHADVPCMPWSGTGIKETMMSDQGFLTVSDDVYQQACIHTAEE
GLEKAEKIGYPVMIKASEGGGGKGIRKCTNGEEFKQLYNAVLG
EVPGSPVFVMKLAGQARHLEVQLLADQYGNAISIFGRDCSVQR
RHQKIIEEAPVTIAPEDARESMEKAAVRLAKLVGYVSAGTVEW
LYSPESGEFAFLELNPRLQVEHPTTEMVSGVNIPAAQLQVAMG
IPLYSIRDIRTLYGMDPRGNEVIDFDFSSPESFKTQRKPQPQG
HVVACRITAENPDTGFKPGMGALTELNFRSSTSTWGYFSVAAS
GALHEYADSQFGHIFAYGADRSEARKQMVISLKELSIRGDFRT
TVEYLIKLLETDAFESNKITTGWLDGLIQDRLTAERPPADLAV
```

Figure 6. Amino acid sequence of *Ustilago maydis* ACCase BC Domain (Amino Acids 2-560) (also SEQ

```
MVAEEAPPAADVAAYAETRSDSNPLNYASMEEYVRLQKGTRPITSVL
IANNGISAVKAIRSIRSWSYEMFADEHVVTFVVMATPEDLKANAEYI
RMAEHVVEVPGGSNNHNYANVSLIIEIAERFNVDAVWAGWGHASENP
LLPDTLAQTERKIVFIGPPGKPMRALGDKIGSTIIAQSAKVPTIAWN
GDGMEVDYKEHDGIPDEIYNAAMLRDGQHCLDECKRIGFPVMIKASE
GGGGKGIRMVHEESQVLSAWEAVRGEIPGSPIFVMKLAPKSRHLEVQ
LLADTYGNAIALSGRDCSVQRRHQKIVEEGPVLAPTQEVWEKMMRAA
TRLAQEVEYVNAGTVEYLFSELPEDNGNSFFFLELNPRLQVEHPVTE
MITHVNLPAAQLQVAMGIPLHCIPDVRRLYNKDAFETTVIDFDAEKQ
KPPHGHVIAARITAEDPNAGFQPTSGAIQELNFRSTPDVWGYFSVDS
SGQVHEFADSQIGHLFSWSPTREKARKNMVLALKELSIRGDIHTTVE
YIVNMMESDDFKYNRISTSWLDERISHHNEVRLQGRPD
```

Figure 7: Amino acid sequence of *Phytophthora infestans* ACCase BC Domain (Amino Acids 1-555) (also SEQ ID NO:4)

Figure 8: Anion Exchange Chromatography of pCS8 showing the Ni-NTA-agarose input and the peak fractions (F) off of the UNO-Q column (anion exchange column).
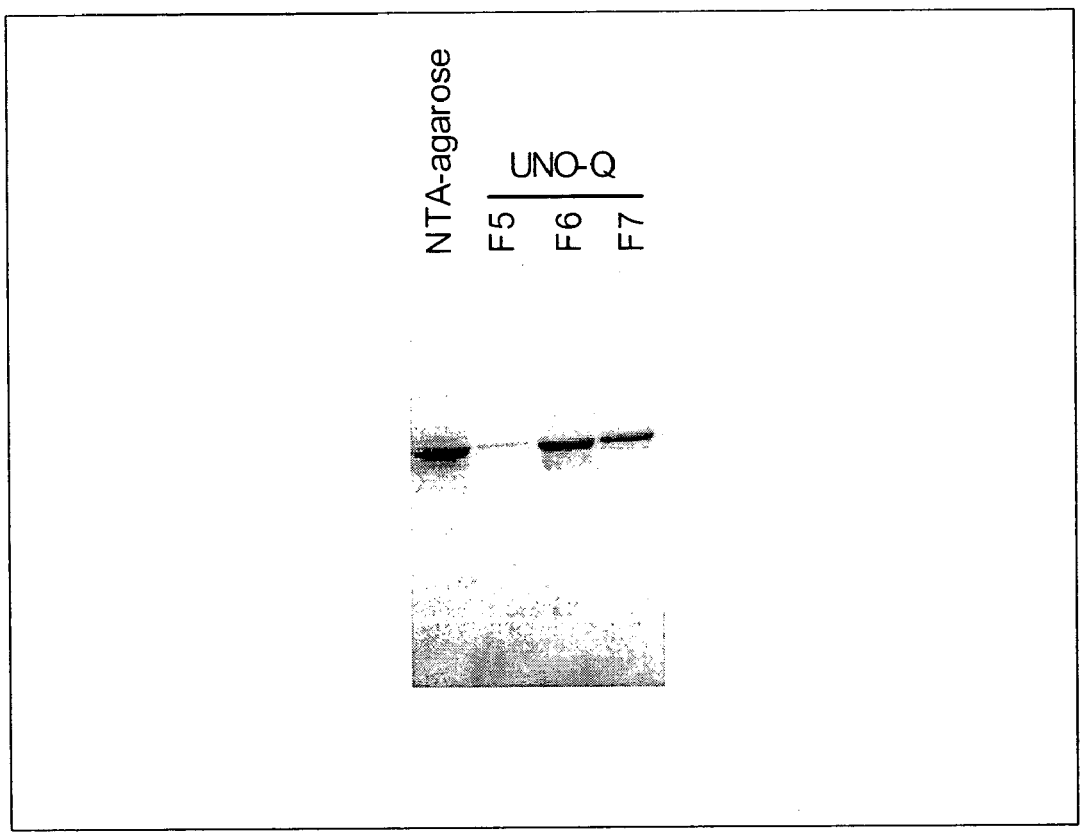

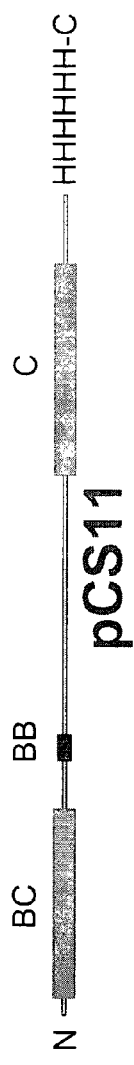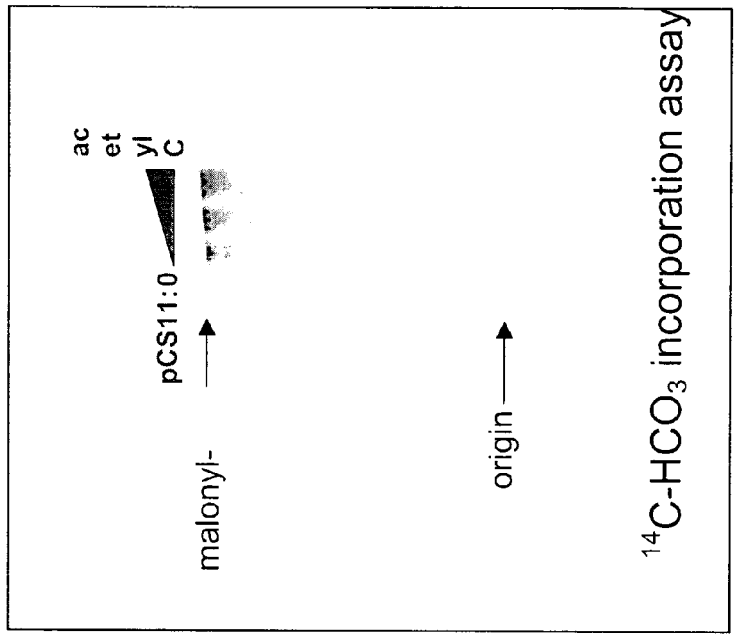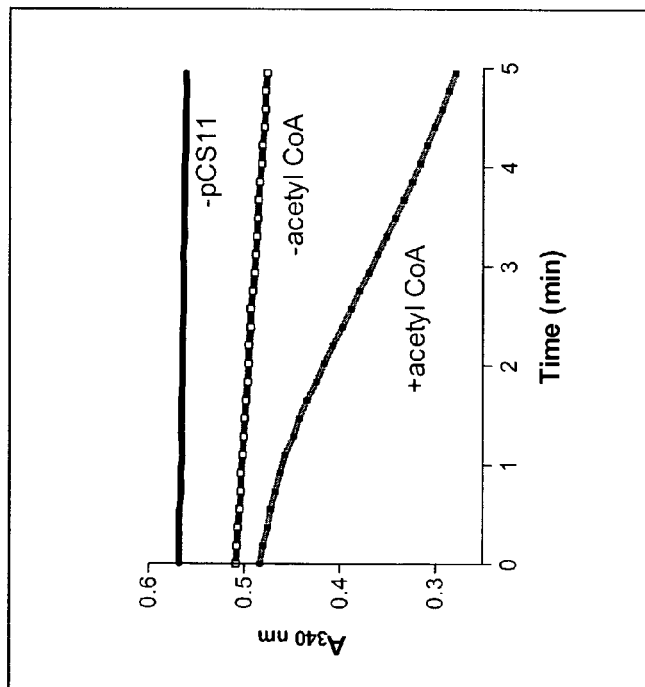
Figure 9B

Alignment of fungal ACCase BC Domains

```
ustilago      ------------------------PPPD------------HKAVSQ---------FIG-GNP
phytophthora  -VAEEAP-----------------PAAD------------VAAYAE---------TRSDSNP
yeast         SEESLFESS---------------PQKM------EYEITNYSERHTELPGHFIG-LNT
magnaporthe   TETNGTAAAANSSRQRNGANGVTVPVANGKATYAQRHKIADH-------------FIG-GNR
                                      *                                 *

Y
ustilago      LETAPASPVADFIRKQGGHSVITKVLICNNGIAAVKEIRSIRKWAYETFGDERAIEFTVM
phytophthora  LNYA---SMEEYVRLQKGTRPITSVLIANNGISAVKAIRSIRSWSYEMFADEHVVTFVVM
yeast         VDKLEESPLRDFVKSHGGHTVISKILIANNGIAAVKEIRSVRKWAYETFGDDRTVQFVAM
magnaporthe   LENAPPSKVKEWVAAHDGHTVITNVLIANNGIAAVKEIRSVRKWAYETFGDERAIQFTVM
                           *       **   * ***      *  *  * ustilago      ATPEDLKVNADYIRMADQYVEVPGGSNNNNYANVDLIVDVAERAGVHAVWAGWGHASENP
phytophthora  ATPEDLKANAEYIRMAEHVVEVPGGSNNHNYANVSLIIEIAERFNVDAVWAGWGHASENP
yeast         ATPEDLEANAEYIRMADQYIEVPGGTNNNNYANVDLIVDIAERADVDAVWAGWGHASENP
magnaporthe   ATPEDLQANADYIRMADHYVEVPGGTNNNNYANVELIVDVAERMNVHAVWAGWGHASENP
              ******    * ****** * **** ** *****  *  ***     **********
```

FIG. 10 (part 1 of 4)

```
ustilago       RLPESLAASKHKIIFIGPPGSAMRSLGDKISSTIVAQHADVPCMPWSGTGIKETMMSDQ-
phytophthora   LLPDTLAQTERKIVFIGPPGKPMRALGDKIGSTIIAQSAKVPTIAWNGDGMEVDYKEHD-
yeast          LLPEKLSQSKRKVIFIGPPGNAMRSLGDKISSTIVAQSAKVPCIPWSGTGV-DTVHVDEK
magnaporthe    KLPESLAASPKKIIFIGPPGSAMRSLGDKISSTIVAQHAQVPCIPWSGTGVDAVQIDKK-
                **  *   ****   ****   *     ***    * ustilago       -GFLTVSDDVYQQACIHTAEEGLEKAEKIGYPVMIKASEGGGGKGIRKCTNGEEFKQLYN
phytophthora   -G---IPDEIYNAAMLRDGQHCLDECKRIGFPVMIKASEGGGGKGIRMVHEESQVLSAWE
yeast          TGLVSVDDDIYQKGCCTSPEDGLQKAKRIGFPVMIKASEGGGGKGIRQVEREEDFIALYH
magnaporthe    -GIVTVDDDTYAKGCVTSWQEGLEKARQIGFPVMIKASEGGGGKGIRKAVSEEGFEELYK
                *          *           *   ************* * ustilago       AVLGEVPGSPVFVMKLAGQARHLEVQLLADQYGNAISIFGRDCSVQRRHQKIIEEAPVTI
phytophthora   AVRGEIPGSPIFVMKLAPKSRHLEVQLLADTYGNAIALSGRDCSVQRRHQKIVEEGPVLA
yeast          QAANEIPGSPIFVMKLAGRARHLEVQLLADQYGTNISLFGRDCSVQRRHQKIIEEAPVTI
magnaporthe    AAASEIPGSPIFIMKLAGNARHLEVQLLADQYGNNISLFGRDCSVQRRHQKIIEEAPVTI
                *   ****  *****   ********** ** *   *********** ** ***
```

*FIG. 10 (part 2 of 4)*

```
ustilago        APEDARESMEKAAVRLAKLVGYVSAGTVEWLYS--PESG--EFAFLELNPRLQVEHPTTE
phytophthora    PTQEVWEKMMRAATRLAQEVEYVNAGTVEYLFSELPEDNGNSFFFLELNPRLQVEHPVTE
yeast           AKAETFHEMEKAAVRLGKLVGYVSAGTVEYLYS--HDDG--KFYFLELNPRLQVEHPTTE
magnaporthe     AKPDTFKAMEEAAVRLGRLVGYVSAGTVEYLYS--HADD--KFYFLELNPRLQVEHPTTE
                        *  ** **   * ** ***** * *         * ************* ** ustilago        MVSGVNIPAAQLQVAMGIPLYSIRDIRTLYGMDPRGNEVIDFDFSSPESFKTQRKPQPQG
phytophthora    MITHVNLPAAQLQVAMGIPLHCIPDVRRLYNKDAFETTVIDFD--------AEKQKPPHG
yeast           MVSGVNLPAAQLQIAMGIPMHRISDIRTLYGMNPHSASEIDFEFKTQDATKKQRRPIPKG
magnaporthe     GVSGVNLPASQLQIAMGIPLHRISDIRLLYGVDPKLSTEIDFDFKNPDSEKTQRRPSPKG
                    ** ** *** *****   * * * **         ***               * * ustilago        HVVACRITAENPDTGFKPGMGALTELNFRSSTSTWGYFSVGTSGALHEYADSQFGHIFAY
phytophthora    HVIAARITAEDPNAGFQPTSGAIQELNFRSTPDVWGYFSVDSSGQVHEFADSQIGHLFSW
yeast           HCTACRITSEDPNDGFKPSGGTLHELNFRSSSNVWGYFSVGNNGNIHSFSDSQFGHIFAF
magnaporthe     HLTACRITSEDPGEGFKPSNGVMHELNFRSSSNVWGYFSVGTQGGIHSFSDSQFGHIFAY
                *  * *** * *  ** *  *   ******    ******   *  *   *** ** *
```

FIG. 10 (part 3 of 4)

```
ustilago        GADRSEARKQMVISLKELSIRGDFRTTVEYLIKLLETDAFESNKITTGWLDGLIQDRLTA
phytophthora    SPTREKARKNMVLALKELSIRGDIHTTVEYIVNMMESDDFKYNRISTSWLDERISHHNEV
yeast           GENRQASRKHMVVALKELSIRGDFRTTVEYLIKLLETEDFEDNTITTGWLDDLITHKMTA
magnaporthe     GENRSASRKHMVIALKELSIRGDFRTTVEYLIKLLETEAFEENTITTGWLDELISKKLTA
                   *   ** **  *********  *****     *   *  * * * ***  * ustilago        E---RPPADLAV  (SEQ ID NO: 2)
phytophthora    RLQGRPD-----  (SEQ ID NO: 4)
yeast           E---KPDPTLAV  (SEQ ID NO: 8)
magnaporthe     E---RPDKMLAV  (SEQ ID NO: 6)
               *
```

*FIG. 10 (part 4 of 4)*

Alignment of the ustilago and human ACCase BC domains

```
ustilagoBC  ------------------------------------------------------------
ACC1BC      MDE---------------------------------------------------------
ACC2BC      MVLLLCLSCLIFSCLTFSWLKIWGKMTDSKPITKSKSEANLIPSQEPFPASDNSGETPQR ustilagoBC  ---------------PPPDHKAV--------S---------------QFIGGNPLET-----
ACC1BC      ---------------PSPLAQPLELNQHS----------RFIIGSVSEDNSEDEISNL
ACC2BC      NGEGHTLPKTPSQAEPASHKGP------KDAGRRRNSLPPSHQKPPRNPLSS-------- ustilagoBC  ----------------APAS----------------------------------------
ACC1BC      VKLDLLEEKEGSLSPASVGSDTLSDLGISSLQDGLALHIRSSMSGLHLVKQGRDRKKIDS
ACC2BC      --------SDAA------------------------------------------------
                            *
```

*FIG. 13 (part 1 of 5)*

```
ustilagoBC   ------PV----------------------------------------
ACC1BC       QRDFTVASP---------------------------------------
ACC2BC       ------PSPELQANGTGTQGLEATDTNGLSSSARPQGQQAGSPSKEDKKQANIKRQLMT ustilagoBC   ------------------------------------------------
ACC1BC       ------------------------------------------------
ACC2BC       NFILGSFDDYSSDEDSVAGSSRESTRKGSRASLGALSLEAYLTTGEAETRVPTMRPSMSG ustilagoBC   ------------ADFIRKQGGHSVITKVLICNNGIAAVKEIRSIRKWA
ACC1BC       ------------AEFVTRFGGNKVIEKVLIANNGIAAVKCMRSIRRWS
ACC2BC       LHLVKRGREHKKLDLHRDFTVASPAEFVTRFGGDRVIEKVLIANNGIAAVKCMRSIRRWA
                          *  **  ** ***** ********* **** *
```

FIG. 13 (part 2 of 5)

```
ustilagoBC  YETFGDERAIEFTVMATPEDLKVNADYIRMADQYVEVPGGSNNNNYANVDLIVDVAERAG
ACC1BC      YEMFRNERAIRFVVMVTPEDLKANAEYIKMADHYVPVPGGPNNNNYANVELILDIAKRIP
ACC2BC      YEMFRNERAIRFVVMVTPEDLKANAEYIKMADHYVPVPGGPNNNNYANVELIVDIAKRIP
             **   ********  **  ******** *  ***** ustilagoBC  VHAVWAGWGHASENPRLPESLAASKHKIIFIGPPGSAMRSLGDKISSTIVAQHADVPCMP
ACC1BC      VQAVWAGWGHASENPKLPELLL--KNGIAFMGPPSQAMWALGDKIASSIVAQTAGIPTLP
ACC2BC      LQAVWAGWGHASENPKLPELLC--KNGVAFLGPPSEAMWALGDKIASTVVAQTLQVPTLP
             ********** * *      *   ****      * ustilagoBC  WSGTGIKETMMSD---QGF-LTVSDDVYQQACIHTAEEGLEKAEKIGYPVMIKASEGGGG
ACC1BC      WSGSGLRVDWQENDFSKRI-LNVPQELYEKGYVKDVDDGLKAAEEVGYPVMIKASEGGGG
ACC2BC      RSGSGLTVEWTEDDLQQGKRISVPEDVYDKGCVKDVDEGLEAAERIGFPLMIKASEGGGG
             ** *            *      *  *      *   **    *  *  *********
```

*FIG. 13 (part 3 of 5)*

```
ustilagoBC   KGIRKCTNGEEFKQLYNAVLGEVPGSPVFVMKLAGQARHLEVQLLADQYGNAISIFGRDC
ACC1BC       KGIRKVNNADDFPNLFRQVQAEVPGSPIFVMRLAKQSRHLEVQILADQYGNAISLFGRDC
ACC2BC       KGIRKAESAEDFPILFRQVQSEIPGSPIFLMKLAQHARHLEVQILADQYGNAVSLFGRDC
             *****   *  * *  *****  * *  *  *   *****  ***** **** ustilagoBC   SVQRRHQKIIEEAPVTIAPEDARESMEKAAVRLAKLVGYVSAGTVEWLYSPESGEFAFLE
ACC1BC       SVQRRHQKIIEEAPATIATPAVFEHMEQCAVKLAKMVGYVSAGTVEYLYS-QDGSFYFLE
ACC2BC       SIQRRHQKIVEEAPATIAPLAIFEFMEQCAIRLAKTVGYVSAGTVEYLYS-QDGSFHFLE
             * *****   *    *  **  * * ***** * *  * *** ustilagoBC   LNPRLQVEHPTTEMVSGVNIPAAQLQVAMGIPLYSIRDIRTLYGMDPRGNEVIDFDFSSP
ACC1BC       LNPRLQVEHPCTEMVADVNLPAAQLQIAMGIPLYRIKDIRMMYGVSPWGDSPIDFEDSA-
ACC2BC       LNPRLQVEHPCTEMIADVNLPAAQLQIAMGVPLHRLKDIRLLYGESPWG-------VTP
             ********** ***   * *******:***:**  : **  *    *       *
```

FIG. 13 (part 4 of 5)

```
ustilagoBC    ESFKTQRKPQ-PQGHVVACRITAENPDTGFKPGMGALTELNFRSSTSTWGYFSVGTSGAL
ACC1BC        -----HVPC-PRGHVIAARITSENPDEGFKPSSGTVQELNFRSNKNVWGYFSVAAAGGL
ACC2BC        ISFETPSNPPLARGHVIAARITSENPDEGFKPSSGTVQELNFRSSKNVWGYFSVAATGGL
                   *   **      * ****  **  ** **  * ustilagoBC    HEYADSQFGHIFAYGADRSEARKQMVISLKELSIRGDFRTTVEYLIKLLETDAFESNKIT
ACC1BC        HEFADSQFGHCFSWGENREEAISNMVALKELSIRGDFRTTVEYLIKLLETESFQMNRID
ACC2BC        HEFADSQFGHCFSWGENRKEAISNMVVALKELSIRGDFRTTVEYLINLLETESFQNNDID
               ***** *  *  *  *   *  ***************** **** *  * ustilagoBC    TGWLDGLIQDRLTAERPPADLAV     (SEQ ID NO: 2)
ACC1BC        TGWLDRLIAEKVQAERPDTMLGV     (SEQ ID NO: 10)
ACC2BC        TGWLDYLIAEKVQ-EKPDIMLGV     (SEQ ID NO: 12)
              *****  *  *    *  * *
```

*FIG. 13 (part 5 of 5)*

A
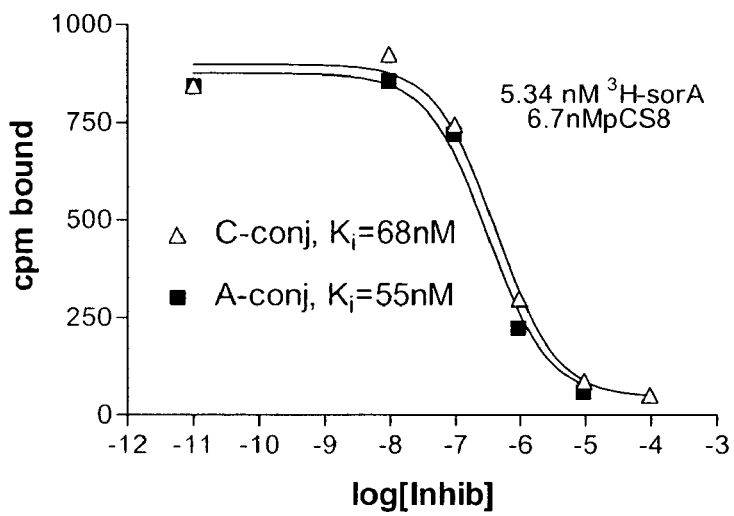
B
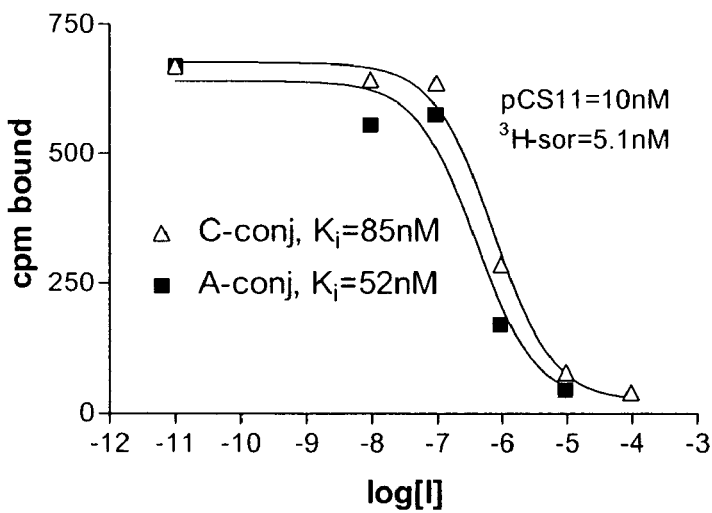
FIG. 15

SEQUENCE LISTING

<160> NUMBER OF SEQ ID NOS: 71

<210> SEQ ID NO 1
<211> LENGTH: 1677
<212> TYPE: DNA
<213> ORGANISM: Ustilago maydis
<220> FEATURE:
<221> NAME/KEY: CDS
<222> LOCATION: (1)..(1677)
<223> OTHER INFORMATION: ACCase BC domain (aa 2-560)

<400> SEQUENCE: 1

| | | | | | | | | | | | | | | | | |
|---|---|---|---|---|---|---|---|---|---|---|---|---|---|---|---|---|
| ccg | cct | ccg | gat | cac | aag | gca | gtc | agc | cag | ttt | atc | ggc | ggc | aac | ccg | 48 |
| Pro | Pro | Pro | Asp | His | Lys | Ala | Val | Ser | Gln | Phe | Ile | Gly | Gly | Asn | Pro | |
| 1 | | | | 5 | | | | | 10 | | | | | 15 | | |
| ctt | gaa | acc | gct | ccc | gcc | agc | cct | gtt | gcc | gac | ttt | att | cgc | aaa | cag | 96 |
| Leu | Glu | Thr | Ala | Pro | Ala | Ser | Pro | Val | Ala | Asp | Phe | Ile | Arg | Lys | Gln | |
| | | | 20 | | | | | 25 | | | | | 30 | | | |
| ggt | ggt | cac | agt | gtc | atc | acc | aag | gtc | ctc | att | tgc | aac | aac | ggt | atc | 144 |
| Gly | Gly | His | Ser | Val | Ile | Thr | Lys | Val | Leu | Ile | Cys | Asn | Asn | Gly | Ile | |
| | | 35 | | | | | 40 | | | | | 45 | | | | |
| gcc | gcc | gtc | aag | gag | att | cgc | tcc | atc | cga | aaa | tgg | gcc | tac | gag | acc | 192 |
| Ala | Ala | Val | Lys | Glu | Ile | Arg | Ser | Ile | Arg | Lys | Trp | Ala | Tyr | Glu | Thr | |
| | 50 | | | | | 55 | | | | | 60 | | | | | |
| ttt | ggc | gat | gag | cgt | gcc | att | gaa | ttt | acc | gtc | atg | gcc | acc | cct | gag | 240 |
| Phe | Gly | Asp | Glu | Arg | Ala | Ile | Glu | Phe | Thr | Val | Met | Ala | Thr | Pro | Glu | |
| 65 | | | | | 70 | | | | | 75 | | | | | 80 | |
| gac | ctc | aaa | gtc | aat | gcc | gac | tac | atc | cgc | atg | gcc | gac | caa | tac | gtc | 288 |
| Asp | Leu | Lys | Val | Asn | Ala | Asp | Tyr | Ile | Arg | Met | Ala | Asp | Gln | Tyr | Val | |
| | | | | 85 | | | | | 90 | | | | | 95 | | |
| gag | gta | ccc | ggt | ggc | tct | aac | aac | aac | aac | tac | gct | aac | gtc | gac | ctc | 336 |
| Glu | Val | Pro | Gly | Gly | Ser | Asn | Asn | Asn | Asn | Tyr | Ala | Asn | Val | Asp | Leu | |
| | | | 100 | | | | | 105 | | | | | 110 | | | |
| atc | gtc | gat | gtc | gct | gag | cga | gcc | ggt | gtt | cac | gcc | gta | tgg | gct | ggc | 384 |
| Ile | Val | Asp | Val | Ala | Glu | Arg | Ala | Gly | Val | His | Ala | Val | Trp | Ala | Gly | |
| | | 115 | | | | | 120 | | | | | 125 | | | | |
| tgg | ggt | cac | gcc | tcc | gag | aac | cca | cgc | cta | cct | gaa | tcg | ctc | gcc | gcc | 432 |
| Trp | Gly | His | Ala | Ser | Glu | Asn | Pro | Arg | Leu | Pro | Glu | Ser | Leu | Ala | Ala | |
| | 130 | | | | | 135 | | | | | 140 | | | | | |
| tcc | aag | cac | aag | atc | atc | ttt | atc | ggt | ccc | ccc | ggc | tcc | gcc | atg | cgc | 480 |
| Ser | Lys | His | Lys | Ile | Ile | Phe | Ile | Gly | Pro | Pro | Gly | Ser | Ala | Met | Arg | |
| 145 | | | | | 150 | | | | | 155 | | | | | 160 | |
| tcg | ctt | ggt | gac | aag | atc | tcg | tcc | acc | atc | gtc | gca | cag | cac | gcc | gac | 528 |
| Ser | Leu | Gly | Asp | Lys | Ile | Ser | Ser | Thr | Ile | Val | Ala | Gln | His | Ala | Asp | |
| | | | | 165 | | | | | 170 | | | | | 175 | | |
| gtg | cca | tgc | atg | ccc | tgg | tcc | ggt | acc | ggc | atc | aag | gag | acc | atg | atg | 576 |
| Val | Pro | Cys | Met | Pro | Trp | Ser | Gly | Thr | Gly | Ile | Lys | Glu | Thr | Met | Met | |
| | | | 180 | | | | | 185 | | | | | 190 | | | |
| agc | gat | cag | ggt | ttc | ctg | acc | gtc | tcg | gac | gac | gtc | tac | caa | cag | gcc | 624 |
| Ser | Asp | Gln | Gly | Phe | Leu | Thr | Val | Ser | Asp | Asp | Val | Tyr | Gln | Gln | Ala | |
| | | 195 | | | | | 200 | | | | | 205 | | | | |
| tgc | atc | cac | acc | gct | gaa | gaa | ggt | ctt | gag | aag | gcc | gaa | aag | atc | ggc | 672 |
| Cys | Ile | His | Thr | Ala | Glu | Glu | Gly | Leu | Glu | Lys | Ala | Glu | Lys | Ile | Gly | |
| | 210 | | | | | 215 | | | | | 220 | | | | | |
| tac | ccc | gtc | atg | atc | aag | gcc | tcc | gaa | ggt | gga | gga | gga | aag | ggt | atc | 720 |
| Tyr | Pro | Val | Met | Ile | Lys | Ala | Ser | Glu | Gly | Gly | Gly | Gly | Lys | Gly | Ile | |
| 225 | | | | | 230 | | | | | 235 | | | | | 240 | |
| cga | aag | tgt | acc | aac | ggc | gaa | gaa | ttc | aag | cag | ctc | tac | aac | gcc | gtt | 768 |
| Arg | Lys | Cys | Thr | Asn | Gly | Glu | Glu | Phe | Lys | Gln | Leu | Tyr | Asn | Ala | Val | |
| | | | | 245 | | | | | 250 | | | | | 255 | | |
| ctc | ggt | gaa | gtg | ccc | ggc | tcg | ccc | gtt | ttc | gtt | atg | aaa | ctc | gcc | ggc | 816 |
| Leu | Gly | Glu | Val | Pro | Gly | Ser | Pro | Val | Phe | Val | Met | Lys | Leu | Ala | Gly | |
| | | | 260 | | | | | 265 | | | | | 270 | | | |
| cag | gcg | cgt | cat | ctc | gag | gtg | cag | ctg | ctg | gcc | gat | cag | tac | ggc | aac | 864 |
| Gln | Ala | Arg | His | Leu | Glu | Val | Gln | Leu | Leu | Ala | Asp | Gln | Tyr | Gly | Asn | |
| | | 275 | | | | | 280 | | | | | 285 | | | | |

```
gcc atc agc atc ttt ggt cgt gac tgc tct gtc cag cgt cgt cac caa      912
Ala Ile Ser Ile Phe Gly Arg Asp Cys Ser Val Gln Arg Arg His Gln
    290             295                 300 aag atc atc gag gag gct cct gtc act atc gct cct gag gat gcc cgc      960
Lys Ile Ile Glu Glu Ala Pro Val Thr Ile Ala Pro Glu Asp Ala Arg
305             310                 315                 320 gag tcc atg gag aag gct gcc gtg cgt ctc gcc aaa ctg gtt ggc tac     1008
Glu Ser Met Glu Lys Ala Ala Val Arg Leu Ala Lys Leu Val Gly Tyr
                325                 330                 335 gtc tct gcc ggt acc gtc gaa tgg ctc tac tct ccc gag tcg ggc gag     1056
Val Ser Ala Gly Thr Val Glu Trp Leu Tyr Ser Pro Glu Ser Gly Glu
            340                 345                 350 ttt gcc ttc ctc gag ctc aac ccc cgt ctt cag gtc gag cac cct act     1104
Phe Ala Phe Leu Glu Leu Asn Pro Arg Leu Gln Val Glu His Pro Thr
        355                 360                 365 acc gag atg gtc tcg ggt gtc aac att ccc gct gcc cag ctt cag gtc     1152
Thr Glu Met Val Ser Gly Val Asn Ile Pro Ala Ala Gln Leu Gln Val
370                 375                 380 gcc atg ggt atc cct ctc tac tcg atc cgc gac atc cga acc ctt tac     1200
Ala Met Gly Ile Pro Leu Tyr Ser Ile Arg Asp Ile Arg Thr Leu Tyr
385                 390                 395                 400 ggc atg gac cct cgc ggt aat gag gtc atc gac ttt gac ttc tct agc     1248
Gly Met Asp Pro Arg Gly Asn Glu Val Ile Asp Phe Asp Phe Ser Ser
                405                 410                 415 ccc gag tcg ttc aag acc cag cgc aag cct cag ccc cag ggc cac gta     1296
Pro Glu Ser Phe Lys Thr Gln Arg Lys Pro Gln Pro Gln Gly His Val
            420                 425                 430 gtc gcc tgc cgt atc act gcc gaa aac ccc gac acc ggc ttc aag cct     1344
Val Ala Cys Arg Ile Thr Ala Glu Asn Pro Asp Thr Gly Phe Lys Pro
        435                 440                 445 ggc atg ggt gcc ctc act gag ctc aac ttc cgc tcc agc acc tcc acc     1392
Gly Met Gly Ala Leu Thr Glu Leu Asn Phe Arg Ser Ser Thr Ser Thr
    450                 455                 460 tgg ggt tac ttc tcc gtc ggc acc agc ggt gct ctc cac gag tac gcc     1440
Trp Gly Tyr Phe Ser Val Gly Thr Ser Gly Ala Leu His Glu Tyr Ala
465                 470                 475                 480 gat tcg cag ttc gga cac atc ttt gcc tat ggt gcc gac cga tcc gag     1488
Asp Ser Gln Phe Gly His Ile Phe Ala Tyr Gly Ala Asp Arg Ser Glu
                485                 490                 495 gcg cga aaa cag atg gtc atc tcg ctc aag gag ctc tcc att cgc ggt     1536
Ala Arg Lys Gln Met Val Ile Ser Leu Lys Glu Leu Ser Ile Arg Gly
            500                 505                 510 gac ttc cgt acc acc gtc gaa tac ctc atc aag ttg ctc gag acc gac     1584
Asp Phe Arg Thr Thr Val Glu Tyr Leu Ile Lys Leu Leu Glu Thr Asp
        515                 520                 525 gcc ttc gag tcc aac aag atc acc act gga tgg ctc gat ggt ctc att     1632
Ala Phe Glu Ser Asn Lys Ile Thr Thr Gly Trp Leu Asp Gly Leu Ile
    530                 535                 540 cag gac cgt ctc act gcc gaa cga cct cct gcg gac ctc gct gtc          1677
Gln Asp Arg Leu Thr Ala Glu Arg Pro Pro Ala Asp Leu Ala Val
545                 550                 555

<210> SEQ ID NO 2
<211> LENGTH: 559
<212> TYPE: PRT
<213> ORGANISM: Ustilago maydis

<400> SEQUENCE: 2

Pro Pro Pro Asp His Lys Ala Val Ser Gln Phe Ile Gly Gly Asn Pro
1               5                   10                  15
```

-continued

```
Leu Glu Thr Ala Pro Ala Ser Pro Val Ala Asp Phe Ile Arg Lys Gln
         20                  25                  30

Gly Gly His Ser Val Ile Thr Lys Val Leu Ile Cys Asn Asn Gly Ile
             35                  40                  45

Ala Ala Val Lys Glu Ile Arg Ser Ile Arg Lys Trp Ala Tyr Glu Thr
 50                  55                  60

Phe Gly Asp Glu Arg Ala Ile Glu Phe Thr Val Met Ala Thr Pro Glu
 65                  70                  75                  80

Asp Leu Lys Val Asn Ala Asp Tyr Ile Arg Met Ala Asp Gln Tyr Val
                 85                  90                  95

Glu Val Pro Gly Gly Ser Asn Asn Asn Tyr Ala Asn Val Asp Leu
                100                 105                 110

Ile Val Asp Val Ala Glu Arg Ala Gly Val His Ala Val Trp Ala Gly
             115                 120                 125

Trp Gly His Ala Ser Glu Asn Pro Arg Leu Pro Glu Ser Leu Ala Ala
130                 135                 140

Ser Lys His Lys Ile Ile Phe Ile Gly Pro Pro Gly Ser Ala Met Arg
145                 150                 155                 160

Ser Leu Gly Asp Lys Ile Ser Ser Thr Ile Val Ala Gln His Ala Asp
                165                 170                 175

Val Pro Cys Met Pro Trp Ser Gly Thr Gly Ile Lys Glu Thr Met Met
             180                 185                 190

Ser Asp Gln Gly Phe Leu Thr Val Ser Asp Asp Val Tyr Gln Gln Ala
         195                 200                 205

Cys Ile His Thr Ala Glu Glu Gly Leu Glu Lys Ala Glu Lys Ile Gly
210                 215                 220

Tyr Pro Val Met Ile Lys Ala Ser Glu Gly Gly Gly Lys Gly Ile
225                 230                 235                 240

Arg Lys Cys Thr Asn Gly Glu Glu Phe Lys Gln Leu Tyr Asn Ala Val
                245                 250                 255

Leu Gly Glu Val Pro Gly Ser Pro Val Phe Val Met Lys Leu Ala Gly
             260                 265                 270

Gln Ala Arg His Leu Glu Val Gln Leu Leu Ala Asp Gln Tyr Gly Asn
         275                 280                 285

Ala Ile Ser Ile Phe Gly Arg Asp Cys Ser Val Gln Arg Arg His Gln
290                 295                 300

Lys Ile Ile Glu Glu Ala Pro Val Thr Ile Ala Pro Glu Asp Ala Arg
305                 310                 315                 320

Glu Ser Met Glu Lys Ala Ala Val Arg Leu Ala Lys Leu Val Gly Tyr
                325                 330                 335

Val Ser Ala Gly Thr Val Glu Trp Leu Tyr Ser Pro Glu Ser Gly Glu
             340                 345                 350

Phe Ala Phe Leu Glu Leu Asn Pro Arg Leu Gln Val Glu His Pro Thr
         355                 360                 365

Thr Glu Met Val Ser Gly Val Asn Ile Pro Ala Ala Gln Leu Gln Val
370                 375                 380

Ala Met Gly Ile Pro Leu Tyr Ser Ile Arg Asp Ile Arg Thr Leu Tyr
385                 390                 395                 400

Gly Met Asp Pro Arg Gly Asn Glu Val Ile Asp Phe Asp Phe Ser Ser
                405                 410                 415

Pro Glu Ser Phe Lys Thr Gln Arg Lys Pro Gln Pro Gln Gly His Val
             420                 425                 430

Val Ala Cys Arg Ile Thr Ala Glu Asn Pro Asp Thr Gly Phe Lys Pro
```

-continued

```
                435                 440                 445
    Gly Met Gly Ala Leu Thr Glu Leu Asn Phe Arg Ser Ser Thr Ser Thr
        450                 455                 460

Trp Gly Tyr Phe Ser Val Gly Thr Ser Gly Ala Leu His Glu Tyr Ala
    465                 470                 475                 480

Asp Ser Gln Phe Gly His Ile Phe Ala Tyr Gly Ala Asp Arg Ser Glu
                        485                 490                 495

Ala Arg Lys Gln Met Val Ile Ser Leu Lys Glu Leu Ser Ile Arg Gly
                    500                 505                 510

Asp Phe Arg Thr Thr Val Glu Tyr Leu Ile Lys Leu Leu Glu Thr Asp
                515                 520                 525

Ala Phe Glu Ser Asn Lys Ile Thr Thr Gly Trp Leu Asp Gly Leu Ile
            530                 535                 540

Gln Asp Arg Leu Thr Ala Glu Arg Pro Pro Ala Asp Leu Ala Val
    545                 550                 555

<210> SEQ ID NO 3
    <211> LENGTH: 1665
    <212> TYPE: DNA
    <213> ORGANISM: Phytophthora infestans
    <220> FEATURE:
    <221> NAME/KEY: CDS
    <222> LOCATION: (1)..(1665)
    <223> OTHER INFORMATION: ACCase BC domain (aa 1-555)

<400> SEQUENCE: 3 atg gtg gcc gag gaa gcg ccc ccc gcc gct gat gtt gcg gct tac gcg     48
    Met Val Ala Glu Glu Ala Pro Pro Ala Ala Asp Val Ala Ala Tyr Ala
    1               5                   10                  15 gag acg cgc agc gac agc aac ccg ctg aac tac gcg agc atg gag gag     96
    Glu Thr Arg Ser Asp Ser Asn Pro Leu Asn Tyr Ala Ser Met Glu Glu
                    20                  25                  30 tat gtg cgt ctg cag aag ggt acg cgc ccc att acg tcc gtt ctg atc    144
    Tyr Val Arg Leu Gln Lys Gly Thr Arg Pro Ile Thr Ser Val Leu Ile
                35                  40                  45 gcc aac aac ggt atc tcg gcc gtc aag gcc atc cgc agc atc cgc agc    192
    Ala Asn Asn Gly Ile Ser Ala Val Lys Ala Ile Arg Ser Ile Arg Ser
        50                  55                  60 tgg agc tac gag atg ttc gct gac gaa cac gtc gtg acc ttc gtc gtc    240
    Trp Ser Tyr Glu Met Phe Ala Asp Glu His Val Val Thr Phe Val Val
    65                  70                  75                  80 atg gct acg ccc gag gat ctt aag gct aat gca gag tac att cgc atg    288
    Met Ala Thr Pro Glu Asp Leu Lys Ala Asn Ala Glu Tyr Ile Arg Met
                    85                  90                  95 gcc gaa cac gtc gtc gaa gtg ccc ggc ggc tcc aac aac cac aac tac    336
    Ala Glu His Val Val Glu Val Pro Gly Gly Ser Asn Asn His Asn Tyr
                    100                 105                 110 gcc aac gta tct ctc atc att gag atc gcc gag cgc ttc aac gtc gac    384
    Ala Asn Val Ser Leu Ile Ile Glu Ile Ala Glu Arg Phe Asn Val Asp
                115                 120                 125 gcc gtc tgg gcc ggc tgg ggc cac gcc tct gag aat ccg ctt ctg ccc    432
    Ala Val Trp Ala Gly Trp Gly His Ala Ser Glu Asn Pro Leu Leu Pro
        130                 135                 140 gac acc ctc gct cag act gag cgt aag atc gtc ttt atc ggc ccc ccg    480
    Asp Thr Leu Ala Gln Thr Glu Arg Lys Ile Val Phe Ile Gly Pro Pro
    145                 150                 155                 160 ggc aag ccc atg cgt gca ttg ggc gac aag atc ggc tcc act atc atc    528
    Gly Lys Pro Met Arg Ala Leu Gly Asp Lys Ile Gly Ser Thr Ile Ile
                    165                 170                 175
```

-continued

| | | |
|---|---|---|
| gcg cag agc gct aag gtg cct aca atc gcc tgg aac ggc gac ggc atg<br>Ala Gln Ser Ala Lys Val Pro Thr Ile Ala Trp Asn Gly Asp Gly Met<br>           180                    185                    190 | 576 |
| gaa gtc gac tac aag gaa cac gac gga atc ccc gac gag atc tac aac<br>Glu Val Asp Tyr Lys Glu His Asp Gly Ile Pro Asp Glu Ile Tyr Asn<br>       195                    200                    205 | 624 |
| gcc gct atg ttg cgt gac ggc cag cac tgt ctg gac gaa tgc aaa cgt<br>Ala Ala Met Leu Arg Asp Gly Gln His Cys Leu Asp Glu Cys Lys Arg<br>210                    215                    220 | 672 |
| atc ggc ttc ccc gtc atg att aaa gcc agc gaa ggc gga ggt ggc aag<br>Ile Gly Phe Pro Val Met Ile Lys Ala Ser Glu Gly Gly Gly Gly Lys<br>225                    230                    235                    240 | 720 |
| ggt atc cgt atg gtt cac gaa gag tcc cag gtg ctc agt gcc tgg gaa<br>Gly Ile Arg Met Val His Glu Glu Ser Gln Val Leu Ser Ala Trp Glu<br>                    245                    250                    255 | 768 |
| gct gtg cgt ggt gag atc cct ggg tct cct atc ttc gtc atg aag ctg<br>Ala Val Arg Gly Glu Ile Pro Gly Ser Pro Ile Phe Val Met Lys Leu<br>                  260                    265                    270 | 816 |
| gca ccc aag tcg cgt cac ttg gaa gtg cag cta ttg gcg gat acg tac<br>Ala Pro Lys Ser Arg His Leu Glu Val Gln Leu Leu Ala Asp Thr Tyr<br>275                    280                    285 | 864 |
| ggc aat gcc atc gct ctc agt ggc cgt gat tgc tcc gtg cag cgt cgt<br>Gly Asn Ala Ile Ala Leu Ser Gly Arg Asp Cys Ser Val Gln Arg Arg<br>290                    295                    300 | 912 |
| cac caa aag atc gtc gag gaa ggt ccc gtt ctt gcg ccc acc caa gaa<br>His Gln Lys Ile Val Glu Glu Gly Pro Val Leu Ala Pro Thr Gln Glu<br>305                    310                    315                    320 | 960 |
| gtg tgg gag aag atg atg cgc gcc gcc act cgc ctc gct cag gag gtc<br>Val Trp Glu Lys Met Met Arg Ala Ala Thr Arg Leu Ala Gln Glu Val<br>                          325                    330                    335 | 1008 |
| gag tac gtc aac gcc ggt acc gtc gag tac ctg ttc agt gag ctg ccg<br>Glu Tyr Val Asn Ala Gly Thr Val Glu Tyr Leu Phe Ser Glu Leu Pro<br>                  340                    345                    350 | 1056 |
| gaa gac aac ggc aac tcg ttc ttc ttc ctg gaa ctc aac ccg cgt ttg<br>Glu Asp Asn Gly Asn Ser Phe Phe Phe Leu Glu Leu Asn Pro Arg Leu<br>       355                    360                    365 | 1104 |
| cag gtg gaa cac ccc gtc aca gag atg atc act cat gtg aat ctc cca<br>Gln Val Glu His Pro Val Thr Glu Met Ile Thr His Val Asn Leu Pro<br>370                    375                    380 | 1152 |
| gct gct caa ctg caa gtg gct atg ggt att ccg ctg cac tgc atc ccg<br>Ala Ala Gln Leu Gln Val Ala Met Gly Ile Pro Leu His Cys Ile Pro<br>385                    390                    395                    400 | 1200 |
| gat gtg cgt cgt ctg tac aac aag gat gcg ttt gag acg aca gtt att<br>Asp Val Arg Arg Leu Tyr Asn Lys Asp Ala Phe Glu Thr Thr Val Ile<br>                          405                    410                    415 | 1248 |
| gac ttc gac gcg gag aag cag aag cca ccg cat gga cac gtt atc gcc<br>Asp Phe Asp Ala Glu Lys Gln Lys Pro Pro His Gly His Val Ile Ala<br>                  420                    425                    430 | 1296 |
| gcg cgt att acc gcc gag gat ccg aac gcc ggt ttc cag cct acc agt<br>Ala Arg Ile Thr Ala Glu Asp Pro Asn Ala Gly Phe Gln Pro Thr Ser<br>                          435                    440                    445 | 1344 |
| gga gcc atc cag gag ctt aac ttc cgt agt acg ccc gat gta tgg ggt<br>Gly Ala Ile Gln Glu Leu Asn Phe Arg Ser Thr Pro Asp Val Trp Gly<br>                  450                    455                    460 | 1392 |
| tac ttc tcg gtg gac tcg tcc gga cag gtg cac gag ttc gct gac tca<br>Tyr Phe Ser Val Asp Ser Ser Gly Gln Val His Glu Phe Ala Asp Ser<br>465                    470                    475                    480 | 1440 |
| cag att ggt cac ctg ttc tcg tgg agt ccg act cgt gaa aag gcc cgt<br>Gln Ile Gly His Leu Phe Ser Trp Ser Pro Thr Arg Glu Lys Ala Arg<br>                          485                    490                    495 | 1488 |

```
aag aac atg gtt cta gcg ctc aag gag ttg tcg att cgt ggt gat att    1536
Lys Asn Met Val Leu Ala Leu Lys Glu Leu Ser Ile Arg Gly Asp Ile
        500                 505                 510 cac acg acg gtc gag tac atc gtt aac atg atg gag tct gat gat ttc    1584
His Thr Thr Val Glu Tyr Ile Val Asn Met Met Glu Ser Asp Asp Phe
        515                 520                 525 aag tac aac cgc atc tcc acg tcg tgg ctg gat gag cgt atc tcg cac    1632
Lys Tyr Asn Arg Ile Ser Thr Ser Trp Leu Asp Glu Arg Ile Ser His
        530                 535                 540 cac aat gaa gtg cgt cta cag ggt cgg ccg gac                        1665
His Asn Glu Val Arg Leu Gln Gly Arg Pro Asp
545                 550                 555

<210> SEQ ID NO 4
<211> LENGTH: 555
<212> TYPE: PRT
<213> ORGANISM: Phytophthora infestans

<400> SEQUENCE: 4

Met Val Ala Glu Glu Ala Pro Pro Ala Ala Asp Val Ala Ala Tyr Ala
1               5                   10                  15

Glu Thr Arg Ser Asp Ser Asn Pro Leu Asn Tyr Ala Ser Met Glu Glu
            20                  25                  30

Tyr Val Arg Leu Gln Lys Gly Thr Arg Pro Ile Thr Ser Val Leu Ile
        35                  40                  45

Ala Asn Asn Gly Ile Ser Ala Val Lys Ala Ile Arg Ser Ile Arg Ser
    50                  55                  60

Trp Ser Tyr Glu Met Phe Ala Asp Gl

```
Gly Asn Ala Ile Ala Leu Ser Gly Arg Asp Cys Ser Val Gln Arg Arg
        290                 295                 300

His Gln Lys Ile Val Glu Glu Gly Pro Val Leu Ala Pro Thr Gln Glu
305                 310                 315                 320

Val Trp Glu Lys Met Met Arg Ala Ala Thr Arg Leu Ala Gln Glu Val
                325                 330                 335

Glu Tyr Val Asn Ala Gly Thr Val Glu Tyr Leu Phe Ser Glu Leu Pro
            340                 345                 350

Glu Asp Asn Gly Asn Ser Phe Phe Leu Glu Leu Asn Pro Arg Leu
        355                 360                 365

Gln Val Glu His Pro Val Thr Glu Met Ile Thr His Val Asn Leu Pro
    370                 375                 380

Ala Ala Gln Leu Gln Val Ala Met Gly Ile Pro Leu His Cys Ile Pro
385                 390                 395                 400

Asp Val Arg Arg Leu Tyr Asn Lys Asp Ala Phe Glu Thr Thr Val Ile
                405                 410                 415

Asp Phe Asp Ala Glu Lys Gln Lys Pro Pro His Gly His Val Ile Ala
            420                 425                 430

Ala Arg Ile Thr Ala Glu Asp Pro Asn Ala Gly Phe Gln Pro Thr Ser
        435                 440                 445

Gly Ala Ile Gln Glu Leu Asn Phe Arg Ser Thr Pro Asp Val Trp Gly
    450                 455                 460

Tyr Phe Ser Val Asp Ser Ser Gly Gln Val His Glu Phe Ala Asp Ser
465                 470                 475                 480

Gln Ile Gly His Leu Phe Ser Trp Ser Pro Thr Arg Glu Lys Ala Arg
                485                 490                 495

Lys Asn Met Val Leu Ala Leu Lys Glu Leu Ser Ile Arg Gly Asp Ile
            500                 505                 510

His Thr Thr Val Glu Tyr Ile Val Asn Met Met Glu Ser Asp Asp Phe
        515                 520                 525

Lys Tyr Asn Arg Ile Ser Thr Ser Trp Leu Asp Glu Arg Ile Ser His
    530                 535                 540

His Asn Glu Val Arg Leu Gln Gly Arg Pro Asp
545                 550                 555

<210> SEQ ID NO 5
<211> LENGTH: 1773
<212> TYPE: DNA
<213> ORGANISM: Magnaporthe grisea
<220> FEATURE:
<221> NAME/KEY: CDS
<222> LOCATION: (1)..(1773)
<223> OTHER INFORMATION: ACCase BC domain (aa 2-592)

<400> SEQUENCE: 5 act gag aca aat gga acc gct gcg gct gct aac agc tcc cgt cag cgc      48
Thr Glu Thr Asn Gly Thr Ala Ala Ala Ala Asn Ser Ser Arg Gln Arg
1               5                   10                  15 aac ggc gcc aac ggc gtc acc gtg cct gtg gcc aac ggc aag gct act      96
Asn Gly Ala Asn Gly Val Thr Val Pro Val Ala Asn Gly Lys Ala Thr
            20                  25                  30 tac gct cag agg cac aag att gcc gac cac ttt att ggc ggc aac agg     144
Tyr Ala Gln Arg His Lys Ile Ala Asp His Phe Ile Gly Gly Asn Arg
        35                  40                  45 cta gag aat gcc cct ccg tcc aag gtc aag gag tgg gtt gcc gca cac     192
Leu Glu Asn Ala Pro Pro Ser Lys Val Lys Glu Trp Val Ala Ala His
    50                  55                  60
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gac | ggc | cac | aca | gtc | atc | acc | aac | gtc | ctg | att | gcc | aac | aac | ggt | atc | 240 |
| Asp | Gly | His | Thr | Val | Ile | Thr | Asn | Val | Leu | Ile | Ala | Asn | Asn | Gly | Ile |     |
| 65  |     |     |     | 70  |     |     |     | 75  |     |     |     | 80  |     |     |     |     |

| gct | gcc | gtc | aag | gag | att | cga | tcc | gtg | cga | aaa | tgg | gca | tac | gag | acg | 288 |
| --- | --- | --- | --- | --- | --- | --- | --- | --- | --- | --- | --- | --- | --- | --- | --- | --- |
| Ala | Ala | Val | Lys | Glu | Ile | Arg | Ser | Val | Arg | Lys | Trp | Ala | Tyr | Glu | Thr |     |
|     |     |     |     | 85  |     |     |     |     | 90  |     |     |     |     | 95  |     |     |

| ttc | gga | gac | gaa | agg | gcc | att | cag | ttc | act | gtg | atg | gcc | act | ccc | gag | 336 |
| --- | --- | --- | --- | --- | --- | --- | --- | --- | --- | --- | --- | --- | --- | --- | --- | --- |
| Phe | Gly | Asp | Glu | Arg | Ala | Ile | Gln | Phe | Thr | Val | Met | Ala | Thr | Pro | Glu |     |
|     |     |     | 100 |     |     |     |     | 105 |     |     |     |     | 110 |     |     |     |

| gat | ttg | caa | gca | aac | gca | gac | tac | att | cgc | atg | gca | gac | cac | tac | gtc | 384 |
| --- | --- | --- | --- | --- | --- | --- | --- | --- | --- | --- | --- | --- | --- | --- | --- | --- |
| Asp | Leu | Gln | Ala | Asn | Ala | Asp | Tyr | Ile | Arg | Met | Ala | Asp | His | Tyr | Val |     |
|     |     | 115 |     |     |     |     | 120 |     |     |     |     | 125 |     |     |     |     |

| gag | gtc | cct | ggt | ggt | aca | aac | aac | aac | tat | gcg | aac | gtc | gag | ttg |     | 432 |
| --- | --- | --- | --- | --- | --- | --- | --- | --- | --- | --- | --- | --- | --- | --- | --- | --- |
| Glu | Val | Pro | Gly | Gly | Thr | Asn | Asn | Asn | Tyr | Ala | Asn | Val | Glu | Leu |     |     |
| 130 |     |     |     |     | 135 |     |     |     |     | 140 |     |     |     |     |     |     |

| atc | gtc | gat | gtt | gcg | gag | cgc | atg | aac | gtg | cac | gcc | gtt | tgg | gcc | ggt | 480 |
| --- | --- | --- | --- | --- | --- | --- | --- | --- | --- | --- | --- | --- | --- | --- | --- | --- |
| Ile | Val | Asp | Val | Ala | Glu | Arg | Met | Asn | Val | His | Ala | Val | Trp | Ala | Gly |     |
| 145 |     |     |     | 150 |     |     |     | 155 |     |     |     | 160 |     |     |     |     |

| tgg | gga | cac | gca | tcg | gag | aac | cca | aag | ctc | cct | gag | tct | ctc | gct | gcc | 528 |
| --- | --- | --- | --- | --- | --- | --- | --- | --- | --- | --- | --- | --- | --- | --- | --- | --- |
| Trp | Gly | His | Ala | Ser | Glu | Asn | Pro | Lys | Leu | Pro | Glu | Ser | Leu | Ala | Ala |     |
|     |     |     |     | 165 |     |     |     |     | 170 |     |     |     |     | 175 |     |     |

| tcg | cct | aag | aaa | att | att | ttc | atc | ggc | cct | ccc | ggc | tcc | gcg | atg | cgc | 576 |
| --- | --- | --- | --- | --- | --- | --- | --- | --- | --- | --- | --- | --- | --- | --- | --- | --- |
| Ser | Pro | Lys | Lys | Ile | Ile | Phe | Ile | Gly | Pro | Pro | Gly | Ser | Ala | Met | Arg |     |
|     |     | 180 |     |     |     |     | 185 |     |     |     |     | 190 |     |     |     |     |

| tcg | ctc | ggt | gac | aag | atc | tct | tct | acc | att | gtc | gct | caa | cat | gcc | cag | 624 |
| --- | --- | --- | --- | --- | --- | --- | --- | --- | --- | --- | --- | --- | --- | --- | --- | --- |
| Ser | Leu | Gly | Asp | Lys | Ile | Ser | Ser | Thr | Ile | Val | Ala | Gln | His | Ala | Gln |     |
|     |     | 195 |     |     |     |     | 200 |     |     |     |     | 205 |     |     |     |     |

| gtc | cca | tgt | atc | ccc | tgg | tcg | gga | act | ggt | gtt | gat | gcg | gtc | caa | atc | 672 |
| --- | --- | --- | --- | --- | --- | --- | --- | --- | --- | --- | --- | --- | --- | --- | --- | --- |
| Val | Pro | Cys | Ile | Pro | Trp | Ser | Gly | Thr | Gly | Val | Asp | Ala | Val | Gln | Ile |     |
| 210 |     |     |     |     | 215 |     |     |     |     | 220 |     |     |     |     |     |     |

| gac | aag | aag | gga | att | gtc | acc | gtc | gac | gac | gac | act | tat | gcc | aaa | gga | 720 |
| --- | --- | --- | --- | --- | --- | --- | --- | --- | --- | --- | --- | --- | --- | --- | --- | --- |
| Asp | Lys | Lys | Gly | Ile | Val | Thr | Val | Asp | Asp | Asp | Thr | Tyr | Ala | Lys | Gly |     |
| 225 |     |     |     |     | 230 |     |     |     |     | 235 |     |     |     |     | 240 |     |

| tgc | gtc | act | tca | tgg | cag | gag | ggt | ctt | gag | aag | gcc | aga | caa | att | ggt | 768 |
| --- | --- | --- | --- | --- | --- | --- | --- | --- | --- | --- | --- | --- | --- | --- | --- | --- |
| Cys | Val | Thr | Ser | Trp | Gln | Glu | Gly | Leu | Glu | Lys | Ala | Arg | Gln | Ile | Gly |     |
|     |     |     |     | 245 |     |     |     |     | 250 |     |     |     |     | 255 |     |     |

| ttc | ccg | gtc | atg | atc | aag | gct | tct | gag | ggt | ggt | ggt | ggc | aag | ggt | atc | 816 |
| --- | --- | --- | --- | --- | --- | --- | --- | --- | --- | --- | --- | --- | --- | --- | --- | --- |
| Phe | Pro | Val | Met | Ile | Lys | Ala | Ser | Glu | Gly | Gly | Gly | Gly | Lys | Gly | Ile |     |
|     |     |     | 260 |     |     |     |     | 265 |     |     |     |     | 270 |     |     |     |

| cgt | aag | gct | gtc | tcc | gag | gag | ggc | ttc | gag | gag | ctc | tac | aag | gcc | gct | 864 |
| --- | --- | --- | --- | --- | --- | --- | --- | --- | --- | --- | --- | --- | --- | --- | --- | --- |
| Arg | Lys | Ala | Val | Ser | Glu | Glu | Gly | Phe | Glu | Glu | Leu | Tyr | Lys | Ala | Ala |     |
|     |     | 275 |     |     |     |     | 280 |     |     |     |     | 285 |     |     |     |     |

| gcc | agt | gaa | atc | ccc | ggt | tcg | ccc | atc | ttc | atc | atg | aag | ctt | gca | ggc | 912 |
| --- | --- | --- | --- | --- | --- | --- | --- | --- | --- | --- | --- | --- | --- | --- | --- | --- |
| Ala | Ser | Glu | Ile | Pro | Gly | Ser | Pro | Ile | Phe | Ile | Met | Lys | Leu | Ala | Gly |     |
|     | 290 |     |     |     |     | 295 |     |     |     |     | 300 |     |     |     |     |     |

| aac | gcc | agg | cat | ttg | gaa | gtg | cag | ctt | ctc | gct | gat | cag | tac | ggc | aac | 960 |
| --- | --- | --- | --- | --- | --- | --- | --- | --- | --- | --- | --- | --- | --- | --- | --- | --- |
| Asn | Ala | Arg | His | Leu | Glu | Val | Gln | Leu | Leu | Ala | Asp | Gln | Tyr | Gly | Asn |     |
| 305 |     |     |     |     | 310 |     |     |     |     | 315 |     |     |     |     | 320 |     |

| aac | atc | tcc | ctc | ttt | ggt | cgt | gat | tgt | tcc | gtc | cag | cga | agg | cac | caa | 1008 |
| --- | --- | --- | --- | --- | --- | --- | --- | --- | --- | --- | --- | --- | --- | --- | --- | --- |
| Asn | Ile | Ser | Leu | Phe | Gly | Arg | Asp | Cys | Ser | Val | Gln | Arg | Arg | His | Gln |     |
|     |     |     |     | 325 |     |     |     |     | 330 |     |     |     |     | 335 |     |     |

| aag | att | atc | gag | gaa | gct | ccc | gtg | acc | atc | gcc | aag | ccc | gac | acg | ttc | 1056 |
| --- | --- | --- | --- | --- | --- | --- | --- | --- | --- | --- | --- | --- | --- | --- | --- | --- |
| Lys | Ile | Ile | Glu | Glu | Ala | Pro | Val | Thr | Ile | Ala | Lys | Pro | Asp | Thr | Phe |     |
|     |     |     | 340 |     |     |     |     | 345 |     |     |     |     | 350 |     |     |     |

| aag | gcc | atg | gag | gag | gcc | gct | gtt | cgt | ctt | ggt | cgt | ctt | gtc | ggt | tac | 1104 |
| --- | --- | --- | --- | --- | --- | --- | --- | --- | --- | --- | --- | --- | --- | --- | --- | --- |
| Lys | Ala | Met | Glu | Glu | Ala | Ala | Val | Arg | Leu | Gly | Arg | Leu | Val | Gly | Tyr |     |
|     |     | 355 |     |     |     |     | 360 |     |     |     |     | 365 |     |     |     |     |

| gtc | tct | gct | ggt | acc | gtc | gag | tac | ctg | tac | tcg | cac | gcc | gac | gac | aag | 1152 |
| --- | --- | --- | --- | --- | --- | --- | --- | --- | --- | --- | --- | --- | --- | --- | --- | --- |
| Val | Ser | Ala | Gly | Thr | Val | Glu | Tyr | Leu | Tyr | Ser | His | Ala | Asp | Asp | Lys |     |
|     | 370 |     |     |     |     | 375 |     |     |     |     | 380 |     |     |     |     |     |

-continued

```
ttc tac ttc ctg gag ctc aac cct cgt ctt cag gtc gag cat cct acc      1200
Phe Tyr Phe Leu Glu Leu Asn Pro Arg Leu Gln Val Glu His Pro Thr
385                 390                 395                 400 act gag ggt gtc agt ggt gtc aac ctc ccc gct tcg cag ctt cag att      1248
Thr Glu Gly Val Ser Gly Val Asn Leu Pro Ala Ser Gln Leu Gln Ile
            405                 410                 415 gcc atg ggt atc cct ctc cac agg ata tct gac att agg ctc ctt tac      1296
Ala Met Gly Ile Pro Leu His Arg Ile Ser Asp Ile Arg Leu Leu Tyr
        420                 425                 430 ggt gtg gac ccc aag ctc tcg act gag atc gac ttt gac ttc aag aac      1344
Gly Val Asp Pro Lys Leu Ser Thr Glu Ile Asp Phe Asp Phe Lys Asn
    435                 440                 445 ccc gac agc gag aag acg cag agg agg cca tcg ccc aaa ggc cac ctt      1392
Pro Asp Ser Glu Lys Thr Gln Arg Arg Pro Ser Pro Lys Gly His Leu
450                 455                 460 act gcc tgc cgt att acc tca gag gac cct gga gag ggc ttc aag ccg      1440
Thr Ala Cys Arg Ile Thr Ser Glu Asp Pro Gly Glu Gly Phe Lys Pro
465                 470                 475                 480 tcc aac ggt gtc atg cac gag ctg aac ttc cgc agt agt tca aac gtg      1488
Ser Asn Gly Val Met His Glu Leu Asn Phe Arg Ser Ser Ser Asn Val
            485                 490                 495 tgg ggt tac ttc tca gtc ggt acg cag ggt gga att cac agt ttc tcc      1536
Trp Gly Tyr Phe Ser Val Gly Thr Gln Gly Gly Ile His Ser Phe Ser
        500                 505                 510 gac agt cag ttc ggt cac att ttc gcc tat ggc gag aac cga tcc gcg      1584
Asp Ser Gln Phe Gly His Ile Phe Ala Tyr Gly Glu Asn Arg Ser Ala
    515                 520                 525 tca agg aag cac atg gtt atc gcc ttg aag gaa ctt agc att cgt ggt      1632
Ser Arg Lys His Met Val Ile Ala Leu Lys Glu Leu Ser Ile Arg Gly
530                 535                 540 gat ttc cgc acc acg gtc gag tac cta atc aag ctt ctg gag acg gag      1680
Asp Phe Arg Thr Thr Val Glu Tyr Leu Ile Lys Leu Leu Glu Thr Glu
545                 550                 555                 560 gct ttc gag gag aac acc att acc act ggc tgg ctg gac gag ctt att      1728
Ala Phe Glu Glu Asn Thr Ile Thr Thr Gly Trp Leu Asp Glu Leu Ile
            565                 570                 575 tcg aag aag ctc act gcg gag agg ccc gac aag atg ctt gct gtt           1773
Ser Lys Lys Leu Thr Ala Glu Arg Pro Asp Lys Met Leu Ala Val
        580                 585                 590

<210> SEQ ID NO 6
<211> LENGTH: 591
<212> TYPE: PRT
<213> ORGANISM: Magnaporthe grisea

<400> SEQUENCE: 6

Thr Glu Thr Asn Gly Thr Ala Ala Ala Asn Ser Ser Arg Gln Arg
1               5                   10                  15

Asn Gly Ala Asn Gly Val Thr Val Pro Val Ala Asn Gly Lys Ala Thr
            20                  25                  30

Tyr Ala Gln Arg His Lys Ile Ala Asp His Phe Ile Gly Gly Asn Arg
        35                  40                  45

Leu Glu Asn Ala Pro Pro Ser Lys Val Lys Glu Trp Val Ala Ala His
    50                  55                  60

Asp Gly His Thr Val Ile Thr Asn Val Leu Ile Ala Asn Asn Gly Ile
65                  70                  75                  80

Ala Ala Val Lys Glu Ile Arg Ser Val Arg Lys Trp Ala Tyr Glu Thr
                85                  90                  95
```

-continued

```
Phe Gly Asp Glu Arg Ala Ile Gln Phe Thr Val Met Ala Thr Pro Glu
            100                 105                 110

Asp Leu Gln Ala Asn Ala Asp Tyr Ile Arg Met Ala Asp His Tyr Val
        115                 120                 125

Glu Val Pro Gly Gly Thr Asn Asn Asn Tyr Ala Asn Val Glu Leu
    130                 135                 140

Ile Val Asp Val Ala Glu Arg Met Asn Val His Ala Val Trp Ala Gly
145                 150                 155                 160

Trp Gly His Ala Ser Glu Asn Pro Lys Leu Pro Glu Ser Leu Ala Ala
                165                 170                 175

Ser Pro Lys Lys Ile Ile Phe Ile Gly Pro Pro Gly Ser Ala Met Arg
            180                 185                 190

Ser Leu Gly Asp Lys Ile Ser Ser Thr Ile Val Ala Gln His Ala Gln
        195                 200                 205

Val Pro Cys Ile Pro Trp Ser Gly Thr Gly Val Asp Ala Val Gln Ile
    210                 215                 220

Asp Lys Lys Gly Ile Val Thr Val Asp Asp Thr Tyr Ala Lys Gly
225                 230                 235                 240

Cys Val Thr Ser Trp Gln Glu Gly Leu Glu Lys Ala Arg Gln Ile Gly
                245                 250                 255

Phe Pro Val Met Ile Lys Ala Ser Glu Gly Gly Gly Lys Gly Ile
            260                 265                 270

Arg Lys Ala Val Ser Glu Glu Gly Phe Glu Glu Leu Tyr Lys Ala Ala
        275                 280                 285

Ala Ser Glu Ile Pro Gly Ser Pro Ile Phe Ile Met Lys Leu Ala Gly
    290                 295                 300

Asn Ala Arg His Leu Glu Val Gln Leu Leu Ala Asp Gln Tyr Gly Asn
305                 310                 315                 320

Asn Ile Ser Leu Phe Gly Arg Asp Cys Ser Val Gln Arg Arg His Gln
                325                 330                 335

Lys Ile Ile Glu Glu Ala Pro Val Thr Ile Ala Lys Pro Asp Thr Phe
            340                 345                 350

Lys Ala Met Glu Glu Ala Ala Val Arg Leu Gly Arg Leu Val Gly Tyr
        355                 360                 365

Val Ser Ala Gly Thr Val Glu Tyr Leu Tyr Ser His Ala Asp Asp Lys
    370                 375                 380

Phe Tyr Phe Leu Glu Leu Asn Pro Arg Leu Gln Val Glu His Pro Thr
385                 390                 395                 400

Thr Glu Gly Val Ser Gly Val Asn Leu Pro Ala Ser Gln Leu Gln Ile
                405                 410                 415

Ala Met Gly Ile Pro Leu His Arg Ile Ser Asp Ile Arg Leu Leu Tyr
            420                 425                 430

Gly Val Asp Pro Lys Leu Ser Thr Glu Ile Asp Phe Asp Phe Lys Asn
        435                 440                 445

Pro Asp Ser Glu Lys Thr Gln Arg Arg Pro Ser Pro Lys Gly His Leu
    450                 455                 460

Thr Ala Cys Arg Ile Thr Ser Glu Asp Pro Gly Glu Gly Phe Lys Pro
465                 470                 475                 480

Ser Asn Gly Val Met His Glu Leu Asn Phe Arg Ser Ser Ser Asn Val
                485                 490                 495

Trp Gly Tyr Phe Ser Val Gly Thr Gln Gly Gly Ile His Ser Phe Ser
            500                 505                 510

Asp Ser Gln Phe Gly His Ile Phe Ala Tyr Gly Glu Asn Arg Ser Ala
```

```
                        515                 520                 525
Ser Arg Lys His Met Val Ile Ala Leu Lys Glu Leu Ser Ile Arg Gly
            530                 535                 540

Asp Phe Arg Thr Thr Val Glu Tyr Leu Ile Lys Leu Leu Glu Thr Glu
545                 550                 555                 560

Ala Phe Glu Glu Asn Thr Ile Thr Thr Gly Trp Leu Asp Leu Ile
                565                 570                 575

Ser Lys Lys Leu Thr Ala Glu Arg Pro Asp Lys Met Leu Ala Val
            580                 585                 590

<210> SEQ ID NO 7
<211> LENGTH: 1740
<212> TYPE: DNA
<213> ORGANISM: Saccharomyces cerevisiae
<220> FEATURE:
<221> NAME/KEY: CDS
<222> LOCATION: (1)..(1740)
<223> OTHER INFORMATION: ACCase BC domain (aa 2-581)
<220> FEATURE:
<221> NAME/KEY: misc_feature
<222> LOCATION: (226)..(228)
<223> OTHER INFORMATION: Alteration of Ser-77 codon results in Ser to
      Tyr mutation that eliminates soraphen binding

<400> SEQUENCE: 7 tct gaa gaa agc tta ttc gag tct tct cca cag aag atg gag tac gaa    48
Ser Glu Glu Ser Leu Phe Glu Ser Ser Pro Gln Lys Met Glu Tyr Glu
1               5                  10                  15 att aca aac tac tca gaa aga cat aca gaa ctt cca ggt cat ttc att    96
Ile Thr Asn Tyr Ser Glu Arg His Thr Glu Leu Pro Gly His Phe Ile
                20                  25                  30 ggc ctc aat aca gta gat aaa cta gag gag tcc ccg tta agg gac ttt   144
Gly Leu Asn Thr Val Asp Lys Leu Glu Glu Ser Pro Leu Arg Asp Phe
            35                  40                  45 gtt aag agt cac ggt ggt cac acg gtc ata tcc aag atc ctg ata gca   192
Val Lys Ser His Gly Gly His Thr Val Ile Ser Lys Ile Leu Ile Ala
    50                  55                  60 aat aat ggt att gcc gcc gtg aaa gaa att aga tcc gtc aga aaa tgg   240
Asn Asn Gly Ile Ala Ala Val Lys Glu Ile Arg Ser Val Arg Lys Trp
65                  70                  75                  80 gca tac gag acg ttc ggc gat gac aga acc gtc caa ttc gtc gcc atg   288
Ala Tyr Glu Thr Phe Gly Asp Asp Arg Thr Val Gln Phe Val Ala Met
                85                  90                  95 gcc acc cca gaa gat ctg gag gcc aac gca gaa tat atc cgt atg gcc   336
Ala Thr Pro Glu Asp Leu Glu Ala Asn Ala Glu Tyr Ile Arg Met Ala
                100                 105                 110 gat caa tac att gaa gtg cca ggt ggt act aat aat aac aac tac gct   384
Asp Gln Tyr Ile Glu Val Pro Gly Gly Thr Asn Asn Asn Asn Tyr Ala
            115                 120                 125 aac gta gac ttg atc gta gac atc gcc gaa aga gca gac gta gac gcc   432
Asn Val Asp Leu Ile Val Asp Ile Ala Glu Arg Ala Asp Val Asp Ala
        130                 135                 140 gta tgg gct ggc tgg ggt cac gcc tcc gag aat cca cta ttg cct gaa   480
Val Trp Ala Gly Trp Gly His Ala Ser Glu Asn Pro Leu Leu Pro Glu
145                 150                 155                 160 aaa ttg tcc cag tct aag agg aaa gtc atc ttt att ggg cct cca ggt   528
Lys Leu Ser Gln Ser Lys Arg Lys Val Ile Phe Ile Gly Pro Pro Gly
                165                 170                 175 aac gcc atg agg tct tta ggt gat aaa atc tcc tct acc att gtc gct   576
Asn Ala Met Arg Ser Leu Gly Asp Lys Ile Ser Ser Thr Ile Val Ala
                180                 185                 190
```

```
caa agt gct aaa gtc cca tgt att cca tgg tct ggt acc ggt gtt gac      624
Gln Ser Ala Lys Val Pro Cys Ile Pro Trp Ser Gly Thr Gly Val Asp
            195                 200                 205 acc gtt cac gtg gac gag aaa acc ggt ctg gtc tct gtc gac gat gac      672
Thr Val His Val Asp Glu Lys Thr Gly Leu Val Ser Val Asp Asp Asp
    210                 215                 220 atc tat caa aag ggt tgt tgt acc tct cct gaa gat ggt tta caa aag      720
Ile Tyr Gln Lys Gly Cys Cys Thr Ser Pro Glu Asp Gly Leu Gln Lys
225                 230                 235                 240 gcc aag cgt att ggt ttt cct gtc atg att aag gca tcc gaa ggt ggt      768
Ala Lys Arg Ile Gly Phe Pro Val Met Ile Lys Ala Ser Glu Gly Gly
                245                 250                 255 ggt ggt aaa ggt atc aga caa gtt gaa cgt gaa gaa gat ttc atc gct      816
Gly Gly Lys Gly Ile Arg Gln Val Glu Arg Glu Glu Asp Phe Ile Ala
            260                 265                 270 tta tac cac cag gca gcc aac gaa att cca ggc tcc ccc att ttc atc      864
Leu Tyr His Gln Ala Ala Asn Glu Ile Pro Gly Ser Pro Ile Phe Ile
        275                 280                 285 atg aag ttg gcc ggt aga gcg cgt cac ttg gaa gtt caa ctg cta gca      912
Met Lys Leu Ala Gly Arg Ala Arg His Leu Glu Val Gln Leu Leu Ala
    290                 295                 300 gat cag tac ggt aca aat att tcc ttg ttc ggt aga gac tgt tcc gtt      960
Asp Gln Tyr Gly Thr Asn Ile Ser Leu Phe Gly Arg Asp Cys Ser Val
305                 310                 315                 320 cag aga cgt cat caa aaa att atc gaa gaa gca cca gtt aca att gcc     1008
Gln Arg Arg His Gln Lys Ile Ile Glu Glu Ala Pro Val Thr Ile Ala
                325                 330                 335 aag gct gaa aca ttt cac gag atg gaa aag gct gcc gtc aga ctg ggg     1056
Lys Ala Glu Thr Phe His Glu Met Glu Lys Ala Ala Val Arg Leu Gly
            340                 345                 350 aaa cta gtc ggt tat gtc tct gcc ggt acc gtg gag tat cta tat tct     1104
Lys Leu Val Gly Tyr Val Ser Ala Gly Thr Val Glu Tyr Leu Tyr Ser
        355                 360                 365 cat gat gat gga aaa ttc tac ttt tta gaa ttg aac cca aga tta caa     1152
His Asp Asp Gly Lys Phe Tyr Phe Leu Glu Leu Asn Pro Arg Leu Gln
    370                 375                 380 gtc gag cat cca aca acg gaa atg gtc tcc ggt gtt aac tta cct gca     1200
Val Glu His Pro Thr Thr Glu Met Val Ser Gly Val Asn Leu Pro Ala
385                 390                 395                 400 gct caa tta caa atc gct atg ggt atc cct atg cat aga ata agt gac     1248
Ala Gln Leu Gln Ile Ala Met Gly Ile Pro Met His Arg Ile Ser Asp
                405                 410                 415 att aga act tta tat ggt atg aat cct cat tct gcc tca gaa atc gat     1296
Ile Arg Thr Leu Tyr Gly Met Asn Pro His Ser Ala Ser Glu Ile Asp
            420                 425                 430 ttc gaa ttc aaa act caa gat gcc acc aag aaa caa aga aga cct att     1344
Phe Glu Phe Lys Thr Gln Asp Ala Thr Lys Lys Gln Arg Arg Pro Ile
        435                 440                 445 cca aag ggt cat tgt acc gct tgt cgt atc aca tca gaa gat cca aac     1392
Pro Lys Gly His Cys Thr Ala Cys Arg Ile Thr Ser Glu Asp Pro Asn
    450                 455                 460 gat gga ttc aag cca tcg ggt ggt act ttg cat gaa cta aac ttc cgt     1440
Asp Gly Phe Lys Pro Ser Gly Gly Thr Leu His Glu Leu Asn Phe Arg
465                 470                 475                 480 tct tcc tct aat gtt tgg ggt tac ttc tcc gtg ggt aac aat ggt aat     1488
Ser Ser Ser Asn Val Trp Gly Tyr Phe Ser Val Gly Asn Asn Gly Asn
                485                 490                 495 att cac tcc ttt tcg gac tct cag ttc ggc cat att ttt gct ttt ggt     1536
Ile His Ser Phe Ser Asp Ser Gln Phe Gly His Ile Phe Ala Phe Gly
            500                 505                 510
```

-continued

```
gaa aat aga caa gct tcc agg aaa cac atg gtt gtt gcc ctg aag gaa    1584
Glu Asn Arg Gln Ala Ser Arg Lys His Met Val Val Ala Leu Lys Glu
        515                 520                 525 ttg tcc att agg ggt gat ttc aga act act gtg gaa tac ttg atc aaa    1632
Leu Ser Ile Arg Gly Asp Phe Arg Thr Thr Val Glu Tyr Leu Ile Lys
530                 535                 540 ctt ttg gaa act gaa gat ttc gag gat aac act att acc acc ggt tgg    1680
Leu Leu Glu Thr Glu Asp Phe Glu Asp Asn Thr Ile Thr Thr Gly Trp
545                 550                 555                 560 ttg gac gat ttg att act cat aaa atg acc gct gaa aag cct gat cca    1728
Leu Asp Asp Leu Ile Thr His Lys Met Thr Ala Glu Lys Pro Asp Pro
                565                 570                 575 act ctt gcc gtc                                                    1740
Thr Leu Ala Val
            580

<210> SEQ ID NO 8
<211> LENGTH: 580
<212> TYPE: PRT
<213> ORGANISM: Saccharomyces cerevisiae

<400> SEQUENCE: 8

Ser Glu Glu Ser Leu Phe Glu Ser Ser Pro Gln Lys Met Glu Tyr Glu
1               5                   10                  15

Ile Thr Asn Tyr Ser Glu Arg His Thr Glu Leu Pro Gly His Phe Ile
            20                  25                  30

Gly Leu Asn Thr Val Asp Lys Leu Glu Glu Ser Pro Leu Arg Asp Phe
        35                  40                  45

Val Lys Ser His Gly Gly His Thr Val Ile Ser Lys Ile Leu Ile Ala
    50                  55                  60

Asn Asn Gly Ile Ala Ala Val Lys Glu Ile Arg Ser Val Arg Lys Trp
65                  70                  75                  80

Ala Tyr Glu Thr Phe Gly Asp Asp Arg Thr Val Gln Phe Val Ala Met
                85                  90                  95

Ala Thr Pro Glu Asp Leu Glu Ala Asn Ala Glu Tyr Ile Arg Met Ala
            100                 105                 110

Asp Gln Tyr Ile Glu Val Pro Gly Gly Thr Asn Asn Asn Tyr Ala
        115                 120                 125

Asn Val Asp Leu Ile Val Asp Ile Ala Glu Arg Ala Asp Val Asp Ala
    130                 135                 140

Val Trp Ala Gly Trp Gly His Ala Ser Glu Asn Pro Leu Leu Pro Glu
145                 150                 155                 160

Lys Leu Ser Gln Ser Lys Arg Lys Val Ile Phe Ile Gly Pro Pro Gly
                165                 170                 175

Asn Ala Met Arg Ser Leu Gly Asp Lys Ile Ser Ser Thr Ile Val Ala
            180                 185                 190

Gln Ser Ala Lys Val Pro Cys Ile Pro Trp Ser Gly Thr Gly Val Asp
        195                 200                 205

Thr Val His Val Asp Glu Lys Thr Gly Leu Val Ser Val Asp Asp
    210                 215                 220

Ile Tyr Gln Lys Gly Cys Cys Thr Ser Pro Glu Asp Gly Leu Gln Lys
225                 230                 235                 240

Ala Lys Arg Ile Gly Phe Pro Val Met Ile Lys Ala Ser Glu Gly Gly
                245                 250                 255

Gly Gly Lys Gly Ile Arg Gln Val Glu Arg Glu Glu Asp Phe Ile Ala
            260                 265                 270
```

```
Leu Tyr His Gln Ala Ala Asn Glu Ile Pro Gly Ser Pro Ile Phe Ile
        275                 280                 285

Met Lys Leu Ala Gly Arg Ala Arg His Leu Glu Val Gln Leu Leu Ala
        290                 295                 300

Asp Gln Tyr Gly Thr Asn Ile Ser Leu Phe Gly Arg Asp Cys Ser Val
305                 310                 315                 320

Gln Arg Arg His Gln Lys Ile Ile Glu Glu Ala Pro Val Thr Ile Ala
                325                 330                 335

Lys Ala Glu Thr Phe His Glu Met Glu Lys Ala Val Arg Leu Gly
                340                 345                 350

Lys Leu Val Gly Tyr Val Ser Ala Gly Thr Val Glu Tyr Leu Tyr Ser
        355                 360                 365

His Asp Asp Gly Lys Phe Tyr Phe Leu Glu Leu Asn Pro Arg Leu Gln
        370                 375                 380

Val Glu His Pro Thr Thr Glu Met Val Ser Gly Val Asn Leu Pro Ala
385                 390                 395                 400

Ala Gln Leu Gln Ile Ala Met Gly Ile Pro Met His Arg Ile Ser Asp
                405                 410                 415

Ile Arg Thr Leu Tyr Gly Met Asn Pro His Ser Ala Ser Glu Ile Asp
                420                 425                 430

Phe Glu Phe Lys Thr Gln Asp Ala Thr Lys Lys Gln Arg Arg Pro Ile
        435                 440                 445

Pro Lys Gly His Cys Thr Ala Cys Arg Ile Thr Ser Glu Asp Pro Asn
        450                 455                 460

Asp Gly Phe Lys Pro Ser Gly Gly Thr Leu His Glu Leu Asn Phe Arg
465                 470                 475                 480

Ser Ser Ser Asn Val Trp Gly Tyr Phe Ser Val Gly Asn Asn Gly Asn
                485                 490                 495

Ile His Ser Phe Ser Asp Ser Gln Phe Gly His Ile Phe Ala Phe Gly
        500                 505                 510

Glu Asn Arg Gln Ala Ser Arg Lys His Met Val Val Ala Leu Lys Glu
        515                 520                 525

Leu Ser Ile Arg Gly Asp Phe Arg Thr Thr Val Glu Tyr Leu Ile Lys
        530                 535                 540

Leu Leu Glu Thr Glu Asp Phe Glu Asp Asn Thr Ile Thr Thr Gly Trp
545                 550                 555                 560

Leu Asp Asp Leu Ile Thr His Lys Met Thr Ala Glu Lys Pro Asp Pro
                565                 570                 575

Thr Leu Ala Val
        580

<210> SEQ ID NO 9
<211> LENGTH: 1896
<212> TYPE: DNA
<213> ORGANISM: Homo sapiens
<220> FEATURE:
<221> NAME/KEY: CDS
<222> LOCATION: (1)..(1896)
<223> OTHER INFORMATION: Human ACCase1 (alpha) BC domain (aa 1-632)

<400> SEQUENCE: 9 atg gat gaa cca tct ccc ttg gcc caa cct ctg gag ctg aac cag cac      48
Met Asp Glu Pro Ser Pro Leu Ala Gln Pro Leu Glu Leu Asn Gln His
1               5                   10                  15 tct cga ttc ata ata ggt tct gtg tct gaa gat aac tca gag gat gag      96
Ser Arg Phe Ile Ile Gly Ser Val Ser Glu Asp Asn Ser Glu Asp Glu
```

-continued

```
              20                  25                  30
atc agc aac ctg gtg aag ttg gac cta ctg gag gag aag gag ggc tcc    144
Ile Ser Asn Leu Val Lys Leu Asp Leu Leu Glu Glu Lys Glu Gly Ser
         35                  40                  45 ttg tca cct gct tct gtt ggc tca gat aca ctc tct gat ttg ggg atc    192
Leu Ser Pro Ala Ser Val Gly Ser Asp Thr Leu Ser Asp Leu Gly Ile
 50                  55                  60 tct agc cta cag gat ggc ttg gcc ttg cac ata agg tcc agc atg tct    240
Ser Ser Leu Gln Asp Gly Leu Ala Leu His Ile Arg Ser Ser Met Ser
 65                  70                  75                  80 ggc ttg cac cta gta aag cag ggc cga gac aga aag aaa ata gat tct    288
Gly Leu His Leu Val Lys Gln Gly Arg Asp Arg Lys Lys Ile Asp Ser
                 85                  90                  95 caa cga gat ttc act gtg gct tct cca gca gaa ttt gtt act cgc ttt    336
Gln Arg Asp Phe Thr Val Ala Ser Pro Ala Glu Phe Val Thr Arg Phe
            100                 105                 110 ggg gga aat aaa gtg att gag aag gtt ctt att gct aac aat ggc att    384
Gly Gly Asn Lys Val Ile Glu Lys Val Leu Ile Ala Asn Asn Gly Ile
        115                 120                 125 gca gca gtg aaa tgc atg cgg tct atc cgt agg tgg tct tat gaa atg    432
Ala Ala Val Lys Cys Met Arg Ser Ile Arg Arg Trp Ser Tyr Glu Met
130                 135                 140 ttt cga aat gaa cgt gca att aga ttc gtt gtc atg gtc aca cct gaa    480
Phe Arg Asn Glu Arg Ala Ile Arg Phe Val Val Met Val Thr Pro Glu
145                 150                 155                 160 gac ctt aaa gcc aat gca gaa tac att aag atg gca gat cac tat gtg    528
Asp Leu Lys Ala Asn Ala Glu Tyr Ile Lys Met Ala Asp His Tyr Val
                165                 170                 175 cca gtg cct gga gga cca aac aac aac aac tat gca aat gtg gaa tta    576
Pro Val Pro Gly Gly Pro Asn Asn Asn Asn Tyr Ala Asn Val Glu Leu
            180                 185                 190 att ctt gat att gct aaa agg atc cca gtg cag gca gtg tgg gct ggc    624
Ile Leu Asp Ile Ala Lys Arg Ile Pro Val Gln Ala Val Trp Ala Gly
        195                 200                 205 tgg ggt cat gct tct gag aat ccc aaa cta ccg gaa ctt ctc ttg aaa    672
Trp Gly His Ala Ser Glu Asn Pro Lys Leu Pro Glu Leu Leu Leu Lys
210                 215                 220 aat ggc att gcc ttc atg ggt cct cca agc cag gcc atg tgg gct tta    720
Asn Gly Ile Ala Phe Met Gly Pro Pro Ser Gln Ala Met Trp Ala Leu
225                 230                 235                 240 ggg gat aag att gca tct tcc ata gtg gct caa act gca ggt atc cca    768
Gly Asp Lys Ile Ala Ser Ser Ile Val Ala Gln Thr Ala Gly Ile Pro
                245                 250                 255 act ctt ccc tgg agc ggc agt ggt ctt cgt gtg gac tgg cag gaa aat    816
Thr Leu Pro Trp Ser Gly Ser Gly Leu Arg Val Asp Trp Gln Glu Asn
            260                 265                 270 gat ttt tca aaa cgt atc tta aat gtt ccc cag gag cta tat gaa aaa    864
Asp Phe Ser Lys Arg Ile Leu Asn Val Pro Gln Glu Leu Tyr Glu Lys
        275                 280                 285 ggt tat gtg aaa gat gtg gat gat ggg cta aag gca gct gag gaa gtt    912
Gly Tyr Val Lys Asp Val Asp Asp Gly Leu Lys Ala Ala Glu Glu Val
290                 295                 300 gga tat cca gta atg atc aag gcc tca gag gga gga gga ggg aag gga    960
Gly Tyr Pro Val Met Ile Lys Ala Ser Glu Gly Gly Gly Gly Lys Gly
305                 310                 315                 320 att aga aaa gtc aac aat gca gat gac ttc cct aat ctc ttc aga cag    1008
Ile Arg Lys Val Asn Asn Ala Asp Asp Phe Pro Asn Leu Phe Arg Gln
                325                 330                 335 gtt caa gct gaa gtt cct gga tct ccc ata ttt gtg atg aga cta gcc    1056
Val Gln Ala Glu Val Pro Gly Ser Pro Ile Phe Val Met Arg Leu Ala
```

|     |     |     |     |     |     |     |     |     |     |     |     |     |     |
|---|---|---|---|---|---|---|---|---|---|---|---|---|---|
| Val | Gln | Ala | Glu | Val | Pro | Gly | Ser | Pro | Ile | Phe | Val | Met | Arg | Leu | Ala |
|     |     |     | 340 |     |     |     | 345 |     |     |     |     | 350 |     |

```
aaa caa tct cgt cat ctg gag gtg cag atc tta gcg gac caa tat ggc        1104
Lys Gln Ser Arg His Leu Glu Val Gln Ile Leu Ala Asp Gln Tyr Gly
        355                 360                 365 aat gct atc tct ttg ttt ggt cgt gat tgc tct gta caa cgc agg cat        1152
Asn Ala Ile Ser Leu Phe Gly Arg Asp Cys Ser Val Gln Arg Arg His
370                 375                 380 cag aag att att gaa gaa gca cct gct act att gct act cca gca gta        1200
Gln Lys Ile Ile Glu Glu Ala Pro Ala Thr Ile Ala Thr Pro Ala Val
385                 390                 395                 400 ttt gaa cac atg gaa cag tgt gcg gtg aaa ctt gcc aaa atg gtg ggt        1248
Phe Glu His Met Glu Gln Cys Ala Val Lys Leu Ala Lys Met Val Gly
                405                 410                 415 tat gtg agt gct ggg act gtg gaa tac ctg tac agc cag gat ggc agc        1296
Tyr Val Ser Ala Gly Thr Val Glu Tyr Leu Tyr Ser Gln Asp Gly Ser
            420                 425                 430 ttc tac ttt ctg gaa ttg aat cct cgg ctg cag gta gag cac cct tgt        1344
Phe Tyr Phe Leu Glu Leu Asn Pro Arg Leu Gln Val Glu His Pro Cys
        435                 440                 445 aca gag atg gtg gct gat gtc aat ctc cct gca gca cag ctc cag att        1392
Thr Glu Met Val Ala Asp Val Asn Leu Pro Ala Ala Gln Leu Gln Ile
450                 455                 460 gcc atg ggg att cct cta tat aga atc aag gat atc cgt atg atg tat        1440
Ala Met Gly Ile Pro Leu Tyr Arg Ile Lys Asp Ile Arg Met Met Tyr
465                 470                 475                 480 ggg gta tct ccc tgg ggt gat tct ccc att gat ttt gaa gat tct gca        1488
Gly Val Ser Pro Trp Gly Asp Ser Pro Ile Asp Phe Glu Asp Ser Ala
                485                 490                 495 cac gtt cct tgt cca agg ggc cat gtt att gct gct cgg atc act agt        1536
His Val Pro Cys Pro Arg Gly His Val Ile Ala Ala Arg Ile Thr Ser
            500                 505                 510 gaa aat cca gat gag ggt ttt aag ccc agc tca gga aca gtt cag gag        1584
Glu Asn Pro Asp Glu Gly Phe Lys Pro Ser Ser Gly Thr Val Gln Glu
        515                 520                 525 cta aat ttc cgc agc aat aag aat gtt tgg gga tat ttc agt gtt gct        1632
Leu Asn Phe Arg Ser Asn Lys Asn Val Trp Gly Tyr Phe Ser Val Ala
530                 535                 540 gct gca ggg gga ctt cat gaa ttt gct gat tct cag ttt ggt cac tgc        1680
Ala Ala Gly Gly Leu His Glu Phe Ala Asp Ser Gln Phe Gly His Cys
545                 550                 555                 560 ttt tct tgg gga gaa aac aga gaa gag gca att tca aac atg gtg gtg        1728
Phe Ser Trp Gly Glu Asn Arg Glu Glu Ala Ile Ser Asn Met Val Val
                565                 570                 575 gct ttg aag gag ctg tct att cgg ggt gac ttt cga act aca gtt gaa        1776
Ala Leu Lys Glu Leu Ser Ile Arg Gly Asp Phe Arg Thr Thr Val Glu
            580                 585                 590 tac ctg atc aaa ttg tta gag act gaa agc ttt cag atg aac aga att        1824
Tyr Leu Ile Lys Leu Leu Glu Thr Glu Ser Phe Gln Met Asn Arg Ile
        595                 600                 605 gat act ggc tgg ctg gac aga ctg ata gca gaa aaa gta cag gct gag        1872
Asp Thr Gly Trp Leu Asp Arg Leu Ile Ala Glu Lys Val Gln Ala Glu
610                 615                 620 cga cct gac acc atg ttg ggg gtt                                        1896
Arg Pro Asp Thr Met Leu Gly Val
625                 630

<210> SEQ ID NO 10
<211> LENGTH: 632
<212> TYPE: PRT
```

<213> ORGANISM: Homo sapiens

<400> SEQUENCE: 10

```
Met Asp Glu Pro Ser Pro Leu Ala Gln Pro Leu Glu Leu Asn Gln His
1               5                   10                  15

Ser Arg Phe Ile Ile Gly Ser Val Ser Glu Asp Asn Ser Glu Asp Glu
            20                  25                  30

Ile Ser Asn Leu Val Lys Leu Asp Leu Leu Glu Glu Lys Glu Gly Ser
        35                  40                  45

Leu Ser Pro Ala Ser Val Gly Ser Asp Thr Leu Ser Asp Leu Gly Ile
    50                  55                  60

Ser Ser Leu Gln Asp Gly Leu Ala Leu His Ile Arg Ser Ser Met Ser
65                  70                  75                  80

Gly Leu His Leu Val Lys Gln Gly Arg Asp Arg Lys Lys Ile Asp Ser
                85                  90                  95

Gln Arg Asp Phe Thr Val Ala Ser Pro Ala Glu Phe Val Thr Arg Phe
            100                 105                 110

Gly Gly Asn Lys Val Ile Glu Lys Val Leu Ile Ala Asn Asn Gly Ile
        115                 120                 125

Ala Ala Val Lys Cys Met Arg Ser Ile Arg Arg Trp Ser Tyr Glu Met
    130                 135                 140

Phe Arg Asn Glu Arg Ala Ile Arg Phe Val Val Met Val Thr Pro Glu
145                 150                 155                 160

Asp Leu Lys Ala Asn Ala Glu Tyr Ile Lys Met Ala Asp His Tyr Val
                165                 170                 175

Pro Val Pro Gly Gly Pro Asn Asn Asn Tyr Ala Asn Val Glu Leu
            180                 185                 190

Ile Leu Asp Ile Ala Lys Arg Ile Pro Val Gln Ala Val Trp Ala Gly
        195                 200                 205

Trp Gly His Ala Ser Glu Asn Pro Lys Leu Pro Glu Leu Leu Leu Lys
    210                 215                 220

Asn Gly Ile Ala Phe Met Gly Pro Pro Ser Gln Ala Met Trp Ala Leu
225                 230                 235                 240

Gly Asp Lys Ile Ala Ser Ser Ile Val Ala Gln Thr Ala Gly Ile Pro
                245                 250                 255

Thr Leu Pro Trp Ser Gly Ser Gly Leu Arg Val Asp Trp Gln Glu Asn
            260                 265                 270

Asp Phe Ser Lys Arg Ile Leu Asn Val Pro Gln Glu Leu Tyr Glu Lys
        275                 280                 285

Gly Tyr Val Lys Asp Val Asp Asp Gly Leu Lys Ala Ala Glu Glu Val
    290                 295                 300

Gly Tyr Pro Val Met Ile Lys Ala Ser Glu Gly Gly Gly Gly Lys Gly
305                 310                 315                 320

Ile Arg Lys Val Asn Asn Ala Asp Asp Phe Pro Asn Leu Phe Arg Gln
                325                 330                 335

Val Gln Ala Glu Val Pro Gly Ser Pro Ile Phe Val Met Arg Leu Ala
            340                 345                 350

Lys Gln Ser Arg His Leu Glu Val Gln Ile Leu Ala Asp Gln Tyr Gly
        355                 360                 365

Asn Ala Ile Ser Leu Phe Gly Arg Asp Cys Ser Val Gln Arg Arg His
    370                 375                 380

Gln Lys Ile Ile Glu Glu Ala Pro Ala Thr Ile Ala Thr Pro Ala Val
385                 390                 395                 400
```

-continued

```
Phe Glu His Met Glu Gln Cys Ala Val Lys Leu Ala Lys Met Val Gly
            405                 410                 415

Tyr Val Ser Ala Gly Thr Val Glu Tyr Leu Tyr Ser Gln Asp Gly Ser
        420                 425                 430

Phe Tyr Phe Leu Glu Leu Asn Pro Arg Leu Gln Val Glu His Pro Cys
    435                 440                 445

Thr Glu Met Val Ala Asp Val Asn Leu Pro Ala Ala Gln Leu Gln Ile
450                 455                 460

Ala Met Gly Ile Pro Leu Tyr Arg Ile Lys Asp Ile Arg Met Met Tyr
465                 470                 475                 480

Gly Val Ser Pro Trp Gly Asp Ser Pro Ile Asp Phe Glu Asp Ser Ala
                485                 490                 495

His Val Pro Cys Pro Arg Gly His Val Ile Ala Arg Ile Thr Ser
            500                 505                 510

Glu Asn Pro Asp Glu Gly Phe Lys Pro Ser Ser Gly Thr Val Gln Glu
        515                 520                 525

Leu Asn Phe Arg Ser Asn Lys Asn Val Trp Gly Tyr Phe Ser Val Ala
    530                 535                 540

Ala Ala Gly Gly Leu His Glu Phe Ala Asp Ser Gln Phe Gly His Cys
545                 550                 555                 560

Phe Ser Trp Gly Glu Asn Arg Glu Glu Ala Ile Ser Asn Met Val Val
                565                 570                 575

Ala Leu Lys Glu Leu Ser Ile Arg Gly Asp Phe Arg Thr Thr Val Glu
            580                 585                 590

Tyr Leu Ile Lys Leu Leu Glu Thr Glu Ser Phe Gln Met Asn Arg Ile
        595                 600                 605

Asp Thr Gly Trp Leu Asp Arg Leu Ile Ala Glu Lys Val Gln Ala Glu
    610                 615                 620

Arg Pro Asp Thr Met Leu Gly Val
625                 630

<210> SEQ ID NO 11
<211> LENGTH: 2322
<212> TYPE: DNA
<213> ORGANISM: Homo sapiens
<220> FEATURE:
<221> NAME/KEY: CDS
<222> LOCATION: (1)..(2322)
<223> OTHER INFORMATION: Human ACCase2 (beta) BC domain (aa 1-774)

<400> SEQUENCE: 11 atg gtc ttg ctt ctt tgt cta tct tgt ctg att ttc tcc tgt ctg acc      48
Met Val Leu Leu Leu Cys Leu Ser Cys Leu Ile Phe Ser Cys Leu Thr
1               5                   10                  15 ttt tcc tgg tta aaa atc tgg ggg aaa atg acg gac tcc aag ccg atc      96
Phe Ser Trp Leu Lys Ile Trp Gly Lys Met Thr Asp Ser Lys Pro Ile
            20                  25                  30 acc aag agt aaa tca gaa gca aac ctc atc ccg agc cag gag ccc ttt     144
Thr Lys Ser Lys Ser Glu Ala Asn Leu Ile Pro Ser Gln Glu Pro Phe
        35                  40                  45 cca gcc tct gat aac tca ggg gag aca ccg cag aga aat ggg gag ggc     192
Pro Ala Ser Asp Asn Ser Gly Glu Thr Pro Gln Arg Asn Gly Glu Gly
    50                  55                  60 cac act ctg ccc aag aca ccc agc cag gcc gag cca gcc tcc cac aaa     240
His Thr Leu Pro Lys Thr Pro Ser Gln Ala Glu Pro Ala Ser His Lys
65                  70                  75                  80 ggc ccc aaa gat gcc ggt cgg cgg aga aac tcc cta cca ccc tcc cac     288
Gly Pro Lys Asp Ala Gly Arg Arg Arg Asn Ser Leu Pro Pro Ser His
```

-continued

|  |  |  |  |  |  |  |  |  |  |  |  |  |  |  |  |
|---|---|---|---|---|---|---|---|---|---|---|---|---|---|---|---|
|  |  | 85 |  |  |  | 90 |  |  |  | 95 |  |  |  |  |  |

```
cag aag ccc cca aga aac ccc ctt tct tcc agt gac gca gca ccc tcc     336
Gln Lys Pro Pro Arg Asn Pro Leu Ser Ser Ser Asp Ala Ala Pro Ser
        100                 105                 110 cca gag ctt caa gcc aac ggg act ggg aca caa ggt ctg gag gcc aca     384
Pro Glu Leu Gln Ala Asn Gly Thr Gly Thr Gln Gly Leu Glu Ala Thr
            115                 120                 125 gat acc aat ggc ctg tcc tcc tca gcc agg ccc cag ggc cag caa gct     432
Asp Thr Asn Gly Leu Ser Ser Ser Ala Arg Pro Gln Gly Gln Gln Ala
130                 135                 140 ggc tcc ccc tcc aaa gaa gac aag aag cag gca aac atc aag agg cag     480
Gly Ser Pro Ser Lys Glu Asp Lys Lys Gln Ala Asn Ile Lys Arg Gln
145                 150                 155                 160 ctg atg acc aac ttc atc ctg ggc tct ttt gat gac tac tcc tct gac     528
Leu Met Thr Asn Phe Ile Leu Gly Ser Phe Asp Asp Tyr Ser Ser Asp
                165                 170                 175 gag gac tct gtt gct ggc tca tct cgt gag tct acc cgg aag ggc agc     576
Glu Asp Ser Val Ala Gly Ser Ser Arg Glu Ser Thr Arg Lys Gly Ser
            180                 185                 190 cgg gcc agc ttg ggg gcc ctg tcc ctg gag gct tat ctg acc aca ggt     624
Arg Ala Ser Leu Gly Ala Leu Ser Leu Glu Ala Tyr Leu Thr Thr Gly
        195                 200                 205 gaa gct gag acc cgc gtc ccc act atg agg ccg agc atg tcg gga ctc     672
Glu Ala Glu Thr Arg Val Pro Thr Met Arg Pro Ser Met Ser Gly Leu
210                 215                 220 cac ctg gtg aag agg gga cgg gaa cac aag aag ctg gac ctg cac aga     720
His Leu Val Lys Arg Gly Arg Glu His Lys Lys Leu Asp Leu His Arg
225                 230                 235                 240 gac ttt acc gtg gct tct ccc gct gag ttt gtc aca cgc ttt ggg ggg     768
Asp Phe Thr Val Ala Ser Pro Ala Glu Phe Val Thr Arg Phe Gly Gly
                245                 250                 255 gat cgg gtc atc gag aag gtg ctt att gcc aac aac ggg att gcc gcc     816
Asp Arg Val Ile Glu Lys Val Leu Ile Ala Asn Asn Gly Ile Ala Ala
            260                 265                 270 gtg aag tgc atg cgc tcc atc cgc agg tgg gcc tat gag atg ttc cgc     864
Val Lys Cys Met Arg Ser Ile Arg Arg Trp Ala Tyr Glu Met Phe Arg
        275                 280                 285 aac gag cgg gcc atc cgg ttt gtt gtg atg gtg acc ccc gag gac ctt     912
Asn Glu Arg Ala Ile Arg Phe Val Val Met Val Thr Pro Glu Asp Leu
290                 295                 300 aag gcc aac gca gag tac atc aag atg gcg gat cat tac gtc ccc gtc     960
Lys Ala Asn Ala Glu Tyr Ile Lys Met Ala Asp His Tyr Val Pro Val
305                 310                 315                 320 cca gga ggg ccc aat aac aac aac tat gcc aac gtg gag ctg att gtg    1008
Pro Gly Gly Pro Asn Asn Asn Asn Tyr Ala Asn Val Glu Leu Ile Val
                325                 330                 335 gac att gcc aag aga att cct ttg cag gcg gtg tgg gct ggc tgg ggc    1056
Asp Ile Ala Lys Arg Ile Pro Leu Gln Ala Val Trp Ala Gly Trp Gly
            340                 345                 350 cat gct tca gaa aac cct aaa ctt ccg gag ctg ctg tgc aag aat gga    1104
His Ala Ser Glu Asn Pro Lys Leu Pro Glu Leu Leu Cys Lys Asn Gly
        355                 360                 365 gtt gct ttc tta ggc cct ccc agt gag gcc atg tgg gcc tta gga gat    1152
Val Ala Phe Leu Gly Pro Pro Ser Glu Ala Met Trp Ala Leu Gly Asp
370                 375                 380 aag atc gcc tcc acc gtt gtc gcc cag acg cta cag gtc cca acc ctg    1200
Lys Ile Ala Ser Thr Val Val Ala Gln Thr Leu Gln Val Pro Thr Leu
385                 390                 395                 400 ccc agg agt gga agc ggc ctg aca gtg gag tgg aca gaa gat gat ctg    1248
```

-continued

| | | |
|---|---|---|
| Pro Arg Ser Gly Ser Gly Leu Thr Val Glu Trp Thr Glu Asp Asp Leu<br>405                               410                        415 | | |
| cag cag gga aaa aga atc agt gtc cca gaa gat gtt tat gac aag ggt<br>Gln Gln Gly Lys Arg Ile Ser Val Pro Glu Asp Val Tyr Asp Lys Gly<br>                420                        425                        430 | 1296 |
| tgc gtg aaa gac gta gat gag ggc ttg gag gca gca gaa aga att ggt<br>Cys Val Lys Asp Val Asp Glu Gly Leu Glu Ala Ala Glu Arg Ile Gly<br>                435                        440                        445 | 1344 |
| ttt cca ttg atg atc aaa gct tct gaa ggt ggc gga ggg aag gga atc<br>Phe Pro Leu Met Ile Lys Ala Ser Glu Gly Gly Gly Gly Lys Gly Ile<br>450                            455                        460 | 1392 |
| cgg aag gct gag agt gcg gag gac ttc ccg atc ctt ttc aga caa gta<br>Arg Lys Ala Glu Ser Ala Glu Asp Phe Pro Ile Leu Phe Arg Gln Val<br>465                            470                        475                        480 | 1440 |
| cag agt gag atc cca ggc tcg ccc atc ttt ctc atg aag ctg gcc cag<br>Gln Ser Glu Ile Pro Gly Ser Pro Ile Phe Leu Met Lys Leu Ala Gln<br>                                      485                        490                        495 | 1488 |
| cac gcc cgt cac ctg gaa gtt cag atc ctc gct gac cag tat ggg aat<br>His Ala Arg His Leu Glu Val Gln Ile Leu Ala Asp Gln Tyr Gly Asn<br>                              500                        505                        510 | 1536 |
| gct gtg tct ctg ttt ggt cgc gac tgc tcc atc cag cgg cgg cat cag<br>Ala Val Ser Leu Phe Gly Arg Asp Cys Ser Ile Gln Arg Arg His Gln<br>              515                        520                        525 | 1584 |
| aag atc gtt gag gaa gca ccg gcc acc atc gcc ccg ctg gcc ata ttc<br>Lys Ile Val Glu Glu Ala Pro Ala Thr Ile Ala Pro Leu Ala Ile Phe<br>530                            535                        540 | 1632 |
| gag ttc atg gag cag tgt gcc atc cgc ctg gcc aag acc gtg ggc tat<br>Glu Phe Met Glu Gln Cys Ala Ile Arg Leu Ala Lys Thr Val Gly Tyr<br>545                            550                        555                        560 | 1680 |
| gtg agt gca ggg aca gtg gaa tac ctc tat agt cag gat ggc agc ttc<br>Val Ser Ala Gly Thr Val Glu Tyr Leu Tyr Ser Gln Asp Gly Ser Phe<br>                              565                        570                        575 | 1728 |
| cac ttc ttg gag ctg aat cct cgc ttg cag gtg gaa cat ccc tgc aca<br>His Phe Leu Glu Leu Asn Pro Arg Leu Gln Val Glu His Pro Cys Thr<br>                            580                        585                        590 | 1776 |
| gaa atg att gct gat gtt aat ctg ccg gcc gcc cag cta cag atc gcc<br>Glu Met Ile Ala Asp Val Asn Leu Pro Ala Ala Gln Leu Gln Ile Ala<br>              595                        600                        605 | 1824 |
| atg ggc gtg cca ctg cac cgg ctg aag gat atc cgg ctt ctg tat gga<br>Met Gly Val Pro Leu His Arg Leu Lys Asp Ile Arg Leu Leu Tyr Gly<br>610                            615                        620 | 1872 |
| gag tca cca tgg gga gtg act ccc att tct ttt gaa acc ccc tca aac<br>Glu Ser Pro Trp Gly Val Thr Pro Ile Ser Phe Glu Thr Pro Ser Asn<br>625                            630                        635                        640 | 1920 |
| cct ccc ctc gcc cga ggc cac gtc att gcc gcc aga atc acc agc gaa<br>Pro Pro Leu Ala Arg Gly His Val Ile Ala Ala Arg Ile Thr Ser Glu<br>                              645                        650                        655 | 1968 |
| aac cca gac gag ggt ttt aag ccg agc tcc ggg act gtc cag gaa ctg<br>Asn Pro Asp Glu Gly Phe Lys Pro Ser Ser Gly Thr Val Gln Glu Leu<br>                              660                        665                        670 | 2016 |
| aat ttc cgg agc agc aag aac gtg tgg ggt tac ttc agc gtg gcc gct<br>Asn Phe Arg Ser Ser Lys Asn Val Trp Gly Tyr Phe Ser Val Ala Ala<br>              675                        680                        685 | 2064 |
| act gga ggc ctg cac gag ttt gcg gat tcc caa ttt ggg cac tgc ttc<br>Thr Gly Gly Leu His Glu Phe Ala Asp Ser Gln Phe Gly His Cys Phe<br>690                            695                        700 | 2112 |
| tcc tgg gga gag aac cgg aaa gag gcc att tcg aac atg gtg gtg gct<br>Ser Trp Gly Glu Asn Arg Lys Glu Ala Ile Ser Asn Met Val Val Ala<br>705                            710                        715                        720 | 2160 |

```
ttg aag gaa ctg tcc atc cga ggt gac ttt agg act acc gtg gaa tac    2208
Leu Lys Glu Leu Ser Ile Arg Gly Asp Phe Arg Thr Thr Val Glu Tyr
            725                 730                 735 ctc att aac ctc ctg gag acc gag agc ttc cag aac aac gac atc gac    2256
Leu Ile Asn Leu Leu Glu Thr Glu Ser Phe Gln Asn Asn Asp Ile Asp
        740                 745                 750 acc ggg tgg ttg gac tac ctc att gct gag aaa gtg cag gag aaa ccg    2304
Thr Gly Trp Leu Asp Tyr Leu Ile Ala Glu Lys Val Gln Glu Lys Pro
    755                 760                 765 gat atc atg ctt ggg gtg                                            2322
Asp Ile Met Leu Gly Val
    770
```

<210> SEQ ID NO 12
<211> LENGTH: 774
<212> TYPE: PRT
<213> ORGANISM: Homo sapiens

<400> SEQUENCE: 12

```
Met Val Leu Leu Leu Cys Leu Ser Cys Leu Ile Phe Ser Cys Leu Thr
1               5                   10                  15

Phe Ser Trp Leu Lys Ile Trp Gly Lys Met Thr Asp Ser Lys Pro Ile
            20                  25                  30

Thr Lys Ser Lys Ser Glu Ala Asn Leu Ile Pro Ser Gln Glu Pro Phe
        35                  40                  45

Pro Ala Ser Asp Asn Ser Gly Glu Thr Pro Gln Arg Asn Gly Glu Gly
    50                  55                  60

His Thr Leu Pro Lys Thr Pro Ser Gln Ala Glu Pro Ala Ser His Lys
65                  70                  75                  80

Gly Pro Lys Asp Ala Gly Arg Arg Asn Ser Leu Pro Pro Ser His
                85                  90                  95

Gln Lys Pro Pro Arg Asn Pro Leu Ser Ser Ser Asp Ala Ala Pro Ser
            100                 105                 110

Pro Glu Leu Gln Ala Asn Gly Thr Gly Thr Gln Gly Leu Glu Ala Thr
        115                 120                 125

Asp Thr Asn Gly Leu Ser Ser Ser Ala Arg Pro Gln Gly Gln Gln Ala
    130                 135                 140

Gly Ser Pro Ser Lys Glu Asp Lys Lys Gln Ala Asn Ile Lys Arg Gln
145                 150                 155                 160

Leu Met Thr Asn Phe Ile Leu Gly Ser Phe Asp Asp Tyr Ser Ser Asp
                165                 170                 175

Glu Asp Ser Val Ala Gly Ser Ser Arg Glu Ser Thr Arg Lys Gly Ser
            180                 185                 190

Arg Ala Ser Leu Gly Ala Leu Ser Leu Glu Ala Tyr Leu Thr Thr Gly
        195                 200                 205

Glu Ala Glu Thr Arg Val Pro Thr Met Arg Pro Ser Met Ser Gly Leu
    210                 215                 220

His Leu Val Lys Arg Gly Arg Glu His Lys Lys Leu Asp Leu His Arg
225                 230                 235                 240

Asp Phe Thr Val Ala Ser Pro Ala Glu Phe Val Thr Arg Phe Gly Gly
                245                 250                 255

Asp Arg Val Ile Glu Lys Val Leu Ile Ala Asn Asn Gly Ile Ala Ala
            260                 265                 270

Val Lys Cys Met Arg Ser Ile Arg Arg Trp Ala Tyr Glu Met Phe Arg
        275                 280                 285

Asn Glu Arg Ala Ile Arg Phe Val Val Met Val Thr Pro Glu Asp Leu
```

```
              290                 295                 300
Lys Ala Asn Ala Glu Tyr Ile Lys Met Ala Asp His Tyr Val Pro Val
305                 310                 315                 320

Pro Gly Gly Pro Asn Asn Asn Tyr Ala Asn Val Glu Leu Ile Val
                325                 330                 335

Asp Ile Ala Lys Arg Ile Pro Leu Gln Ala Val Trp Ala Gly Trp Gly
                340                 345                 350

His Ala Ser Glu Asn Pro Lys Leu Pro Glu Leu Leu Cys Lys Asn Gly
                355                 360                 365

Val Ala Phe Leu Gly Pro Ser Glu Ala Met Trp Ala Leu Gly Asp
370                 375                 380

Lys Ile Ala Ser Thr Val Val Ala Gln Thr Leu Gln Val Pro Thr Leu
385                 390                 395                 400

Pro Arg Ser Gly Ser Gly Leu Thr Val Glu Trp Thr Glu Asp Asp Leu
                405                 410                 415

Gln Gln Gly Lys Arg Ile Ser Val Pro Glu Asp Val Tyr Asp Lys Gly
                420                 425                 430

Cys Val Lys Asp Val Asp Glu Gly Leu Glu Ala Ala Glu Arg Ile Gly
                435                 440                 445

Phe Pro Leu Met Ile Lys Ala Ser Glu Gly Gly Gly Lys Gly Ile
                450                 455                 460

Arg Lys Ala Glu Ser Ala Glu Asp Phe Pro Ile Leu Phe Arg Gln Val
465                 470                 475                 480

Gln Ser Glu Ile Pro Gly Ser Pro Ile Phe Leu Met Lys Leu Ala Gln
                485                 490                 495

His Ala Arg His Leu Glu Val Gln Ile Leu Ala Asp Gln Tyr Gly Asn
                500                 505                 510

Ala Val Ser Leu Phe Gly Arg Asp Cys Ser Ile Gln Arg Arg His Gln
                515                 520                 525

Lys Ile Val Glu Glu Ala Pro Ala Thr Ile Ala Pro Leu Ala Ile Phe
                530                 535                 540

Glu Phe Met Glu Gln Cys Ala Ile Arg Leu Ala Lys Thr Val Gly Tyr
545                 550                 555                 560

Val Ser Ala Gly Thr Val Glu Tyr Leu Tyr Ser Gln Asp Gly Ser Phe
                565                 570                 575

His Phe Leu Glu Leu Asn Pro Arg Leu Gln Val Glu His Pro Cys Thr
                580                 585                 590

Glu Met Ile Ala Asp Val Asn Leu Pro Ala Ala Gln Leu Gln Ile Ala
                595                 600                 605

Met Gly Val Pro Leu His Arg Leu Lys Asp Ile Arg Leu Leu Tyr Gly
                610                 615                 620

Glu Ser Pro Trp Gly Val Thr Pro Ile Ser Phe Glu Thr Pro Ser Asn
625                 630                 635                 640

Pro Pro Leu Ala Arg Gly His Val Ile Ala Ala Arg Ile Thr Ser Glu
                645                 650                 655

Asn Pro Asp Glu Gly Phe Lys Pro Ser Ser Gly Thr Val Gln Glu Leu
                660                 665                 670

Asn Phe Arg Ser Ser Lys Asn Val Trp Gly Tyr Phe Ser Val Ala Ala
                675                 680                 685

Thr Gly Gly Leu His Glu Phe Ala Asp Ser Gln Phe Gly His Cys Phe
                690                 695                 700

Ser Trp Gly Glu Asn Arg Lys Glu Ala Ile Ser Asn Met Val Val Ala
705                 710                 715                 720
```

```
Leu Lys Glu Leu Ser Ile Arg Gly Asp Phe Arg Thr Thr Val Glu Tyr
            725                 730                 735

Leu Ile Asn Leu Leu Glu Thr Glu Ser Phe Gln Asn Asn Asp Ile Asp
            740                 745                 750

Thr Gly Trp Leu Asp Tyr Leu Ile Ala Glu Lys Val Gln Glu Lys Pro
            755                 760                 765

Asp Ile Met Leu Gly Val
    770

<210> SEQ ID NO 13
<211> LENGTH: 1596
<212> TYPE: DNA
<213> ORGANISM: Homo sapiens
<220> FEATURE:
<221> NAME/KEY: CDS
<222> LOCATION: (1)..(1596)
<223> OTHER INFORMATION: N-terminal deleted Human ACCase1 BC domain
      (AAs 102-632)

<400> SEQUENCE: 13 atg gtg gct tct cca gca gaa ttt gtt act cgc ttt ggg gga aat aaa     48
Met Val Ala Ser Pro Ala Glu Phe Val Thr Arg Phe Gly Gly Asn Lys
1               5                   10                  15 gtg att gag aag gtt ctt att gct aac aat ggc att gca gca gtg aaa     96
Val Ile Glu Lys Val Leu Ile Ala Asn Asn Gly Ile Ala Ala Val Lys
            20                  25                  30 tgc atg cgg tct atc cgt agg tgg tct tat gaa atg ttt cga aat gaa    144
Cys Met Arg Ser Ile Arg Arg Trp Ser Tyr Glu Met Phe Arg Asn Glu
        35                  40                  45 cgt gca att aga ttc gtt gtc atg gtc aca cct gaa gac ctt aaa gcc    192
Arg Ala Ile Arg Phe Val Val Met Val Thr Pro Glu Asp Leu Lys Ala
    50                  55                  60 aat gca gaa tac att aag atg gca gat cac tat gtg cca gtg cct gga    240
Asn Ala Glu Tyr Ile Lys Met Ala Asp His Tyr Val Pro Val Pro Gly
65                  70                  75                  80 gga cca aac aac aac aac tat gca aat gtg gaa tta att ctt gat att    288
Gly Pro Asn Asn Asn Asn Tyr Ala Asn Val Glu Leu Ile Leu Asp Ile
                85                  90                  95 gct aaa agg atc cca gtg cag gca gtg tgg gct ggc tgg ggt cat gct    336
Ala Lys Arg Ile Pro Val Gln Ala Val Trp Ala Gly Trp Gly His Ala
            100                 105                 110 tct gag aat ccc aaa cta ccg gaa ctt ctc ttg aaa aat ggc att gcc    384
Ser Glu Asn Pro Lys Leu Pro Glu Leu Leu Leu Lys Asn Gly Ile Ala
        115                 120                 125 ttc atg ggt cct cca agc cag gcc atg tgg gct tta ggg gat aag att    432
Phe Met Gly Pro Pro Ser Gln Ala Met Trp Ala Leu Gly Asp Lys Ile
    130                 135                 140 gca tct tcc ata gtg gct caa act gca ggt atc cca act ctt ccc tgg    480
Ala Ser Ser Ile Val Ala Gln Thr Ala Gly Ile Pro Thr Leu Pro Trp
145                 150                 155                 160 agc ggc agt ggt ctt cgt gtg gac tgg cag gaa aat gat ttt tca aaa    528
Ser Gly Ser Gly Leu Arg Val Asp Trp Gln Glu Asn Asp Phe Ser Lys
                165                 170                 175 cgt atc tta aat gtt ccc cag gag cta tat gaa aaa ggt tat gtg aaa    576
Arg Ile Leu Asn Val Pro Gln Glu Leu Tyr Glu Lys Gly Tyr Val Lys
            180                 185                 190 gat gtg gat gat ggg cta aag gca gct gag gaa gtt gga tat cca gta    624
Asp Val Asp Asp Gly Leu Lys Ala Ala Glu Glu Val Gly Tyr Pro Val
        195                 200                 205 atg atc aag gcc tca gag gga gga gga ggg aag gga att aga aaa gtc    672
```

```
Met Ile Lys Ala Ser Glu Gly Gly Gly Lys Gly Ile Arg Lys Val
    210             215             220 aac aat gca gat gac ttc cct aat ctc ttc aga cag gtt caa gct gaa      720
Asn Asn Ala Asp Asp Phe Pro Asn Leu Phe Arg Gln Val Gln Ala Glu
225             230             235             240 gtt cct gga tct ccc ata ttt gtg atg aga cta gcc aaa caa tct cgt      768
Val Pro Gly Ser Pro Ile Phe Val Met Arg Leu Ala Lys Gln Ser Arg
                245             250             255 cat ctg gag gtg cag atc tta gcg gac caa tat ggc aat gct atc tct      816
His Leu Glu Val Gln Ile Leu Ala Asp Gln Tyr Gly Asn Ala Ile Ser
            260             265             270 ttg ttt ggt cgt gat tgc tct gta caa cgc agg cat cag aag att att      864
Leu Phe Gly Arg Asp Cys Ser Val Gln Arg Arg His Gln Lys Ile Ile
        275             280             285 gaa gaa gca cct gct act att gct act cca gca gta ttt gaa cac atg      912
Glu Glu Ala Pro Ala Thr Ile Ala Thr Pro Ala Val Phe Glu His Met
    290             295             300 gaa cag tgt gcg gtg aaa ctt gcc aaa atg gtg ggt tat gtg agt gct      960
Glu Gln Cys Ala Val Lys Leu Ala Lys Met Val Gly Tyr Val Ser Ala
305             310             315             320 ggg act gtg gaa tac ctg tac agc cag gat ggc agc ttc tac ttt ctg     1008
Gly Thr Val Glu Tyr Leu Tyr Ser Gln Asp Gly Ser Phe Tyr Phe Leu
                325             330             335 gaa ttg aat cct cgg ctg cag gta gag cac cct tgt aca gag atg gtg     1056
Glu Leu Asn Pro Arg Leu Gln Val Glu His Pro Cys Thr Glu Met Val
            340             345             350 gct gat gtc aat ctc cct gca gca cag ctc cag att gcc atg ggg att     1104
Ala Asp Val Asn Leu Pro Ala Ala Gln Leu Gln Ile Ala Met Gly Ile
        355             360             365 cct cta tat aga atc aag gat atc cgt atg atg tat ggg gta tct ccc     1152
Pro Leu Tyr Arg Ile Lys Asp Ile Arg Met Met Tyr Gly Val Ser Pro
    370             375             380 tgg ggt gat tct ccc att gat ttt gaa gat tct gca cac gtt cct tgt     1200
Trp Gly Asp Ser Pro Ile Asp Phe Glu Asp Ser Ala His Val Pro Cys
385             390             395             400 cca agg ggc cat gtt att gct gct cgg atc act agt gaa aat cca gat     1248
Pro Arg Gly His Val Ile Ala Ala Arg Ile Thr Ser Glu Asn Pro Asp
                405             410             415 gag ggt ttt aag ccc agc tca gga aca gtt cag gag cta aat ttc cgc     1296
Glu Gly Phe Lys Pro Ser Ser Gly Thr Val Gln Glu Leu Asn Phe Arg
            420             425             430 agc aat aag aat gtt tgg gga tat ttc agt gtt gct gct gca ggg gga     1344
Ser Asn Lys Asn Val Trp Gly Tyr Phe Ser Val Ala Ala Ala Gly Gly
        435             440             445 ctt cat gaa ttt gct gat tct cag ttt ggt cac tgc ttt tct tgg gga     1392
Leu His Glu Phe Ala Asp Ser Gln Phe Gly His Cys Phe Ser Trp Gly
    450             455             460 gaa aac aga gaa gag gca att tca aac atg gtg gtg gct ttg aag gag     1440
Glu Asn Arg Glu Glu Ala Ile Ser Asn Met Val Val Ala Leu Lys Glu
465             470             475             480 ctg tct att cgg ggt gac ttt cga act aca gtt gaa tac ctg atc aaa     1488
Leu Ser Ile Arg Gly Asp Phe Arg Thr Thr Val Glu Tyr Leu Ile Lys
                485             490             495 ttg tta gag act gaa agc ttt cag atg aac aga att gat act ggc tgg     1536
Leu Leu Glu Thr Glu Ser Phe Gln Met Asn Arg Ile Asp Thr Gly Trp
            500             505             510 ctg gac aga ctg ata gca gaa aaa gta cag gct gag cga cct gac acc     1584
Leu Asp Arg Leu Ile Ala Glu Lys Val Gln Ala Glu Arg Pro Asp Thr
        515             520             525
```

```
atg ttg ggg gtt                                                    1596
Met Leu Gly Val
    530
```

<210> SEQ ID NO 14
<211> LENGTH: 532
<212> TYPE: PRT
<213> ORGANISM: Homo sapiens

<400> SEQUENCE: 14

```
Met Val Ala Ser Pro Ala Glu Phe Val Thr Arg Phe Gly Gly Asn Lys
1               5                   10                  15

Val Ile Glu Lys Val Leu Ile Ala Asn Asn Gly Ile Ala Ala Val Lys
            20                  25                  30

Cys Met Arg Ser Ile Arg Arg Trp Ser Tyr Glu Met Phe Arg Asn Glu
        35                  40                  45

Arg Ala Ile Arg Phe Val Val Met Val Thr Pro Glu Asp Leu Lys Ala
    50                  55                  60

Asn Ala Glu Tyr Ile Lys Met Ala Asp His Tyr Val Pro Val Pro Gly
65                  70                  75                  80

Gly Pro Asn Asn Asn Tyr Ala Asn Val Glu Leu Ile Leu Asp Ile
                85                  90                  95

Ala Lys Arg Ile Pro Val Gln Ala Val Trp Ala Gly Trp Gly His Ala
            100                 105                 110

Ser Glu Asn Pro Lys Leu Pro Glu Leu Leu Leu Lys Asn Gly Ile Ala
        115                 120                 125

Phe Met Gly Pro Pro Ser Gln Ala Met Trp Ala Leu Gly Asp Lys Ile
130                 135                 140

Ala Ser Ser Ile Val Ala Gln Thr Ala Gly Ile Pro Thr Leu Pro Trp
145                 150                 155                 160

Ser Gly Ser Gly Leu Arg Val Asp Trp Gln Glu Asn Asp Phe Ser Lys
                165                 170                 175

Arg Ile Leu Asn Val Pro Gln Glu Leu Tyr Glu Lys Gly Tyr Val Lys
            180                 185                 190

Asp Val Asp Asp Gly Leu Lys Ala Ala Glu Glu Val Gly Tyr Pro Val
        195                 200                 205

Met Ile Lys Ala Ser Glu Gly Gly Gly Lys Gly Ile Arg Lys Val
    210                 215                 220

Asn Asn Ala Asp Asp Phe Pro Asn Leu Phe Arg Gln Val Gln Ala Glu
225                 230                 235                 240

Val Pro Gly Ser Pro Ile Phe Val Met Arg Leu Ala Lys Gln Ser Arg
                245                 250                 255

His Leu Glu Val Gln Ile Leu Ala Asp Gln Tyr Gly Asn Ala Ile Ser
            260                 265                 270

Leu Phe Gly Arg Asp Cys Ser Val Gln Arg Arg His Gln Lys Ile Ile
        275                 280                 285

Glu Glu Ala Pro Ala Thr Ile Ala Thr Pro Ala Val Phe Glu His Met
    290                 295                 300

Glu Gln Cys Ala Val Lys Leu Ala Lys Met Val Gly Tyr Val Ser Ala
305                 310                 315                 320

Gly Thr Val Glu Tyr Leu Tyr Ser Gln Asp Gly Ser Phe Tyr Phe Leu
                325                 330                 335

Glu Leu Asn Pro Arg Leu Gln Val Glu His Pro Cys Thr Glu Met Val
            340                 345                 350

Ala Asp Val Asn Leu Pro Ala Ala Gln Leu Gln Ile Ala Met Gly Ile
```

```
                355                 360                 365
Pro Leu Tyr Arg Ile Lys Asp Ile Arg Met Met Tyr Gly Val Ser Pro
    370                 375                 380

Trp Gly Asp Ser Pro Ile Asp Phe Glu Asp Ser Ala His Val Pro Cys
385                 390                 395                 400

Pro Arg Gly His Val Ile Ala Ala Arg Ile Thr Ser Glu Asn Pro Asp
                405                 410                 415

Glu Gly Phe Lys Pro Ser Ser Gly Thr Val Gln Glu Leu Asn Phe Arg
            420                 425                 430

Ser Asn Lys Asn Val Trp Gly Tyr Phe Ser Val Ala Ala Ala Gly Gly
        435                 440                 445

Leu His Glu Phe Ala Asp Ser Gln Phe Gly His Cys Phe Ser Trp Gly
    450                 455                 460

Glu Asn Arg Glu Glu Ala Ile Ser Asn Met Val Val Ala Leu Lys Glu
465                 470                 475                 480

Leu Ser Ile Arg Gly Asp Phe Arg Thr Thr Val Glu Tyr Leu Ile Lys
                485                 490                 495

Leu Leu Glu Thr Glu Ser Phe Gln Met Asn Arg Ile Asp Thr Gly Trp
            500                 505                 510

Leu Asp Arg Leu Ile Ala Glu Lys Val Gln Ala Glu Arg Pro Asp Thr
        515                 520                 525

Met Leu Gly Val
    530

<210> SEQ ID NO 15
<211> LENGTH: 1596
<212> TYPE: DNA
<213> ORGANISM: Homo sapiens
<220> FEATURE:
<221> NAME/KEY: CDS
<222> LOCATION: (1)..(1596)
<223> OTHER INFORMATION: N-terminal deleted Human ACCase2 BC domain
      (AAs 244-774)

<400> SEQUENCE: 15 atg gtg gct tct ccc gct gag ttt gtc aca cgc ttt ggg ggg gat cgg       48
Met Val Ala Ser Pro Ala Glu Phe Val Thr Arg Phe Gly Gly Asp Arg
1               5                   10                  15 gtc atc gag aag gtg ctt att gcc aac aac ggg att gcc gcc gtg aag       96
Val Ile Glu Lys Val Leu Ile Ala Asn Asn Gly Ile Ala Ala Val Lys
            20                  25                  30 tgc atg cgc tcc atc cgc agg tgg gcc tat gag atg ttc cgc aac gag      144
Cys Met Arg Ser Ile Arg Arg Trp Ala Tyr Glu Met Phe Arg Asn Glu
        35                  40                  45 cgg gcc atc cgg ttt gtt gtg atg gtg acc ccc gag gac ctt aag gcc      192
Arg Ala Ile Arg Phe Val Val Met Val Thr Pro Glu Asp Leu Lys Ala
    50                  55                  60 aac gca gag tac atc aag atg gcg gat cat tac gtc ccc gtc cca gga      240
Asn Ala Glu Tyr Ile Lys Met Ala Asp His Tyr Val Pro Val Pro Gly
65                  70                  75                  80 ggg ccc aat aac aac aac tat gcc aac gtg gag ctg att gtg gac att      288
Gly Pro Asn Asn Asn Asn Tyr Ala Asn Val Glu Leu Ile Val Asp Ile
                85                  90                  95 gcc aag aga att cct ttg cag gcg gtg tgg gct ggc tgg ggc cat gct      336
Ala Lys Arg Ile Pro Leu Gln Ala Val Trp Ala Gly Trp Gly His Ala
            100                 105                 110 tca gaa aac cct aaa ctt ccg gag ctg ctg tgc aag aat gga gtt gct      384
Ser Glu Asn Pro Lys Leu Pro Glu Leu Leu Cys Lys Asn Gly Val Ala
        115                 120                 125
```

```
ttc tta ggc cct ccc agt gag gcc atg tgg gcc tta gga gat aag atc    432
Phe Leu Gly Pro Pro Ser Glu Ala Met Trp Ala Leu Gly Asp Lys Ile
    130                 135                 140 gcc tcc acc gtt gtc gcc cag acg cta cag gtc cca acc ctg ccc agg    480
Ala Ser Thr Val Val Ala Gln Thr Leu Gln Val Pro Thr Leu Pro Arg
145                 150                 155                 160 agt gga agc ggc ctg aca gtg gag tgg aca gaa gat gat ctg cag cag    528
Ser Gly Ser Gly Leu Thr Val Glu Trp Thr Glu Asp Asp Leu Gln Gln
                165                 170                 175 gga aaa aga atc agt gtc cca gaa gat gtt tat gac aag ggt tgc gtg    576
Gly Lys Arg Ile Ser Val Pro Glu Asp Val Tyr Asp Lys Gly Cys Val
            180                 185                 190 aaa gac gta gat gag ggc ttg gag gca gca gaa aga att ggt ttt cca    624
Lys Asp Val Asp Glu Gly Leu Glu Ala Ala Glu Arg Ile Gly Phe Pro
        195                 200                 205 ttg atg atc aaa gct tct gaa ggt ggc gga ggg aag gga atc cgg aag    672
Leu Met Ile Lys Ala Ser Glu Gly Gly Gly Gly Lys Gly Ile Arg Lys
    210                 215                 220 gct gag agt gcg gag gac ttc ccg atc ctt ttc aga caa gta cag agt    720
Ala Glu Ser Ala Glu Asp Phe Pro Ile Leu Phe Arg Gln Val Gln Ser
225                 230                 235                 240 gag atc cca ggc tcg ccc atc ttt ctc atg aag ctg gcc cag cac gcc    768
Glu Ile Pro Gly Ser Pro Ile Phe Leu Met Lys Leu Ala Gln His Ala
                245                 250                 255 cgt cac ctg gaa gtt cag atc ctc gct gac cag tat ggg aat gct gtg    816
Arg His Leu Glu Val Gln Ile Leu Ala Asp Gln Tyr Gly Asn Ala Val
            260                 265                 270 tct ctg ttt ggt cgc gac tgc tcc atc cag cgg cgg cat cag aag atc    864
Ser Leu Phe Gly Arg Asp Cys Ser Ile Gln Arg Arg His Gln Lys Ile
        275                 280                 285 gtt gag gaa gca ccg gcc acc atc gcc ccg ctg gcc ata ttc gag ttc    912
Val Glu Glu Ala Pro Ala Thr Ile Ala Pro Leu Ala Ile Phe Glu Phe
    290                 295                 300 atg gag cag tgt gcc atc cgc ctg gcc aag acc gtg ggc tat gtg agt    960
Met Glu Gln Cys Ala Ile Arg Leu Ala Lys Thr Val Gly Tyr Val Ser
305                 310                 315                 320 gca ggg aca gtg gaa tac ctc tat agt cag gat ggc agc ttc cac ttc   1008
Ala Gly Thr Val Glu Tyr Leu Tyr Ser Gln Asp Gly Ser Phe His Phe
                325                 330                 335 ttg gag ctg aat cct cgc ttg cag gtg gaa cat ccc tgc aca gaa atg   1056
Leu Glu Leu Asn Pro Arg Leu Gln Val Glu His Pro Cys Thr Glu Met
            340                 345                 350 att gct gat gtt aat ctg ccg gcc gcc cag cta cag atc gcc atg ggc   1104
Ile Ala Asp Val Asn Leu Pro Ala Ala Gln Leu Gln Ile Ala Met Gly
        355                 360                 365 gtg cca ctg cac cgg ctg aag gat atc cgg ctt ctg tat gga gag tca   1152
Val Pro Leu His Arg Leu Lys Asp Ile Arg Leu Leu Tyr Gly Glu Ser
    370                 375                 380 cca tgg gga gtg act ccc att tct ttt gaa acc ccc tca aac cct ccc   1200
Pro Trp Gly Val Thr Pro Ile Ser Phe Glu Thr Pro Ser Asn Pro Pro
385                 390                 395                 400 ctc gcc cga ggc cac gtc att gcc gcc aga atc acc agc gaa aac cca   1248
Leu Ala Arg Gly His Val Ile Ala Ala Arg Ile Thr Ser Glu Asn Pro
                405                 410                 415 gac gag ggt ttt aag ccg agc tcc ggg act gtc cag gaa ctg aat ttc   1296
Asp Glu Gly Phe Lys Pro Ser Ser Gly Thr Val Gln Glu Leu Asn Phe
            420                 425                 430 cgg agc agc aag aac gtg tgg ggt tac ttc agc gtg gcc gct act gga   1344
Arg Ser Ser Lys Asn Val Trp Gly Tyr Phe Ser Val Ala Ala Thr Gly
```

```
                435                 440                 445
ggc ctg cac gag ttt gcg gat tcc caa ttt ggg cac tgc ttc tcc tgg       1392
Gly Leu His Glu Phe Ala Asp Ser Gln Phe Gly His Cys Phe Ser Trp
        450                 455                 460 gga gag aac cgg aaa gag gcc att tcg aac atg gtg gtg gct ttg aag       1440
Gly Glu Asn Arg Lys Glu Ala Ile Ser Asn Met Val Val Ala Leu Lys
465                 470                 475                 480 gaa ctg tcc atc cga ggt gac ttt agg act acc gtg gaa tac ctc att       1488
Glu Leu Ser Ile Arg Gly Asp Phe Arg Thr Thr Val Glu Tyr Leu Ile
                485                 490                 495 aac ctc ctg gag acc gag agc ttc cag aac aac gac atc gac acc ggg       1536
Asn Leu Leu Glu Thr Glu Ser Phe Gln Asn Asn Asp Ile Asp Thr Gly
            500                 505                 510 tgg ttg gac tac ctc att gct gag aaa gtg cag gag aaa ccg gat atc       1584
Trp Leu Asp Tyr Leu Ile Ala Glu Lys Val Gln Glu Lys Pro Asp Ile
        515                 520                 525 atg ctt ggg gtg                                                        1596
Met Leu Gly Val
    530

<210> SEQ ID NO 16
<211> LENGTH: 532
<212> TYPE: PRT
<213> ORGANISM: Homo sapiens

<400> SEQUENCE: 16

Met Val Ala Ser Pro Ala Glu Phe Val Thr Arg Phe Gly Gly Asp Arg
1               5                   10                  15

Val Ile Glu Lys Val Leu Ile Ala Asn Asn Gly Ile Ala Ala Val Lys
            20                  25                  30

Cys Met Arg Ser Ile Arg Arg Trp Ala Tyr Glu Met Phe Arg Asn Glu
        35                  40                  45

Arg Ala Ile Arg Phe Val Val Met Val Thr Pro Glu Asp Leu Lys Ala
    50                  55                  60

Asn Ala Glu Tyr Ile Lys Met Ala Asp His Tyr Val Pro Val Pro Gly
65                  70                  75                  80

Gly Pro Asn Asn Asn Tyr Ala Asn Val Glu Leu Ile Val Asp Ile
            85                  90                  95

Ala Lys Arg Ile Pro Leu Gln Ala Val Trp Ala Gly Trp Gly His Ala
        100                 105                 110

Ser Glu Asn Pro Lys Leu Pro Glu Leu Leu Cys Lys Asn Gly Val Ala
    115                 120                 125

Phe Leu Gly Pro Pro Ser Glu Ala Met Trp Ala Leu Gly Asp Lys Ile
130                 135                 140

Ala Ser Thr Val Val Ala Gln Thr Leu Gln Val Pro Thr Leu Pro Arg
145                 150                 155                 160

Ser Gly Ser Gly Leu Thr Val Glu Trp Thr Glu Asp Leu Gln Gln
            165                 170                 175

Gly Lys Arg Ile Ser Val Pro Glu Asp Val Tyr Asp Lys Gly Cys Val
        180                 185                 190

Lys Asp Val Asp Glu Gly Leu Glu Ala Ala Glu Arg Ile Gly Phe Pro
    195                 200                 205

Leu Met Ile Lys Ala Ser Glu Gly Gly Gly Gly Lys Gly Ile Arg Lys
210                 215                 220

Ala Glu Ser Ala Glu Asp Phe Pro Ile Leu Phe Arg Gln Val Gln Ser
225                 230                 235                 240
```

-continued

Glu Ile Pro Gly Ser Pro Ile Phe Leu Met Lys Leu Ala Gln His Ala
                245                 250                 255

Arg His Leu Glu Val Gln Ile Leu Ala Asp Gln Tyr Gly Asn Ala Val
            260                 265                 270

Ser Leu Phe Gly Arg Asp Cys Ser Ile Gln Arg Arg His Gln Lys Ile
        275                 280                 285

Val Glu Glu Ala Pro Ala Thr Ile Ala Pro Leu Ala Ile Phe Glu Phe
    290                 295                 300

Met Glu Gln Cys Ala Ile Arg Leu Ala Lys Thr Val Gly Tyr Val Ser
305                 310                 315                 320

Ala Gly Thr Val Glu Tyr Leu Tyr Ser Gln Asp Gly Ser Phe His Phe
                325                 330                 335

Leu Glu Leu Asn Pro Arg Leu Gln Val Glu His Pro Cys Thr Glu Met
            340                 345                 350

Ile Ala Asp Val Asn Leu Pro Ala Ala Gln Leu Gln Ile Ala Met Gly
        355                 360                 365

Val Pro Leu His Arg Leu Lys Asp Ile Arg Leu Leu Tyr Gly Glu Ser
    370                 375                 380

Pro Trp Gly Val Thr Pro Ile Ser Phe Glu Thr Pro Ser Asn Pro Pro
385                 390                 395                 400

Leu Ala Arg Gly His Val Ile Ala Ala Arg Ile Thr Ser Glu Asn Pro
                405                 410                 415

Asp Glu Gly Phe Lys Pro Ser Ser Gly Thr Val Gln Glu Leu Asn Phe
            420                 425                 430

Arg Ser Ser Lys Asn Val Trp Gly Tyr Phe Ser Val Ala Ala Thr Gly
        435                 440                 445

Gly Leu His Glu Phe Ala Asp Ser Gln Phe Gly His Cys Phe Ser Trp
    450                 455                 460

Gly Glu Asn Arg Lys Glu Ala Ile Ser Asn Met Val Val Ala Leu Lys
465                 470                 475                 480

Glu Leu Ser Ile Arg Gly Asp Phe Arg Thr Thr Val Glu Tyr Leu Ile
                485                 490                 495

Asn Leu Leu Glu Thr Glu Ser Phe Gln Asn Asn Asp Ile Asp Thr Gly
            500                 505                 510

Trp Leu Asp Tyr Leu Ile Ala Glu Lys Val Gln Glu Lys Pro Asp Ile
        515                 520                 525

Met Leu Gly Val
    530

<210> SEQ ID NO 17
<211> LENGTH: 554
<212> TYPE: PRT
<213> ORGANISM: Ustilago maydis
<220> FEATURE:
<221> NAME/KEY: MISC_FEATURE
<222> LOCATION: (1)..(554)
<223> OTHER INFORMATION: N-terminal deleted Ustilago ACCase BC domain
      (AAs 7-560)

<400> SEQUENCE: 17

Lys Ala Val Ser Gln Phe Ile Gly Gly Asn Pro Leu Glu Thr Ala Pro
1               5                   10                  15

Ala Ser Pro Val Ala Asp Phe Ile Arg Lys Gln Gly Gly His Ser Val
            20                  25                  30

Ile Thr Lys Val Leu Ile Cys Asn Asn Gly Ile Ala Ala Val Lys Glu
        35                  40                  45

```
Ile Arg Ser Ile Arg Lys Trp Ala Tyr Glu Thr Phe Gly Asp Glu Arg
 50                  55                  60

Ala Ile Glu Phe Thr Val Met Ala Thr Pro Glu Asp Leu Lys Val Asn
 65                  70                  75                  80

Ala Asp Tyr Ile Arg Met Ala Asp Gln Tyr Val Glu Val Pro Gly Gly
                 85                  90                  95

Ser Asn Asn Asn Tyr Ala Asn Val Asp Leu Ile Val Asp Val Ala
             100                 105                 110

Glu Arg Ala Gly Val His Ala Val Trp Ala Gly Trp Gly His Ala Ser
         115                 120                 125

Glu Asn Pro Arg Leu Pro Glu Ser Leu Ala Ala Ser Lys His Lys Ile
     130                 135                 140

Ile Phe Ile Gly Pro Pro Gly Ser Ala Met Arg Ser Leu Gly Asp Lys
145                 150                 155                 160

Ile Ser Ser Thr Ile Val Ala Gln His Ala Asp Val Pro Cys Met Pro
                 165                 170                 175

Trp Ser Gly Thr Gly Ile Lys Glu Thr Met Met Ser Asp Gln Gly Phe
             180                 185                 190

Leu Thr Val Ser Asp Asp Val Tyr Gln Gln Ala Cys Ile His Thr Ala
         195                 200                 205

Glu Glu Gly Leu Glu Lys Ala Glu Lys Ile Gly Tyr Pro Val Met Ile
     210                 215                 220

Lys Ala Ser Glu Gly Gly Gly Lys Gly Ile Arg Lys Cys Thr Asn
225                 230                 235                 240

Gly Glu Glu Phe Lys Gln Leu Tyr Asn Ala Val Leu Gly Glu Val Pro
                 245                 250                 255

Gly Ser Pro Val Phe Val Met Lys Leu Ala Gly Gln Ala Arg His Leu
             260                 265                 270

Glu Val Gln Leu Leu Ala Asp Gln Tyr Gly Asn Ala Ile Ser Ile Phe
         275                 280                 285

Gly Arg Asp Cys Ser Val Gln Arg Arg His Gln Lys Ile Ile Glu Glu
     290                 295                 300

Ala Pro Val Thr Ile Ala Pro Glu Asp Ala Arg Glu Ser Met Glu Lys
305                 310                 315                 320

Ala Ala Val Arg Leu Ala Lys Leu Val Gly Tyr Val Ser Ala Gly Thr
                 325                 330                 335

Val Glu Trp Leu Tyr Ser Pro Glu Ser Gly Glu Phe Ala Phe Leu Glu
             340                 345                 350

Leu Asn Pro Arg Leu Gln Val Glu His Pro Thr Thr Glu Met Val Ser
         355                 360                 365

Gly Val Asn Ile Pro Ala Ala Gln Leu Gln Val Ala Met Gly Ile Pro
     370                 375                 380

Leu Tyr Ser Ile Arg Asp Ile Arg Thr Leu Tyr Gly Met Asp Pro Arg
385                 390                 395                 400

Gly Asn Glu Val Ile Asp Phe Asp Phe Ser Ser Pro Glu Ser Phe Lys
                 405                 410                 415

Thr Gln Arg Lys Pro Gln Pro Gln Gly His Val Val Ala Cys Arg Ile
             420                 425                 430

Thr Ala Glu Asn Pro Asp Thr Gly Phe Lys Pro Gly Met Gly Ala Leu
         435                 440                 445

Thr Glu Leu Asn Phe Arg Ser Ser Thr Ser Thr Trp Gly Tyr Phe Ser
     450                 455                 460

Val Gly Thr Ser Gly Ala Leu His Glu Tyr Ala Asp Ser Gln Phe Gly
```

```
                465                 470                 475                 480
His Ile Phe Ala Tyr Gly Ala Asp Arg Ser Glu Ala Arg Lys Gln Met
                    485                 490                 495

Val Ile Ser Leu Lys Glu Leu Ser Ile Arg Gly Asp Phe Arg Thr Thr
                500                 505                 510

Val Glu Tyr Leu Ile Lys Leu Leu Glu Thr Asp Ala Phe Glu Ser Asn
                515                 520                 525

Lys Ile Thr Thr Gly Trp Leu Asp Gly Leu Ile Gln Asp Arg Leu Thr
                530                 535                 540

Ala Glu Arg Pro Pro Ala Asp Leu Ala Val
545                 550

<210> SEQ ID NO 18
<211> LENGTH: 549
<212> TYPE: PRT
<213> ORGANISM: Ustilago maydis
<220> FEATURE:
<221> NAME/KEY: MISC_FEATURE
<222> LOCATION: (1)..(549)
<223> OTHER INFORMATION: N-terminal deleted Ustilago ACCase BC domain
      (AAs 12-560)

<400> SEQUENCE: 18

Phe Ile Gly Gly Asn Pro Leu Glu Thr Ala Pro Ala Ser Pro Val Ala
1               5                   10                  15

Asp Phe Ile Arg Lys Gln Gly Gly His Ser Val Ile Thr Lys Val Leu
                20                  25                  30

Ile Cys Asn Asn Gly Ile Ala Ala Val Lys Glu Ile Arg Ser Ile Arg
            35                  40                  45

Lys Trp Ala Tyr Glu Thr Phe Gly Asp Glu Arg Ala Ile Glu Phe Thr
        50                  55                  60

Val Met Ala Thr Pro Glu Asp Leu Lys Val Asn Ala Asp Tyr Ile Arg
65                  70                  75                  80

Met Ala Asp Gln Tyr Val Glu Val Pro Gly Gly Ser Asn Asn Asn Asn
                85                  90                  95

Tyr Ala Asn Val Asp Leu Ile Val Asp Val Ala Glu Arg Ala Gly Val
                100                 105                 110

His Ala Val Trp Ala Gly Trp Gly His Ala Ser Glu Asn Pro Arg Leu
            115                 120                 125

Pro Glu Ser Leu Ala Ala Ser Lys His Lys Ile Ile Phe Ile Gly Pro
        130                 135                 140

Pro Gly Ser Ala Met Arg Ser Leu Gly Asp Lys Ile Ser Ser Thr Ile
145                 150                 155                 160

Val Ala Gln His Ala Asp Val Pro Cys Met Pro Trp Ser Gly Thr Gly
                165                 170                 175

Ile Lys Glu Thr Met Met Ser Asp Gln Gly Phe Leu Thr Val Ser Asp
            180                 185                 190

Asp Val Tyr Gln Gln Ala Cys Ile His Thr Ala Glu Glu Gly Leu Glu
        195                 200                 205

Lys Ala Glu Lys Ile Gly Tyr Pro Val Met Ile Lys Ala Ser Glu Gly
    210                 215                 220

Gly Gly Gly Lys Gly Ile Arg Lys Cys Thr Asn Gly Glu Glu Phe Lys
225                 230                 235                 240

Gln Leu Tyr Asn Ala Val Leu Gly Glu Val Pro Gly Ser Pro Val Phe
                245                 250                 255

Val Met Lys Leu Ala Gly Gln Ala Arg His Leu Glu Val Gln Leu Leu
```

-continued

```
                260                 265                 270
Ala Asp Gln Tyr Gly Asn Ala Ile Ser Ile Phe Gly Arg Asp Cys Ser
            275                 280                 285
Val Gln Arg Arg His Gln Lys Ile Ile Glu Glu Ala Pro Val Thr Ile
        290                 295                 300
Ala Pro Glu Asp Ala Arg Glu Ser Met Glu Lys Ala Ala Val Arg Leu
305                 310                 315                 320
Ala Lys Leu Val Gly Tyr Val Ser Ala Gly Thr Val Glu Trp Leu Tyr
            325                 330                 335
Ser Pro Glu Ser Gly Glu Phe Ala Phe Leu Glu Leu Asn Pro Arg Leu
        340                 345                 350
Gln Val Glu His Pro Thr Thr Glu Met Val Ser Gly Val Asn Ile Pro
        355                 360                 365
Ala Ala Gln Leu Gln Val Ala Met Gly Ile Pro Leu Tyr Ser Ile Arg
        370                 375                 380
Asp Ile Arg Thr Leu Tyr Gly Met Asp Pro Arg Gly Asn Glu Val Ile
385                 390                 395                 400
Asp Phe Asp Phe Ser Ser Pro Glu Ser Phe Lys Thr Gln Arg Lys Pro
            405                 410                 415
Gln Pro Gln Gly His Val Val Ala Cys Arg Ile Thr Ala Glu Asn Pro
        420                 425                 430
Asp Thr Gly Phe Lys Pro Gly Met Gly Ala Leu Thr Glu Leu Asn Phe
        435                 440                 445
Arg Ser Ser Thr Ser Thr Trp Gly Tyr Phe Ser Val Gly Thr Ser Gly
        450                 455                 460
Ala Leu His Glu Tyr Ala Asp Ser Gln Phe Gly His Ile Phe Ala Tyr
465                 470                 475                 480
Gly Ala Asp Arg Ser Glu Ala Arg Lys Gln Met Val Ile Ser Leu Lys
            485                 490                 495
Glu Leu Ser Ile Arg Gly Asp Phe Arg Thr Thr Val Glu Tyr Leu Ile
            500                 505                 510
Lys Leu Leu Glu Thr Asp Ala Phe Glu Ser Asn Lys Ile Thr Thr Gly
        515                 520                 525
Trp Leu Asp Gly Leu Ile Gln Asp Arg Leu Thr Ala Glu Arg Pro Pro
        530                 535                 540
Ala Asp Leu Ala Val
545

<210> SEQ ID NO 19
<211> LENGTH: 539
<212> TYPE: PRT
<213> ORGANISM: Ustilago maydis
<220> FEATURE:
<221> NAME/KEY: MISC_FEATURE
<222> LOCATION: (1)..(539)
<223> OTHER INFORMATION: N-terminal deleted Ustilago ACCse BC domain
      (AAs 22-560)

<400> SEQUENCE: 19

Pro Ala Ser Pro Val Ala Asp Phe Ile Arg Lys Gln Gly Gly His Ser
1               5                   10                  15
Val Ile Thr Lys Val Leu Ile Cys Asn Asn Gly Ile Ala Ala Val Lys
            20                  25                  30
Glu Ile Arg Ser Ile Arg Lys Trp Ala Tyr Glu Thr Phe Gly Asp Glu
        35                  40                  45
Arg Ala Ile Glu Phe Thr Val Met Ala Thr Pro Glu Asp Leu Lys Val
```

-continued

```
            50                  55                  60
Asn Ala Asp Tyr Ile Arg Met Ala Asp Gln Tyr Val Glu Val Pro Gly
 65                  70                  75                  80
Gly Ser Asn Asn Asn Tyr Ala Asn Val Asp Leu Ile Val Asp Val
                 85                  90                  95
Ala Glu Arg Ala Gly Val His Ala Val Trp Ala Gly Trp Gly His Ala
                100                 105                 110
Ser Glu Asn Pro Arg Leu Pro Glu Ser Leu Ala Ala Ser Lys His Lys
                115                 120                 125
Ile Ile Phe Ile Gly Pro Pro Gly Ser Ala Met Arg Ser Leu Gly Asp
            130                 135                 140
Lys Ile Ser Ser Thr Ile Val Ala Gln His Ala Asp Val Pro Cys Met
145                 150                 155                 160
Pro Trp Ser Gly Thr Gly Ile Lys Glu Thr Met Met Ser Asp Gln Gly
                165                 170                 175
Phe Leu Thr Val Ser Asp Asp Val Tyr Gln Gln Ala Cys Ile His Thr
            180                 185                 190
Ala Glu Glu Gly Leu Glu Lys Ala Glu Lys Ile Gly Tyr Pro Val Met
            195                 200                 205
Ile Lys Ala Ser Glu Gly Gly Gly Lys Gly Ile Arg Lys Cys Thr
210                 215                 220
Asn Gly Glu Glu Phe Lys Gln Leu Tyr Asn Ala Val Leu Gly Glu Val
225                 230                 235                 240
Pro Gly Ser Pro Val Phe Val Met Lys Leu Ala Gly Gln Ala Arg His
                245                 250                 255
Leu Glu Val Gln Leu Leu Ala Asp Gln Tyr Gly Asn Ala Ile Ser Ile
                260                 265                 270
Phe Gly Arg Asp Cys Ser Val Gln Arg Arg His Gln Lys Ile Ile Glu
            275                 280                 285
Glu Ala Pro Val Thr Ile Ala Pro Glu Asp Ala Arg Glu Ser Met Glu
            290                 295                 300
Lys Ala Ala Val Arg Leu Ala Lys Leu Val Gly Tyr Val Ser Ala Gly
305                 310                 315                 320
Thr Val Glu Trp Leu Tyr Ser Pro Glu Ser Gly Glu Phe Ala Phe Leu
                325                 330                 335
Glu Leu Asn Pro Arg Leu Gln Val Glu His Pro Thr Thr Glu Met Val
                340                 345                 350
Ser Gly Val Asn Ile Pro Ala Ala Gln Leu Gln Val Ala Met Gly Ile
            355                 360                 365
Pro Leu Tyr Ser Ile Arg Asp Ile Arg Thr Leu Tyr Gly Met Asp Pro
            370                 375                 380
Arg Gly Asn Glu Val Ile Asp Phe Asp Phe Ser Ser Pro Glu Ser Phe
385                 390                 395                 400
Lys Thr Gln Arg Lys Pro Gln Pro Gln Gly His Val Val Ala Cys Arg
                405                 410                 415
Ile Thr Ala Glu Asn Pro Asp Thr Gly Phe Lys Pro Gly Met Gly Ala
            420                 425                 430
Leu Thr Glu Leu Asn Phe Arg Ser Ser Thr Thr Trp Gly Tyr Phe
            435                 440                 445
Ser Val Gly Thr Ser Gly Ala Leu His Glu Tyr Ala Asp Ser Gln Phe
            450                 455                 460
Gly His Ile Phe Ala Tyr Gly Ala Asp Arg Ser Glu Ala Arg Lys Gln
465                 470                 475                 480
```

```
Met Val Ile Ser Leu Lys Glu Leu Ser Ile Arg Gly Asp Phe Arg Thr
                485                 490                 495

Thr Val Glu Tyr Leu Ile Lys Leu Leu Glu Thr Asp Ala Phe Glu Ser
                500                 505                 510

Asn Lys Ile Thr Thr Gly Trp Leu Asp Gly Leu Ile Gln Asp Arg Leu
                515                 520                 525

Thr Ala Glu Arg Pro Pro Ala Asp Leu Ala Val
                530                 535

<210> SEQ ID NO 20
<211> LENGTH: 529
<212> TYPE: PRT
<213> ORGANISM: Ustilago maydis
<220> FEATURE:
<221> NAME/KEY: MISC_FEATURE
<222> LOCATION: (1)..(529)
<223> OTHER INFORMATION: N-terminal deleted Ustilago ACCase BC domain
      (AAs 32-560)

<400> SEQUENCE: 20

Lys Gln Gly Gly His Ser Val Ile Thr Lys Val Leu Ile Cys Asn Asn
1               5                   10                  15

Gly Ile Ala Ala Val Lys Glu Ile Arg Ser Ile Arg Lys Trp Ala Tyr
                20                  25                  30

Glu Thr Phe Gly Asp Glu Arg Ala Ile Glu Phe Thr Val Met Ala Thr
                35                  40                  45

Pro Glu Asp Leu Lys Val Asn Ala Asp Tyr Ile Arg Met Ala Asp Gln
            50                  55                  60

Tyr Val Glu Val Pro Gly Gly Ser Asn Asn Asn Tyr Ala Asn Val
65              70                  75                  80

Asp Leu Ile Val Asp Val Ala Glu Arg Ala Gly Val His Ala Val Trp
                85                  90                  95

Ala Gly Trp Gly His Ala Ser Glu Asn Pro Arg Leu Pro Glu Ser Leu
                100                 105                 110

Ala Ala Ser Lys His Lys Ile Ile Phe Ile Gly Pro Pro Gly Ser Ala
                115                 120                 125

Met Arg Ser Leu Gly Asp Lys Ile Ser Ser Thr Ile Val Ala Gln His
                130                 135                 140

Ala Asp Val Pro Cys Met Pro Trp Ser Gly Thr Gly Ile Lys Glu Thr
145                 150                 155                 160

Met Met Ser Asp Gln Gly Phe Leu Thr Val Ser Asp Asp Val Tyr Gln
                165                 170                 175

Gln Ala Cys Ile His Thr Ala Glu Glu Gly Leu Glu Lys Ala Glu Lys
                180                 185                 190

Ile Gly Tyr Pro Val Met Ile Lys Ala Ser Glu Gly Gly Gly Gly Lys
                195                 200                 205

Gly Ile Arg Lys Cys Thr Asn Gly Glu Glu Phe Lys Gln Leu Tyr Asn
                210                 215                 220

Ala Val Leu Gly Glu Val Pro Gly Ser Pro Val Phe Val Met Lys Leu
225                 230                 235                 240

Ala Gly Gln Ala Arg His Leu Glu Val Gln Leu Leu Ala Asp Gln Tyr
                245                 250                 255

Gly Asn Ala Ile Ser Ile Phe Gly Arg Asp Cys Ser Val Gln Arg Arg
                260                 265                 270

His Gln Lys Ile Ile Glu Glu Ala Pro Val Thr Ile Ala Pro Glu Asp
                275                 280                 285
```

```
Ala Arg Glu Ser Met Glu Lys Ala Ala Val Arg Leu Ala Lys Leu Val
    290                 295                 300

Gly Tyr Val Ser Ala Gly Thr Val Glu Trp Leu Tyr Ser Pro Glu Ser
305                 310                 315                 320

Gly Glu Phe Ala Phe Leu Glu Leu Asn Pro Arg Leu Gln Val Glu His
                325                 330                 335

Pro Thr Thr Glu Met Val Ser Gly Val Asn Ile Pro Ala Ala Gln Leu
            340                 345                 350

Gln Val Ala Met Gly Ile Pro Leu Tyr Ser Ile Arg Asp Ile Arg Thr
        355                 360                 365

Leu Tyr Gly Met Asp Pro Arg Gly Asn Glu Val Ile Asp Phe Asp Phe
    370                 375                 380

Ser Ser Pro Glu Ser Phe Lys Thr Gln Arg Lys Pro Gln Pro Gln Gly
385                 390                 395                 400

His Val Val Ala Cys Arg Ile Thr Ala Glu Asn Pro Asp Thr Gly Phe
                405                 410                 415

Lys Pro Gly Met Gly Ala Leu Thr Glu Leu Asn Phe Arg Ser Ser Thr
            420                 425                 430

Ser Thr Trp Gly Tyr Phe Ser Val Gly Thr Ser Gly Ala Leu His Glu
        435                 440                 445

Tyr Ala Asp Ser Gln Phe Gly His Ile Phe Ala Tyr Gly Ala Asp Arg
    450                 455                 460

Ser Glu Ala Arg Lys Gln Met Val Ile Ser Leu Lys Glu Leu Ser Ile
465                 470                 475                 480

Arg Gly Asp Phe Arg Thr Thr Val Glu Tyr Leu Ile Lys Leu Leu Glu
                485                 490                 495

Thr Asp Ala Phe Glu Ser Asn Lys Ile Thr Thr Gly Trp Leu Asp Gly
            500                 505                 510

Leu Ile Gln Asp Arg Leu Thr Ala Glu Arg Pro Pro Ala Asp Leu Ala
        515                 520                 525

Val

<210> SEQ ID NO 21
<211> LENGTH: 519
<212> TYPE: PRT
<213> ORGANISM: Ustilago maydis
<220> FEATURE:
<221> NAME/KEY: MISC_FEATURE
<222> LOCATION: (1)..(519)
<223> OTHER INFORMATION: N-terminal deleted Ustilago ACCase BC domain
      (AAs 42-560)

<400> SEQUENCE: 21

Val Leu Ile Cys Asn Asn Gly Ile Ala Ala Val Lys Glu Ile Arg Ser
1               5                   10                  15

Ile Arg Lys Trp Ala Tyr Glu Thr Phe Gly Asp Glu Arg Ala Ile Glu
            20                  25                  30

Phe Thr Val Met Ala Thr Pro Glu Asp Leu Lys Val Asn Ala Asp Tyr
        35                  40                  45

Ile Arg Met Ala Asp Gln Tyr Val Glu Val Pro Gly Gly Ser Asn Asn
    50                  55                  60

Asn Asn Tyr Ala Asn Val Asp Leu Ile Val Asp Val Ala Glu Arg Ala
65                  70                  75                  80

Gly Val His Ala Val Trp Ala Gly Trp Gly His Ala Ser Glu Asn Pro
                85                  90                  95
```

-continued

```
Arg Leu Pro Glu Ser Leu Ala Ala Ser Lys His Lys Ile Ile Phe Ile
            100                 105                 110
Gly Pro Pro Gly Ser Ala Met Arg Ser Leu Gly Asp Lys Ile Ser Ser
        115                 120                 125
Thr Ile Val Ala Gln His Ala Asp Val Pro Cys Met Pro Trp Ser Gly
    130                 135                 140
Thr Gly Ile Lys Glu Thr Met Met Ser Asp Gln Gly Phe Leu Thr Val
145                 150                 155                 160
Ser Asp Asp Val Tyr Gln Gln Ala Cys Ile His Thr Ala Glu Glu Gly
                165                 170                 175
Leu Glu Lys Ala Glu Lys Ile Gly Tyr Pro Val Met Ile Lys Ala Ser
            180                 185                 190
Glu Gly Gly Gly Gly Lys Gly Ile Arg Lys Cys Thr Asn Gly Glu Glu
        195                 200                 205
Phe Lys Gln Leu Tyr Asn Ala Val Leu Gly Glu Val Pro Gly Ser Pro
    210                 215                 220
Val Phe Val Met Lys Leu Ala Gly Gln Ala Arg His Leu Glu Val Gln
225                 230                 235                 240
Leu Leu Ala Asp Gln Tyr Gly Asn Ala Ile Ser Ile Phe Gly Arg Asp
                245                 250                 255
Cys Ser Val Gln Arg Arg His Gln Lys Ile Ile Glu Glu Ala Pro Val
            260                 265                 270
Thr Ile Ala Pro Glu Asp Ala Arg Glu Ser Met Glu Lys Ala Ala Val
        275                 280                 285
Arg Leu Ala Lys Leu Val Gly Tyr Val Ser Ala Gly Thr Val Glu Trp
    290                 295                 300
Leu Tyr Ser Pro Glu Ser Gly Glu Phe Ala Phe Leu Glu Leu Asn Pro
305                 310                 315                 320
Arg Leu Gln Val Glu His Pro Thr Thr Glu Met Val Ser Gly Val Asn
                325                 330                 335
Ile Pro Ala Ala Gln Leu Gln Val Ala Met Gly Ile Pro Leu Tyr Ser
            340                 345                 350
Ile Arg Asp Ile Arg Thr Leu Tyr Gly Met Asp Pro Arg Gly Asn Glu
        355                 360                 365
Val Ile Asp Phe Asp Phe Ser Ser Pro Glu Ser Phe Lys Thr Gln Arg
    370                 375                 380
Lys Pro Gln Pro Gln Gly His Val Val Ala Cys Arg Ile Thr Ala Glu
385                 390                 395                 400
Asn Pro Asp Thr Gly Phe Lys Pro Gly Met Gly Ala Leu Thr Glu Leu
                405                 410                 415
Asn Phe Arg Ser Ser Thr Ser Thr Trp Gly Tyr Phe Ser Val Gly Thr
            420                 425                 430
Ser Gly Ala Leu His Glu Tyr Ala Asp Ser Gln Phe Gly His Ile Phe
        435                 440                 445
Ala Tyr Gly Ala Asp Arg Ser Glu Ala Arg Lys Gln Met Val Ile Ser
    450                 455                 460
Leu Lys Glu Leu Ser Ile Arg Gly Asp Phe Arg Thr Thr Val Glu Tyr
465                 470                 475                 480
Leu Ile Lys Leu Leu Glu Thr Asp Ala Phe Glu Ser Asn Lys Ile Thr
                485                 490                 495
Thr Gly Trp Leu Asp Gly Leu Ile Gln Asp Arg Leu Thr Ala Glu Arg
            500                 505                 510
Pro Pro Ala Asp Leu Ala Val
```

515

<210> SEQ ID NO 22
<211> LENGTH: 554
<212> TYPE: PRT
<213> ORGANISM: Ustilago maydis
<220> FEATURE:
<221> NAME/KEY: MISC_FEATURE
<222> LOCATION: (1)..(554)
<223> OTHER INFORMATION: C-terminal deleted Ustilago ACCase BC domain
      (AAs 2-555)

<400> SEQUENCE: 22

```
Pro Pro Pro Asp His Lys Ala Val Ser Gln Phe Ile Gly Gly Asn Pro
1               5                   10                  15

Leu Glu Thr Ala Pro Ala Ser Pro Val Ala Asp Phe Ile Arg Lys Gln
            20                  25                  30

Gly Gly His Ser Val Ile Thr Lys Val Leu Ile Cys Asn Asn Gly Ile
        35                  40                  45

Ala Ala Val Lys Glu Ile Arg Ser Ile Arg Lys Trp Ala Tyr Glu Thr
    50                  55                  60

Phe Gly Asp Glu Arg Ala Ile Glu Phe Thr Val Met Ala Thr Pro Glu
65                  70                  75                  80

Asp Leu Lys Val Asn Ala Asp Tyr Ile Arg Met Ala Asp Gln Tyr Val
                85                  90                  95

Glu Val Pro Gly Gly Ser Asn Asn Asn Tyr Ala Asn Val Asp Leu
            100                 105                 110

Ile Val Asp Val Ala Glu Arg Ala Gly Val His Ala Val Trp Ala Gly
        115                 120                 125

Trp Gly His Ala Ser Glu Asn Pro Arg Leu Pro Glu Ser Leu Ala Ala
    130                 135                 140

Ser Lys His Lys Ile Ile Phe Ile Gly Pro Pro Gly Ser Ala Met Arg
145                 150                 155                 160

Ser Leu Gly Asp Lys Ile Ser Ser Thr Ile Val Ala Gln His Ala Asp
                165                 170                 175

Val Pro Cys Met Pro Trp Ser Gly Thr Gly Ile Lys Glu Thr Met Met
            180                 185                 190

Ser Asp Gln Gly Phe Leu Thr Val Ser Asp Asp Val Tyr Gln Gln Ala
        195                 200                 205

Cys Ile His Thr Ala Glu Glu Gly Leu Glu Lys Ala Glu Lys Ile Gly
    210                 215                 220

Tyr Pro Val Met Ile Lys Ala Ser Glu Gly Gly Gly Lys Gly Ile
225                 230                 235                 240

Arg Lys Cys Thr Asn Gly Glu Glu Phe Lys Gln Leu Tyr Asn Ala Val
                245                 250                 255

Leu Gly Glu Val Pro Gly Ser Pro Val Phe Val Met Lys Leu Ala Gly
            260                 265                 270

Gln Ala Arg His Leu Glu Val Gln Leu Leu Ala Asp Gln Tyr Gly Asn
        275                 280                 285

Ala Ile Ser Ile Phe Gly Arg Asp Cys Ser Val Gln Arg Arg His Gln
    290                 295                 300

Lys Ile Ile Glu Glu Ala Pro Val Thr Ile Ala Pro Glu Asp Ala Arg
305                 310                 315                 320

Glu Ser Met Glu Lys Ala Ala Val Arg Leu Ala Lys Leu Val Gly Tyr
                325                 330                 335

Val Ser Ala Gly Thr Val Glu Trp Leu Tyr Ser Pro Glu Ser Gly Glu
```

-continued

```
                340             345             350
Phe Ala Phe Leu Glu Leu Asn Pro Arg Leu Gln Val Glu His Pro Thr
            355                 360                 365

Thr Glu Met Val Ser Gly Val Asn Ile Pro Ala Gln Leu Gln Val
        370                 375                 380

Ala Met Gly Ile Pro Leu Tyr Ser Ile Arg Asp Ile Arg Thr Leu Tyr
385                 390                 395                 400

Gly Met Asp Pro Arg Gly Asn Glu Val Ile Asp Phe Asp Phe Ser Ser
                405                 410                 415

Pro Glu Ser Phe Lys Thr Gln Arg Lys Pro Gln Pro Gln Gly His Val
            420                 425                 430

Val Ala Cys Arg Ile Thr Ala Glu Asn Pro Asp Thr Gly Phe Lys Pro
        435                 440                 445

Gly Met Gly Ala Leu Thr Glu Leu Asn Phe Arg Ser Ser Thr Ser Thr
    450                 455                 460

Trp Gly Tyr Phe Ser Val Gly Thr Ser Gly Ala Leu His Glu Tyr Ala
465                 470                 475                 480

Asp Ser Gln Phe Gly His Ile Phe Ala Tyr Gly Ala Asp Arg Ser Glu
                485                 490                 495

Ala Arg Lys Gln Met Val Ile Ser Leu Lys Glu Leu Ser Ile Arg Gly
            500                 505                 510

Asp Phe Arg Thr Thr Val Glu Tyr Leu Ile Lys Leu Leu Glu Thr Asp
        515                 520                 525

Ala Phe Glu Ser Asn Lys Ile Thr Thr Gly Trp Leu Asp Gly Leu Ile
    530                 535                 540

Gln Asp Arg Leu Thr Ala Glu Arg Pro Pro
545                 550

<210> SEQ ID NO 23
<211> LENGTH: 549
<212> TYPE: PRT
<213> ORGANISM: Ustilago maydis
<220> FEATURE:
<221> NAME/KEY: MISC_FEATURE
<222> LOCATION: (1)..(549)
<223> OTHER INFORMATION: C-terminal deleted Ustilago ACCase BC domain
      (AAs 2-550)

<400> SEQUENCE: 23

Pro Pro Pro Asp His Lys Ala Val Ser Gln Phe Ile Gly Gly Asn Pro
1               5                   10                  15

Leu Glu Thr Ala Pro Ala Ser Pro Val Ala Asp Phe Ile Arg Lys Gln
            20                  25                  30

Gly Gly His Ser Val Ile Thr Lys Val Leu Ile Cys Asn Asn Gly Ile
        35                  40                  45

Ala Ala Val Lys Glu Ile Arg Ser Ile Arg Lys Trp Ala Tyr Glu Thr
    50                  55                  60

Phe Gly Asp Glu Arg Ala Ile Glu Phe Thr Val Met Ala Thr Pro Glu
65                  70                  75                  80

Asp Leu Lys Val Asn Ala Asp Tyr Ile Arg Met Ala Asp Gln Tyr Val
                85                  90                  95

Glu Val Pro Gly Gly Ser Asn Asn Asn Tyr Ala Asn Val Asp Leu
            100                 105                 110

Ile Val Asp Val Ala Glu Arg Ala Gly Val His Ala Val Trp Ala Gly
        115                 120                 125

Trp Gly His Ala Ser Glu Asn Pro Arg Leu Pro Glu Ser Leu Ala Ala
```

-continued

```
                130                 135                 140
Ser Lys His Lys Ile Ile Phe Ile Gly Pro Pro Gly Ser Ala Met Arg
145                 150                 155                 160

Ser Leu Gly Asp Lys Ile Ser Ser Thr Ile Val Ala Gln His Ala Asp
                165                 170                 175

Val Pro Cys Met Pro Trp Ser Gly Thr Gly Ile Lys Glu Thr Met Met
            180                 185                 190

Ser Asp Gln Gly Phe Leu Thr Val Ser Asp Asp Val Tyr Gln Gln Ala
                195                 200                 205

Cys Ile His Thr Ala Glu Glu Gly Leu Glu Lys Ala Glu Lys Ile Gly
210                 215                 220

Tyr Pro Val Met Ile Lys Ala Ser Glu Gly Gly Gly Lys Gly Ile
225                 230                 235                 240

Arg Lys Cys Thr Asn Gly Glu Glu Phe Lys Gln Leu Tyr Asn Ala Val
                245                 250                 255

Leu Gly Glu Val Pro Gly Ser Pro Val Phe Val Met Lys Leu Ala Gly
                260                 265                 270

Gln Ala Arg His Leu Glu Val Gln Leu Leu Ala Asp Gln Tyr Gly Asn
                275                 280                 285

Ala Ile Ser Ile Phe Gly Arg Asp Cys Ser Val Gln Arg Arg His Gln
            290                 295                 300

Lys Ile Ile Glu Glu Ala Pro Val Thr Ile Ala Pro Glu Asp Ala Arg
305                 310                 315                 320

Glu Ser Met Glu Lys Ala Ala Val Arg Leu Ala Lys Leu Val Gly Tyr
                325                 330                 335

Val Ser Ala Gly Thr Val Glu Trp Leu Tyr Ser Pro Glu Ser Gly Glu
            340                 345                 350

Phe Ala Phe Leu Glu Leu Asn Pro Arg Leu Gln Val Glu His Pro Thr
            355                 360                 365

Thr Glu Met Val Ser Gly Val Asn Ile Pro Ala Ala Gln Leu Gln Val
            370                 375                 380

Ala Met Gly Ile Pro Leu Tyr Ser Ile Arg Asp Ile Arg Thr Leu Tyr
385                 390                 395                 400

Gly Met Asp Pro Arg Gly Asn Glu Val Ile Asp Phe Asp Phe Ser Ser
                405                 410                 415

Pro Glu Ser Phe Lys Thr Gln Arg Lys Pro Gln Pro Gln Gly His Val
                420                 425                 430

Val Ala Cys Arg Ile Thr Ala Glu Asn Pro Asp Thr Gly Phe Lys Pro
            435                 440                 445

Gly Met Gly Ala Leu Thr Glu Leu Asn Phe Arg Ser Ser Thr Ser Thr
450                 455                 460

Trp Gly Tyr Phe Ser Val Gly Thr Ser Gly Ala Leu His Glu Tyr Ala
465                 470                 475                 480

Asp Ser Gln Phe Gly His Ile Phe Ala Tyr Gly Ala Asp Arg Ser Glu
                485                 490                 495

Ala Arg Lys Gln Met Val Ile Ser Leu Lys Glu Leu Ser Ile Arg Gly
                500                 505                 510

Asp Phe Arg Thr Thr Val Glu Tyr Leu Ile Lys Leu Leu Glu Thr Asp
                515                 520                 525

Ala Phe Glu Ser Asn Lys Ile Thr Thr Gly Trp Leu Asp Gly Leu Ile
            530                 535                 540

Gln Asp Arg Leu Thr
545
```

<210> SEQ ID NO 24
<211> LENGTH: 539
<212> TYPE: PRT
<213> ORGANISM: Ustilago maydis
<220> FEATURE:
<221> NAME/KEY: MISC_FEATURE
<222> LOCATION: (1)..(539)
<223> OTHER INFORMATION: C-terminal deleted Ustilago ACCase BC domain
(AAs 2-540)

<400> SEQUENCE: 24

```
Pro Pro Pro Asp His Lys Ala Val Ser Gln Phe Ile Gly Gly Asn Pro
1               5                   10                  15

Leu Glu Thr Ala Pro Ala Ser Pro Val Ala Asp Phe Ile Arg Lys Gln
            20                  25                  30

Gly Gly His Ser Val Ile Thr Lys Val Leu Ile Cys Asn Asn Gly Ile
        35                  40                  45

Ala Ala Val Lys Glu Ile Arg Ser Ile Arg Lys Trp Ala Tyr Glu Thr
    50                  55                  60

Phe Gly Asp Glu Arg Ala Ile Glu Phe Thr Val Met Ala Thr Pro Glu
65                  70                  75                  80

Asp Leu Lys Val Asn Ala Asp Tyr Ile Arg Met Ala Asp Gln Tyr Val
                85                  90                  95

Glu Val Pro Gly Gly Ser Asn Asn Asn Asn Tyr Ala Asn Val Asp Leu
            100                 105                 110

Ile Val Asp Val Ala Glu Arg Ala Gly Val His Ala Val Trp Ala Gly
        115                 120                 125

Trp Gly His Ala Ser Glu Asn Pro Arg Leu Pro Glu Ser Leu Ala Ala
    130                 135                 140

Ser Lys His Lys Ile Ile Phe Ile Gly Pro Pro Gly Ser Ala Met Arg
145                 150                 155                 160

Ser Leu Gly Asp Lys Ile Ser Ser Thr Ile Val Ala Gln His Ala Asp
                165                 170                 175

Val Pro Cys Met Pro Trp Ser Gly Thr Gly Ile Lys Glu Thr Met Met
            180                 185                 190

Ser Asp Gln Gly Phe Leu Thr Val Ser Asp Asp Val Tyr Gln Gln Ala
        195                 200                 205

Cys Ile His Thr Ala Glu Glu Gly Leu Glu Lys Ala Glu Lys Ile Gly
    210                 215                 220

Tyr Pro Val Met Ile Lys Ala Ser Glu Gly Gly Gly Gly Lys Gly Ile
225                 230                 235                 240

Arg Lys Cys Thr Asn Gly Glu Glu Phe Lys Gln Leu Tyr Asn Ala Val
                245                 250                 255

Leu Gly Glu Val Pro Gly Ser Pro Val Phe Val Met Lys Leu Ala Gly
            260                 265                 270

Gln Ala Arg His Leu Glu Val Gln Leu Leu Ala Asp Gln Tyr Gly Asn
        275                 280                 285

Ala Ile Ser Ile Phe Gly Arg Asp Cys Ser Val Gln Arg Arg His Gln
    290                 295                 300

Lys Ile Ile Glu Glu Ala Pro Val Thr Ile Ala Pro Glu Asp Ala Arg
305                 310                 315                 320

Glu Ser Met Glu Lys Ala Ala Val Arg Leu Ala Lys Leu Val Gly Tyr
                325                 330                 335

Val Ser Ala Gly Thr Val Glu Trp Leu Tyr Ser Pro Glu Ser Gly Glu
            340                 345                 350
```

```
Phe Ala Phe Leu Glu Leu Asn Pro Arg Leu Gln Val Glu His Pro Thr
        355                 360                 365

Thr Glu Met Val Ser Gly Val Asn Ile Pro Ala Ala Gln Leu Gln Val
    370                 375                 380

Ala Met Gly Ile Pro Leu Tyr Ser Ile Arg Asp Ile Arg Thr Leu Tyr
385                 390                 395                 400

Gly Met Asp Pro Arg Gly Asn Glu Val Ile Asp Phe Asp Phe Ser Ser
                405                 410                 415

Pro Glu Ser Phe Lys Thr Gln Arg Lys Pro Gln Pro Gln Gly His Val
            420                 425                 430

Val Ala Cys Arg Ile Thr Ala Glu Asn Pro Asp Thr Gly Phe Lys Pro
        435                 440                 445

Gly Met Gly Ala Leu Thr Glu Leu Asn Phe Arg Ser Ser Thr Ser Thr
    450                 455                 460

Trp Gly Tyr Phe Ser Val Gly Thr Ser Gly Ala Leu His Glu Tyr Ala
465                 470                 475                 480

Asp Ser Gln Phe Gly His Ile Phe Ala Tyr Gly Ala Asp Arg Ser Glu
                485                 490                 495

Ala Arg Lys Gln Met Val Ile Ser Leu Lys Glu Leu Ser Ile Arg Gly
            500                 505                 510

Asp Phe Arg Thr Thr Val Glu Tyr Leu Ile Lys Leu Leu Glu Thr Asp
        515                 520                 525

Ala Phe Glu Ser Asn Lys Ile Thr Thr Gly Trp
    530                 535

<210> SEQ ID NO 25
<211> LENGTH: 529
<212> TYPE: PRT
<213> ORGANISM: Ustilago maydis
<220> FEATURE:
<221> NAME/KEY: MISC_FEATURE
<222> LOCATION: (1)..(529)
<223> OTHER INFORMATION: C-terminal deleted Ustilago ACCase B

```
Ser Leu Gly Asp Lys Ile Ser Ser Thr Ile Val Ala Gln His Ala Asp
            165                 170                 175

Val Pro Cys Met Pro Trp Ser Gly Thr Gly Ile Lys Glu Thr Met Met
            180                 185                 190

Ser Asp Gln Gly Phe Leu Thr Val Ser Asp Asp Val Tyr Gln Gln Ala
            195                 200                 205

Cys Ile His Thr Ala Glu Glu Gly Leu Glu Lys Ala Glu Lys Ile Gly
    210                 215                 220

Tyr Pro Val Met Ile Lys Ala Ser Glu Gly Gly Gly Lys Gly Ile
225                 230                 235                 240

Arg Lys Cys Thr Asn Gly Glu Glu Phe Lys Gln Leu Tyr Asn Ala Val
                245                 250                 255

Leu Gly Glu Val Pro Gly Ser Pro Val Phe Val Met Lys Leu Ala Gly
                260                 265                 270

Gln Ala Arg His Leu Glu Val Gln Leu Leu Ala Asp Gln Tyr Gly Asn
            275                 280                 285

Ala Ile Ser Ile Phe Gly Arg Asp Cys Ser Val Gln Arg Arg His Gln
    290                 295                 300

Lys Ile Ile Glu Glu Ala Pro Val Thr Ile Ala Pro Glu Asp Ala Arg
305                 310                 315                 320

Glu Ser Met Glu Lys Ala Ala Val Arg Leu Ala Lys Leu Val Gly Tyr
                325                 330                 335

Val Ser Ala Gly Thr Val Glu Trp Leu Tyr Ser Pro Glu Ser Gly Glu
            340                 345                 350

Phe Ala Phe Leu Glu Leu Asn Pro Arg Leu Gln Val Glu His Pro Thr
        355                 360                 365

Thr Glu Met Val Ser Gly Val Asn Ile Pro Ala Ala Gln Leu Gln Val
    370                 375                 380

Ala Met Gly Ile Pro Leu Tyr Ser Ile Arg Asp Ile Arg Thr Leu Tyr
385                 390                 395                 400

Gly Met Asp Pro Arg Gly Asn Glu Val Ile Asp Phe Asp Phe Ser Ser
                405                 410                 415

Pro Glu Ser Phe Lys Thr Gln Arg Lys Pro Gln Pro Gln Gly His Val
            420                 425                 430

Val Ala Cys Arg Ile Thr Ala Glu Asn Pro Asp Thr Gly Phe Lys Pro
        435                 440                 445

Gly Met Gly Ala Leu Thr Glu Leu Asn Phe Arg Ser Ser Thr Ser Thr
    450                 455                 460

Trp Gly Tyr Phe Ser Val Gly Thr Ser Gly Ala Leu His Glu Tyr Ala
465                 470                 475                 480

Asp Ser Gln Phe Gly His Ile Phe Ala Tyr Gly Ala Asp Arg Ser Glu
                485                 490                 495

Ala Arg Lys Gln Met Val Ile Ser Leu Lys Glu Leu Ser Ile Arg Gly
            500                 505                 510

Asp Phe Arg Thr Thr Val Glu Tyr Leu Ile Lys Leu Leu Glu Thr Asp
        515                 520                 525

Ala
```

<210> SEQ ID NO 26
<211> LENGTH: 519
<212> TYPE: PRT
<213> ORGANISM: Ustilago maydis
<220> FEATURE:
<221> NAME/KEY: MISC_FEATURE
<222> LOCATION: (1)..(519)
<223> OTHER INFORMATION: C-terminal deleted Ustilago ACCase BC domain (AAs 2-520)

<400> SEQUENCE: 26

| | | | | | | | | | | | | | | |
|---|---|---|---|---|---|---|---|---|---|---|---|---|---|---|
| Pro | Pro | Pro | Asp | His | Lys | Ala | Val | Ser | Gln | Phe | Ile | Gly | Gly | Asn | Pro |
| 1 | | | | 5 | | | | | 10 | | | | | 15 | |
| Leu | Glu | Thr | Ala | Pro | Ala | Ser | Pro | Val | Ala | Asp | Phe | Ile | Arg | Lys | Gln |
| | | | 20 | | | | | 25 | | | | | 30 | | |
| Gly | Gly | His | Ser | Val | Ile | Thr | Lys | Val | Leu | Ile | Cys | Asn | Asn | Gly | Ile |
| | | | 35 | | | | | 40 | | | | | 45 | | |
| Ala | Ala | Val | Lys | Glu | Ile | Arg | Ser | Ile | Arg | Lys | Trp | Ala | Tyr | Glu | Thr |
| | 50 | | | | | 55 | | | | | 60 | | | | |
| Phe | Gly | Asp | Glu | Arg | Ala | Ile | Glu | Phe | Thr | Val | Met | Ala | Thr | Pro | Glu |
| 65 | | | | | 70 | | | | | 75 | | | | | 80 |
| Asp | Leu | Lys | Val | Asn | Ala | Asp | Tyr | Ile | Arg | Met | Ala | Asp | Gln | Tyr | Val |
| | | | | 85 | | | | | 90 | | | | | 95 | |
| Glu | Val | Pro | Gly | Gly | Ser | Asn | Asn | Asn | Tyr | Ala | Asn | Val | Asp | Leu | |
| | | | | 100 | | | | | 105 | | | | | 110 | |
| Ile | Val | Asp | Val | Ala | Glu | Arg | Ala | Gly | Val | His | Ala | Val | Trp | Ala | Gly |
| | | | | 115 | | | | | 120 | | | | | 125 | |
| Trp | Gly | His | Ala | Ser | Glu | Asn | Pro | Arg | Leu | Pro | Glu | Ser | Leu | Ala | Ala |
| | | 130 | | | | | 135 | | | | | 140 | | | |
| Ser | Lys | His | Lys | Ile | Ile | Phe | Ile | Gly | Pro | Pro | Gly | Ser | Ala | Met | Arg |
| 145 | | | | | 150 | | | | | 155 | | | | | 160 |
| Ser | Leu | Gly | Asp | Lys | Ile | Ser | Ser | Thr | Ile | Val | Ala | Gln | His | Ala | Asp |
| | | | | 165 | | | | | 170 | | | | | 175 | |
| Val | Pro | Cys | Met | Pro | Trp | Ser | Gly | Thr | Gly | Ile | Lys | Glu | Thr | Met | Met |
| | | | 180 | | | | | 185 | | | | | 190 | | |
| Ser | Asp | Gln | Gly | Phe | Leu | Thr | Val | Ser | Asp | Asp | Val | Tyr | Gln | Gln | Ala |
| | | | 195 | | | | | 200 | | | | | 205 | | |
| Cys | Ile | His | Thr | Ala | Glu | Glu | Gly | Leu | Glu | Lys | Ala | Glu | Lys | Ile | Gly |
| | | 210 | | | | | 215 | | | | | 220 | | | |
| Tyr | Pro | Val | Met | Ile | Lys | Ala | Ser | Glu | Gly | Gly | Gly | Lys | Gly | Ile | |
| 225 | | | | | 230 | | | | | 235 | | | | | 240 |
| Arg | Lys | Cys | Thr | Asn | Gly | Glu | Glu | Phe | Lys | Gln | Leu | Tyr | Asn | Ala | Val |
| | | | | 245 | | | | | 250 | | | | | 255 | |
| Leu | Gly | Glu | Val | Pro | Gly | Ser | Pro | Val | Phe | Val | Met | Lys | Leu | Ala | Gly |
| | | | | 260 | | | | | 265 | | | | | 270 | |
| Gln | Ala | Arg | His | Leu | Glu | Val | Gln | Leu | Leu | Ala | Asp | Gln | Tyr | Gly | Asn |
| | | | 275 | | | | | 280 | | | | | 285 | | |
| Ala | Ile | Ser | Ile | Phe | Gly | Arg | Asp | Cys | Ser | Val | Gln | Arg | Arg | His | Gln |
| | | 290 | | | | | 295 | | | | | 300 | | | |
| Lys | Ile | Ile | Glu | Glu | Ala | Pro | Val | Thr | Ile | Ala | Pro | Glu | Asp | Ala | Arg |
| 305 | | | | | 310 | | | | | 315 | | | | | 320 |
| Glu | Ser | Met | Glu | Lys | Ala | Ala | Val | Arg | Leu | Ala | Lys | Leu | Val | Gly | Tyr |
| | | | | 325 | | | | | 330 | | | | | 335 | |
| Val | Ser | Ala | Gly | Thr | Val | Glu | Trp | Leu | Tyr | Ser | Pro | Glu | Ser | Gly | Glu |
| | | | 340 | | | | | 345 | | | | | 350 | | |
| Phe | Ala | Phe | Leu | Glu | Leu | Asn | Pro | Arg | Leu | Gln | Val | Glu | His | Pro | Thr |
| | | | 355 | | | | | 360 | | | | | 365 | | |
| Thr | Glu | Met | Val | Ser | Gly | Val | Asn | Ile | Pro | Ala | Ala | Gln | Leu | Gln | Val |
| | | 370 | | | | | 375 | | | | | 380 | | | |
| Ala | Met | Gly | Ile | Pro | Leu | Tyr | Ser | Ile | Arg | Asp | Ile | Arg | Thr | Leu | Tyr |

```
                385                 390                 395                 400
Gly Met Asp Pro Arg Gly Asn Glu Val Ile Asp Phe Asp Phe Ser Ser
                    405                 410                 415

Pro Glu Ser Phe Lys Thr Gln Arg Lys Pro Gln Pro Gln Gly His Val
                420                 425                 430

Val Ala Cys Arg Ile Thr Ala Glu Asn Pro Asp Thr Gly Phe Lys Pro
                435                 440                 445

Gly Met Gly Ala Leu Thr Glu Leu Asn Phe Arg Ser Ser Thr Ser Thr
            450                 455                 460

Trp Gly Tyr Phe Ser Val Gly Thr Ser Gly Ala Leu His Glu Tyr Ala
465                 470                 475                 480

Asp Ser Gln Phe Gly His Ile Phe Ala Tyr Gly Ala Asp Arg Ser Glu
                485                 490                 495

Ala Arg Lys Gln Met Val Ile Ser Leu Lys Glu Leu Ser Ile Arg Gly
                500                 505                 510

Asp Phe Arg Thr Thr Val Glu
                515

<210> SEQ ID NO 27
<211> LENGTH: 554
<212> TYPE: PRT
<213> ORGANISM: Ustilago maydis
<220> FEATURE:
<221> NAME/KEY: MISC_FEATURE
<222> LOCATION: (1)..(554)
<223> OTHER INFORMATION: N- and C-terminal deleted Ustilago ACCase BC
      domain (AAs 4-547)

<400> SEQUENCE: 27

Pro Asp His Lys Ala Val Ser Gln Phe Ile Gly Gly Asn Pro Leu Glu
1               5                   10                  15

Thr Ala Pro Ala Ser Pro Val Ala Asp Phe Ile Arg Lys Gln Gly Gly
                20                  25                  30

His Ser Val Ile Thr Lys Val Leu Ile Cys Asn Asn Gly Ile Ala Ala
            35                  40                  45

Val Lys Glu Ile Arg Ser Ile Arg Lys Trp Ala Tyr Glu Thr Phe Gly
50                  55                  60

Asp Glu Arg Ala Ile Glu Phe Thr Val Met Ala Thr Pro Glu Asp Leu
65                  70                  75                  80

Lys Val Asn Ala Asp Tyr Ile Arg Met Ala Asp Gln Tyr Val Glu Val
                85                  90                  95

Pro Gly Gly Ser Asn Asn Asn Asn Tyr Ala Asn Val Asp Leu Ile Val
                100                 105                 110

Asp Val Ala Glu Arg Ala Gly Val His Ala Val Trp Ala Gly Trp Gly
            115                 120                 125

His Ala Ser Glu Asn Pro Arg Leu Pro Glu Ser Leu Ala Ala Ser Lys
    130                 135                 140

His Lys Ile Ile Phe Ile Gly Pro Pro Gly Ser Ala Met Arg Ser Leu
145                 150                 155                 160

Gly Asp Lys Ile Ser Ser Thr Ile Val Ala Gln His Ala Asp Val Pro
                165                 170                 175

Cys Met Pro Trp Ser Gly Thr Gly Ile Lys Glu Thr Met Met Ser Asp
                180                 185                 190

Gln Gly Phe Leu Thr Val Ser Asp Asp Val Tyr Gln Gln Ala Cys Ile
            195                 200                 205

His Thr Ala Glu Glu Gly Leu Glu Lys Ala Glu Lys Ile Gly Tyr Pro
```

```
        210                 215                 220
Val Met Ile Lys Ala Ser Glu Gly Gly Gly Lys Gly Ile Arg Lys
225                 230                 235                 240

Cys Thr Asn Gly Glu Glu Phe Lys Gln Leu Tyr Asn Ala Val Leu Gly
                245                 250                 255

Glu Val Pro Gly Ser Pro Val Phe Val Met Lys Leu Ala Gly Gln Ala
            260                 265                 270

Arg His Leu Glu Val Gln Leu Leu Ala Asp Gln Tyr Gly Asn Ala Ile
        275                 280                 285

Ser Ile Phe Gly Arg Asp Cys Ser Val Gln Arg His Gln Lys Ile
290                 295                 300

Ile Glu Glu Ala Pro Val Thr Ile Ala Pro Glu Asp Ala Arg Glu Ser
305                 310                 315                 320

Met Glu Lys Ala Ala Val Arg Leu Ala Lys Leu Val Gly Tyr Val Ser
                325                 330                 335

Ala Gly Thr Val Glu Trp Leu Tyr Ser Pro Glu Ser Gly Glu Phe Ala
            340                 345                 350

Phe Leu Glu Leu Asn Pro Arg Leu Gln Val Glu His Pro Thr Thr Glu
        355                 360                 365

Met Val Ser Gly Val Asn Ile Pro Ala Ala Gln Leu Gln Val Ala Met
370                 375                 380

Gly Ile Pro Leu Tyr Ser Ile Arg Asp Ile Arg Thr Leu Tyr Gly Met
385                 390                 395                 400

Asp Pro Arg Gly Asn Glu Val Ile Asp Phe Asp Phe Ser Ser Pro Glu
                405                 410                 415

Ser Phe Lys Thr Gln Arg Lys Pro Gln Pro Gln Gly His Val Val Ala
            420                 425                 430

Cys Arg Ile Thr Ala Glu Asn Pro Asp Thr Gly Phe Lys Pro Gly Met
        435                 440                 445

Gly Ala Leu Thr Glu Leu Asn Phe Arg Ser Ser Thr Ser Thr Trp Gly
450                 455                 460

Tyr Phe Ser Val Gly Thr Ser Gly Ala Leu His Glu Tyr Ala Asp Ser
465                 470                 475                 480

Gln Phe Gly His Ile Phe Ala Tyr Gly Ala Asp Arg Ser Glu Ala Arg
                485                 490                 495

Lys Gln Met Val Ile Ser Leu Lys Glu Leu Ser Ile Arg Gly Asp Phe
            500                 505                 510

Arg Thr Thr Val Glu Tyr Leu Ile Lys Leu Leu Glu Thr Asp Ala Phe
        515                 520                 525

Glu Ser Asn Lys Ile Thr Thr Gly Trp Leu Asp Gly Leu Ile Gln Asp
530                 535                 540

Arg Leu Thr Ala Glu Arg Pro Pro Ala Asp
545                 550

<210> SEQ ID NO 28
<211> LENGTH: 549
<212> TYPE: PRT
<213> ORGANISM: Ustilago maydis
<220> FEATURE:
<221> NAME/KEY: MISC_FEATURE
<222> LOCATION: (1)..(549)
<223> OTHER INFORMATION: N- and C-terminal deleted Ustilago ACCase BC
      domain (AAs 7-555)

<400> SEQUENCE: 28

Lys Ala Val Ser Gln Phe Ile Gly Gly Asn Pro Leu Glu Thr Ala Pro
```

-continued

```
1               5                   10                  15
Ala Ser Pro Val Ala Asp Phe Ile Arg Lys Gln Gly Gly His Ser Val
                20                  25                  30

Ile Thr Lys Val Leu Ile Cys Asn Asn Gly Ile Ala Ala Val Lys Glu
                35                  40                  45

Ile Arg Ser Ile Arg Lys Trp Ala Tyr Glu Thr Phe Gly Asp Glu Arg
 50                  55                  60

Ala Ile Glu Phe Thr Val Met Ala Thr Pro Glu Asp Leu Lys Val Asn
 65                  70                  75                  80

Ala Asp Tyr Ile Arg Met Ala Asp Gln Tyr Val Glu Val Pro Gly Gly
                85                  90                  95

Ser Asn Asn Asn Tyr Ala Asn Val Asp Leu Ile Val Asp Val Ala
                100                 105                 110

Glu Arg Ala Gly Val His Ala Val Trp Ala Gly Trp Gly His Ala Ser
                115                 120                 125

Glu Asn Pro Arg Leu Pro Glu Ser Leu Ala Ala Ser Lys His Lys Ile
                130                 135                 140

Ile Phe Ile Gly Pro Pro Gly Ser Ala Met Arg Ser Leu Gly Asp Lys
145                 150                 155                 160

Ile Ser Ser Thr Ile Val Ala Gln His Ala Asp Val Pro Cys Met Pro
                165                 170                 175

Trp Ser Gly Thr Gly Ile Lys Glu Thr Met Met Ser Asp Gln Gly Phe
                180                 185                 190

Leu Thr Val Ser Asp Asp Val Tyr Gln Gln Ala Cys Ile His Thr Ala
                195                 200                 205

Glu Glu Gly Leu Glu Lys Ala Glu Lys Ile Gly Tyr Pro Val Met Ile
                210                 215                 220

Lys Ala Ser Glu Gly Gly Gly Lys Gly Ile Arg Lys Cys Thr Asn
225                 230                 235                 240

Gly Glu Glu Phe Lys Gln Leu Tyr Asn Ala Val Leu Gly Glu Val Pro
                245                 250                 255

Gly Ser Pro Val Phe Val Met Lys Leu Ala Gly Gln Ala Arg His Leu
                260                 265                 270

Glu Val Gln Leu Leu Ala Asp Gln Tyr Gly Asn Ala Ile Ser Ile Phe
                275                 280                 285

Gly Arg Asp Cys Ser Val Gln Arg Arg His Gln Lys Ile Ile Glu Glu
                290                 295                 300

Ala Pro Val Thr Ile Ala Pro Glu Asp Ala Arg Glu Ser Met Glu Lys
305                 310                 315                 320

Ala Ala Val Arg Leu Ala Lys Leu Val Gly Tyr Val Ser Ala Gly Thr
                325                 330                 335

Val Glu Trp Leu Tyr Ser Pro Glu Ser Gly Glu Phe Ala Phe Leu Glu
                340                 345                 350

Leu Asn Pro Arg Leu Gln Val Glu His Pro Thr Thr Glu Met Val Ser
                355                 360                 365

Gly Val Asn Ile Pro Ala Ala Gln Leu Gln Val Ala Met Gly Ile Pro
                370                 375                 380

Leu Tyr Ser Ile Arg Asp Ile Arg Thr Leu Tyr Gly Met Asp Pro Arg
385                 390                 395                 400

Gly Asn Glu Val Ile Asp Phe Asp Phe Ser Ser Pro Glu Ser Phe Lys
                405                 410                 415

Thr Gln Arg Lys Pro Gln Pro Gln Gly His Val Val Ala Cys Arg Ile
                420                 425                 430
```

-continued

Thr Ala Glu Asn Pro Asp Thr Gly Phe Lys Pro Gly Met Gly Ala Leu
                435                 440                 445

Thr Glu Leu Asn Phe Arg Ser Ser Thr Ser Thr Trp Gly Tyr Phe Ser
        450                 455                 460

Val Gly Thr Ser Gly Ala Leu His Glu Tyr Ala Asp Ser Gln Phe Gly
465                 470                 475                 480

His Ile Phe Ala Tyr Gly Ala Asp Arg Ser Glu Ala Arg Lys Gln Met
                485                 490                 495

Val Ile Ser Leu Lys Glu Leu Ser Ile Arg Gly Asp Phe Arg Thr Thr
                500                 505                 510

Val Glu Tyr Leu Ile Lys Leu Leu Glu Thr Asp Ala Phe Glu Ser Asn
                515                 520                 525

Lys Ile Thr Thr Gly Trp Leu Asp Gly Leu Ile Gln Asp Arg Leu Thr
                530                 535                 540

Ala Glu Arg Pro Pro
545

<210> SEQ ID NO 29
<211> LENGTH: 539
<212> TYPE: PRT
<213> ORGANISM: Ustilago maydis
<220> FEATURE:
<221> NAME/KEY: MISC_FEATURE
<222> LOCATION: (1)..(539)
<223> OTHER INFORMATION: N- and C-terminal deleted Ustilago ACCase BC
      domain (AAs 12-550)

<400> SEQUENCE: 29

Phe Ile Gly Gly Asn Pro Leu Glu Thr Ala Pro Ala Ser Pro Val Ala
1               5                   10                  15

Asp Phe Ile Arg Lys Gln Gly Gly His Ser Val Ile Thr Lys Val Leu
                20                  25                  30

Ile Cys Asn Asn Gly Ile Ala Ala Val Lys Glu Ile Arg Ser Ile Arg
                35                  40                  45

Lys Trp Ala Tyr Glu Thr Phe Gly Asp Glu Arg Ala Ile Glu Phe Thr
        50                  55                  60

Val Met Ala Thr Pro Glu Asp Leu Lys Val Asn Ala Asp Tyr Ile Arg
65                  70                  75                  80

Met Ala Asp Gln Tyr Val Glu Val Pro Gly Gly Ser Asn Asn Asn Asn
                85                  90                  95

Tyr Ala Asn Val Asp Leu Ile Val Asp Val Ala Glu Arg Ala Gly Val
                100                 105                 110

His Ala Val Trp Ala Gly Trp Gly His Ala Ser Glu Asn Pro Arg Leu
                115                 120                 125

Pro Glu Ser Leu Ala Ala Ser Lys His Lys Ile Ile Phe Ile Gly Pro
        130                 135                 140

Pro Gly Ser Ala Met Arg Ser Leu Gly Asp Lys Ile Ser Ser Thr Ile
145                 150                 155                 160

Val Ala Gln His Ala Asp Val Pro Cys Met Pro Trp Ser Gly Thr Gly
                165                 170                 175

Ile Lys Glu Thr Met Met Ser Asp Gln Gly Phe Leu Thr Val Ser Asp
                180                 185                 190

Asp Val Tyr Gln Gln Ala Cys Ile His Thr Ala Glu Glu Gly Leu Glu
        195                 200                 205

Lys Ala Glu Lys Ile Gly Tyr Pro Val Met Ile Lys Ala Ser Glu Gly
        210                 215                 220

```
Gly Gly Gly Lys Gly Ile Arg Lys Cys Thr Asn Gly Glu Glu Phe Lys
225                 230                 235                 240

Gln Leu Tyr Asn Ala Val Leu Gly Glu Val Pro Gly Ser Pro Val Phe
            245                 250                 255

Val Met Lys Leu Ala Gly Gln Ala Arg His Leu Glu Val Gln Leu Leu
            260                 265                 270

Ala Asp Gln Tyr Gly Asn Ala Ile Ser Ile Phe Gly Arg Asp Cys Ser
            275                 280                 285

Val Gln Arg Arg His Gln Lys Ile Ile Glu Glu Ala Pro Val Thr Ile
290                 295                 300

Ala Pro Glu Asp Ala Arg Glu Ser Met Glu Lys Ala Ala Val Arg Leu
305                 310                 315                 320

Ala Lys Leu Val Gly Tyr Val Ser Ala Gly Thr Val Glu Trp Leu Tyr
                325                 330                 335

Ser Pro Glu Ser Gly Glu Phe Ala Phe Leu Glu Leu Asn Pro Arg Leu
            340                 345                 350

Gln Val Glu His Pro Thr Thr Glu Met Val Ser Gly Val Asn Ile Pro
            355                 360                 365

Ala Ala Gln Leu Gln Val Ala Met Gly Ile Pro Leu Tyr Ser Ile Arg
370                 375                 380

Asp Ile Arg Thr Leu Tyr Gly Met Asp Pro Arg Gly Asn Glu Val Ile
385                 390                 395                 400

Asp Phe Asp Phe Ser Ser Pro Glu Ser Phe Lys Thr Gln Arg Lys Pro
                405                 410                 415

Gln Pro Gln Gly His Val Val Ala Cys Arg Ile Thr Ala Glu Asn Pro
            420                 425                 430

Asp Thr Gly Phe Lys Pro Gly Met Gly Ala Leu Thr Glu Leu Asn Phe
            435                 440                 445

Arg Ser Ser Thr Ser Thr Trp Gly Tyr Phe Ser Val Gly Thr Ser Gly
450                 455                 460

Ala Leu His Glu Tyr Ala Asp Ser Gln Phe Gly His Ile Phe Ala Tyr
465                 470                 475                 480

Gly Ala Asp Arg Ser Glu Ala Arg Lys Gln Met Val Ile Ser Leu Lys
                485                 490                 495

Glu Leu Ser Ile Arg Gly Asp Phe Arg Thr Thr Val Glu Tyr Leu Ile
            500                 505                 510

Lys Leu Leu Glu Thr Asp Ala Phe Glu Ser Asn Lys Ile Thr Thr Gly
            515                 520                 525

Trp Leu Asp Gly Leu Ile Gln Asp Arg Leu Thr
530                 535
```

<210> SEQ ID NO 30
<211> LENGTH: 529
<212> TYPE: PRT
<213> ORGANISM: Ustilago maydis
<220> FEATURE:
<221> NAME/KEY: MISC_FEATURE
<222> LOCATION: (1)..(529)
<223> OTHER INFORMATION: N- and C-terminal deleted Ustilago ACCase BC
      domain (AAs 17-545)

<400> SEQUENCE: 30

```
Pro Leu Glu Thr Ala Pro Ala Ser Pro Val Ala Asp Phe Ile Arg Lys
1               5                   10                  15

Gln Gly Gly His Ser Val Ile Thr Lys Val Leu Ile Cys Asn Asn Gly
            20                  25                  30
```

-continued

```
Ile Ala Ala Val Lys Glu Ile Arg Ser Ile Arg Lys Trp Ala Tyr Glu
             35                  40                  45

Thr Phe Gly Asp Glu Arg Ala Ile Glu Phe Thr Val Met Ala Thr Pro
 50                  55                  60

Glu Asp Leu Lys Val Asn Ala Asp Tyr Ile Arg Met Ala Asp Gln Tyr
 65                  70                  75                  80

Val Glu Val Pro Gly Gly Ser Asn Asn Asn Tyr Ala Asn Val Asp
                 85                  90                  95

Leu Ile Val Asp Val Ala Glu Arg Ala Gly Val His Ala Val Trp Ala
                100                 105                 110

Gly Trp Gly His Ala Ser Glu Asn Pro Arg Leu Pro Glu Ser Leu Ala
                115                 120                 125

Ala Ser Lys His Lys Ile Ile Phe Ile Gly Pro Pro Gly Ser Ala Met
        130                 135                 140

Arg Ser Leu Gly Asp Lys Ile Ser Ser Thr Ile Val Ala Gln His Ala
145                 150                 155                 160

Asp Val Pro Cys Met Pro Trp Ser Gly Thr Gly Ile Lys Glu Thr Met
                165                 170                 175

Met Ser Asp Gln Gly Phe Leu Thr Val Ser Asp Val Tyr Gln Gln
                180                 185                 190

Ala Cys Ile His Thr Ala Glu Glu Gly Leu Glu Lys Ala Glu Lys Ile
            195                 200                 205

Gly Tyr Pro Val Met Ile Lys Ala Ser Glu Gly Gly Gly Lys Gly
        210                 215                 220

Ile Arg Lys Cys Thr Asn Gly Glu Glu Phe Lys Gln Leu Tyr Asn Ala
225                 230                 235                 240

Val Leu Gly Glu Val Pro Gly Ser Pro Val Phe Val Met Lys Leu Ala
                245                 250                 255

Gly Gln Ala Arg His Leu Glu Val Gln Leu Leu Ala Asp Gln Tyr Gly
                260                 265                 270

Asn Ala Ile Ser Ile Phe Gly Arg Asp Cys Ser Val Gln Arg Arg His
            275                 280                 285

Gln Lys Ile Ile Glu Glu Ala Pro Val Thr Ile Ala Pro Glu Asp Ala
        290                 295                 300

Arg Glu Ser Met Glu Lys Ala Ala Val Arg Leu Ala Lys Leu Val Gly
305                 310                 315                 320

Tyr Val Ser Ala Gly Thr Val Glu Trp Leu Tyr Ser Pro Glu Ser Gly
                325                 330                 335

Glu Phe Ala Phe Leu Glu Leu Asn Pro Arg Leu Gln Val Glu His Pro
                340                 345                 350

Thr Thr Glu Met Val Ser Gly Val Asn Ile Pro Ala Ala Gln Leu Gln
            355                 360                 365

Val Ala Met Gly Ile Pro Leu Tyr Ser Ile Arg Asp Ile Arg Thr Leu
        370                 375                 380

Tyr Gly Met Asp Pro Arg Gly Asn Glu Val Ile Asp Phe Asp Phe Ser
385                 390                 395                 400

Ser Pro Glu Ser Phe Lys Thr Gln Arg Lys Pro Gln Pro Gly His
                405                 410                 415

Val Val Ala Cys Arg Ile Thr Ala Glu Asn Pro Asp Thr Gly Phe Lys
            420                 425                 430

Pro Gly Met Gly Ala Leu Thr Glu Leu Asn Phe Arg Ser Ser Thr Ser
        435                 440                 445
```

```
Thr Trp Gly Tyr Phe Ser Val Gly Thr Ser Gly Ala Leu His Glu Tyr
    450                 455                 460

Ala Asp Ser Gln Phe Gly His Ile Phe Ala Tyr Gly Ala Asp Arg Ser
465                 470                 475                 480

Glu Ala Arg Lys Gln Met Val Ile Ser Leu Lys Glu Leu Ser Ile Arg
                485                 490                 495

Gly Asp Phe Arg Thr Thr Val Glu Tyr Leu Ile Lys Leu Leu Glu Thr
                500                 505                 510

Asp Ala Phe Glu Ser Asn Lys Ile Thr Thr Gly Trp Leu Asp Gly Leu
            515                 520                 525

Ile

<210> SEQ ID NO 31
<211> LENGTH: 519
<212> TYPE: PRT
<213> ORGANISM: Ustilago maydis
<220> FEATURE:
<221> NAME/KEY: MISC_FEATURE
<222> LOCATION: (1)..(519)
<223> OTHER INFORMATION: N- and C-terminal deleted Ustilago ACCase BC
      domain (AAs 22-540)

<400> SEQUENCE: 31

Pro Ala Ser Pro Val Ala Asp Phe Ile Arg Lys Gln Gly Gly His Ser
1               5                   10                  15

Val Ile Thr Lys Val Leu Ile Cys Asn Asn Gly Ile Ala Ala Val Lys
                20                  25                  30

Glu Ile Arg Ser Ile Arg Lys Trp Ala Tyr Glu Thr Phe Gly Asp Glu
            35                  40                  45

Arg Ala Ile Glu Phe Thr Val Met Ala Thr Pro Glu Asp Leu Lys Val
        50                  55                  60

Asn Ala Asp Tyr Ile Arg Met Ala Asp Gln Tyr Val Glu Val Pro Gly
65                  70                  75                  80

Gly Ser Asn Asn Asn Tyr Ala Asn Val Asp Leu Ile Val Asp Val
                85                  90                  95

Ala Glu Arg Ala Gly Val His Ala Val Trp Ala Gly Trp Gly His Ala
            100                 105                 110

Ser Glu Asn Pro Arg Leu Pro Glu Ser Leu Ala Ala Ser Lys His Lys
        115                 120                 125

Ile Ile Phe Ile Gly Pro Pro Gly Ser Ala Met Arg Ser Leu Gly Asp
130                 135                 140

Lys Ile Ser Ser Thr Ile Val Ala Gln His Ala Asp Val Pro Cys Met
145                 150                 155                 160

Pro Trp Ser Gly Thr Gly Ile Lys Glu Thr Met Met Ser Asp Gln Gly
                165                 170                 175

Phe Leu Thr Val Ser Asp Asp Val Tyr Gln Gln Ala Cys Ile His Thr
            180                 185                 190

Ala Glu Glu Gly Leu Glu Lys Ala Glu Lys Ile Gly Tyr Pro Val Met
        195                 200                 205

Ile Lys Ala Ser Glu Gly Gly Gly Gly Lys Gly Ile Arg Lys Cys Thr
    210                 215                 220

Asn Gly Glu Glu Phe Lys Gln Leu Tyr Asn Ala Val Leu Gly Glu Val
225                 230                 235                 240

Pro Gly Ser Pro Val Phe Val Met Lys Leu Ala Gly Gln Ala Arg His
                245                 250                 255

Leu Glu Val Gln Leu Leu Ala Asp Gln Tyr Gly Asn Ala Ile Ser Ile
```

```
                260                 265                 270
Phe Gly Arg Asp Cys Ser Val Gln Arg His Gln Lys Ile Ile Glu
            275                 280                 285
Glu Ala Pro Val Thr Ile Ala Pro Glu Asp Ala Arg Glu Ser Met Glu
        290                 295                 300
Lys Ala Val Arg Leu Ala Lys Leu Val Gly Tyr Val Ser Ala Gly
305                 310                 315                 320
Thr Val Glu Trp Leu Tyr Ser Pro Glu Ser Gly Glu Phe Ala Phe Leu
                325                 330                 335
Glu Leu Asn Pro Arg Leu Gln Val Glu His Pro Thr Thr Glu Met Val
            340                 345                 350
Ser Gly Val Asn Ile Pro Ala Ala Gln Leu Gln Val Ala Met Gly Ile
        355                 360                 365
Pro Leu Tyr Ser Ile Arg Asp Ile Arg Thr Leu Tyr Gly Met Asp Pro
    370                 375                 380
Arg Gly Asn Glu Val Ile Asp Phe Asp Phe Ser Ser Pro Glu Ser Phe
385                 390                 395                 400
Lys Thr Gln Arg Lys Pro Gln Pro Gln Gly His Val Val Ala Cys Arg
                405                 410                 415
Ile Thr Ala Glu Asn Pro Asp Thr Gly Phe Lys Pro Gly Met Gly Ala
            420                 425                 430
Leu Thr Glu Leu Asn Phe Arg Ser Ser Thr Ser Thr Trp Gly Tyr Phe
        435                 440                 445
Ser Val Gly Thr Ser Gly Ala Leu His Glu Tyr Ala Asp Ser Gln Phe
    450                 455                 460
Gly His Ile Phe Ala Tyr Gly Ala Asp Arg Ser Glu Ala Arg Lys Gln
465                 470                 475                 480
Met Val Ile Ser Leu Lys Glu Leu Ser Ile Arg Gly Asp Phe Arg Thr
                485                 490                 495
Thr Val Glu Tyr Leu Ile Lys Leu Leu Glu Thr Asp Ala Phe Glu Ser
            500                 505                 510
Asn Lys Ile Thr Thr Gly Trp
        515

<210> SEQ ID NO 32
<211> LENGTH: 580
<212> TYPE: PRT
<213> ORGANISM: Saccharomyces cerevisiae
<220> FEATURE:
<221> NAME/KEY: MISC_FEATURE
<222> LOCATION: (76)..(76)
<223> OTHER INFORMATION: Saccharomyces cerevisiae ACCase BC domain S77Y
      mutation

<400> SEQUENCE: 32

Ser Glu Glu Ser Leu Phe Glu Ser Ser Pro Gln Lys Met Glu Tyr Glu
1               5                   10                  15
Ile Thr Asn Tyr Ser Glu Arg His Thr Glu Leu Pro Gly His Phe Ile
            20                  25                  30
Gly Leu Asn Thr Val Asp Lys Leu Glu Glu Ser Pro Leu Arg Asp Phe
        35                  40                  45
Val Lys Ser His Gly Gly His Thr Val Ile Ser Lys Ile Leu Ile Ala
    50                  55                  60
Asn Asn Gly Ile Ala Ala Val Lys Glu Ile Arg Tyr Val Arg Lys Trp
65                  70                  75                  80
Ala Tyr Glu Thr Phe Gly Asp Asp Arg Thr Val Gln Phe Val Ala Met
```

-continued

```
                85                  90                  95
Ala Thr Pro Glu Asp Leu Glu Ala Asn Ala Glu Tyr Ile Arg Met Ala
            100                 105                 110
Asp Gln Tyr Ile Glu Val Pro Gly Gly Thr Asn Asn Asn Asn Tyr Ala
            115                 120                 125
Asn Val Asp Leu Ile Val Asp Ile Ala Glu Arg Ala Asp Val Asp Ala
            130                 135                 140
Val Trp Ala Gly Trp Gly His Ala Ser Glu Asn Pro Leu Leu Pro Glu
145                 150                 155                 160
Lys Leu Ser Gln Ser Lys Arg Lys Val Ile Phe Ile Gly Pro Pro Gly
            165                 170                 175
Asn Ala Met Arg Ser Leu Gly Asp Lys Ile Ser Ser Thr Ile Val Ala
            180                 185                 190
Gln Ser Ala Lys Val Pro Cys Ile Pro Trp Ser Gly Thr Gly Val Asp
            195                 200                 205
Thr Val His Val Asp Glu Lys Thr Gly Leu Val Ser Val Asp Asp Asp
            210                 215                 220
Ile Tyr Gln Lys Gly Cys Cys Thr Ser Pro Glu Asp Gly Leu Gln Lys
225                 230                 235                 240
Ala Lys Arg Ile Gly Phe Pro Val Met Ile Lys Ala Ser Glu Gly Gly
            245                 250                 255
Gly Gly Lys Gly Ile Arg Gln Val Glu Arg Glu Asp Phe Ile Ala
            260                 265                 270
Leu Tyr His Gln Ala Ala Asn Glu Ile Pro Gly Ser Pro Ile Phe Ile
            275                 280                 285
Met Lys Leu Ala Gly Arg Ala Arg His Leu Glu Val Gln Leu Leu Ala
            290                 295                 300
Asp Gln Tyr Gly Thr Asn Ile Ser Leu Phe Gly Arg Asp Cys Ser Val
305                 310                 315                 320
Gln Arg Arg His Gln Lys Ile Ile Glu Glu Ala Pro Val Thr Ile Ala
            325                 330                 335
Lys Ala Glu Thr Phe His Glu Met Glu Lys Ala Ala Val Arg Leu Gly
            340                 345                 350
Lys Leu Val Gly Tyr Val Ser Ala Gly Thr Val Glu Tyr Leu Tyr Ser
            355                 360                 365
His Asp Asp Gly Lys Phe Tyr Phe Leu Glu Leu Asn Pro Arg Leu Gln
            370                 375                 380
Val Glu His Pro Thr Thr Glu Met Val Ser Gly Val Asn Leu Pro Ala
385                 390                 395                 400
Ala Gln Leu Gln Ile Ala Met Gly Ile Pro Met His Arg Ile Ser Asp
            405                 410                 415
Ile Arg Thr Leu Tyr Gly Met Asn Pro His Ser Ala Ser Glu Ile Asp
            420                 425                 430
Phe Glu Phe Lys Thr Gln Asp Ala Thr Lys Gln Arg Arg Pro Ile
            435                 440                 445
Pro Lys Gly His Cys Thr Ala Cys Arg Ile Thr Ser Glu Asp Pro Asn
            450                 455                 460
Asp Gly Phe Lys Pro Ser Gly Thr Leu His Glu Leu Asn Phe Arg
465                 470                 475                 480
Ser Ser Ser Asn Val Trp Gly Tyr Phe Ser Val Gly Asn Asn Gly Asn
            485                 490                 495
Ile His Ser Phe Ser Asp Ser Gln Phe Gly His Ile Phe Ala Phe Gly
            500                 505                 510
```

```
Glu Asn Arg Gln Ala Ser Arg Lys His Met Val Val Ala Leu Lys Glu
            515                 520                 525

Leu Ser Ile Arg Gly Asp Phe Arg Thr Thr Val Glu Tyr Leu Ile Lys
            530                 535                 540

Leu Leu Glu Thr Glu Asp Phe Glu Asp Asn Thr Ile Thr Thr Gly Trp
545                 550                 555                 560

Leu Asp Asp Leu Ile Thr His Lys Met Thr Ala Glu Lys Pro Asp Pro
                565                 570                 575

Thr Leu Ala Val
            580

<210> SEQ ID NO 33
<211> LENGTH: 575
<212> TYPE: PRT
<213> ORGANISM: Saccharomyces cerevisiae
<220> FEATURE:
<221> NAME/KEY: MISC_FEATURE
<222> LOCATION: (1)..(575)
<223> OTHER INFORMATION: N-terminal deleted Saccharomyces cerevisiae
      ACCase BC domain (AA s7-581)

<400> SEQUENCE: 33

Phe Glu Ser Ser Pro Gln Lys Met Glu Tyr Glu Ile Thr Asn Tyr Ser
1               5                   10                  15

Glu Arg His Thr Glu Leu Pro Gly His Phe Ile Gly Leu Asn Thr Val
            20                  25                  30

Asp Lys Leu Glu Glu Ser Pro Leu Arg Asp Phe Val Lys Ser His Gly
        35                  40                  45

Gly His Thr Val Ile Ser Lys Ile Leu Ile Ala Asn Asn Gly Ile Ala
    50                  55                  60

Ala Val Lys Glu Ile Arg Ser Val Arg Lys Trp Ala Tyr Glu Thr Phe
65                  70                  75                  80

Gly Asp Asp Arg Thr Val Gln Phe Val Ala Met Ala Thr Pro Glu Asp
                85                  90                  95

Leu Glu Ala Asn Ala Glu Tyr Ile Arg Met Ala Asp Gln Tyr Ile Glu
            100                 105                 110

Val Pro Gly Gly Thr Asn Asn Asn Asn Tyr Ala Asn Val Asp Leu Ile
        115                 120                 125

Val Asp Ile Ala Glu Arg Ala Asp Val Asp Ala Val Trp Ala Gly Trp
    130                 135                 140

Gly His Ala Ser Glu Asn Pro Leu Leu Pro Glu Lys Leu Ser Gln Ser
145                 150                 155                 160

Lys Arg Lys Val Ile Phe Ile Gly Pro Pro Gly Asn Ala Met Arg Ser
                165                 170                 175

Leu Gly Asp Lys Ile Ser Ser Thr Ile Val Ala Gln Ser Ala Lys Val
            180                 185                 190

Pro Cys Ile Pro Trp Ser Gly Thr Gly Val Asp Thr His Val Val Asp
        195                 200                 205

Glu Lys Thr Gly Leu Val Ser Val Asp Asp Ile Tyr Gln Lys Gly
    210                 215                 220

Cys Cys Thr Ser Pro Glu Asp Gly Leu Gln Lys Ala Lys Arg Ile Gly
225                 230                 235                 240

Phe Pro Val Met Ile Lys Ala Ser Glu Gly Gly Gly Lys Gly Ile
                245                 250                 255

Arg Gln Val Glu Arg Glu Glu Asp Phe Ile Ala Leu Tyr His Gln Ala
            260                 265                 270
```

```
Ala Asn Glu Ile Pro Gly Ser Pro Ile Phe Ile Met Lys Leu Ala Gly
            275                 280                 285

Arg Ala Arg His Leu Glu Val Gln Leu Leu Ala Asp Gln Tyr Gly Thr
        290                 295                 300

Asn Ile Ser Leu Phe Gly Arg Asp Cys Ser Val Gln Arg Arg His Gln
305                 310                 315                 320

Lys Ile Ile Glu Glu Ala Pro Val Thr Ile Ala Lys Ala Glu Thr Phe
                325                 330                 335

His Glu Met Glu Lys Ala Ala Val Arg Leu Gly Lys Leu Val Gly Tyr
            340                 345                 350

Val Ser Ala Gly Thr Val Glu Tyr Leu Tyr Ser His Asp Asp Gly Lys
        355                 360                 365

Phe Tyr Phe Leu Glu Leu Asn Pro Arg Leu Gln Val Glu His Pro Thr
    370                 375                 380

Thr Glu Met Val Ser Gly Val Asn Leu Pro Ala Ala Gln Leu Gln Ile
385                 390                 395                 400

Ala Met Gly Ile Pro Met His Arg Ile Ser Asp Ile Arg Thr Leu Tyr
                405                 410                 415

Gly Met Asn Pro His Ser Ala Ser Glu Ile Asp Phe Glu Phe Lys Thr
            420                 425                 430

Gln Asp Ala Thr Lys Lys Gln Arg Arg Pro Ile Pro Lys Gly His Cys
        435                 440                 445

Thr Ala Cys Arg Ile Thr Ser Glu Asp Pro Asn Asp Gly Phe Lys Pro
    450                 455                 460

Ser Gly Gly Thr Leu His Glu Leu Asn Phe Arg Ser Ser Ser Asn Val
465                 470                 475                 480

Trp Gly Tyr Phe Ser Val Gly Asn Asn Gly Asn Ile His Ser Phe Ser
                485                 490                 495

Asp Ser Gln Phe Gly His Ile Phe Ala Phe Gly Glu Asn Arg Gln Ala
            500                 505                 510

Ser Arg Lys His Met Val Val Ala Leu Lys Glu Leu Ser Ile Arg Gly
        515                 520                 525

Asp Phe Arg Thr Thr Val Glu Tyr Leu Ile Lys Leu Leu Glu Thr Glu
    530                 535                 540

Asp Phe Glu Asp Asn Thr Ile Thr Thr Gly Trp Leu Asp Asp Leu Ile
545                 550                 555                 560

Thr His Lys Met Thr Ala Glu Lys Pro Asp Pro Thr Leu Ala Val
                565                 570                 575

<210> SEQ ID NO 34
<211> LENGTH: 570
<212> TYPE: PRT
<213> ORGANISM: Saccharomyces cerevisiae
<220> FEATURE:
<221> NAME/KEY: MISC_FEATURE
<222> LOCATION: (1)..(570)
<223> OTHER INFORMATION: N-terminal deleted Saccharomyces cerevisiae
      ACCase BC domain (AAs 12-581)

<400> SEQUENCE: 34

Gln Lys Met Glu Tyr Glu Ile Thr Asn Tyr Ser Glu Arg His Thr Glu
1               5                   10                  15

Leu Pro Gly His Phe Ile Gly Leu Asn Thr Val Asp Lys Leu Glu Glu
            20                  25                  30

Ser Pro Leu Arg Asp Phe Val Lys Ser His Gly Gly His Thr Val Ile
        35                  40                  45
```

-continued

```
Ser Lys Ile Leu Ile Ala Asn Asn Gly Ile Ala Ala Val Lys Glu Ile
 50                  55                  60
Arg Ser Val Arg Lys Trp Ala Tyr Glu Thr Phe Gly Asp Asp Arg Thr
 65                  70                  75                  80
Val Gln Phe Val Ala Met Ala Thr Pro Glu Asp Leu Glu Ala Asn Ala
                 85                  90                  95
Glu Tyr Ile Arg Met Ala Asp Gln Tyr Ile Glu Val Pro Gly Gly Thr
                100                 105                 110
Asn Asn Asn Asn Tyr Ala Asn Val Asp Leu Ile Val Asp Ile Ala Glu
                115                 120                 125
Arg Ala Asp Val Asp Ala Val Trp Ala Gly Trp Gly His Ala Ser Glu
130                 135                 140
Asn Pro Leu Leu Pro Glu Lys Leu Ser Gln Ser Lys Arg Lys Val Ile
145                 150                 155                 160
Phe Ile Gly Pro Pro Gly Asn Ala Met Arg Ser Leu Gly Asp Lys Ile
                165                 170                 175
Ser Ser Thr Ile Val Ala Gln Ser Ala Lys Val Pro Cys Ile Pro Trp
                180                 185                 190
Ser Gly Thr Gly Val Asp Thr Val His Val Asp Glu Lys Thr Gly Leu
                195                 200                 205
Val Ser Val Asp Asp Ile Tyr Gln Lys Gly Cys Cys Thr Ser Pro
210                 215                 220
Glu Asp Gly Leu Gln Lys Ala Lys Arg Ile Gly Phe Pro Val Met Ile
225                 230                 235                 240
Lys Ala Ser Glu Gly Gly Gly Lys Gly Ile Arg Gln Val Glu Arg
                245                 250                 255
Glu Glu Asp Phe Ile Ala Leu Tyr His Gln Ala Ala Asn Glu Ile Pro
                260                 265                 270
Gly Ser Pro Ile Phe Ile Met Lys Leu Ala Gly Arg Ala Arg His Leu
                275                 280                 285
Glu Val Gln Leu Leu Ala Asp Gln Tyr Gly Thr Asn Ile Ser Leu Phe
290                 295                 300
Gly Arg Asp Cys Ser Val Gln Arg Arg His Gln Lys Ile Ile Glu Glu
305                 310                 315                 320
Ala Pro Val Thr Ile Ala Lys Ala Glu Thr Phe His Glu Met Glu Lys
                325                 330                 335
Ala Ala Val Arg Leu Gly Lys Leu Val Gly Tyr Val Ser Ala Gly Thr
                340                 345                 350
Val Glu Tyr Leu Tyr Ser His Asp Asp Gly Lys Phe Tyr Phe Leu Glu
                355                 360                 365
Leu Asn Pro Arg Leu Gln Val Glu His Pro Thr Thr Glu Met Val Ser
370                 375                 380
Gly Val Asn Leu Pro Ala Ala Gln Leu Gln Ile Ala Met Gly Ile Pro
385                 390                 395                 400
Met His Arg Ile Ser Asp Ile Arg Thr Leu Tyr Gly Met Asn Pro His
                405                 410                 415
Ser Ala Ser Glu Ile Asp Phe Glu Phe Lys Thr Gln Asp Ala Thr Lys
                420                 425                 430
Lys Gln Arg Arg Pro Ile Pro Lys Gly His Cys Thr Ala Cys Arg Ile
                435                 440                 445
Thr Ser Glu Asp Pro Asn Asp Gly Phe Lys Pro Ser Gly Gly Thr Leu
450                 455                 460
```

```
His Glu Leu Asn Phe Arg Ser Ser Asn Val Trp Gly Tyr Phe Ser
465                 470                 475                 480

Val Gly Asn Asn Gly Asn Ile His Ser Phe Ser Asp Ser Gln Phe Gly
                485                 490                 495

His Ile Phe Ala Phe Gly Glu Asn Arg Gln Ala Ser Arg Lys His Met
            500                 505                 510

Val Val Ala Leu Lys Glu Leu Ser Ile Arg Gly Asp Phe Arg Thr Thr
        515                 520                 525

Val Glu Tyr Leu Ile Lys Leu Leu Glu Thr Glu Asp Phe Glu Asp Asn
    530                 535                 540

Thr Ile Thr Thr Gly Trp Leu Asp Asp Leu Ile Thr His Lys Met Thr
545                 550                 555                 560

Ala Glu Lys Pro Asp Pro Thr Leu Ala Val
                565                 570

<210> SEQ ID NO 35
<211> LENGTH: 560
<212> TYPE: PRT
<213> ORGANISM: Saccharomyces cerevisiae
<220> FEATURE:
<221> NAME/KEY: MISC_FEATURE
<222> LOCATION: (1)..(560)
<223> OTHER INFORMATION: N-terminal deleted Saccharomyces cerevisiae
      ACCase BC domain (AAs22-581)

<400> SEQUENCE: 35

Ser Glu Arg His Thr Glu Leu Pro Gly His Phe Ile Gly Leu Asn Thr
1               5                   10                  15

Val Asp Lys Leu Glu Glu Ser Pro Leu Arg Asp Phe Val Lys Ser His
            20                  25                  30

Gly Gly His Thr Val Ile Ser Lys Ile Leu Ile Ala Asn Asn Gly Ile
        35                  40                  45

Ala Ala Val Lys Glu Ile Arg Ser Val Arg Lys Trp Ala Tyr Glu Thr
    50                  55                  60

Phe Gly Asp Asp Arg Thr Val Gln Phe Val Ala Met Ala Thr Pro Glu
65                  70                  75                  80

Asp Leu Glu Ala Asn Ala Glu Tyr Ile Arg Met Ala Asp Gln Tyr Ile
                85                  90                  95

Glu Val Pro Gly Gly Thr Asn Asn Asn Tyr Ala Asn Val Asp Leu
            100                 105                 110

Ile Val Asp Ile Ala Glu Arg Ala Asp Val Asp Ala Val Trp Ala Gly
        115                 120                 125

Trp Gly His Ala Ser Glu Asn Pro Leu Leu Pro Glu Lys Leu Ser Gln
    130                 135                 140

Ser Lys Arg Lys Val Ile Phe Ile Gly Pro Pro Gly Asn Ala Met Arg
145                 150                 155                 160

Ser Leu Gly Asp Lys Ile Ser Ser Thr Ile Val Ala Gln Ser Ala Lys
                165                 170                 175

Val Pro Cys Ile Pro Trp Ser Gly Thr Gly Val Asp Thr Val His Val
            180                 185                 190

Asp Glu Lys Thr Gly Leu Val Ser Val Asp Asp Ile Tyr Gln Lys
        195                 200                 205

Gly Cys Cys Thr Ser Pro Glu Asp Gly Leu Gln Lys Ala Lys Arg Ile
    210                 215                 220

Gly Phe Pro Val Met Ile Lys Ala Ser Glu Gly Gly Gly Gly Lys Gly
225                 230                 235                 240
```

```
Ile Arg Gln Val Glu Arg Glu Asp Phe Ile Ala Leu Tyr His Gln
                245                 250                 255

Ala Ala Asn Glu Ile Pro Gly Ser Pro Ile Phe Ile Met Lys Leu Ala
            260                 265                 270

Gly Arg Ala Arg His Leu Glu Val Gln Leu Leu Ala Asp Gln Tyr Gly
        275                 280                 285

Thr Asn Ile Ser Leu Phe Gly Arg Asp Cys Ser Val Gln Arg Arg His
    290                 295                 300

Gln Lys Ile Ile Glu Glu Ala Pro Val Thr Ile Ala Lys Ala Glu Thr
305                 310                 315                 320

Phe His Glu Met Glu Lys Ala Ala Val Arg Leu Gly Lys Leu Val Gly
                325                 330                 335

Tyr Val Ser Ala Gly Thr Val Glu Tyr Leu Tyr Ser His Asp Asp Gly
            340                 345                 350

Lys Phe Tyr Phe Leu Glu Leu Asn Pro Arg Leu Gln Val Glu His Pro
        355                 360                 365

Thr Thr Glu Met Val Ser Gly Val Asn Leu Pro Ala Ala Gln Leu Gln
    370                 375                 380

Ile Ala Met Gly Ile Pro Met His Arg Ile Ser Asp Ile Arg Thr Leu
385                 390                 395                 400

Tyr Gly Met Asn Pro His Ser Ala Ser Glu Ile Asp Phe Glu Phe Lys
                405                 410                 415

Thr Gln Asp Ala Thr Lys Lys Gln Arg Arg Pro Ile Pro Lys Gly His
            420                 425                 430

Cys Thr Ala Cys Arg Ile Thr Ser Glu Asp Pro Asn Asp Gly Phe Lys
        435                 440                 445

Pro Ser Gly Gly Thr Leu His Glu Leu Asn Phe Arg Ser Ser Ser Asn
    450                 455                 460

Val Trp Gly Tyr Phe Ser Val Gly Asn Asn Gly Asn Ile His Ser Phe
465                 470                 475                 480

Ser Asp Ser Gln Phe Gly His Ile Phe Ala Phe Gly Glu Asn Arg Gln
                485                 490                 495

Ala Ser Arg Lys His Met Val Val Ala Leu Lys Glu Leu Ser Ile Arg
            500                 505                 510

Gly Asp Phe Arg Thr Thr Val Glu Tyr Leu Ile Lys Leu Leu Glu Thr
        515                 520                 525

Glu Asp Phe Glu Asp Asn Thr Ile Thr Thr Gly Trp Leu Asp Asp Leu
    530                 535                 540

Ile Thr His Lys Met Thr Ala Glu Lys Pro Asp Pro Thr Leu Ala Val
545                 550                 555                 560
```

<210> SEQ ID NO 36
<211> LENGTH: 550
<212> TYPE: PRT
<213> ORGANISM: Saccharomyces cerevisiae
<220> FEATURE:
<221> NAME/KEY: MISC_FEATURE
<222> LOCATION: (1)..(550)
<223> OTHER INFORMATION: N-terminal deleted Saccharomyces cerevisiae
      ACCase BC domain (AA s32-581

<400> SEQUENCE: 36

```
Phe Ile Gly Leu Asn Thr Val Asp Lys Leu Glu Glu Ser Pro Leu Arg
1               5                   10                  15

Asp Phe Val Lys Ser His Gly Gly His Thr Val Ile Ser Lys Ile Leu
            20                  25                  30
```

-continued

```
Ile Ala Asn Asn Gly Ile Ala Ala Val Lys Glu Ile Arg Ser Val Arg
         35                  40                  45

Lys Trp Ala Tyr Glu Thr Phe Gly Asp Asp Arg Thr Val Gln Phe Val
     50                  55                  60

Ala Met Ala Thr Pro Glu Asp Leu Glu Ala Asn Ala Glu Tyr Ile Arg
 65                  70                  75                  80

Met Ala Asp Gln Tyr Ile Glu Val Pro Gly Gly Thr Asn Asn Asn Asn
                 85                  90                  95

Tyr Ala Asn Val Asp Leu Ile Val Asp Ile Ala Glu Arg Ala Asp Val
             100                 105                 110

Asp Ala Val Trp Ala Gly Trp Gly His Ala Ser Glu Asn Pro Leu Leu
             115                 120                 125

Pro Glu Lys Leu Ser Gln Ser Lys Arg Lys Val Ile Phe Ile Gly Pro
         130                 135                 140

Pro Gly Asn Ala Met Arg Ser Leu Gly Asp Lys Ile Ser Ser Thr Ile
145                 150                 155                 160

Val Ala Gln Ser Ala Lys Val Pro Cys Ile Pro Trp Ser Gly Thr Gly
                 165                 170                 175

Val Asp Thr Val His Val Asp Glu Lys Thr Gly Leu Val Ser Val Asp
             180                 185                 190

Asp Asp Ile Tyr Gln Lys Gly Cys Cys Thr Ser Pro Glu Asp Gly Leu
         195                 200                 205

Gln Lys Ala Lys Arg Ile Gly Phe Pro Val Met Ile Lys Ala Ser Glu
     210                 215                 220

Gly Gly Gly Gly Lys Gly Ile Arg Gln Val Glu Arg Glu Glu Asp Phe
225                 230                 235                 240

Ile Ala Leu Tyr His Gln Ala Ala Asn Glu Ile Pro Gly Ser Pro Ile
                 245                 250                 255

Phe Ile Met Lys Leu Ala Gly Arg Ala Arg His Leu Glu Val Gln Leu
             260                 265                 270

Leu Ala Asp Gln Tyr Gly Thr Asn Ile Ser Leu Phe Gly Arg Asp Cys
         275                 280                 285

Ser Val Gln Arg Arg His Gln Lys Ile Ile Glu Glu Ala Pro Val Thr
     290                 295                 300

Ile Ala Lys Ala Glu Thr Phe His Glu Met Glu Lys Ala Ala Val Arg
305                 310                 315                 320

Leu Gly Lys Leu Val Gly Tyr Val Ser Ala Gly Thr Val Glu Tyr Leu
                 325                 330                 335

Tyr Ser His Asp Asp Gly Lys Phe Tyr Phe Leu Glu Leu Asn Pro Arg
             340                 345                 350

Leu Gln Val Glu His Pro Thr Thr Glu Met Val Ser Gly Val Asn Leu
         355                 360                 365

Pro Ala Ala Gln Leu Gln Ile Ala Met Gly Ile Pro Met His Arg Ile
     370                 375                 380

Ser Asp Ile Arg Thr Leu Tyr Gly Met Asn Pro His Ser Ala Ser Glu
385                 390                 395                 400

Ile Asp Phe Glu Phe Lys Thr Gln Asp Ala Thr Lys Lys Gln Arg Arg
                 405                 410                 415

Pro Ile Pro Lys Gly His Cys Thr Ala Cys Arg Ile Thr Ser Glu Asp
             420                 425                 430

Pro Asn Asp Gly Phe Lys Pro Ser Gly Gly Thr Leu His Glu Leu Asn
         435                 440                 445

Phe Arg Ser Ser Ser Asn Val Trp Gly Tyr Phe Ser Val Gly Asn Asn
```

```
              450                 455                 460
Gly Asn Ile His Ser Phe Ser Asp Ser Gln Phe Gly His Ile Phe Ala
465                 470                 475                 480

Phe Gly Glu Asn Arg Gln Ala Ser Arg Lys His Met Val Val Ala Leu
                485                 490                 495

Lys Glu Leu Ser Ile Arg Gly Asp Phe Arg Thr Thr Val Glu Tyr Leu
                500                 505                 510

Ile Lys Leu Leu Glu Thr Glu Asp Phe Glu Asp Asn Thr Ile Thr Thr
                515                 520                 525

Gly Trp Leu Asp Asp Leu Ile Thr His Lys Met Thr Ala Glu Lys Pro
                530                 535                 540

Asp Pro Thr Leu Ala Val
545                 550

<210> SEQ ID NO 37
<211> LENGTH: 540
<212> TYPE: PRT
<213> ORGANISM: Saccharomyces cerevisiae
<220> FEATURE:
<221> NAME/KEY: MISC_FEATURE
<222> LOCATION: (1)..(540)
<223> OTHER INFORMATION: N-terminal deleted Saccharomyces cerevisiae
      ACCase BC domain (AAs 42-581)

<400> SEQUENCE: 37

Glu Glu Ser Pro Leu Arg Asp Phe Val Lys Ser His Gly Gly His Thr
1               5                   10                  15

Val Ile Ser Lys Ile Leu Ile Ala Asn Asn Gly Ile Ala Ala Val Lys
                20                  25                  30

Glu Ile Arg Ser Val Arg Lys Trp Ala Tyr Glu Thr Phe Gly Asp Asp
            35                  40                  45

Arg Thr Val Gln Phe Val Ala Met Ala Thr Pro Glu Asp Leu Glu Ala
        50                  55                  60

Asn Ala Glu Tyr Ile Arg Met Ala Asp Gln Tyr Ile Glu Val Pro Gly
65                  70                  75                  80

Gly Thr Asn Asn Asn Asn Tyr Ala Asn Val Asp Leu Ile Val Asp Ile
                85                  90                  95

Ala Glu Arg Ala Asp Val Asp Ala Val Trp Ala Gly Trp Gly His Ala
            100                 105                 110

Ser Glu Asn Pro Leu Leu Pro Glu Lys Leu Ser Gln Ser Lys Arg Lys
        115                 120                 125

Val Ile Phe Ile Gly Pro Pro Gly Asn Ala Met Arg Ser Leu Gly Asp
    130                 135                 140

Lys Ile Ser Ser Thr Ile Val Ala Gln Ser Ala Lys Val Pro Cys Ile
145                 150                 155                 160

Pro Trp Ser Gly Thr Gly Val Asp Thr Val His Val Asp Glu Lys Thr
                165                 170                 175

Gly Leu Val Ser Val Asp Asp Asp Ile Tyr Gln Lys Gly Cys Cys Thr
            180                 185                 190

Ser Pro Glu Asp Gly Leu Gln Lys Ala Lys Arg Ile Gly Phe Pro Val
        195                 200                 205

Met Ile Lys Ala Ser Glu Gly Gly Gly Gly Lys Gly Ile Arg Gln Val
    210                 215                 220

Glu Arg Glu Glu Asp Phe Ile Ala Leu Tyr His Gln Ala Ala Asn Glu
225                 230                 235                 240

Ile Pro Gly Ser Pro Ile Phe Ile Met Lys Leu Ala Gly Arg Ala Arg
```

```
                    245                 250                 255
His Leu Glu Val Gln Leu Leu Ala Asp Gln Tyr Gly Thr Asn Ile Ser
            260                 265                 270

Leu Phe Gly Arg Asp Cys Ser Val Gln Arg Arg His Gln Lys Ile Ile
        275                 280                 285

Glu Glu Ala Pro Val Thr Ile Ala Lys Ala Glu Thr Phe His Glu Met
    290                 295                 300

Glu Lys Ala Ala Val Arg Leu Gly Lys Leu Val Gly Tyr Val Ser Ala
305                 310                 315                 320

Gly Thr Val Glu Tyr Leu Tyr Ser His Asp Asp Gly Lys Phe Tyr Phe
                325                 330                 335

Leu Glu Leu Asn Pro Arg Leu Gln Val Glu His Pro Thr Thr Glu Met
            340                 345                 350

Val Ser Gly Val Asn Leu Pro Ala Ala Gln Leu Gln Ile Ala Met Gly
        355                 360                 365

Ile Pro Met His Arg Ile Ser Asp Ile Arg Thr Leu Tyr Gly Met Asn
    370                 375                 380

Pro His Ser Ala Ser Glu Ile Asp Phe Glu Phe Lys Thr Gln Asp Ala
385                 390                 395                 400

Thr Lys Lys Gln Arg Arg Pro Ile Pro Lys Gly His Cys Thr Ala Cys
                405                 410                 415

Arg Ile Thr Ser Glu Asp Pro Asn Asp Gly Phe Lys Pro Ser Gly Gly
            420                 425                 430

Thr Leu His Glu Leu Asn Phe Arg Ser Ser Asn Val Trp Gly Tyr
        435                 440                 445

Phe Ser Val Gly Asn Asn Gly Asn Ile His Ser Phe Ser Asp Ser Gln
450                 455                 460

Phe Gly His Ile Phe Ala Phe Gly Glu Asn Arg Gln Ala Ser Arg Lys
465                 470                 475                 480

His Met Val Val Ala Leu Lys Glu Leu Ser Ile Arg Gly Asp Phe Arg
                485                 490                 495

Thr Thr Val Glu Tyr Leu Ile Lys Leu Leu Glu Thr Glu Asp Phe Glu
            500                 505                 510

Asp Asn Thr Ile Thr Thr Gly Trp Leu Asp Asp Leu Ile Thr His Lys
        515                 520                 525

Met Thr Ala Glu Lys Pro Asp Pro Thr Leu Ala Val
    530                 535                 540

<210> SEQ ID NO 38
<211> LENGTH: 575
<212> TYPE: PRT
<213> ORGANISM: Saccharomyces cerevisiae
<220> FEATURE:
<221> NAME/KEY: MISC_FEATURE
<222> LOCATION: (1)..(575)
<223> OTHER INFORMATION: C-terminal deleted Saccharomyces cerevisiae
      ACCase BC domain (AAs 2-576)

<400> SEQUENCE: 38

Ser Glu Glu Ser Leu Phe Glu Ser Ser Pro Gln Lys Met Glu Tyr Glu
1               5                   10                  15

Ile Thr Asn Tyr Ser Glu Arg His Thr Glu Leu Pro Gly His Phe Ile
            20                  25                  30

Gly Leu Asn Thr Val Asp Lys Leu Glu Glu Ser Pro Leu Arg Asp Phe
        35                  40                  45

Val Lys Ser His Gly Gly His Thr Val Ile Ser Lys Ile Leu Ile Ala
```

-continued

```
                50                  55                  60
Asn Asn Gly Ile Ala Ala Val Lys Glu Ile Arg Ser Val Arg Lys Trp
 65                  70                  75                  80
Ala Tyr Glu Thr Phe Gly Asp Asp Arg Thr Val Gln Phe Val Ala Met
                 85                  90                  95
Ala Thr Pro Glu Asp Leu Glu Ala Asn Ala Glu Tyr Ile Arg Met Ala
            100                 105                 110
Asp Gln Tyr Ile Glu Val Pro Gly Gly Thr Asn Asn Asn Asn Tyr Ala
            115                 120                 125
Asn Val Asp Leu Ile Val Asp Ile Ala Glu Arg Ala Asp Val Asp Ala
        130                 135                 140
Val Trp Ala Gly Trp Gly His Ala Ser Glu Asn Pro Leu Leu Pro Glu
145                 150                 155                 160
Lys Leu Ser Gln Ser Lys Arg Lys Val Ile Phe Ile Gly Pro Pro Gly
            165                 170                 175
Asn Ala Met Arg Ser Leu Gly Asp Lys Ile Ser Ser Thr Ile Val Ala
            180                 185                 190
Gln Ser Ala Lys Val Pro Cys Ile Pro Trp Ser Gly Thr Gly Val Asp
        195                 200                 205
Thr Val His Val Asp Glu Lys Thr Gly Leu Val Ser Val Asp Asp Asp
210                 215                 220
Ile Tyr Gln Lys Gly Cys Cys Thr Ser Pro Glu Asp Gly Leu Gln Lys
225                 230                 235                 240
Ala Lys Arg Ile Gly Phe Pro Val Met Ile Lys Ala Ser Glu Gly Gly
            245                 250                 255
Gly Gly Lys Gly Ile Arg Gln Val Glu Arg Glu Glu Asp Phe Ile Ala
            260                 265                 270
Leu Tyr His Gln Ala Ala Asn Glu Ile Pro Gly Ser Pro Ile Phe Ile
        275                 280                 285
Met Lys Leu Ala Gly Arg Ala Arg His Leu Glu Val Gln Leu Leu Ala
290                 295                 300
Asp Gln Tyr Gly Thr Asn Ile Ser Leu Phe Gly Arg Asp Cys Ser Val
305                 310                 315                 320
Gln Arg Arg His Gln Lys Ile Ile Glu Glu Ala Pro Val Thr Ile Ala
            325                 330                 335
Lys Ala Glu Thr Phe His Glu Met Glu Lys Ala Ala Val Arg Leu Gly
            340                 345                 350
Lys Leu Val Gly Tyr Val Ser Ala Gly Thr Val Glu Tyr Leu Tyr Ser
        355                 360                 365
His Asp Asp Gly Lys Phe Tyr Phe Leu Glu Leu Asn Pro Arg Leu Gln
370                 375                 380
Val Glu His Pro Thr Thr Glu Met Val Ser Gly Val Asn Leu Pro Ala
385                 390                 395                 400
Ala Gln Leu Gln Ile Ala Met Gly Ile Pro Met His Arg Ile Ser Asp
            405                 410                 415
Ile Arg Thr Leu Tyr Gly Met Asn Pro His Ser Ala Ser Glu Ile Asp
            420                 425                 430
Phe Glu Phe Lys Thr Gln Asp Ala Thr Lys Lys Gln Arg Arg Pro Ile
        435                 440                 445
Pro Lys Gly His Cys Thr Ala Cys Arg Ile Thr Ser Glu Asp Pro Asn
450                 455                 460
Asp Gly Phe Lys Pro Ser Gly Thr Leu His Glu Leu Asn Phe Arg
465                 470                 475                 480
```

-continued

```
Ser Ser Ser Asn Val Trp Gly Tyr Phe Ser Val Gly Asn Asn Gly Asn
            485                 490                 495

Ile His Ser Phe Ser Asp Ser Gln Phe Gly His Ile Phe Ala Phe Gly
            500                 505                 510

Glu Asn Arg Gln Ala Ser Arg Lys His Met Val Val Ala Leu Lys Glu
            515                 520                 525

Leu Ser Ile Arg Gly Asp Phe Arg Thr Thr Val Glu Tyr Leu Ile Lys
            530                 535                 540

Leu Leu Glu Thr Glu Asp Phe Glu Asp Asn Thr Ile Thr Thr Gly Trp
545                 550                 555                 560

Leu Asp Asp Leu Ile Thr His Lys Met Thr Ala Glu Lys Pro Asp
                565                 570                 575

<210> SEQ ID NO 39
<211> LENGTH: 570
<212> TYPE: PRT
<213> ORGANISM: Saccharomyces cerevisiae
<220> FEATURE:
<221> NAME/KEY: MISC_FEATURE
<222> LOCATION: (1)..(570)
<223> OTHER INFORMATION: C-terminal deleted Saccharomyces cerevisiae
      ACCase BC domain (AAs 2-571)

<400> SEQUENCE: 39

Ser Glu Glu Ser Leu Phe Glu Ser Ser Pro Gln Lys Met Glu Tyr Glu
1               5                   10                  15

Ile Thr Asn Tyr Ser Glu Arg His Thr Glu Leu Pro Gly His Phe Ile
            20                  25                  30

Gly Leu Asn Thr Val Asp Lys Leu Glu Glu Ser Pro Leu Arg Asp Phe
            35                  40                  45

Val Lys Ser His Gly Gly His Thr Val Ile Ser Lys Ile Leu Ile Ala
        50                  55                  60

Asn Asn Gly Ile Ala Ala Val Lys Glu Ile Arg Ser Val Arg Lys Trp
65                  70                  75                  80

Ala Tyr Glu Thr Phe Gly Asp Asp Arg Thr Val Gln Phe Val Ala Met
                85                  90                  95

Ala Thr Pro Glu Asp Leu Glu Ala Asn Ala Glu Tyr Ile Arg Met Ala
            100                 105                 110

Asp Gln Tyr Ile Glu Val Pro Gly Gly Thr Asn Asn Asn Tyr Ala
            115                 120                 125

Asn Val Asp Leu Ile Val Asp Ile Ala Glu Arg Ala Asp Val Asp Ala
        130                 135                 140

Val Trp Ala Gly Trp Gly His Ala Ser Glu Asn Pro Leu Leu Pro Glu
145                 150                 155                 160

Lys Leu Ser Gln Ser Lys Arg Lys Val Ile Phe Ile Gly Pro Pro Gly
                165                 170                 175

Asn Ala Met Arg Ser Leu Gly Asp Lys Ile Ser Ser Thr Ile Val Ala
            180                 185                 190

Gln Ser Ala Lys Val Pro Cys Ile Pro Trp Ser Gly Thr Gly Val Asp
            195                 200                 205

Thr Val His Val Asp Glu Lys Thr Gly Leu Val Ser Val Asp Asp
        210                 215                 220

Ile Tyr Gln Lys Gly Cys Cys Thr Ser Pro Glu Asp Gly Leu Gln Lys
225                 230                 235                 240

Ala Lys Arg Ile Gly Phe Pro Val Met Ile Lys Ala Ser Glu Gly Gly
                245                 250                 255
```

```
Gly Gly Lys Gly Ile Arg Gln Val Glu Arg Glu Asp Phe Ile Ala
            260                 265                 270

Leu Tyr His Gln Ala Ala Asn Glu Ile Pro Gly Ser Pro Ile Phe Ile
        275                 280                 285

Met Lys Leu Ala Gly Arg Ala Arg His Leu Glu Val Gln Leu Leu Ala
        290                 295                 300

Asp Gln Tyr Gly Thr Asn Ile Ser Leu Phe Gly Arg Asp Cys Ser Val
305                 310                 315                 320

Gln Arg Arg His Gln Lys Ile Ile Glu Ala Pro Val Thr Ile Ala
            325                 330                 335

Lys Ala Glu Thr Phe His Glu Met Glu Lys Ala Ala Val Arg Leu Gly
        340                 345                 350

Lys Leu Val Gly Tyr Val Ser Ala Gly Thr Val Glu Tyr Leu Tyr Ser
        355                 360                 365

His Asp Asp Gly Lys Phe Tyr Phe Leu Glu Leu Asn Pro Arg Leu Gln
        370                 375                 380

Val Glu His Pro Thr Thr Glu Met Val Ser Gly Val Asn Leu Pro Ala
385                 390                 395                 400

Ala Gln Leu Gln Ile Ala Met Gly Ile Pro Met His Arg Ile Ser Asp
            405                 410                 415

Ile Arg Thr Leu Tyr Gly Met Asn Pro His Ser Ala Ser Glu Ile Asp
            420                 425                 430

Phe Glu Phe Lys Thr Gln Asp Ala Thr Lys Lys Gln Arg Arg Pro Ile
        435                 440                 445

Pro Lys Gly His Cys Thr Ala Cys Arg Ile Thr Ser Glu Asp Pro Asn
450                 455                 460

Asp Gly Phe Lys Pro Ser Gly Gly Thr Leu His Glu Leu Asn Phe Arg
465                 470                 475                 480

Ser Ser Ser Asn Val Trp Gly Tyr Phe Ser Val Gly Asn Asn Gly Asn
            485                 490                 495

Ile His Ser Phe Ser Asp Ser Gln Phe Gly His Ile Phe Ala Phe Gly
        500                 505                 510

Glu Asn Arg Gln Ala Ser Arg Lys His Met Val Val Ala Leu Lys Glu
        515                 520                 525

Leu Ser Ile Arg Gly Asp Phe Arg Thr Thr Val Glu Tyr Leu Ile Lys
        530                 535                 540

Leu Leu Glu Thr Glu Asp Phe Glu Asp Asn Thr Ile Thr Thr Gly Trp
545                 550                 555                 560

Leu Asp Asp Leu Ile Thr His Lys Met Thr
            565                 570

<210> SEQ ID NO 40
<211> LENGTH: 560
<212> TYPE: PRT
<213> ORGANISM: Saccharomyces cerevisiae
<220> FEATURE:
<221> NAME/KEY: MISC_FEATURE
<222> LOCATION: (1)..(560)
<223> OTHER INFORMATION: C-terminal deleted Saccharomyces cerevisiae
      ACCase BC domain (AAs 2-561)

<400> SEQUENCE: 40

Ser Glu Glu Ser Leu Phe Glu Ser Ser Pro Gln Lys Met Glu Tyr Glu
1               5                   10                  15

Ile Thr Asn Tyr Ser Glu Arg His Thr Glu Leu Pro Gly His Phe Ile
            20                  25                  30
```

```
Gly Leu Asn Thr Val Asp Lys Leu Glu Glu Ser Pro Leu Arg Asp Phe
                35                  40                  45
Val Lys Ser His Gly His Thr Val Ile Ser Lys Ile Leu Ile Ala
 50                  55                  60
Asn Asn Gly Ile Ala Ala Val Lys Glu Ile Arg Ser Val Arg Lys Trp
 65                  70                  75                  80
Ala Tyr Glu Thr Phe Gly Asp Asp Arg Thr Val Gln Phe Val Ala Met
                85                  90                  95
Ala Thr Pro Glu Asp Leu Glu Ala Asn Ala Glu Tyr Ile Arg Met Ala
               100                 105                 110
Asp Gln Tyr Ile Glu Val Pro Gly Gly Thr Asn Asn Asn Tyr Ala
               115                 120                 125
Asn Val Asp Leu Ile Val Asp Ile Ala Glu Arg Ala Asp Val Asp Ala
130                 135                 140
Val Trp Ala Gly Trp Gly His Ala Ser Glu Asn Pro Leu Leu Pro Glu
145                 150                 155                 160
Lys Leu Ser Gln Ser Lys Arg Lys Val Ile Phe Ile Gly Pro Pro Gly
               165                 170                 175
Asn Ala Met Arg Ser Leu Gly Asp Lys Ile Ser Ser Thr Ile Val Ala
               180                 185                 190
Gln Ser Ala Lys Val Pro Cys Ile Pro Trp Ser Gly Thr Gly Val Asp
               195                 200                 205
Thr Val His Val Asp Glu Lys Thr Gly Leu Val Ser Val Asp Asp Asp
210                 215                 220
Ile Tyr Gln Lys Gly Cys Cys Thr Ser Pro Glu Asp Gly Leu Gln Lys
225                 230                 235                 240
Ala Lys Arg Ile Gly Phe Pro Val Met Ile Lys Ala Ser Glu Gly Gly
               245                 250                 255
Gly Gly Lys Gly Ile Arg Gln Val Glu Arg Glu Glu Asp Phe Ile Ala
               260                 265                 270
Leu Tyr His Gln Ala Ala Asn Glu Ile Pro Gly Ser Pro Ile Phe Ile
               275                 280                 285
Met Lys Leu Ala Gly Arg Ala Arg His Leu Glu Val Gln Leu Leu Ala
290                 295                 300
Asp Gln Tyr Gly Thr Asn Ile Ser Leu Phe Gly Arg Asp Cys Ser Val
305                 310                 315                 320
Gln Arg Arg His Gln Lys Ile Ile Glu Glu Ala Pro Val Thr Ile Ala
               325                 330                 335
Lys Ala Glu Thr Phe His Glu Met Glu Lys Ala Ala Val Arg Leu Gly
               340                 345                 350
Lys Leu Val Gly Tyr Val Ser Ala Gly Thr Val Glu Tyr Leu Tyr Ser
               355                 360                 365
His Asp Asp Gly Lys Phe Tyr Phe Leu Glu Leu Asn Pro Arg Leu Gln
               370                 375                 380
Val Glu His Pro Thr Thr Glu Met Val Ser Gly Val Asn Leu Pro Ala
385                 390                 395                 400
Ala Gln Leu Gln Ile Ala Met Gly Ile Pro Met His Arg Ile Ser Asp
               405                 410                 415
Ile Arg Thr Leu Tyr Gly Met Asn Pro His Ser Ala Ser Glu Ile Asp
               420                 425                 430
Phe Glu Phe Lys Thr Gln Asp Ala Thr Lys Lys Gln Arg Arg Pro Ile
               435                 440                 445
```

```
Pro Lys Gly His Cys Thr Ala Cys Arg Ile Thr Ser Glu Asp Pro Asn
    450                 455                 460

Asp Gly Phe Lys Pro Ser Gly Gly Thr Leu His Glu Leu Asn Phe Arg
465                 470                 475                 480

Ser Ser Ser Asn Val Trp Gly Tyr Phe Ser Val Gly Asn Asn Gly Asn
                485                 490                 495

Ile His Ser Phe Ser Asp Ser Gln Phe Gly His Ile Phe Ala Phe Gly
            500                 505                 510

Glu Asn Arg Gln Ala Ser Arg Lys His Met Val Val Ala Leu Lys Glu
        515                 520                 525

Leu Ser Ile Arg Gly Asp Phe Arg Thr Thr Val Glu Tyr Leu Ile Lys
    530                 535                 540

Leu Leu Glu Thr Glu Asp Phe Glu Asp Asn Thr Ile Thr Thr Gly Trp
545                 550                 555                 560

<210> SEQ ID NO 41
<211> LENGTH: 550
<212> TYPE: PRT
<213> ORGANISM: Saccharomyces cerevisiae
<220> FEATURE:
<221> NAME/KEY: MISC_FEATURE
<222> LOCATION: (1)..(550)
<223> OTHER INFORMATION: C-terminal deleted Saccharomyces cerevisiae
      ACCase BC domain (AAs 2-551)

<400> SEQUENCE: 41

Ser Glu Glu Ser Leu Phe Glu Ser Ser Pro Gln Lys Met Glu Tyr Glu
1               5                   10                  15

Ile Thr Asn Tyr Ser Glu Arg His Thr Glu Leu Pro Gly His Phe Ile
            20                  25                  30

Gly Leu Asn Thr Val Asp Lys Leu Glu Glu Ser Pro Leu Arg Asp Phe
        35                  40                  45

Val Lys Ser His Gly Gly His Thr Val Ile Ser Lys Ile Leu Ile Ala
    50                  55                  60

Asn Asn Gly Ile Ala Ala Val Lys Glu Ile Arg Ser Val Arg Lys Trp
65                  70                  75                  80

Ala Tyr Glu Thr Phe Gly Asp Asp Arg Thr Val Gln Phe Val Ala Met
                85                  90                  95

Ala Thr Pro Glu Asp Leu Glu Ala Asn Ala Glu Tyr Ile Arg Met Ala
            100                 105                 110

Asp Gln Tyr Ile Glu Val Pro Gly Gly Thr Asn Asn Asn Asn Tyr Ala
        115                 120                 125

Asn Val Asp Leu Ile Val Asp Ile Ala Glu Arg Ala Asp Val Asp Ala
130                 135                 140

Val Trp Ala Gly Trp Gly His Ala Ser Glu Asn Pro Leu Leu Pro Glu
145                 150                 155                 160

Lys Leu Ser Gln Ser Lys Arg Lys Val Ile Phe Ile Gly Pro Pro Gly
                165                 170                 175

Asn Ala Met Arg Ser Leu Gly Asp Lys Ile Ser Ser Thr Ile Val Ala
            180                 185                 190

Gln Ser Ala Lys Val Pro Cys Ile Pro Trp Ser Gly Thr Gly Val Asp
        195                 200                 205

Thr Val His Val Asp Glu Lys Thr Gly Leu Val Ser Val Asp Asp Asp
    210                 215                 220

Ile Tyr Gln Lys Gly Cys Cys Thr Ser Pro Glu Asp Gly Leu Gln Lys
225                 230                 235                 240
```

Ala Lys Arg Ile Gly Phe Pro Val Met Ile Lys Ala Ser Glu Gly Gly
            245                 250                 255

Gly Gly Lys Gly Ile Arg Gln Val Glu Arg Glu Asp Phe Ile Ala
        260                 265                 270

Leu Tyr His Gln Ala Ala Asn Glu Ile Pro Gly Ser Pro Ile Phe Ile
        275                 280                 285

Met Lys Leu Ala Gly Arg Ala Arg His Leu Glu Val Gln Leu Leu Ala
290                 295                 300

Asp Gln Tyr Gly Thr Asn Ile Ser Leu Phe Gly Arg Asp Cys Ser Val
305                 310                 315                 320

Gln Arg Arg His Gln Lys Ile Ile Glu Glu Ala Pro Val Thr Ile Ala
                325                 330                 335

Lys Ala Glu Thr Phe His Glu Met Glu Lys Ala Ala Val Arg Leu Gly
                340                 345                 350

Lys Leu Val Gly Tyr Val Ser Ala Gly Thr Val Glu Tyr Leu Tyr Ser
            355                 360                 365

His Asp Asp Gly Lys Phe Tyr Phe Leu Glu Leu Asn Pro Arg Leu Gln
        370                 375                 380

Val Glu His Pro Thr Thr Glu Met Val Ser Gly Val Asn Leu Pro Ala
385                 390                 395                 400

Ala Gln Leu Gln Ile Ala Met Gly Ile Pro Met His Arg Ile Ser Asp
                405                 410                 415

Ile Arg Thr Leu Tyr Gly Met Asn Pro His Ser Ala Ser Glu Ile Asp
                420                 425                 430

Phe Glu Phe Lys Thr Gln Asp Ala Thr Lys Lys Gln Arg Arg Pro Ile
            435                 440                 445

Pro Lys Gly His Cys Thr Ala Cys Arg Ile Thr Ser Glu Asp Pro Asn
        450                 455                 460

Asp Gly Phe Lys Pro Ser Gly Gly Thr Leu His Glu Leu Asn Phe Arg
465                 470                 475                 480

Ser Ser Ser Asn Val Trp Gly Tyr Phe Ser Val Gly Asn Asn Gly Asn
                485                 490                 495

Ile His Ser Phe Ser Asp Ser Gln Phe Gly His Ile Phe Ala Phe Gly
            500                 505                 510

Glu Asn Arg Gln Ala Ser Arg Lys His Met Val Val Ala Leu Lys Glu
        515                 520                 525

Leu Ser Ile Arg Gly Asp Phe Arg Thr Thr Val Glu Tyr Leu Ile Lys
    530                 535                 540

Leu Leu Glu Thr Glu Asp
545                 550

<210> SEQ ID NO 42
<211> LENGTH: 540
<212> TYPE: PRT
<213> ORGANISM: Saccharomyces cerevisiae
<220> FEATURE:
<221> NAME/KEY: MISC_FEATURE
<222> LOCATION: (1)..(540)
<223> OTHER INFORMATION: C-terminal deleted Saccharomyces cerevisiae
      ACCase BC domain (AAs 2-541)

<400> SEQUENCE: 42

Ser Glu Glu Ser Leu Phe Glu Ser Pro Gln Lys Met Glu Tyr Glu
1               5                   10                  15

Ile Thr Asn Tyr Ser Glu Arg His Thr Glu Leu Pro Gly His Phe Ile
            20                  25                  30

-continued

```
Gly Leu Asn Thr Val Asp Lys Leu Glu Glu Ser Pro Leu Arg Asp Phe
             35                  40                  45

Val Lys Ser His Gly Gly His Thr Val Ile Ser Lys Ile Leu Ile Ala
 50                  55                  60

Asn Asn Gly Ile Ala Ala Val Lys Glu Ile Arg Ser Val Arg Lys Trp
 65                  70                  75                  80

Ala Tyr Glu Thr Phe Gly Asp Asp Arg Thr Val Gln Phe Val Ala Met
                 85                  90                  95

Ala Thr Pro Glu Asp Leu Glu Ala Asn Ala Glu Tyr Ile Arg Met Ala
            100                 105                 110

Asp Gln Tyr Ile Glu Val Pro Gly Gly Thr Asn Asn Asn Tyr Ala
            115                 120                 125

Asn Val Asp Leu Ile Val Asp Ile Ala Glu Arg Ala Asp Val Asp Ala
        130                 135                 140

Val Trp Ala Gly Trp Gly His Ala Ser Glu Asn Pro Leu Leu Pro Glu
145                 150                 155                 160

Lys Leu Ser Gln Ser Lys Arg Lys Val Ile Phe Ile Gly Pro Pro Gly
                165                 170                 175

Asn Ala Met Arg Ser Leu Gly Asp Lys Ile Ser Thr Ile Val Ala
            180                 185                 190

Gln Ser Ala Lys Val Pro Cys Ile Pro Trp Ser Gly Thr Gly Val Asp
        195                 200                 205

Thr Val His Val Asp Glu Lys Thr Gly Leu Val Ser Val Asp Asp Asp
        210                 215                 220

Ile Tyr Gln Lys Gly Cys Cys Thr Ser Pro Glu Asp Gly Leu Gln Lys
225                 230                 235                 240

Ala Lys Arg Ile Gly Phe Pro Val Met Ile Lys Ala Ser Glu Gly Gly
                245                 250                 255

Gly Gly Lys Gly Ile Arg Gln Val Glu Arg Glu Glu Asp Phe Ile Ala
            260                 265                 270

Leu Tyr His Gln Ala Ala Asn Glu Ile Pro Gly Ser Pro Ile Phe Ile
        275                 280                 285

Met Lys Leu Ala Gly Arg Ala Arg His Leu Glu Val Gln Leu Leu Ala
290                 295                 300

Asp Gln Tyr Gly Thr Asn Ile Ser Leu Phe Gly Arg Asp Cys Ser Val
305                 310                 315                 320

Gln Arg Arg His Gln Lys Ile Ile Glu Glu Ala Pro Val Thr Ile Ala
                325                 330                 335

Lys Ala Glu Thr Phe His Glu Met Glu Lys Ala Ala Val Arg Leu Gly
            340                 345                 350

Lys Leu Val Gly Tyr Val Ser Ala Gly Thr Val Glu Tyr Leu Tyr Ser
        355                 360                 365

His Asp Asp Gly Lys Phe Tyr Phe Leu Glu Leu Asn Pro Arg Leu Gln
        370                 375                 380

Val Glu His Pro Thr Thr Glu Met Val Ser Gly Val Asn Leu Pro Ala
385                 390                 395                 400

Ala Gln Leu Gln Ile Ala Met Gly Ile Pro Met His Arg Ile Ser Asp
                405                 410                 415

Ile Arg Thr Leu Tyr Gly Met Asn Pro His Ser Ala Ser Glu Ile Asp
            420                 425                 430

Phe Glu Phe Lys Thr Gln Asp Ala Thr Lys Lys Gln Arg Arg Pro Ile
        435                 440                 445

Pro Lys Gly His Cys Thr Ala Cys Arg Ile Thr Ser Glu Asp Pro Asn
```

```
                    450                 455                 460
Asp Gly Phe Lys Pro Ser Gly Gly Thr Leu His Glu Leu Asn Phe Arg
465                 470                 475                 480

Ser Ser Ser Asn Val Trp Gly Tyr Phe Ser Val Gly Asn Asn Gly Asn
                485                 490                 495

Ile His Ser Phe Ser Asp Ser Gln Phe Gly His Ile Phe Ala Phe Gly
                500                 505                 510

Glu Asn Arg Gln Ala Ser Arg Lys His Met Val Val Ala Leu Lys Glu
            515                 520                 525

Leu Ser Ile Arg Gly Asp Phe Arg Thr Thr Val Glu
        530                 535                 540

<210> SEQ ID NO 43
<211> LENGTH: 575
<212> TYPE: PRT
<213> ORGANISM: Saccharomyces cerevisiae
<220> FEATURE:
<221> NAME/KEY: MISC_FEATURE
<222> LOCATION: (1)..(575)
<223> OTHER INFORMATION: N- and C-terminal deleted Saccharomyces
      cerevisiae ACCase BC domain (AAs 4-578)

<400> SEQUENCE: 43

Glu Ser Leu Phe Glu Ser Ser Pro Gln Lys Met Glu Tyr Glu Ile Thr
1               5                   10                  15

Asn Tyr Ser Glu Arg His Thr Glu Leu Pro Gly His Phe Ile Gly Leu
            20                  25                  30

Asn Thr Val Asp Lys Leu Glu Glu Ser Pro Leu Arg Asp Phe Val Lys
        35                  40                  45

Ser His Gly Gly His Thr Val Ile Ser Lys Ile Leu Ile Ala Asn Asn
    50                  55                  60

Gly Ile Ala Ala Val Lys Glu Ile Arg Ser Val Arg Lys Trp Ala Tyr
65                  70                  75                  80

Glu Thr Phe Gly Asp Asp Arg Thr Val Gln Phe Val Ala Met Ala Thr
                85                  90                  95

Pro Glu Asp Leu Glu Ala Asn Ala Glu Tyr Ile Arg Met Ala Asp Gln
            100                 105                 110

Tyr Ile Glu Val Pro Gly Gly Thr Asn Asn Asn Asn Tyr Ala Asn Val
        115                 120                 125

Asp Leu Ile Val Asp Ile Ala Glu Arg Ala Asp Val Asp Ala Val Trp
    130                 135                 140

Ala Gly Trp Gly His Ala Ser Glu Asn Pro Leu Leu Pro Glu Lys Leu
145                 150                 155                 160

Ser Gln Ser Lys Arg Lys Val Ile Phe Ile Gly Pro Pro Gly Asn Ala
                165                 170                 175

Met Arg Ser Leu Gly Asp Lys Ile Ser Ser Thr Ile Val Ala Gln Ser
            180                 185                 190

Ala Lys Val Pro Cys Ile Pro Trp Ser Gly Thr Gly Val Asp Thr Val
        195                 200                 205

His Val Asp Glu Lys Thr Gly Leu Val Ser Val Asp Asp Asp Ile Tyr
    210                 215                 220

Gln Lys Gly Cys Cys Thr Ser Pro Glu Asp Gly Leu Gln Lys Ala Lys
225                 230                 235                 240

Arg Ile Gly Phe Pro Val Met Ile Lys Ala Ser Glu Gly Gly Gly Gly
                245                 250                 255

Lys Gly Ile Arg Gln Val Glu Arg Glu Glu Asp Phe Ile Ala Leu Tyr
```

```
                260                 265                 270
His Gln Ala Ala Asn Glu Ile Pro Gly Ser Pro Ile Phe Ile Met Lys
        275                 280                 285
Leu Ala Gly Arg Ala Arg His Leu Glu Val Gln Leu Leu Ala Asp Gln
        290                 295                 300
Tyr Gly Thr Asn Ile Ser Leu Phe Gly Arg Asp Cys Ser Val Gln Arg
305                 310                 315                 320
Arg His Gln Lys Ile Ile Glu Glu Ala Pro Val Thr Ile Ala Lys Ala
                325                 330                 335
Glu Thr Phe His Glu Met Glu Lys Ala Ala Val Arg Leu Gly Lys Leu
        340                 345                 350
Val Gly Tyr Val Ser Ala Gly Thr Val Glu Tyr Leu Tyr Ser His Asp
        355                 360                 365
Asp Gly Lys Phe Tyr Phe Leu Glu Leu Asn Pro Arg Leu Gln Val Glu
        370                 375                 380
His Pro Thr Thr Glu Met Val Ser Gly Val Asn Leu Pro Ala Ala Gln
385                 390                 395                 400
Leu Gln Ile Ala Met Gly Ile Pro Met His Arg Ile Ser Asp Ile Arg
                405                 410                 415
Thr Leu Tyr Gly Met Asn Pro His Ser Ala Ser Glu Ile Asp Phe Glu
        420                 425                 430
Phe Lys Thr Gln Asp Ala Thr Lys Lys Gln Arg Arg Pro Ile Pro Lys
        435                 440                 445
Gly His Cys Thr Ala Cys Arg Ile Thr Ser Glu Asp Pro Asn Asp Gly
        450                 455                 460
Phe Lys Pro Ser Gly Gly Thr Leu His Glu Leu Asn Phe Arg Ser Ser
465                 470                 475                 480
Ser Asn Val Trp Gly Tyr Phe Ser Val Gly Asn Asn Gly Asn Ile His
                485                 490                 495
Ser Phe Ser Asp Ser Gln Phe Gly His Ile Phe Ala Phe Gly Glu Asn
        500                 505                 510
Arg Gln Ala Ser Arg Lys His Met Val Val Ala Leu Lys Glu Leu Ser
        515                 520                 525
Ile Arg Gly Asp Phe Arg Thr Thr Val Glu Tyr Leu Ile Lys Leu Leu
        530                 535                 540
Glu Thr Glu Asp Phe Glu Asp Asn Thr Ile Thr Thr Gly Trp Leu Asp
545                 550                 555                 560
Asp Leu Ile Thr His Lys Met Thr Ala Glu Lys Pro Asp Pro Thr
                565                 570                 575

<210> SEQ ID NO 44
<211> LENGTH: 570
<212> TYPE: PRT
<213> ORGANISM: Saccharomyces cerevisiae
<220> FEATURE:
<221> NAME/KEY: MISC_FEATURE
<222> LOCATION: (1)..(570)
<223> OTHER INFORMATION: N- and C-terminal deleted Saccharomyces
      cerevisiae ACCase BC domain (AAs 7-576)

<400> SEQUENCE: 44

Phe Glu Ser Ser Pro Gln Lys Met Glu Tyr Glu Ile Thr Asn Tyr Ser
1               5                   10                  15
Glu Arg His Thr Glu Leu Pro Gly His Phe Ile Gly Leu Asn Thr Val
                20                  25                  30
Asp Lys Leu Glu Glu Ser Pro Leu Arg Asp Phe Val Lys Ser His Gly
```

-continued

```
                35                  40                  45
Gly His Thr Val Ile Ser Lys Ile Leu Ile Ala Asn Asn Gly Ile Ala
 50                  55                  60
Ala Val Lys Glu Ile Arg Ser Val Arg Lys Trp Ala Tyr Glu Thr Phe
 65                  70                  75                  80
Gly Asp Asp Arg Thr Val Gln Phe Val Ala Met Ala Thr Pro Glu Asp
                 85                  90                  95
Leu Glu Ala Asn Ala Glu Tyr Ile Arg Met Ala Asp Gln Tyr Ile Glu
                100                 105                 110
Val Pro Gly Gly Thr Asn Asn Asn Tyr Ala Asn Val Asp Leu Ile
                115                 120                 125
Val Asp Ile Ala Glu Arg Ala Asp Val Asp Ala Val Trp Ala Gly Trp
130                 135                 140
Gly His Ala Ser Glu Asn Pro Leu Leu Pro Glu Lys Leu Ser Gln Ser
145                 150                 155                 160
Lys Arg Lys Val Ile Phe Ile Gly Pro Pro Gly Asn Ala Met Arg Ser
                165                 170                 175
Leu Gly Asp Lys Ile Ser Ser Thr Ile Val Ala Gln Ser Ala Lys Val
                180                 185                 190
Pro Cys Ile Pro Trp Ser Gly Thr Gly Val Asp Thr Val His Val Asp
                195                 200                 205
Glu Lys Thr Gly Leu Val Ser Val Asp Asp Asp Ile Tyr Gln Lys Gly
                210                 215                 220
Cys Cys Thr Ser Pro Glu Asp Gly Leu Gln Lys Ala Lys Arg Ile Gly
225                 230                 235                 240
Phe Pro Val Met Ile Lys Ala Ser Glu Gly Gly Gly Lys Gly Ile
                245                 250                 255
Arg Gln Val Glu Arg Glu Glu Asp Phe Ile Ala Leu Tyr His Gln Ala
                260                 265                 270
Ala Asn Glu Ile Pro Gly Ser Pro Ile Phe Ile Met Lys Leu Ala Gly
                275                 280                 285
Arg Ala Arg His Leu Glu Val Gln Leu Leu Ala Asp Gln Tyr Gly Thr
290                 295                 300
Asn Ile Ser Leu Phe Gly Arg Asp Cys Ser Val Gln Arg Arg His Gln
305                 310                 315                 320
Lys Ile Ile Glu Glu Ala Pro Val Thr Ile Ala Lys Ala Glu Thr Phe
                325                 330                 335
His Glu Met Glu Lys Ala Ala Val Arg Leu Gly Lys Leu Val Gly Tyr
                340                 345                 350
Val Ser Ala Gly Thr Val Glu Tyr Leu Tyr Ser His Asp Asp Gly Lys
                355                 360                 365
Phe Tyr Phe Leu Glu Leu Asn Pro Arg Leu Gln Val Glu His Pro Thr
                370                 375                 380
Thr Glu Met Val Ser Gly Val Asn Leu Pro Ala Ala Gln Leu Gln Ile
385                 390                 395                 400
Ala Met Gly Ile Pro Met His Arg Ile Ser Asp Ile Arg Thr Leu Tyr
                405                 410                 415
Gly Met Asn Pro His Ser Ala Ser Glu Ile Asp Phe Glu Phe Lys Thr
                420                 425                 430
Gln Asp Ala Thr Lys Lys Gln Arg Arg Pro Ile Pro Lys Gly His Cys
                435                 440                 445
Thr Ala Cys Arg Ile Thr Ser Glu Asp Pro Asn Asp Gly Phe Lys Pro
450                 455                 460
```

```
Ser Gly Gly Thr Leu His Glu Leu Asn Phe Arg Ser Ser Ser Asn Val
465                 470                 475                 480

Trp Gly Tyr Phe Ser Val Gly Asn Asn Gly Asn Ile His Ser Phe Ser
                485                 490                 495

Asp Ser Gln Phe Gly His Ile Phe Ala Phe Gly Glu Asn Arg Gln Ala
                500                 505                 510

Ser Arg Lys His Met Val Ala Leu Lys Glu Leu Ser Ile Arg Gly
                515                 520                 525

Asp Phe Arg Thr Thr Val Glu Tyr Leu Ile Lys Leu Leu Glu Thr Glu
                530                 535                 540

Asp Phe Glu Asp Asn Thr Ile Thr Thr Gly Trp Leu Asp Asp Leu Ile
545                 550                 555                 560

Thr His Lys Met Thr Ala Glu Lys Pro Asp
                565                 570

<210> SEQ ID NO 45
<211> LENGTH: 560
<212> TYPE: PRT
<213> ORGANISM: Saccharomyces cerevisiae
<220> FEATURE:
<221> NAME/KEY: MISC_FEATURE
<222> LOCATION: (1)..(560)
<223> OTHER INFORMATION: N- and C-terminal deleted Saccharomyces
      cerevisiae ACCase BC domain (AAs 12-571)

<400> SEQUENCE: 45

Gln Lys Met Glu Tyr Glu Ile Thr Asn Tyr Ser Glu Arg His Thr Glu
1               5                   10                  15

Leu Pro Gly His Phe Ile Gly Leu Asn Thr Val Asp Lys Leu Glu Glu
                20                  25                  30

Ser Pro Leu Arg Asp Phe Val Lys Ser His Gly Gly His Thr Val Ile
                35                  40                  45

Ser Lys Ile Leu Ile Ala Asn Asn Gly Ile Ala Ala Val Lys Glu Ile
                50                  55                  60

Arg Ser Val Arg Lys Trp Ala Tyr Glu Thr Phe Gly Asp Asp Arg Thr
65                  70                  75                  80

Val Gln Phe Val Ala Met Ala Thr Pro Glu Asp Leu Glu Ala Asn Ala
                85                  90                  95

Glu Tyr Ile Arg Met Ala Asp Gln Tyr Ile Glu Val Pro Gly Gly Thr
                100                 105                 110

Asn Asn Asn Asn Tyr Ala Asn Val Asp Leu Ile Val Asp Ile Ala Glu
                115                 120                 125

Arg Ala Asp Val Asp Ala Val Trp Ala Gly Trp Gly His Ala Ser Glu
130                 135                 140

Asn Pro Leu Leu Pro Glu Lys Leu Ser Gln Ser Lys Arg Lys Val Ile
145                 150                 155                 160

Phe Ile Gly Pro Pro Gly Asn Ala Met Arg Ser Leu Gly Asp Lys Ile
                165                 170                 175

Ser Ser Thr Ile Val Ala Gln Ser Ala Lys Val Pro Cys Ile Pro Trp
                180                 185                 190

Ser Gly Thr Gly Val Asp Thr Val His Val Asp Glu Lys Thr Gly Leu
                195                 200                 205

Val Ser Val Asp Asp Asp Ile Tyr Gln Lys Gly Cys Cys Thr Ser Pro
210                 215                 220

Glu Asp Gly Leu Gln Lys Ala Lys Arg Ile Gly Phe Pro Val Met Ile
225                 230                 235                 240
```

```
Lys Ala Ser Glu Gly Gly Gly Lys Gly Ile Arg Gln Val Glu Arg
                245                 250                 255

Glu Glu Asp Phe Ile Ala Leu Tyr His Gln Ala Ala Asn Glu Ile Pro
            260                 265                 270

Gly Ser Pro Ile Phe Ile Met Lys Leu Ala Gly Arg Ala Arg His Leu
        275                 280                 285

Glu Val Gln Leu Leu Ala Asp Gln Tyr Gly Thr Asn Ile Ser Leu Phe
    290                 295                 300

Gly Arg Asp Cys Ser Val Gln Arg Arg His Gln Lys Ile Ile Glu Glu
305                 310                 315                 320

Ala Pro Val Thr Ile Ala Lys Ala Glu Thr Phe His Glu Met Glu Lys
                325                 330                 335

Ala Ala Val Arg Leu Gly Lys Leu Val Gly Tyr Val Ser Ala Gly Thr
            340                 345                 350

Val Glu Tyr Leu Tyr Ser His Asp Asp Gly Lys Phe Tyr Phe Leu Glu
        355                 360                 365

Leu Asn Pro Arg Leu Gln Val Glu His Pro Thr Thr Glu Met Val Ser
    370                 375                 380

Gly Val Asn Leu Pro Ala Ala Gln Leu Gln Ile Ala Met Gly Ile Pro
385                 390                 395                 400

Met His Arg Ile Ser Asp Ile Arg Thr Leu Tyr Gly Met Asn Pro His
                405                 410                 415

Ser Ala Ser Glu Ile Asp Phe Glu Phe Lys Thr Gln Asp Ala Thr Lys
            420                 425                 430

Lys Gln Arg Arg Pro Ile Pro Lys Gly His Cys Thr Ala Cys Arg Ile
        435                 440                 445

Thr Ser Glu Asp Pro Asn Asp Gly Phe Lys Pro Ser Gly Gly Thr Leu
    450                 455                 460

His Glu Leu Asn Phe Arg Ser Ser Asn Val Trp Gly Tyr Phe Ser
465                 470                 475                 480

Val Gly Asn Asn Gly Asn Ile His Ser Phe Ser Asp Ser Gln Phe Gly
                485                 490                 495

His Ile Phe Ala Phe Gly Glu Asn Arg Gln Ala Ser Arg Lys His Met
            500                 505                 510

Val Val Ala Leu Lys Glu Leu Ser Ile Arg Gly Asp Phe Arg Thr Thr
        515                 520                 525

Val Glu Tyr Leu Ile Lys Leu Leu Glu Thr Glu Asp Phe Glu Asp Asn
    530                 535                 540

Thr Ile Thr Thr Gly Trp Leu Asp Asp Leu Ile Thr His Lys Met Thr
545                 550                 555                 560

<210> SEQ ID NO 46
<211> LENGTH: 550
<212> TYPE: PRT
<213> ORGANISM: Saccharomyces cerevisiae
<220> FEATURE:
<221> NAME/KEY: MISC_FEATURE
<222> LOCATION: (1)..(550)
<223> OTHER INFORMATION: N- and C-terminal deleted Saccharomyces
      cerevisiae ACCase BC domain (AAs 17-566)

<400> SEQUENCE: 46

Glu Ile Thr Asn Tyr Ser Glu Arg His Thr Glu Leu Pro Gly His Phe
1               5                   10                  15

Ile Gly Leu Asn Thr Val Asp Lys Leu Glu Glu Ser Pro Leu Arg Asp
                20                  25                  30
```

```
Phe Val Lys Ser His Gly Gly His Thr Val Ile Ser Lys Ile Leu Ile
             35                  40                  45

Ala Asn Asn Gly Ile Ala Ala Val Lys Glu Ile Arg Ser Val Arg Lys
 50                  55                  60

Trp Ala Tyr Glu Thr Phe Gly Asp Asp Arg Thr Val Gln Phe Val Ala
 65                  70                  75                  80

Met Ala Thr Pro Glu Asp Leu Glu Ala Asn Ala Glu Tyr Ile Arg Met
                 85                  90                  95

Ala Asp Gln Tyr Ile Glu Val Pro Gly Gly Thr Asn Asn Asn Asn Tyr
                100                 105                 110

Ala Asn Val Asp Leu Ile Val Asp Ile Ala Glu Arg Ala Asp Val Asp
                115                 120                 125

Ala Val Trp Ala Gly Trp Gly His Ala Ser Glu Asn Pro Leu Leu Pro
130                 135                 140

Glu Lys Leu Ser Gln Ser Lys Arg Lys Val Ile Phe Ile Gly Pro Pro
145                 150                 155                 160

Gly Asn Ala Met Arg Ser Leu Gly Asp Lys Ile Ser Ser Thr Ile Val
                165                 170                 175

Ala Gln Ser Ala Lys Val Pro Cys Ile Pro Trp Ser Gly Thr Gly Val
                180                 185                 190

Asp Thr Val His Val Asp Glu Lys Thr Gly Leu Val Ser Val Asp Asp
                195                 200                 205

Asp Ile Tyr Gln Lys Gly Cys Cys Thr Ser Pro Glu Asp Gly Leu Gln
                210                 215                 220

Lys Ala Lys Arg Ile Gly Phe Pro Val Met Ile Lys Ala Ser Glu Gly
225                 230                 235                 240

Gly Gly Gly Lys Gly Ile Arg Gln Val Glu Arg Glu Glu Asp Phe Ile
                245                 250                 255

Ala Leu Tyr His Gln Ala Ala Asn Glu Ile Pro Gly Ser Pro Ile Phe
                260                 265                 270

Ile Met Lys Leu Ala Gly Arg Ala Arg His Leu Glu Val Gln Leu Leu
                275                 280                 285

Ala Asp Gln Tyr Gly Thr Asn Ile Ser Leu Phe Gly Arg Asp Cys Ser
                290                 295                 300

Val Gln Arg Arg His Gln Lys Ile Ile Glu Glu Ala Pro Val Thr Ile
305                 310                 315                 320

Ala Lys Ala Glu Thr Phe His Glu Met Glu Lys Ala Ala Val Arg Leu
                325                 330                 335

Gly Lys Leu Val Gly Tyr Val Ser Ala Gly Thr Val Glu Tyr Leu Tyr
                340                 345                 350

Ser His Asp Asp Gly Lys Phe Tyr Phe Leu Glu Leu Asn Pro Arg Leu
                355                 360                 365

Gln Val Glu His Pro Thr Thr Glu Met Val Ser Gly Val Asn Leu Pro
                370                 375                 380

Ala Ala Gln Leu Gln Ile Ala Met Gly Ile Pro Met His Arg Ile Ser
385                 390                 395                 400

Asp Ile Arg Thr Leu Tyr Gly Met Asn Pro His Ser Ala Ser Glu Ile
                405                 410                 415

Asp Phe Glu Phe Lys Thr Gln Asp Ala Thr Lys Lys Gln Arg Arg Pro
                420                 425                 430

Ile Pro Lys Gly His Cys Thr Ala Cys Arg Ile Thr Ser Glu Asp Pro
                435                 440                 445
```

```
Asn Asp Gly Phe Lys Pro Ser Gly Gly Thr Leu His Glu Leu Asn Phe
    450                 455                 460
Arg Ser Ser Ser Asn Val Trp Gly Tyr Phe Ser Val Gly Asn Asn Gly
465                 470                 475                 480
Asn Ile His Ser Phe Ser Asp Ser Gln Phe Gly His Ile Phe Ala Phe
                485                 490                 495
Gly Glu Asn Arg Gln Ala Ser Arg Lys His Met Val Val Ala Leu Lys
                500                 505                 510
Glu Leu Ser Ile Arg Gly Asp Phe Arg Thr Thr Val Glu Tyr Leu Ile
                515                 520                 525
Lys Leu Leu Glu Thr Glu Asp Phe Glu Asp Asn Thr Ile Thr Thr Gly
    530                 535                 540
Trp Leu Asp Asp Leu Ile
545                 550

<210> SEQ ID NO 47
<211> LENGTH: 540
<212> TYPE: PRT
<213> ORGANISM: Saccharomyces cerevisiae
<220> FEATURE:
<221> NAME/KEY: MISC_FEATURE
<222> LOCATION: (1)..(540)
<223> OTHER INFORMATION: N- and C-terminal deleted Saccharomyces
      cerevisiae ACCase BC domain (AAs 22-561)

<400> SEQUENCE: 47

Ser Glu Arg His Thr Glu Leu Pro Gly His Phe Ile Gly Leu Asn Thr
1               5                   10                  15
Val Asp Lys Leu Glu Glu Ser Pro Leu Arg Asp Phe Val Lys Ser His
                20                  25                  30
Gly Gly His Thr Val Ile Ser Lys Ile Leu Ile Ala Asn Asn Gly Ile
            35                  40                  45
Ala Ala Val Lys Glu Ile Arg Ser Val Arg Lys Trp Ala Tyr Glu Thr
        50                  55                  60
Phe Gly Asp Asp Arg Thr Val Gln Phe Val Ala Met Ala Thr Pro Glu
65                  70                  75                  80
Asp Leu Glu Ala Asn Ala Glu Tyr Ile Arg Met Ala Asp Gln Tyr Ile
                85                  90                  95
Glu Val Pro Gly Gly Thr Asn Asn Asn Tyr Ala Asn Val Asp Leu
                100                 105                 110
Ile Val Asp Ile Ala Glu Arg Ala Asp Val Asp Ala Val Trp Ala Gly
            115                 120                 125
Trp Gly His Ala Ser Glu Asn Pro Leu Leu Pro Glu Lys Leu Ser Gln
    130                 135                 140
Ser Lys Arg Lys Val Ile Phe Ile Gly Pro Pro Gly Asn Ala Met Arg
145                 150                 155                 160
Ser Leu Gly Asp Lys Ile Ser Ser Thr Ile Val Ala Gln Ser Ala Lys
                165                 170                 175
Val Pro Cys Ile Pro Trp Ser Gly Thr Gly Val Asp Thr Val His Val
                180                 185                 190
Asp Glu Lys Thr Gly Leu Val Ser Val Asp Asp Ile Tyr Gln Lys
            195                 200                 205
Gly Cys Cys Thr Ser Pro Glu Asp Gly Leu Gln Lys Ala Lys Arg Ile
    210                 215                 220
Gly Phe Pro Val Met Ile Lys Ala Ser Glu Gly Gly Gly Gly Lys Gly
225                 230                 235                 240
```

-continued

```
Ile Arg Gln Val Glu Arg Glu Glu Asp Phe Ile Ala Leu Tyr His Gln
                245                 250                 255

Ala Ala Asn Glu Ile Pro Gly Ser Pro Ile Phe Ile Met Lys Leu Ala
            260                 265                 270

Gly Arg Ala Arg His Leu Glu Val Gln Leu Leu Ala Asp Gln Tyr Gly
        275                 280                 285

Thr Asn Ile Ser Leu Phe Gly Arg Asp Cys Ser Val Gln Arg Arg His
    290                 295                 300

Gln Lys Ile Ile Glu Glu Ala Pro Val Thr Ile Ala Lys Ala Glu Thr
305                 310                 315                 320

Phe His Glu Met Glu Lys Ala Ala Val Arg Leu Gly Lys Leu Val Gly
                325                 330                 335

Tyr Val Ser Ala Gly Thr Val Glu Tyr Leu Tyr Ser His Asp Asp Gly
            340                 345                 350

Lys Phe Tyr Phe Leu Glu Leu Asn Pro Arg Leu Gln Val Glu His Pro
        355                 360                 365

Thr Thr Glu Met Val Ser Gly Val Asn Leu Pro Ala Ala Gln Leu Gln
    370                 375                 380

Ile Ala Met Gly Ile Pro Met His Arg Ile Ser Asp Ile Arg Thr Leu
385                 390                 395                 400

Tyr Gly Met Asn Pro His Ser Ala Ser Glu Ile Asp Phe Glu Phe Lys
                405                 410                 415

Thr Gln Asp Ala Thr Lys Lys Gln Arg Arg Pro Ile Pro Lys Gly His
            420                 425                 430

Cys Thr Ala Cys Arg Ile Thr Ser Glu Asp Pro Asn Asp Gly Phe Lys
        435                 440                 445

Pro Ser Gly Gly Thr Leu His Glu Leu Asn Phe Arg Ser Ser Ser Asn
    450                 455                 460

Val Trp Gly Tyr Phe Ser Val Gly Asn Asn Gly Asn Ile His Ser Phe
465                 470                 475                 480

Ser Asp Ser Gln Phe Gly His Ile Phe Ala Phe Gly Glu Asn Arg Gln
                485                 490                 495

Ala Ser Arg Lys His Met Val Val Ala Leu Lys Glu Leu Ser Ile Arg
            500                 505                 510

Gly Asp Phe Arg Thr Thr Val Glu Tyr Leu Ile Lys Leu Leu Glu Thr
        515                 520                 525

Glu Asp Phe Glu Asp Asn Thr Ile Thr Thr Gly Trp
    530                 535                 540
```

<210> SEQ ID NO 48
<211> LENGTH: 545
<212> TYPE: PRT
<213> ORGANISM: Phytophthora infestans
<220> FEATURE:
<221> NAME/KEY: MISC_FEATURE
<222> LOCATION: (1)..(545)
<223> OTHER INFORMATION: N-terminal deleted Phytophthora ACCase BC domain (AAs 11-555)

<400> SEQUENCE: 48

```
Asp Val Ala Ala Tyr Ala Glu Thr Arg Ser Asp Ser Asn Pro Leu Asn
1               5                   10                  15

Tyr Ala Ser Met Glu Glu Tyr Val Arg Leu Gln Lys Gly Thr Arg Pro
            20                  25                  30

Ile Thr Ser Val Leu Ile Ala Asn Asn Gly Ile Ser Ala Val Lys Ala
        35                  40                  45
```

```
Ile Arg Ser Ile Arg Ser Trp Ser Tyr Glu Met Phe Ala Asp Glu His
 50                  55                  60

Val Val Thr Phe Val Val Met Ala Thr Pro Glu Asp Leu Lys Ala Asn
 65                  70                  75                  80

Ala Glu Tyr Ile Arg Met Ala Glu His Val Val Glu Val Pro Gly Gly
                 85                  90                  95

Ser Asn Asn His Asn Tyr Ala Asn Val Ser Leu Ile Ile Glu Ile Ala
                100                 105                 110

Glu Arg Phe Asn Val Asp Ala Val Trp Ala Gly Trp Gly His Ala Ser
            115                 120                 125

Glu Asn Pro Leu Leu Pro Asp Thr Leu Ala Gln Thr Glu Arg Lys Ile
130                 135                 140

Val Phe Ile Gly Pro Pro Gly Lys Pro Met Arg Ala Leu Gly Asp Lys
145                 150                 155                 160

Ile Gly Ser Thr Ile Ile Ala Gln Ser Ala Lys Val Pro Thr Ile Ala
                165                 170                 175

Trp Asn Gly Asp Gly Met Glu Val Asp Tyr Lys Glu His Asp Gly Ile
                180                 185                 190

Pro Asp Glu Ile Tyr Asn Ala Ala Met Leu Arg Asp Gly Gln His Cys
            195                 200                 205

Leu Asp Glu Cys Lys Arg Ile Gly Phe Pro Val Met Ile Lys Ala Ser
210                 215                 220

Glu Gly Gly Gly Gly Lys Gly Ile Arg Met Val His Glu Glu Ser Gln
225                 230                 235                 240

Val Leu Ser Ala Trp Glu Ala Val Arg Gly Glu Ile Pro Gly Ser Pro
                245                 250                 255

Ile Phe Val Met Lys Leu Ala Pro Lys Ser Arg His Leu Glu Val Gln
                260                 265                 270

Leu Leu Ala Asp Thr Tyr Gly Asn Ala Ile Ala Leu Ser Gly Arg Asp
            275                 280                 285

Cys Ser Val Gln Arg Arg His Gln Lys Ile Val Glu Glu Gly Pro Val
290                 295                 300

Leu Ala Pro Thr Gln Glu Val Trp Glu Lys Met Met Arg Ala Ala Thr
305                 310                 315                 320

Arg Leu Ala Gln Glu Val Glu Tyr Val Asn Ala Gly Thr Val Glu Tyr
                325                 330                 335

Leu Phe Ser Glu Leu Pro Glu Asp Asn Gly Asn Ser Phe Phe Phe Leu
            340                 345                 350

Glu Leu Asn Pro Arg Leu Gln Val Glu His Pro Val Thr Glu Met Ile
            355                 360                 365

Thr His Val Asn Leu Pro Ala Ala Gln Leu Gln Val Ala Met Gly Ile
370                 375                 380

Pro Leu His Cys Ile Pro Asp Val Arg Arg Leu Tyr Asn Lys Asp Ala
385                 390                 395                 400

Phe Glu Thr Thr Val Ile Asp Phe Asp Ala Glu Lys Gln Lys Pro Pro
                405                 410                 415

His Gly His Val Ile Ala Ala Arg Ile Thr Ala Glu Asp Pro Asn Ala
                420                 425                 430

Gly Phe Gln Pro Thr Ser Gly Ala Ile Gln Glu Leu Asn Phe Arg Ser
            435                 440                 445

Thr Pro Asp Val Trp Gly Tyr Phe Ser Val Asp Ser Ser Gly Gln Val
450                 455                 460

His Glu Phe Ala Asp Ser Gln Ile Gly His Leu Phe Ser Trp Ser Pro
```

-continued

```
465                 470                 475                 480

Thr Arg Glu Lys Ala Arg Lys Asn Met Val Leu Ala Leu Lys Glu Leu
                485                 490                 495

Ser Ile Arg Gly Asp Ile His Thr Thr Val Glu Tyr Ile Val Asn Met
            500                 505                 510

Met Glu Ser Asp Asp Phe Lys Tyr Asn Arg Ile Ser Thr Ser Trp Leu
        515                 520                 525

Asp Glu Arg Ile Ser His His Asn Glu Val Arg Leu Gln Gly Arg Pro
    530                 535                 540

Asp
545

<210> SEQ ID NO 49
<211> LENGTH: 535
<212> TYPE: PRT
<213> ORGANISM: Phytophthora infestans
<220> FEATURE:
<221> NAME/KEY: MISC_FEATURE
<222> LOCATION: (1)..(535)
<223> OTHER INFORMATION: N-terminal deleted Phytophthora ACCase BC
      domain (AAs 21-555)

<400> SEQUENCE: 49

Asp Ser Asn Pro Leu Asn Tyr Ala Ser Met Glu Glu Tyr Val Arg Leu
1               5                   10                  15

Gln Lys Gly Thr Arg Pro Ile Thr Ser Val Leu Ile Ala Asn Asn Gly
            20                  25                  30

Ile Ser Ala Val Lys Ala Ile Arg Ser Ile Arg Ser Trp Ser Tyr Glu
        35                  40                  45

Met Phe Ala Asp Glu His Val Val Thr Phe Val Val Met Ala Thr Pro
    50                  55                  60

Glu Asp Leu Lys Ala Asn Ala Glu Tyr Ile Arg Met Ala Glu His Val
65                  70                  75                  80

Val Glu Val Pro Gly Gly Ser Asn Asn His Asn Tyr Ala Asn Val Ser
                85                  90                  95

Leu Ile Ile Glu Ile Ala Glu Arg Phe Asn Val Asp Ala Val Trp Ala
            100                 105                 110

Gly Trp Gly His Ala Ser Glu Asn Pro Leu Leu Pro Asp Thr Leu Ala
        115                 120                 125

Gln Thr Glu Arg Lys Ile Val Phe Ile Gly Pro Pro Gly Lys Pro Met
    130                 135                 140

Arg Ala Leu Gly Asp Lys Ile Gly Ser Thr Ile Ile Ala Gln Ser Ala
145                 150                 155                 160

Lys Val Pro Thr Ile Ala Trp Asn Gly Asp Gly Met Glu Val Asp Tyr
                165                 170                 175

Lys Glu His Asp Gly Ile Pro Asp Glu Ile Tyr Asn Ala Ala Met Leu
            180                 185                 190

Arg Asp Gly Gln His Cys Leu Asp Glu Cys Lys Arg Ile Gly Phe Pro
        195                 200                 205

Val Met Ile Lys Ala Ser Glu Gly Gly Gly Gly Lys Gly Ile Arg Met
    210                 215                 220

Val His Glu Glu Ser Gln Val Leu Ser Ala Trp Glu Ala Val Arg Gly
225                 230                 235                 240

Glu Ile Pro Gly Ser Pro Ile Phe Val Met Lys Leu Ala Pro Lys Ser
                245                 250                 255

Arg His Leu Glu Val Gln Leu Leu Ala Asp Thr Tyr Gly Asn Ala Ile
```

```
            260                 265                 270

Ala Leu Ser Gly Arg Asp Cys Ser Val Gln Arg Arg His Gln Lys Ile
        275                 280                 285
Val Glu Glu Gly Pro Val Leu Ala Pro Thr Gln Glu Val Trp Glu Lys
    290                 295                 300
Met Met Arg Ala Ala Thr Arg Leu Ala Gln Glu Val Glu Tyr Val Asn
305                 310                 315                 320
Ala Gly Thr Val Glu Tyr Leu Phe Ser Glu Leu Pro Glu Asp Asn Gly
                325                 330                 335

Asn Ser Phe Phe Phe Leu Glu Leu Asn Pro Arg Leu Gln Val Glu His
            340                 345                 350
Pro Val Thr Glu Met Ile Thr His Val Asn Leu Pro Ala Ala Gln Leu
        355                 360                 365
Gln Val Ala Met Gly Ile Pro Leu His Cys Ile Pro Asp Val Arg Arg
    370                 375                 380
Leu Tyr Asn Lys Asp Ala Phe Glu Thr Thr Val Ile Asp Phe Asp Ala
385                 390                 395                 400
Glu Lys Gln Lys Pro Pro His Gly His Val Ile Ala Ala Arg Ile Thr
                405                 410                 415

Ala Glu Asp Pro Asn Ala Gly Phe Gln Pro Thr Ser Gly Ala Ile Gln
            420                 425                 430
Glu Leu Asn Phe Arg Ser Thr Pro Asp Val Trp Gly Tyr Phe Ser Val
        435                 440                 445
Asp Ser Ser Gly Gln Val His Glu Phe Ala Asp Ser Gln Ile Gly His
    450                 455                 460
Leu Phe Ser Trp Ser Pro Thr Arg Glu Lys Ala Arg Lys Asn Met Val
465                 470                 475                 480
Leu Ala Leu Lys Glu Leu Ser Ile Arg Gly Asp Ile His Thr Thr Val
                485                 490                 495

Glu Tyr Ile Val Asn Met Met Glu Ser Asp Asp Phe Lys Tyr Asn Arg
            500                 505                 510
Ile Ser Thr Ser Trp Leu Asp Glu Arg Ile Ser His His Asn Glu Val
        515                 520                 525
Arg Leu Gln Gly Arg Pro Asp
    530                 535

<210> SEQ ID NO 50
<211> LENGTH: 545
<212> TYPE: PRT
<213> ORGANISM: Phytophthora infestans
<220> FEATURE:
<221> NAME/KEY: MISC_FEATURE
<222> LOCATION: (1)..(545)
<223> OTHER INFORMATION: C-terminal deleted Phytophthora ACCase BC
      domain (AAs 1-545)

<400> SEQUENCE: 50

Met Val Ala Glu Glu Ala Pro Pro Ala Ala Asp Val Ala Ala Tyr Ala
1               5                   10                  15
Glu Thr Arg Ser Asp Ser Asn Pro Leu Asn Tyr Ala Ser Met Glu Glu
            20                  25                  30

Tyr Val Arg Leu Gln Lys Gly Thr Arg Pro Ile Thr Ser Val Leu Ile
        35                  40                  45

Ala Asn Asn Gly Ile Ser Ala Val Lys Ala Ile Arg Ser Ile Arg Ser
    50                  55                  60

Trp Ser Tyr Glu Met Phe Ala Asp Glu His Val Val Thr Phe Val Val
```

-continued

```
             65                  70                  75                  80
Met Ala Thr Pro Glu Asp Leu Lys Ala Asn Ala Glu Tyr Ile Arg Met
                    85                  90                  95
Ala Glu His Val Val Glu Val Pro Gly Gly Ser Asn Asn His Asn Tyr
                   100                 105                 110
Ala Asn Val Ser Leu Ile Ile Glu Ile Ala Glu Arg Phe Asn Val Asp
                   115                 120                 125
Ala Val Trp Ala Gly Trp Gly His Ala Ser Glu Asn Pro Leu Leu Pro
               130                 135                 140
Asp Thr Leu Ala Gln Thr Glu Arg Lys Ile Val Phe Ile Gly Pro Pro
145                 150                 155                 160
Gly Lys Pro Met Arg Ala Leu Gly Asp Lys Ile Gly Ser Thr Ile Ile
                   165                 170                 175
Ala Gln Ser Ala Lys Val Pro Thr Ile Ala Trp Asn Gly Asp Gly Met
               180                 185                 190
Glu Val Asp Tyr Lys Glu His Asp Gly Ile Pro Asp Glu Ile Tyr Asn
               195                 200                 205
Ala Ala Met Leu Arg Asp Gly Gln His Cys Leu Asp Glu Cys Lys Arg
210                 215                 220
Ile Gly Phe Pro Val Met Ile Lys Ala Ser Glu Gly Gly Gly Gly Lys
225                 230                 235                 240
Gly Ile Arg Met Val His Glu Glu Ser Gln Val Leu Ser Ala Trp Glu
                   245                 250                 255
Ala Val Arg Gly Glu Ile Pro Gly Ser Pro Ile Phe Val Met Lys Leu
               260                 265                 270
Ala Pro Lys Ser Arg His Leu Glu Val Gln Leu Leu Ala Asp Thr Tyr
               275                 280                 285
Gly Asn Ala Ile Ala Leu Ser Gly Arg Asp Cys Ser Val Gln Arg Arg
               290                 295                 300
His Gln Lys Ile Val Glu Glu Gly Pro Val Leu Ala Pro Thr Gln Glu
305                 310                 315                 320
Val Trp Glu Lys Met Met Arg Ala Ala Thr Arg Leu Ala Gln Glu Val
                   325                 330                 335
Glu Tyr Val Asn Ala Gly Thr Val Glu Tyr Leu Phe Ser Glu Leu Pro
                   340                 345                 350
Glu Asp Asn Gly Asn Ser Phe Phe Phe Leu Glu Leu Asn Pro Arg Leu
               355                 360                 365
Gln Val Glu His Pro Val Thr Glu Met Ile Thr His Val Asn Leu Pro
               370                 375                 380
Ala Ala Gln Leu Gln Val Ala Met Gly Ile Pro Leu His Cys Ile Pro
385                 390                 395                 400
Asp Val Arg Arg Leu Tyr Asn Lys Asp Ala Phe Glu Thr Thr Val Ile
                   405                 410                 415
Asp Phe Asp Ala Glu Lys Gln Lys Pro Pro His Gly His Val Ile Ala
               420                 425                 430
Ala Arg Ile Thr Ala Glu Asp Pro Asn Ala Gly Phe Gln Pro Thr Ser
               435                 440                 445
Gly Ala Ile Gln Glu Leu Asn Phe Arg Ser Thr Pro Asp Val Trp Gly
               450                 455                 460
Tyr Phe Ser Val Asp Ser Ser Gly Gln Val His Glu Phe Ala Asp Ser
465                 470                 475                 480
Gln Ile Gly His Leu Phe Ser Trp Ser Pro Thr Arg Glu Lys Ala Arg
                   485                 490                 495
```

```
Lys Asn Met Val Leu Ala Leu Lys Glu Leu Ser Ile Arg Gly Asp Ile
            500                 505                 510

His Thr Thr Val Glu Tyr Ile Val Asn Met Met Glu Ser Asp Asp Phe
            515                 520                 525

Lys Tyr Asn Arg Ile Ser Thr Ser Trp Leu Asp Glu Arg Ile Ser His
            530                 535                 540

His
545

<210> SEQ ID NO 51
<211> LENGTH: 535
<212> TYPE: PRT
<213> ORGANISM: Phytophthora infestans
<220> FEATURE:
<221> NAME/KEY: MISC_FEATURE
<222> LOCATION: (1)..(535)
<223> OTHER INFORMATION: C-terminal deleted Phytophthora ACCase BC -continued Gly Asn Ala Ile Ala Leu Ser Gly Arg Asp Cys Ser Val Gln Arg Arg
290 295 300

His Gln Lys Ile Val Glu Glu Gly Pro Val Leu Ala Pro Thr Gln Glu
305 310 315 320

Val Trp Glu Lys Met Met Arg Ala Ala Thr Arg Leu Ala Gln Glu Val
325 330 335

Glu Tyr Val Asn Ala Gly Thr Val Glu Tyr Leu Phe Ser Glu Leu Pro
340 345 350

Glu Asp Asn Gly Asn Ser Phe Phe Phe Leu Glu Leu Asn Pro Arg Leu
355 360 365

Gln Val Glu His Pro Val Thr Glu Met Ile Thr His Val Asn Leu Pro
370 375 380

Ala Ala Gln Leu Gln Val Ala Met Gly Ile Pro Leu His Cys Ile Pro
385 390 395 400

Asp Val Arg Arg Leu Tyr Asn Lys Asp Ala Phe Glu Thr Thr Val Ile
405 410 415

Asp Phe Asp Ala Glu Lys Gln Lys Pro Pro His Gly His Val Ile Ala
420 425 430

Ala Arg Ile Thr Ala Glu Asp Pro Asn Ala Gly Phe Gln Pro Thr Ser
435 440 445

Gly Ala Ile Gln Glu Leu Asn Phe Arg Ser Thr Pro Asp Val Trp Gly
450 455 460

Tyr Phe Ser Val Asp Ser Ser Gly Gln Val His Glu Phe Ala Asp Ser
465 470 475 480

Gln Ile Gly His Leu Phe Ser Trp Ser Pro Thr Arg Glu Lys Ala Arg
485 490 495

Lys Asn Met Val Leu Ala Leu Lys Glu Leu Ser Ile Arg Gly Asp Ile
500 505 510

His Thr Thr Val Glu Tyr Ile Val Asn Met Met Glu Ser Asp Asp Phe
515 520 525

Lys Tyr Asn Arg Ile Ser Thr
530 535

<210> SEQ ID NO 52
<211> LENGTH: 581
<212> TYPE: PRT
<213> ORGANISM: Magnaporthe grisea
<220> FEATURE:
<221> NAME/KEY: MISC_FEATURE
<222> LOCATION: (1)..(581)
<223> OTHER INFORMATION: N-terminal deleted Magnaporthe ACCase BC domain
(AAs 12-592

<400> SEQUENCE: 52

Asn Ser Ser Arg Gln Arg Asn Gly Ala Asn Gly Val Thr Val Pro Val
1 5 10 15

Ala Asn Gly Lys Ala Thr Tyr Ala Gln Arg His Lys Ile Ala Asp His
20 25 30

Phe Ile Gly Gly Asn Arg Leu Glu Asn Ala Pro Pro Ser Lys Val Lys
35 40 45

Glu Trp Val Ala Ala His Asp Gly His Thr Val Ile Thr Asn Val Leu
50 55 60

Ile Ala Asn Asn Gly Ile Ala Ala Val Lys Glu Ile Arg Ser Val Arg
65 70 75 80

Lys Trp Ala Tyr Glu Thr Phe Gly Asp Glu Arg Ala Ile Gln Phe Thr
85 90 95

```
Val Met Ala Thr Pro Glu Asp Leu Gln Ala Asn Ala Asp Tyr Ile Arg
            100                 105                 110

Met Ala Asp His Tyr Val Glu Val Pro Gly Gly Thr Asn Asn Asn Asn
        115                 120                 125

Tyr Ala Asn Val Glu Leu Ile Val Asp Val Ala Glu Arg Met Asn Val
    130                 135                 140

His Ala Val Trp Ala Gly Trp Gly His Ala Ser Glu Asn Pro Lys Leu
145                 150                 155                 160

Pro Glu Ser Leu Ala Ala Ser Pro Lys Lys Ile Ile Phe Ile Gly Pro
                165                 170                 175

Pro Gly Ser Ala Met Arg Ser Leu Gly Asp Lys Ile Ser Ser Thr Ile
            180                 185                 190

Val Ala Gln His Ala Gln Val Pro Cys Ile Pro Trp Ser Gly Thr Gly
        195                 200                 205

Val Asp Ala Val Gln Ile Asp Lys Lys Gly Ile Val Thr Val Asp Asp
    210                 215                 220

Asp Thr Tyr Ala Lys Gly Cys Val Thr Ser Trp Gln Glu Gly Leu Glu
225                 230                 235                 240

Lys Ala Arg Gln Ile Gly Phe Pro Val Met Ile Lys Ala Ser Glu Gly
                245                 250                 255

Gly Gly Gly Lys Gly Ile Arg Lys Ala Val Ser Glu Glu Gly Phe Glu
            260                 265                 270

Glu Leu Tyr Lys Ala Ala Ala Ser Glu Ile Pro Gly Ser Pro Ile Phe
        275                 280                 285

Ile Met Lys Leu Ala Gly Asn Ala Arg His Leu Glu Val Gln Leu Leu
    290                 295                 300

Ala Asp Gln Tyr Gly Asn Asn Ile Ser Leu Phe Gly Arg Asp Cys Ser
305                 310                 315                 320

Val Gln Arg Arg His Gln Lys Ile Ile Glu Glu Ala Pro Val Thr Ile
                325                 330                 335

Ala Lys Pro Asp Thr Phe Lys Ala Met Glu Glu Ala Ala Val Arg Leu
            340                 345                 350

Gly Arg Leu Val Gly Tyr Val Ser Ala Gly Thr Val Glu Tyr Leu Tyr
        355                 360                 365

Ser His Ala Asp Asp Lys Phe Tyr Phe Leu Glu Leu Asn Pro Arg Leu
    370                 375                 380

Gln Val Glu His Pro Thr Thr Glu Gly Val Ser Gly Val Asn Leu Pro
385                 390                 395                 400

Ala Ser Gln Leu Gln Ile Ala Met Gly Ile Pro Leu His Arg Ile Ser
                405                 410                 415

Asp Ile Arg Leu Leu Tyr Gly Val Asp Pro Lys Leu Ser Thr Glu Ile
            420                 425                 430

Asp Phe Asp Phe Lys Asn Pro Asp Ser Glu Lys Thr Gln Arg Arg Pro
        435                 440                 445

Ser Pro Lys Gly His Leu Thr Ala Cys Arg Ile Thr Ser Glu Asp Pro
    450                 455                 460

Gly Glu Gly Phe Lys Pro Ser Asn Gly Val Met His Glu Leu Asn Phe
465                 470                 475                 480

Arg Ser Ser Ser Asn Val Trp Gly Tyr Phe Ser Val Gly Thr Gln Gly
                485                 490                 495

Gly Ile His Ser Phe Ser Asp Ser Gln Phe Gly His Ile Phe Ala Tyr
            500                 505                 510
```

-continued

```
Gly Glu Asn Arg Ser Ala Ser Arg Lys His Met Val Ile Ala Leu Lys
        515                 520                 525

Glu Leu Ser Ile Arg Gly Asp Phe Arg Thr Thr Val Glu Tyr Leu Ile
    530                 535                 540

Lys Leu Leu Glu Thr Glu Ala Phe Glu Glu Asn Thr Ile Thr Thr Gly
545                 550                 555                 560

Trp Leu Asp Glu Leu Ile Ser Lys Lys Leu Thr Ala Glu Arg Pro Asp
                565                 570                 575

Lys Met Leu Ala Val
            580

<210> SEQ ID NO 53
<211> LENGTH: 571
<212> TYPE: PRT
<213> ORGANISM: Magnaporthe grisea
<220> FEATURE:
<221> NAME/KEY: MISC_FEATURE
<222> LOCATION: (1)..(571)
<223> OTHER INFORMATION: N-terminal deleted Magnaporthe ACCase BC domain
      (AAs 22-591)

<400> SEQUENCE: 53

Gly Val Thr Val Pro Val Ala Asn Gly Lys Ala Thr Tyr Ala Gln Arg
1               5                   10                  15

His Lys Ile Ala Asp His Phe Ile Gly Gly Asn Arg Leu Glu Asn Ala
            20                  25                  30

Pro Pro Ser Lys Val Lys Glu Trp Val Ala Ala His Asp Gly His Thr
        35                  40                  45

Val Ile Thr Asn Val Leu Ile Ala Asn Asn Gly Ile Ala Ala Val Lys
    50                  55                  60

Glu Ile Arg Ser Val Arg Lys Trp Ala Tyr Glu Thr Phe Gly Asp Glu
65                  70                  75                  80

Arg Ala Ile Gln Phe Thr Val Met Ala Thr Pro Glu Asp Leu Gln Ala
                85                  90                  95

Asn Ala Asp Tyr Ile Arg Met Ala Asp His Tyr Val Glu Val Pro Gly
            100                 105                 110

Gly Thr Asn Asn Asn Asn Tyr Ala Asn Val Glu Leu Ile Val Asp Val
        115                 120                 125

Ala Glu Arg Met Asn Val His Ala Val Trp Ala Gly Trp Gly His Ala
    130                 135                 140

Ser Glu Asn Pro Lys Leu Pro Glu Ser Leu Ala Ala Ser Pro Lys Lys
145                 150                 155                 160

Ile Ile Phe Ile Gly Pro Pro Gly Ser Ala Met Arg Ser Leu Gly Asp
                165                 170                 175

Lys Ile Ser Ser Thr Ile Val Ala Gln His Ala Gln Val Pro Cys Ile
            180                 185                 190

Pro Trp Ser Gly Thr Gly Val Asp Ala Val Gln Ile Asp Lys Lys Gly
        195                 200                 205

Ile Val Thr Val Asp Asp Asp Thr Tyr Ala Lys Gly Cys Val Thr Ser
    210                 215                 220

Trp Gln Glu Gly Leu Glu Lys Ala Arg Gln Ile Gly Phe Pro Val Met
225                 230                 235                 240

Ile Lys Ala Ser Glu Gly Gly Gly Gly Lys Gly Ile Arg Lys Ala Val
                245                 250                 255

Ser Glu Glu Gly Phe Glu Glu Leu Tyr Lys Ala Ala Ala Ser Glu Ile
            260                 265                 270
```

-continued

```
Pro Gly Ser Pro Ile Phe Ile Met Lys Leu Ala Gly Asn Ala Arg His
        275                 280                 285

Leu Glu Val Gln Leu Leu Ala Asp Gln Tyr Gly Asn Asn Ile Ser Leu
    290                 295                 300

Phe Gly Arg Asp Cys Ser Val Gln Arg Arg His Gln Lys Ile Ile Glu
305                 310                 315                 320

Glu Ala Pro Val Thr Ile Ala Lys Pro Asp Thr Phe Lys Ala Met Glu
                325                 330                 335

Glu Ala Ala Val Arg Leu Gly Arg Leu Val Gly Tyr Val Ser Ala Gly
            340                 345                 350

Thr Val Glu Tyr Leu Tyr Ser His Ala Asp Asp Lys Phe Tyr Phe Leu
        355                 360                 365

Glu Leu Asn Pro Arg Leu Gln Val Glu His Pro Thr Thr Glu Gly Val
    370                 375                 380

Ser Gly Val Asn Leu Pro Ala Ser Gln Leu Gln Ile Ala Met Gly Ile
385                 390                 395                 400

Pro Leu His Arg Ile Ser Asp Ile Arg Leu Leu Tyr Gly Val Asp Pro
                405                 410                 415

Lys Leu Ser Thr Glu Ile Asp Phe Asp Phe Lys Asn Pro Asp Ser Glu
            420                 425                 430

Lys Thr Gln Arg Arg Pro Ser Pro Lys Gly His Leu Thr Ala Cys Arg
        435                 440                 445

Ile Thr Ser Glu Asp Pro Gly Glu Gly Phe Lys Pro Ser Asn Gly Val
    450                 455                 460

Met His Glu Leu Asn Phe Arg Ser Ser Ser Asn Val Trp Gly Tyr Phe
465                 470                 475                 480

Ser Val Gly Thr Gln Gly Gly Ile His Ser Phe Ser Asp Ser Gln Phe
                485                 490                 495

Gly His Ile Phe Ala Tyr Gly Glu Asn Arg Ser Ala Ser Arg Lys His
            500                 505                 510

Met Val Ile Ala Leu Lys Glu Leu Ser Ile Arg Gly Asp Phe Arg Thr
        515                 520                 525

Thr Val Glu Tyr Leu Ile Lys Leu Leu Glu Thr Glu Ala Phe Glu Glu
    530                 535                 540

Asn Thr Ile Thr Thr Gly Trp Leu Asp Glu Leu Ile Ser Lys Lys Leu
545                 550                 555                 560

Thr Ala Glu Arg Pro Asp Lys Met Leu Ala Val
                565                 570

<210> SEQ ID NO 54
<211> LENGTH: 581
<212> TYPE: PRT
<213> ORGANISM: Magnaporthe grisea
<220> FEATURE:
<221> NAME/KEY: MISC_FEATURE
<222> LOCATION: (1)..(581)
<223> OTHER INFORMATION: C-terminal deleted Magnaporthe ACCase
      (AAs 2-582)

<400> SEQUENCE: 54

Thr Glu Thr Asn Gly Thr Ala Ala Ala Ala Asn Ser Ser Arg Gln Arg
1               5                   10                  15

Asn Gly Ala Asn Gly Val Thr Val Pro Val Ala Asn Gly Lys Ala Thr
            20                  25                  30

Tyr Ala Gln Arg His Lys Ile Ala Asp His Phe Ile Gly Gly Asn Arg
        35                  40                  45
```

```
Leu Glu Asn Ala Pro Pro Ser Lys Val Lys Glu Trp Val Ala His
 50                  55                  60

Asp Gly His Thr Val Ile Thr Asn Val Leu Ile Ala Asn Asn Gly Ile
 65                      70                  75                  80

Ala Ala Val Lys Glu Ile Arg Ser Val Arg Lys Trp Ala Tyr Glu Thr
                 85                  90                  95

Phe Gly Asp Glu Arg Ala Ile Gln Phe Thr Val Met Ala Thr Pro Glu
                100                 105                 110

Asp Leu Gln Ala Asn Ala Asp Tyr Ile Arg Met Ala Asp His Tyr Val
                115                 120                 125

Glu Val Pro Gly Gly Thr Asn Asn Asn Tyr Ala Asn Val Glu Leu
130                 135                 140

Ile Val Asp Val Ala Glu Arg Met Asn Val His Ala Val Trp Ala Gly
145                 150                 155                 160

Trp Gly His Ala Ser Glu Asn Pro Lys Leu Pro Glu Ser Leu Ala Ala
                165                 170                 175

Ser Pro Lys Lys Ile Ile Phe Ile Gly Pro Pro Gly Ser Ala Met Arg
                180                 185                 190

Ser Leu Gly Asp Lys Ile Ser Ser Thr Ile Val Ala Gln His Ala Gln
                195                 200                 205

Val Pro Cys Ile Pro Trp Ser Gly Thr Gly Val Asp Ala Val Gln Ile
210                 215                 220

Asp Lys Lys Gly Ile Val Thr Val Asp Asp Thr Tyr Ala Lys Gly
225                 230                 235                 240

Cys Val Thr Ser Trp Gln Glu Gly Leu Glu Lys Ala Arg Gln Ile Gly
                245                 250                 255

Phe Pro Val Met Ile Lys Ala Ser Glu Gly Gly Gly Lys Gly Ile
                260                 265                 270

Arg Lys Ala Val Ser Glu Glu Gly Phe Glu Glu Leu Tyr Lys Ala Ala
                275                 280                 285

Ala Ser Glu Ile Pro Gly Ser Pro Ile Phe Ile Met Lys Leu Ala Gly
                290                 295                 300

Asn Ala Arg His Leu Glu Val Gln Leu Leu Ala Asp Gln Tyr Gly Asn
305                 310                 315                 320

Asn Ile Ser Leu Phe Gly Arg Asp Cys Ser Val Gln Arg Arg His Gln
                325                 330                 335

Lys Ile Ile Glu Glu Ala Pro Val Thr Ile Ala Lys Pro Asp Thr Phe
                340                 345                 350

Lys Ala Met Glu Glu Ala Ala Val Arg Leu Gly Arg Leu Val Gly Tyr
                355                 360                 365

Val Ser Ala Gly Thr Val Glu Tyr Leu Tyr Ser His Ala Asp Asp Lys
370                 375                 380

Phe Tyr Phe Leu Glu Leu Asn Pro Arg Leu Gln Val Glu His Pro Thr
385                 390                 395                 400

Thr Glu Gly Val Ser Gly Val Asn Leu Pro Ala Ser Gln Leu Gln Ile
                405                 410                 415

Ala Met Gly Ile Pro Leu His Arg Ile Ser Asp Ile Arg Leu Leu Tyr
                420                 425                 430

Gly Val Asp Pro Lys Leu Ser Thr Glu Ile Asp Phe Asp Phe Lys Asn
                435                 440                 445

Pro Asp Ser Glu Lys Thr Gln Arg Arg Pro Ser Pro Lys Gly His Leu
450                 455                 460

Thr Ala Cys Arg Ile Thr Ser Glu Asp Pro Gly Glu Gly Phe Lys Pro
```

-continued

```
                465                 470                 475                 480
Ser Asn Gly Val Met His Glu Leu Asn Phe Arg Ser Ser Asn Val
                    485                 490                 495

Trp Gly Tyr Phe Ser Val Gly Thr Gln Gly Gly Ile His Ser Phe Ser
                500                 505                 510

Asp Ser Gln Phe Gly His Ile Phe Ala Tyr Gly Glu Asn Arg Ser Ala
                515                 520                 525

Ser Arg Lys His Met Val Ile Ala Leu Lys Glu Leu Ser Ile Arg Gly
            530                 535                 540

Asp Phe Arg Thr Thr Val Glu Tyr Leu Ile Lys Leu Leu Glu Thr Glu
545                 550                 555                 560

Ala Phe Glu Glu Asn Thr Ile Thr Thr Gly Trp Leu Asp Glu Leu Ile
                565                 570                 575

Ser Lys Lys Leu Thr
            580

<210> SEQ ID NO 55
<211> LENGTH: 571
<212> TYPE: PRT
<213> ORGANISM: Magnaporthe grisea
<220> FEATURE:
<221> NAME/KEY: MISC_FEATURE
<222> LOCATION: (1)..(571)
<223> OTHER INFORMATION: C-terminal deleted Magnaporthe ACCase BC domain
      (AAs 2-572)

<400> SEQUENCE: 55

Thr Glu Thr Asn Gly Thr Ala Ala Ala Ala Asn Ser Ser Arg Gln Ar

```
              225                 230                 235                 240
Cys Val Thr Ser Trp Gln Glu Gly Leu Glu Lys Ala Arg Gln Ile Gly
                245                 250                 255

Phe Pro Val Met Ile Lys Ala Ser Glu Gly Gly Gly Lys Gly Ile
            260                 265                 270

Arg Lys Ala Val Ser Glu Gly Phe Glu Glu Leu Tyr Lys Ala Ala
        275                 280                 285

Ala Ser Glu Ile Pro Gly Ser Pro Ile Phe Ile Met Lys Leu Ala Gly
    290                 295                 300

Asn Ala Arg His Leu Glu Val Gln Leu Leu Ala Asp Gln Tyr Gly Asn
305                 310                 315                 320

Asn Ile Ser Leu Phe Gly Arg Asp Cys Ser Val Gln Arg Arg His Gln
                325                 330                 335

Lys Ile Ile Glu Glu Ala Pro Val Thr Ile Ala Lys Pro Asp Thr Phe
            340                 345                 350

Lys Ala Met Glu Glu Ala Ala Val Arg Leu Gly Arg Leu Val Gly Tyr
        355                 360                 365

Val Ser Ala Gly Thr Val Glu Tyr Leu Tyr Ser His Ala Asp Asp Lys
    370                 375                 380

Phe Tyr Phe Leu Glu Leu Asn Pro Arg Leu Gln Val Glu His Pro Thr
385                 390                 395                 400

Thr Glu Gly Val Ser Gly Val Asn Leu Pro Ala Ser Gln Leu Gln Ile
                405                 410                 415

Ala Met Gly Ile Pro Leu His Arg Ile Ser Asp Ile Arg Leu Leu Tyr
            420                 425                 430

Gly Val Asp Pro Lys Leu Ser Thr Glu Ile Asp Phe Asp Phe Lys Asn
        435                 440                 445

Pro Asp Ser Glu Lys Thr Gln Arg Arg Pro Ser Pro Lys Gly His Leu
    450                 455                 460

Thr Ala Cys Arg Ile Thr Ser Glu Asp Pro Gly Glu Gly Phe Lys Pro
465                 470                 475                 480

Ser Asn Gly Val Met His Glu Leu Asn Phe Arg Ser Ser Ser Asn Val
                485                 490                 495

Trp Gly Tyr Phe Ser Val Gly Thr Gln Gly Gly Ile His Ser Phe Ser
            500                 505                 510

Asp Ser Gln Phe Gly His Ile Phe Ala Tyr Gly Glu Asn Arg Ser Ala
        515                 520                 525

Ser Arg Lys His Met Val Ile Ala Leu Lys Glu Leu Ser Ile Arg Gly
    530                 535                 540

Asp Phe Arg Thr Thr Val Glu Tyr Leu Ile Lys Leu Leu Glu Thr Glu
545                 550                 555                 560

Ala Phe Glu Glu Asn Thr Ile Thr Thr Gly Trp
                565                 570

<210> SEQ ID NO 56
<211> LENGTH: 622
<212> TYPE: PRT
<213> ORGANISM: Homo sapiens
<220> FEATURE:
<221> NAME/KEY: MISC_FEATURE
<222> LOCATION: (1)..(622)
<223> OTHER INFORMATION: C-terminal deleted Human ACCase1 BC domain
      (AAs 1-622)

<400> SEQUENCE: 56

Met Asp Glu Pro Ser Pro Leu Ala Gln Pro Leu Glu Leu Asn Gln His
```

-continued

```
1               5                   10                  15
Ser Arg Phe Ile Ile Gly Ser Val Ser Glu Asp Asn Ser Glu Asp Glu
                20                  25                  30
Ile Ser Asn Leu Val Lys Leu Asp Leu Leu Glu Glu Lys Glu Gly Ser
                35                  40                  45
Leu Ser Pro Ala Ser Val Gly Ser Asp Thr Leu Ser Asp Leu Gly Ile
 50                 55                  60
Ser Ser Leu Gln Asp Gly Leu Ala Leu His Ile Arg Ser Ser Met Ser
 65                 70                  75                  80
Gly Leu His Leu Val Lys Gln Gly Arg Asp Arg Lys Lys Ile Asp Ser
                85                  90                  95
Gln Arg Asp Phe Thr Val Ala Ser Pro Ala Glu Phe Val Thr Arg Phe
                100                 105                 110
Gly Gly Asn Lys Val Ile Glu Lys Val Leu Ile Ala Asn Asn Gly Ile
                115                 120                 125
Ala Ala Val Lys Cys Met Arg Ser Ile Arg Arg Trp Ser Tyr Glu Met
                130                 135                 140
Phe Arg Asn Glu Arg Ala Ile Arg Phe Val Val Met Val Thr Pro Glu
145                 150                 155                 160
Asp Leu Lys Ala Asn Ala Glu Tyr Ile Lys Met Ala Asp His Tyr Val
                165                 170                 175
Pro Val Pro Gly Gly Pro Asn Asn Asn Tyr Ala Asn Val Glu Leu
                180                 185                 190
Ile Leu Asp Ile Ala Lys Arg Ile Pro Val Gln Ala Val Trp Ala Gly
                195                 200                 205
Trp Gly His Ala Ser Glu Asn Pro Lys Leu Pro Glu Leu Leu Leu Lys
                210                 215                 220
Asn Gly Ile Ala Phe Met Gly Pro Pro Ser Gln Ala Met Trp Ala Leu
225                 230                 235                 240
Gly Asp Lys Ile Ala Ser Ser Ile Val Ala Gln Thr Ala Gly Ile Pro
                245                 250                 255
Thr Leu Pro Trp Ser Gly Ser Gly Leu Arg Val Asp Trp Gln Glu Asn
                260                 265                 270
Asp Phe Ser Lys Arg Ile Leu Asn Val Pro Gln Glu Leu Tyr Glu Lys
                275                 280                 285
Gly Tyr Val Lys Asp Val Asp Asp Gly Leu Lys Ala Ala Glu Glu Val
                290                 295                 300
Gly Tyr Pro Val Met Ile Lys Ala Ser Glu Gly Gly Gly Gly Lys Gly
305                 310                 315                 320
Ile Arg Lys Val Asn Asn Ala Asp Asp Phe Pro Asn Leu Phe Arg Gln
                325                 330                 335
Val Gln Ala Glu Val Pro Gly Ser Pro Ile Phe Val Met Arg Leu Ala
                340                 345                 350
Lys Gln Ser Arg His Leu Glu Val Gln Ile Leu Ala Asp Gln Tyr Gly
                355                 360                 365
Asn Ala Ile Ser Leu Phe Gly Arg Asp Cys Ser Val Gln Arg Arg His
                370                 375                 380
Gln Lys Ile Ile Glu Glu Ala Pro Ala Thr Ile Ala Thr Pro Ala Val
385                 390                 395                 400
Phe Glu His Met Glu Gln Cys Ala Val Lys Leu Ala Lys Met Val Gly
                405                 410                 415
Tyr Val Ser Ala Gly Thr Val Glu Tyr Leu Tyr Ser Gln Asp Gly Ser
                420                 425                 430
```

-continued

Phe Tyr Phe Leu Glu Leu Asn Pro Arg Leu Gln Val Glu His Pro Cys
            435                 440                 445

Thr Glu Met Val Ala Asp Val Asn Leu Pro Ala Ala Gln Leu Gln Ile
    450                 455                 460

Ala Met Gly Ile Pro Leu Tyr Arg Ile Lys Asp Ile Arg Met Met Tyr
465                 470                 475                 480

Gly Val Ser Pro Trp Gly Asp Ser Pro Ile Asp Phe Glu Asp Ser Ala
                485                 490                 495

His Val Pro Cys Pro Arg Gly His Val Ile Ala Ala Arg Ile Thr Ser
            500                 505                 510

Glu Asn Pro Asp Glu Gly Phe Lys Pro Ser Ser Gly Thr Val Gln Glu
        515                 520                 525

Leu Asn Phe Arg Ser Asn Lys Asn Val Trp Gly Tyr Phe Ser Val Ala
    530                 535                 540

Ala Ala Gly Gly Leu His Glu Phe Ala Asp Ser Gln Phe Gly His Cys
545                 550                 555                 560

Phe Ser Trp Gly Glu Asn Arg Glu Glu Ala Ile Ser Asn Met Val Val
                565                 570                 575

Ala Leu Lys Glu Leu Ser Ile Arg Gly Asp Phe Arg Thr Thr Val Glu
            580                 585                 590

Tyr Leu Ile Lys Leu Leu Glu Thr Glu Ser Phe Gln Met Asn Arg Ile
        595                 600                 605

Asp Thr Gly Trp Leu Asp Arg Leu Ile Ala Glu Lys Val Gln
    610                 615                 620

<210> SEQ ID NO 57
<211> LENGTH: 612
<212> TYPE: PRT
<213> ORGANISM: Homo sapiens
<220> FEATURE:
<221> NAME/KEY: MISC_FEATURE
<222> LOCATION: (1)..(612)
<223> OTHER INFORMATION: C-terminal deleted Human ACCase1 BC domain
      (AAs 1-612)

<400> SEQUENCE: 57

Met Asp Glu Pro Ser Pro Leu Ala Gln Pro Leu Glu Leu Asn Gln His
1               5                   10                  15

Ser Arg Phe Ile Ile Gly Ser Val Ser Glu Asp Asn Ser Glu Asp Glu
            20                  25                  30

Ile Ser Asn Leu Val Lys Leu Asp Leu Leu Glu Glu Lys Glu Gly Ser
        35                  40                  45

Leu Ser Pro Ala Ser Val Gly Ser Asp Thr Leu Ser Asp Leu Gly Ile
    50                  55                  60

Ser Ser Leu Gln Asp Gly Leu Ala Leu His Ile Arg Ser Ser Met Ser
65                  70                  75                  80

Gly Leu His Leu Val Lys Gln Gly Arg Asp Arg Lys Lys Ile Asp Ser
                85                  90                  95

Gln Arg Asp Phe Thr Val Ala Ser Pro Ala Glu Phe Val Thr Arg Phe
            100                 105                 110

Gly Gly Asn Lys Val Ile Glu Lys Val Leu Ile Ala Asn Asn Gly Ile
        115                 120                 125

Ala Ala Val Lys Cys Met Arg Ser Ile Arg Arg Trp Ser Tyr Glu Met
    130                 135                 140

Phe Arg Asn Glu Arg Ala Ile Arg Phe Val Val Met Val Thr Pro Glu
145                 150                 155                 160

```
Asp Leu Lys Ala Asn Ala Glu Tyr Ile Lys Met Ala Asp His Tyr Val
            165                 170                 175
Pro Val Pro Gly Gly Pro Asn Asn Asn Tyr Ala Asn Val Glu Leu
        180                 185                 190
Ile Leu Asp Ile Ala Lys Arg Ile Pro Val Gln Ala Val Trp Ala Gly
            195                 200                 205
Trp Gly His Ala Ser Glu Asn Pro Lys Leu Pro Glu Leu Leu Leu Lys
        210                 215                 220
Asn Gly Ile Ala Phe Met Gly Pro Pro Ser Gln Ala Met Trp Ala Leu
225                 230                 235                 240
Gly Asp Lys Ile Ala Ser Ser Ile Val Ala Gln Thr Ala Gly Ile Pro
            245                 250                 255
Thr Leu Pro Trp Ser Gly Ser Gly Leu Arg Val Asp Trp Gln Glu Asn
            260                 265                 270
Asp Phe Ser Lys Arg Ile Leu Asn Val Pro Gln Glu Leu Tyr Glu Lys
        275                 280                 285
Gly Tyr Val Lys Asp Val Asp Asp Gly Leu Lys Ala Ala Glu Glu Val
    290                 295                 300
Gly Tyr Pro Val Met Ile Lys Ala Ser Glu Gly Gly Gly Lys Gly
305                 310                 315                 320
Ile Arg Lys Val Asn Asn Ala Asp Asp Phe Pro Asn Leu Phe Arg Gln
            325                 330                 335
Val Gln Ala Glu Val Pro Gly Ser Pro Ile Phe Val Met Arg Leu Ala
            340                 345                 350
Lys Gln Ser Arg His Leu Glu Val Gln Ile Leu Ala Asp Gln Tyr Gly
            355                 360                 365
Asn Ala Ile Ser Leu Phe Gly Arg Asp Cys Ser Val Gln Arg Arg His
            370                 375                 380
Gln Lys Ile Ile Glu Glu Ala Pro Ala Thr Ile Ala Thr Pro Ala Val
385                 390                 395                 400
Phe Glu His Met Glu Gln Cys Ala Val Lys Leu Ala Lys Met Val Gly
            405                 410                 415
Tyr Val Ser Ala Gly Thr Val Glu Tyr Leu Tyr Ser Gln Asp Gly Ser
            420                 425                 430
Phe Tyr Phe Leu Glu Leu Asn Pro Arg Leu Gln Val Glu His Pro Cys
        435                 440                 445
Thr Glu Met Val Ala Asp Val Asn Leu Pro Ala Ala Gln Leu Gln Ile
        450                 455                 460
Ala Met Gly Ile Pro Leu Tyr Arg Ile Lys Asp Ile Arg Met Met Tyr
465                 470                 475                 480
Gly Val Ser Pro Trp Gly Asp Ser Pro Ile Asp Phe Glu Asp Ser Ala
            485                 490                 495
His Val Pro Cys Pro Arg Gly His Val Ile Ala Ala Arg Ile Thr Ser
            500                 505                 510
Glu Asn Pro Asp Glu Gly Phe Lys Pro Ser Ser Gly Thr Val Gln Glu
        515                 520                 525
Leu Asn Phe Arg Ser Asn Lys Asn Val Trp Gly Tyr Phe Ser Val Ala
        530                 535                 540
Ala Ala Gly Gly Leu His Glu Phe Ala Asp Ser Gln Phe Gly His Cys
545                 550                 555                 560
Phe Ser Trp Gly Glu Asn Arg Glu Glu Ala Ile Ser Asn Met Val Val
            565                 570                 575
```

```
Ala Leu Lys Glu Leu Ser Ile Arg Gly Asp Phe Arg Thr Thr Val Glu
            580                 585                 590

Tyr Leu Ile Lys Leu Leu Glu Thr Glu Ser Phe Gln Met Asn Arg Ile
        595                 600                 605

Asp Thr Gly Trp
    610

<210> SEQ ID NO 58
<211> LENGTH: 522
<212> TYPE: PRT
<213> ORGANISM: Homo sapiens
<220> FEATURE:
<221> NAME/KEY: MISC_FEATURE
<222> LOCATION: (2)..(632)
<223> OTHER INFORMATION: N- and C-terminal deleted Human ACCase1
      (AAs 102-622)

<400> SEQUENCE: 58

Met Val Ala Ser Pro Ala Glu Phe Val Thr Arg Phe Gly Gly Asn Lys
1               5                   10                  15

Val Ile Glu Lys Val Leu Ile Ala Asn Asn Gly Ile Ala Ala Val Lys
            20                  25                  30

Cys Met Arg Ser Ile Arg Arg Trp Ser Tyr Glu Met Phe Arg Asn Glu
        35                  40                  45

Arg Ala Ile Arg Phe Val Val Met Val Thr Pro Glu Asp Leu Lys Ala
    50                  55                  60

Asn Ala Glu Tyr Ile Lys Met Ala Asp His Tyr Val Pro Val Pro Gly
65                  70                  75                  80

Gly Pro Asn Asn Asn Tyr Ala Asn Val Glu Leu Ile Leu Asp Ile
                85                  90                  95

Ala Lys Arg Ile Pro Val Gln Ala Val Trp Ala Gly Trp Gly His Ala
            100                 105                 110

Ser Glu Asn Pro Lys Leu Pro Glu Leu Leu Lys Asn Gly Ile Ala
        115                 120                 125

Phe Met Gly Pro Pro Ser Gln Ala Met Trp Ala Leu Gly Asp Lys Ile
    130                 135                 140

Ala Ser Ser Ile Val Ala Gln Thr Ala Gly Ile Pro Thr Leu Pro Trp
145                 150                 155                 160

Ser Gly Ser Gly Leu Arg Val Asp Trp Gln Glu Asn Asp Phe Ser Lys
                165                 170                 175

Arg Ile Leu Asn Val Pro Gln Glu Leu Tyr Glu Lys Gly Tyr Val Lys
            180                 185                 190

Asp Val Asp Asp Gly Leu Lys Ala Ala Glu Glu Val Gly Tyr Pro Val
        195                 200                 205

Met Ile Lys Ala Ser Glu Gly Gly Gly Lys Gly Ile Arg Lys Val
    210                 215                 220

Asn Asn Ala Asp Asp Phe Pro Asn Leu Phe Arg Gln Val Gln Ala Glu
225                 230                 235                 240

Val Pro Gly Ser Pro Ile Phe Val Met Arg Leu Ala Lys Gln Ser Arg
                245                 250                 255

His Leu Glu Val Gln Ile Leu Ala Asp Gln Tyr Gly Asn Ala Ile Ser
            260                 265                 270

Leu Phe Gly Arg Asp Cys Ser Val Gln Arg Arg His Gln Lys Ile Ile
        275                 280                 285

Glu Glu Ala Pro Ala Thr Ile Ala Thr Pro Ala Val Phe Glu His Met
    290                 295                 300
```

-continued

```
Glu Gln Cys Ala Val Lys Leu Ala Lys Met Val Gly Tyr Val Ser Ala
305                 310                 315                 320

Gly Thr Val Glu Tyr Leu Tyr Ser Gln Asp Gly Ser Phe Tyr Phe Leu
                325                 330                 335

Glu Leu Asn Pro Arg Leu Gln Val Glu His Pro Cys Thr Glu Met Val
                340                 345                 350

Ala Asp Val Asn Leu Pro Ala Ala Gln Leu Gln Ile Ala Met Gly Ile
                355                 360                 365

Pro Leu Tyr Arg Ile Lys Asp Ile Arg Met Met Tyr Gly Val Ser Pro
370                 375                 380

Trp Gly Asp Ser Pro Ile Asp Phe Glu Asp Ser Ala His Val Pro Cys
385                 390                 395                 400

Pro Arg Gly His Val Ile Ala Ala Arg Ile Thr Ser Glu Asn Pro Asp
                405                 410                 415

Glu Gly Phe Lys Pro Ser Ser Gly Thr Val Gln Glu Leu Asn Phe Arg
                420                 425                 430

Ser Asn Lys Asn Val Trp Gly Tyr Phe Ser Val Ala Ala Ala Gly Gly
                435                 440                 445

Leu His Glu Phe Ala Asp Ser Gln Phe Gly His Cys Phe Ser Trp Gly
                450                 455                 460

Glu Asn Arg Glu Glu Ala Ile Ser Asn Met Val Val Ala Leu Lys Glu
465                 470                 475                 480

Leu Ser Ile Arg Gly Asp Phe Arg Thr Thr Val Glu Tyr Leu Ile Lys
                485                 490                 495

Leu Leu Glu Thr Glu Ser Phe Gln Met Asn Arg Ile Asp Thr Gly Trp
                500                 505                 510

Leu Asp Arg Leu Ile Ala Glu Lys Val Gln
                515                 520

<210> SEQ ID NO 59
<211> LENGTH: 512
<212> TYPE: PRT
<213> ORGANISM: Homo sapiens
<220> FEATURE:
<221> NAME/KEY: MISC_FEATURE
<222> LOCATION: (2)..(512)
<223> OTHER INFORMATION: N- and C-terminal deleted Human ACCase1 BC
      domain (AAs 102-512)

<400> SEQUENCE: 59

Met Val Ala Ser Pro Ala Glu Phe Val Thr Arg Phe Gly Gly Asn Lys
1               5                   10                  15

Val Ile Glu Lys Val Leu Ile Ala Asn Asn Gly Ile Ala Ala Val Lys
                20                  25                  30

Cys Met Arg Ser Ile Arg Arg Trp Ser Tyr Glu Met Phe Arg Asn Glu
            35                  40                  45

Arg Ala Ile Arg Phe Val Val Met Val Thr Pro Glu Asp Leu Lys Ala
        50                  55                  60

Asn Ala Glu Tyr Ile Lys Met Ala Asp His Tyr Val Pro Val Pro Gly
65              70                  75                  80

Gly Pro Asn Asn Asn Tyr Ala Asn Val Glu Leu Ile Leu Asp Ile
                85                  90                  95

Ala Lys Arg Ile Pro Val Gln Ala Val Trp Ala Gly Trp Gly His Ala
            100                 105                 110

Ser Glu Asn Pro Lys Leu Pro Glu Leu Leu Leu Lys Asn Gly Ile Ala
            115                 120                 125
```

```
Phe Met Gly Pro Pro Ser Gln Ala Met Trp Ala Leu Gly Asp Lys Ile
    130                 135                 140
Ala Ser Ser Ile Val Ala Gln Thr Ala Gly Ile Pro Thr Leu Pro Trp
145                 150                 155                 160
Ser Gly Ser Gly Leu Arg Val Asp Trp Gln Glu Asn Asp Phe Ser Lys
                165                 170                 175
Arg Ile Leu Asn Val Pro Gln Glu Leu Tyr Glu Lys Gly Tyr Val Lys
            180                 185                 190
Asp Val Asp Asp Gly Leu Lys Ala Ala Glu Glu Val Gly Tyr Pro Val
        195                 200                 205
Met Ile Lys Ala Ser Glu Gly Gly Gly Gly Lys Gly Ile Arg Lys Val
    210                 215                 220
Asn Asn Ala Asp Asp Phe Pro Asn Leu Phe Arg Gln Val Gln Ala Glu
225                 230                 235                 240
Val Pro Gly Ser Pro Ile Phe Val Met Arg Leu Ala Lys Gln Ser Arg
                245                 250                 255
His Leu Glu Val Gln Ile Leu Ala Asp Gln Tyr Gly Asn Ala Ile Ser
            260                 265                 270
Leu Phe Gly Arg Asp Cys Ser Val Gln Arg Arg His Gln Lys Ile Ile
        275                 280                 285
Glu Glu Ala Pro Ala Thr Ile Ala Thr Pro Ala Val Phe Glu His Met
    290                 295                 300
Glu Gln Cys Ala Val Lys Leu Ala Lys Met Val Gly Tyr Val Ser Ala
305                 310                 315                 320
Gly Thr Val Glu Tyr Leu Tyr Ser Gln Asp Gly Ser Phe Tyr Phe Leu
                325                 330                 335
Glu Leu Asn Pro Arg Leu Gln Val Glu His Pro Cys Thr Glu Met Val
            340                 345                 350
Ala Asp Val Asn Leu Pro Ala Ala Gln Leu Gln Ile Ala Met Gly Ile
        355                 360                 365
Pro Leu Tyr Arg Ile Lys Asp Ile Arg Met Met Tyr Gly Val Ser Pro
    370                 375                 380
Trp Gly Asp Ser Pro Ile Asp Phe Glu Asp Ser Ala His Val Pro Cys
385                 390                 395                 400
Pro Arg Gly His Val Ile Ala Ala Arg Ile Thr Ser Glu Asn Pro Asp
                405                 410                 415
Glu Gly Phe Lys Pro Ser Ser Gly Thr Val Gln Glu Leu Asn Phe Arg
            420                 425                 430
Ser Asn Lys Asn Val Trp Gly Tyr Phe Ser Val Ala Ala Ala Gly Gly
        435                 440                 445
Leu His Glu Phe Ala Asp Ser Gln Phe Gly His Cys Phe Ser Trp Gly
    450                 455                 460
Glu Asn Arg Glu Glu Ala Ile Ser Asn Met Val Val Ala Leu Lys Glu
465                 470                 475                 480
Leu Ser Ile Arg Gly Asp Phe Arg Thr Thr Val Glu Tyr Leu Ile Lys
                485                 490                 495
Leu Leu Glu Thr Glu Ser Phe Gln Met Asn Arg Ile Asp Thr Gly Trp
            500                 505                 510

<210> SEQ ID NO 60
<211> LENGTH: 764
<212> TYPE: PRT
<213> ORGANISM: Homo sapiens
<220> FEATURE:
<221> NAME/KEY: MISC_FEATURE
```

<222> LOCATION: (1)..(764)
<223> OTHER INFORMATION: C-terminal deleted Human ACCase2 BC domain
      (AAs 1-764)

<400> SEQUENCE: 60

Met Val Leu Leu Leu Cys Leu Ser Cys Leu Ile Phe Ser Cys Leu Thr
1               5                   10                  15

Phe Ser Trp Leu Lys Ile Trp Gly Lys Met Thr Asp Ser Lys Pro Ile
            20                  25                  30

Thr Lys Ser Lys Ser Glu Ala Asn Leu Ile Pro Ser Gln Glu Pro Phe
        35                  40                  45

Pro Ala Ser Asp Asn Ser Gly Glu Thr Pro Gln Arg Asn Gly Glu Gly
    50                  55                  60

His Thr Leu Pro Lys Thr Pro Ser Gln Ala Glu Pro Ala Ser His Lys
65                  70                  75                  80

Gly Pro Lys Asp Ala Gly Arg Arg Asn Ser Leu Pro Pro Ser His
                85                  90                  95

Gln Lys Pro Pro Arg Asn Pro Leu Ser Ser Ser Asp Ala Ala Pro Ser
                100                 105                 110

Pro Glu Leu Gln Ala Asn Gly Thr Gly Thr Gln Gly Leu Glu Ala Thr
            115                 120                 125

Asp Thr Asn Gly Leu Ser Ser Ser Ala Arg Pro Gln Gly Gln Gln Ala
    130                 135                 140

Gly Ser Pro Ser Lys Glu Asp Lys Lys Gln Ala Asn Ile Lys Arg Gln
145                 150                 155                 160

Leu Met Thr Asn Phe Ile Leu Gly Ser Phe Asp Asp Tyr Ser Ser Asp
                165                 170                 175

Glu Asp Ser Val Ala Gly Ser Ser Arg Glu Ser Thr Arg Lys Gly Ser
            180                 185                 190

Arg Ala Ser Leu Gly Ala Leu Ser Leu Glu Ala Tyr Leu Thr Thr Gly
        195                 200                 205

Glu Ala Glu Thr Arg Val Pro Thr Met Arg Pro Ser Met Ser Gly Leu
    210                 215                 220

His Leu Val Lys Arg Gly Arg Glu His Lys Lys Leu Asp Leu His Arg
225                 230                 235                 240

Asp Phe Thr Val Ala Ser Pro Ala Glu Phe Val Thr Arg Phe Gly Gly
                245                 250                 255

Asp Arg Val Ile Glu Lys Val Leu Ile Ala Asn Asn Gly Ile Ala Ala
            260                 265                 270

Val Lys Cys Met Arg Ser Ile Arg Arg Trp Ala Tyr Glu Met Phe Arg
        275                 280                 285

Asn Glu Arg Ala Ile Arg Phe Val Val Met Val Thr Pro Glu Asp Leu
    290                 295                 300

Lys Ala Asn Ala Glu Tyr Ile Lys Met Ala Asp His Tyr Val Pro Val
305                 310                 315                 320

Pro Gly Gly Pro Asn Asn Asn Asn Tyr Ala Asn Val Glu Leu Ile Val
                325                 330                 335

Asp Ile Ala Lys Arg Ile Pro Leu Gln Ala Val Trp Ala Gly Trp Gly
            340                 345                 350

His Ala Ser Glu Asn Pro Lys Leu Pro Glu Leu Leu Cys Lys Asn Gly
        355                 360                 365

Val Ala Phe Leu Gly Pro Pro Ser Glu Ala Met Trp Ala Leu Gly Asp
    370                 375                 380

Lys Ile Ala Ser Thr Val Val Ala Gln Thr Leu Gln Val Pro Thr Leu

```
                385                 390                 395                 400
Pro Arg Ser Gly Ser Gly Leu Thr Val Glu Trp Thr Glu Asp Asp Leu
                405                 410                 415
Gln Gln Gly Lys Arg Ile Ser Val Pro Glu Asp Val Tyr Asp Lys Gly
                420                 425                 430
Cys Val Lys Asp Val Asp Glu Gly Leu Glu Ala Ala Glu Arg Ile Gly
                435                 440                 445
Phe Pro Leu Met Ile Lys Ala Ser Glu Gly Gly Gly Lys Gly Ile
                450                 455                 460
Arg Lys Ala Glu Ser Ala Glu Asp Phe Pro Ile Leu Phe Arg Gln Val
465                 470                 475                 480
Gln Ser Glu Ile Pro Gly Ser Pro Ile Phe Leu Met Lys Leu Ala Gln
                485                 490                 495
His Ala Arg His Leu Glu Val Gln Ile Leu Ala Asp Gln Tyr Gly Asn
                500                 505                 510
Ala Val Ser Leu Phe Gly Arg Asp Cys Ser Ile Gln Arg Arg His Gln
                515                 520                 525
Lys Ile Val Glu Glu Ala Pro Ala Thr Ile Ala Pro Leu Ala Ile Phe
                530                 535                 540
Glu Phe Met Glu Gln Cys Ala Ile Arg Leu Ala Lys Thr Val Gly Tyr
545                 550                 555                 560
Val Ser Ala Gly Thr Val Glu Tyr Leu Tyr Ser Gln Asp Gly Ser Phe
                565                 570                 575
His Phe Leu Glu Leu Asn Pro Arg Leu Gln Val Glu His Pro Cys Thr
                580                 585                 590
Glu Met Ile Ala Asp Val Asn Leu Pro Ala Ala Gln Leu Gln Ile Ala
                595                 600                 605
Met Gly Val Pro Leu His Arg Leu Lys Asp Ile Arg Leu Leu Tyr Gly
                610                 615                 620
Glu Ser Pro Trp Gly Val Thr Pro Ile Ser Phe Glu Thr Pro Ser Asn
625                 630                 635                 640
Pro Pro Leu Ala Arg Gly His Val Ile Ala Ala Arg Ile Thr Ser Glu
                645                 650                 655
Asn Pro Asp Glu Gly Phe Lys Pro Ser Ser Gly Thr Val Gln Glu Leu
                660                 665                 670
Asn Phe Arg Ser Ser Lys Asn Val Trp Gly Tyr Phe Ser Val Ala Ala
                675                 680                 685
Thr Gly Gly Leu His Glu Phe Ala Asp Ser Gln Phe Gly His Cys Phe
                690                 695                 700
Ser Trp Gly Glu Asn Arg Lys Glu Ala Ile Ser Asn Met Val Val Ala
705                 710                 715                 720
Leu Lys Glu Leu Ser Ile Arg Gly Asp Phe Arg Thr Thr Val Glu Tyr
                725                 730                 735
Leu Ile Asn Leu Leu Glu Thr Glu Ser Phe Gln Asn Asn Asp Ile Asp
                740                 745                 750
Thr Gly Trp Leu Asp Tyr Leu Ile Ala Glu Lys Val
                755                 760

<210> SEQ ID NO 61
<211> LENGTH: 754
<212> TYPE: PRT
<213> ORGANISM: Homo sapiens
<220> FEATURE:
<221> NAME/KEY: MISC_FEATURE
<222> LOCATION: (1)..(754)
```

<223> OTHER INFORMATION: C-terminal deleted Human ACCase2 BC domain (AAs 1-754)

<400> SEQUENCE: 61

```
Met Val Leu Leu Leu Cys Leu Ser Cys Leu Ile Phe Ser Cys Leu Thr
1               5                   10                  15

Phe Ser Trp Leu Lys Ile Trp Gly Lys Met Thr Asp Ser Lys Pro Ile
            20                  25                  30

Thr Lys Ser Lys Ser Glu Ala Asn Leu Ile Pro Ser Gln Glu Pro Phe
        35                  40                  45

Pro Ala Ser Asp Asn Ser Gly Glu Thr Pro Gln Arg Asn Gly Glu Gly
    50                  55                  60

His Thr Leu Pro Lys Thr Pro Ser Gln Ala Glu Pro Ala Ser His Lys
65                  70                  75                  80

Gly Pro Lys Asp Ala Gly Arg Arg Asn Ser Leu Pro Pro Ser His
                85                  90                  95

Gln Lys Pro Pro Arg Asn Pro Leu Ser Ser Ser Asp Ala Ala Pro Ser
            100                 105                 110

Pro Glu Leu Gln Ala Asn Gly Thr Gly Thr Gln Gly Leu Glu Ala Thr
            115                 120                 125

Asp Thr Asn Gly Leu Ser Ser Ser Ala Arg Pro Gln Gly Gln Gln Ala
130                 135                 140

Gly Ser Pro Ser Lys Glu Asp Lys Lys Gln Ala Asn Ile Lys Arg Gln
145                 150                 155                 160

Leu Met Thr Asn Phe Ile Leu Gly Ser Phe Asp Asp Tyr Ser Ser Asp
                165                 170                 175

Glu Asp Ser Val Ala Gly Ser Ser Arg Glu Ser Thr Arg Lys Gly Ser
            180                 185                 190

Arg Ala Ser Leu Gly Ala Leu Ser Leu Glu Ala Tyr Leu Thr Thr Gly
        195                 200                 205

Glu Ala Glu Thr Arg Val Pro Thr Met Arg Pro Ser Met Ser Gly Leu
    210                 215                 220

His Leu Val Lys Arg Gly Arg Glu His Lys Lys Leu Asp Leu His Arg
225                 230                 235                 240

Asp Phe Thr Val Ala Ser Pro Ala Glu Phe Val Thr Arg Phe Gly Gly
                245                 250                 255

Asp Arg Val Ile Glu Lys Val Leu Ile Ala Asn Asn Gly Ile Ala Ala
            260                 265                 270

Val Lys Cys Met Arg Ser Ile Arg Arg Trp Ala Tyr Glu Met Phe Arg
        275                 280                 285

Asn Glu Arg Ala Ile Arg Phe Val Val Met Val Thr Pro Glu Asp Leu
    290                 295                 300

Lys Ala Asn Ala Glu Tyr Ile Lys Met Ala Asp His Tyr Val Pro Val
305                 310                 315                 320

Pro Gly Gly Pro Asn Asn Asn Tyr Ala Asn Val Glu Leu Ile Val
                325                 330                 335

Asp Ile Ala Lys Arg Ile Pro Leu Gln Ala Val Trp Ala Gly Trp Gly
            340                 345                 350

His Ala Ser Glu Asn Pro Lys Leu Pro Glu Leu Leu Cys Lys Asn Gly
        355                 360                 365

Val Ala Phe Leu Gly Pro Pro Ser Glu Ala Met Trp Ala Leu Gly Asp
    370                 375                 380

Lys Ile Ala Ser Thr Val Val Ala Gln Thr Leu Gln Val Pro Thr Leu
385                 390                 395                 400
```

```
Pro Arg Ser Gly Ser Gly Leu Thr Val Glu Trp Thr Glu Asp Asp Leu
                405                 410                 415
Gln Gln Gly Lys Arg Ile Ser Val Pro Glu Asp Val Tyr Asp Lys Gly
            420                 425                 430
Cys Val Lys Asp Val Asp Gly Leu Glu Ala Ala Glu Arg Ile Gly
        435                 440                 445
Phe Pro Leu Met Ile Lys Ala Ser Glu Gly Gly Gly Lys Gly Ile
450                 455                 460
Arg Lys Ala Glu Ser Ala Glu Asp Phe Pro Ile Leu Phe Arg Gln Val
465                 470                 475                 480
Gln Ser Glu Ile Pro Gly Ser Pro Ile Phe Leu Met Lys Leu Ala Gln
                485                 490                 495
His Ala Arg His Leu Glu Val Gln Ile Leu Ala Asp Gln Tyr Gly Asn
            500                 505                 510
Ala Val Ser Leu Phe Gly Arg Asp Cys Ser Ile Gln Arg Arg His Gln
        515                 520                 525
Lys Ile Val Glu Glu Ala Pro Ala Thr Ile Ala Pro Leu Ala Ile Phe
530                 535                 540
Glu Phe Met Glu Gln Cys Ala Ile Arg Leu Ala Lys Thr Val Gly Tyr
545                 550                 555                 560
Val Ser Ala Gly Thr Val Glu Tyr Leu Tyr Ser Gln Asp Gly Ser Phe
                565                 570                 575
His Phe Leu Glu Leu Asn Pro Arg Leu Gln Val Glu His Pro Cys Thr
            580                 585                 590
Glu Met Ile Ala Asp Val Asn Leu Pro Ala Ala Gln Leu Gln Ile Ala
        595                 600                 605
Met Gly Val Pro Leu His Arg Leu Lys Asp Ile Arg Leu Leu Tyr Gly
610                 615                 620
Glu Ser Pro Trp Gly Val Thr Pro Ile Ser Phe Glu Thr Pro Ser Asn
625                 630                 635                 640
Pro Pro Leu Ala Arg Gly His Val Ile Ala Ala Arg Ile Thr Ser Glu
                645                 650                 655
Asn Pro Asp Glu Gly Phe Lys Pro Ser Ser Gly Thr Val Gln Glu Leu
            660                 665                 670
Asn Phe Arg Ser Ser Lys Asn Val Trp Gly Tyr Phe Ser Val Ala Ala
        675                 680                 685
Thr Gly Gly Leu His Glu Phe Ala Asp Ser Gln Phe Gly His Cys Phe
690                 695                 700
Ser Trp Gly Glu Asn Arg Lys Glu Ala Ile Ser Asn Met Val Val Ala
705                 710                 715                 720
Leu Lys Glu Leu Ser Ile Arg Gly Asp Phe Arg Thr Thr Val Glu Tyr
                725                 730                 735
Leu Ile Asn Leu Leu Glu Thr Glu Ser Phe Gln Asn Asn Asp Ile Asp
            740                 745                 750
Thr Gly

<210> SEQ ID NO 62
<211> LENGTH: 522
<212> TYPE: PRT
<213> ORGANISM: Homo sapiens
<220> FEATURE:
<221> NAME/KEY: MISC_FEATURE
<222> LOCATION: (2)..(522)
<223> OTHER INFORMATION: N- and C-terminal Human ACCase2 BC domain
      (AAs 224-764)
```

<400> SEQUENCE: 62

```
Met Val Ala Ser Pro Ala Glu Phe Val Thr Arg Phe Gly Gly Asp Arg
1               5                   10                  15
Val Ile Glu Lys Val Leu Ile Ala Asn Asn Gly Ile Ala Ala Val Lys
            20                  25                  30
Cys Met Arg Ser Ile Arg Arg Trp Ala Tyr Glu Met Phe Arg Asn Glu
        35                  40                  45
Arg Ala Ile Arg Phe Val Val Met Val Thr Pro Glu Asp Leu Lys Ala
    50                  55                  60
Asn Ala Glu Tyr Ile Lys Met Ala Asp His Tyr Val Pro Val Pro Gly
65                  70                  75                  80
Gly Pro Asn Asn Asn Tyr Ala Asn Val Glu Leu Ile Val Asp Ile
                85                  90                  95
Ala Lys Arg Ile Pro Leu Gln Ala Val Trp Ala Gly Trp Gly His Ala
            100                 105                 110
Ser Glu Asn Pro Lys Leu Pro Glu Leu Leu Cys Lys Asn Gly Val Ala
        115                 120                 125
Phe Leu Gly Pro Pro Ser Glu Ala Met Trp Ala Leu Gly Asp Lys Ile
    130                 135                 140
Ala Ser Thr Val Val Ala Gln Thr Leu Gln Val Pro Thr Leu Pro Arg
145                 150                 155                 160
Ser Gly Ser Gly Leu Thr Val Glu Trp Thr Glu Asp Leu Gln Gln
                165                 170                 175
Gly Lys Arg Ile Ser Val Pro Glu Asp Val Tyr Asp Lys Gly Cys Val
            180                 185                 190
Lys Asp Val Asp Glu Gly Leu Glu Ala Ala Glu Arg Ile Gly Phe Pro
        195                 200                 205
Leu Met Ile Lys Ala Ser Glu Gly Gly Gly Lys Gly Ile Arg Lys
    210                 215                 220
Ala Glu Ser Ala Glu Asp Phe Pro Ile Leu Phe Arg Gln Val Gln Ser
225                 230                 235                 240
Glu Ile Pro Gly Ser Pro Ile Phe Leu Met Lys Leu Ala Gln His Ala
                245                 250                 255
Arg His Leu Glu Val Gln Ile Leu Ala Asp Gln Tyr Gly Asn Ala Val
            260                 265                 270
Ser Leu Phe Gly Arg Asp Cys Ser Ile Gln Arg Arg His Gln Lys Ile
        275                 280                 285
Val Glu Glu Ala Pro Ala Thr Ile Ala Pro Leu Ala Ile Phe Glu Phe
    290                 295                 300
Met Glu Gln Cys Ala Ile Arg Leu Ala Lys Thr Val Gly Tyr Val Ser
305                 310                 315                 320
Ala Gly Thr Val Glu Tyr Leu Tyr Ser Gln Asp Gly Ser Phe His Phe
                325                 330                 335
Leu Glu Leu Asn Pro Arg Leu Gln Val Glu His Pro Cys Thr Glu Met
            340                 345                 350
Ile Ala Asp Val Asn Leu Pro Ala Ala Gln Leu Gln Ile Ala Met Gly
        355                 360                 365
Val Pro Leu His Arg Leu Lys Asp Ile Arg Leu Leu Tyr Gly Glu Ser
    370                 375                 380
Pro Trp Gly Val Thr Pro Ile Ser Phe Glu Thr Pro Ser Asn Pro Pro
385                 390                 395                 400
Leu Ala Arg Gly His Val Ile Ala Ala Arg Ile Thr Ser Glu Asn Pro
```

```
                    405                 410                 415
Asp Glu Gly Phe Lys Pro Ser Ser Gly Thr Val Gln Glu Leu Asn Phe
            420                 425                 430

Arg Ser Ser Lys Asn Val Trp Gly Tyr Phe Ser Val Ala Ala Thr Gly
        435                 440                 445

Gly Leu His Glu Phe Ala Asp Ser Gln Phe Gly His Cys Phe Ser Trp
    450                 455                 460

Gly Glu Asn Arg Lys Glu Ala Ile Ser Asn Met Val Val Ala Leu Lys
465                 470                 475                 480

Glu Leu Ser Ile Arg Gly Asp Phe Arg Thr Thr Val Glu Tyr Leu Ile
                485                 490                 495

Asn Leu Leu Glu Thr Glu Ser Phe Gln Asn Asn Asp Ile Asp Thr Gly
            500                 505                 510

Trp Leu Asp Tyr Leu Ile Ala Glu Lys Val
        515                 520

<210> SEQ ID NO 63
<211> LENGTH: 512
<212> TYPE: PRT
<213> ORGANISM: Homo sapiens
<220> FEATURE:
<221> NAME/KEY: MIC_FEATURE
<222> LOCATION: (2)..(512)
<223> OTHER INFORMATION: N- and C-terminal deleted Human ACCase2 BC
      domain (AAs 224-754)

<400> SEQUENCE: 63

Met Val Ala Ser Pro Ala Glu Phe Val Thr Arg Phe Gly Gly Asp Arg
1               5                   10                  15

Val Ile Glu Lys Val Leu Ile Ala Asn Asn Gly Ile Ala Ala Val Lys
            20                  25                  30

Cys Met Arg Ser Ile Arg Arg Trp Ala Tyr Glu Met Phe Arg Asn Glu
        35                  40                  45

Arg Ala Ile Arg Phe Val Val Met Val Thr Pro Glu Asp Leu Lys Ala
    50                  55                  60

Asn Ala Glu Tyr Ile Lys Met Ala Asp His Tyr Val Pro Val Pro Gly
65                  70                  75                  80

Gly Pro Asn Asn Asn Tyr Ala Asn Val Glu Leu Ile Val Asp Ile
                85                  90                  95

Ala Lys Arg Ile Pro Leu Gln Ala Val Trp Ala Gly Trp Gly His Ala
            100                 105                 110

Ser Glu Asn Pro Lys Leu Pro Glu Leu Leu Cys Lys Asn Gly Val Ala
        115                 120                 125

Phe Leu Gly Pro Pro Ser Glu Ala Met Trp Ala Leu Gly Asp Lys Ile
    130                 135                 140

Ala Ser Thr Val Val Ala Gln Thr Leu Gln Val Pro Thr Leu Pro Arg
145                 150                 155                 160

Ser Gly Ser Gly Leu Thr Val Glu Trp Thr Glu Asp Asp Leu Gln Gln
                165                 170                 175

Gly Lys Arg Ile Ser Val Pro Glu Asp Val Tyr Asp Lys Gly Cys Val
            180                 185                 190

Lys Asp Val Asp Glu Gly Leu Glu Ala Ala Glu Arg Ile Gly Phe Pro
        195                 200                 205

Leu Met Ile Lys Ala Ser Glu Gly Gly Gly Gly Lys Gly Ile Arg Lys
    210                 215                 220

Ala Glu Ser Ala Glu Asp Phe Pro Ile Leu Phe Arg Gln Val Gln Ser
```

```
            225                 230                 235                 240
Glu Ile Pro Gly Ser Pro Ile Phe Leu Met Lys Leu Ala Gln His Ala
                245                 250                 255

Arg His Leu Glu Val Gln Ile Leu Ala Asp Gln Tyr Gly Asn Ala Val
            260                 265                 270

Ser Leu Phe Gly Arg Asp Cys Ser Ile Gln Arg Arg His Gln Lys Ile
        275                 280                 285

Val Glu Glu Ala Pro Ala Thr Ile Ala Pro Leu Ala Ile Phe Glu Phe
    290                 295                 300

Met Glu Gln Cys Ala Ile Arg Leu Ala Lys Thr Val Gly Tyr Val Ser
305                 310                 315                 320

Ala Gly Thr Val Glu Tyr Leu Tyr Ser Gln Asp Gly Ser Phe His Phe
                325                 330                 335

Leu Glu Leu Asn Pro Arg Leu Gln Val Glu His Pro Cys Thr Glu Met
            340                 345                 350

Ile Ala Asp Val Asn Leu Pro Ala Gln Leu Gln Ile Ala Met Gly
        355                 360                 365

Val Pro Leu His Arg Leu Lys Asp Ile Arg Leu Leu Tyr Gly Glu Ser
    370                 375                 380

Pro Trp Gly Val Thr Pro Ile Ser Phe Glu Thr Pro Ser Asn Pro Pro
385                 390                 395                 400

Leu Ala Arg Gly His Val Ala Ala Arg Ile Thr Ser Glu Asn Pro
                405                 410                 415

Asp Glu Gly Phe Lys Pro Ser Ser Gly Thr Val Gln Glu Leu Asn Phe
            420                 425                 430

Arg Ser Ser Lys Asn Val Trp Gly Tyr Phe Ser Val Ala Ala Thr Gly
        435                 440                 445

Gly Leu His Glu Phe Ala Asp Ser Gln Phe Gly His Cys Phe Ser Trp
    450                 455                 460

Gly Glu Asn Arg Lys Glu Ala Ile Ser Asn Met Val Val Ala Leu Lys
465                 470                 475                 480

Glu Leu Ser Ile Arg Gly Asp Phe Arg Thr Thr Val Glu Tyr Leu Ile
                485                 490                 495

Asn Leu Leu Glu Thr Glu Ser Phe Gln Asn Asn Asp Ile Asp Thr Gly
            500                 505                 510

<210> SEQ ID NO 64
<211> LENGTH: 521
<212> TYPE: PRT
<213> ORGANISM: Magnaporthe grisea
<220> FEATURE:
<221> NAME/KEY: MISC_FEATURE
<222> LOCATION: (1)..(521)
<223> OTHER INFORMATION: N-terminal deleted Magnaporthe ACCase B -continued

```
         65                  70                  75                  80
Arg Met Asn Val His Ala Val Trp Ala Gly Trp Gly His Ala Ser Glu
                 85                  90                  95
Asn Pro Lys Leu Pro Glu Ser Leu Ala Ala Ser Pro Lys Lys Ile Ile
            100                 105                 110
Phe Ile Gly Pro Pro Gly Ser Ala Met Arg Ser Leu Gly Asp Lys Ile
            115                 120                 125
Ser Ser Thr Ile Val Ala Gln His Ala Gln Val Pro Cys Ile Pro Trp
            130                 135                 140
Ser Gly Thr Gly Val Asp Ala Val Gln Ile Asp Lys Lys Gly Ile Val
145                 150                 155                 160
Thr Val Asp Asp Asp Thr Tyr Ala Lys Gly Cys Val Thr Ser Trp Gln
                165                 170                 175
Glu Gly Leu Glu Lys Ala Arg Gln Ile Gly Phe Pro Val Met Ile Lys
            180                 185                 190
Ala Ser Glu Gly Gly Gly Gly Lys Gly Ile Arg Lys Ala Val Ser Glu
            195                 200                 205
Glu Gly Phe Glu Glu Leu Tyr Lys Ala Ala Ser Glu Ile Pro Gly
            210                 215                 220
Ser Pro Ile Phe Ile Met Lys Leu Ala Gly Asn Ala Arg His Leu Glu
225                 230                 235                 240
Val Gln Leu Leu Ala Asp Gln Tyr Gly Asn Asn Ile Ser Leu Phe Gly
                245                 250                 255
Arg Asp Cys Ser Val Gln Arg Arg His Gln Lys Ile Ile Glu Glu Ala
            260                 265                 270
Pro Val Thr Ile Ala Lys Pro Asp Thr Phe Lys Ala Met Glu Glu Ala
            275                 280                 285
Ala Val Arg Leu Gly Arg Leu Val Gly Tyr Val Ser Ala Gly Thr Val
            290                 295                 300
Glu Tyr Leu Tyr Ser His Ala Asp Asp Lys Phe Tyr Phe Leu Glu Leu
305                 310                 315                 320
Asn Pro Arg Leu Gln Val Glu His Pro Thr Thr Glu Gly Val Ser Gly
                325                 330                 335
Val Asn Leu Pro Ala Ser Gln Leu Gln Ile Ala Met Gly Ile Pro Leu
            340                 345                 350
His Arg Ile Ser Asp Ile Arg Leu Leu Tyr Gly Val Asp Pro Lys Leu
            355                 360                 365
Ser Thr Glu Ile Asp Phe Asp Phe Lys Asn Pro Asp Ser Glu Lys Thr
            370                 375                 380
Gln Arg Arg Pro Ser Pro Lys Gly His Leu Thr Ala Cys Arg Ile Thr
385                 390                 395                 400
Ser Glu Asp Pro Gly Glu Gly Phe Lys Pro Ser Asn Gly Val Met His
                405                 410                 415
Glu Leu Asn Phe Arg Ser Ser Asn Val Trp Gly Tyr Phe Ser Val
            420                 425                 430
Gly Thr Gln Gly Gly Ile His Ser Phe Ser Asp Ser Gln Phe Gly His
            435                 440                 445
Ile Phe Ala Tyr Gly Glu Asn Arg Ser Ala Ser Arg Lys His Met Val
            450                 455                 460
Ile Ala Leu Lys Glu Leu Ser Ile Arg Gly Asp Phe Arg Thr Thr Val
465                 470                 475                 480
Glu Tyr Leu Ile Lys Leu Leu Glu Thr Glu Ala Phe Glu Glu Asn Thr
                485                 490                 495
```

```
Ile Thr Thr Gly Trp Leu Asp Glu Leu Ile Ser Lys Lys Leu Thr Ala
            500                 505                 510
Glu Arg Pro Asp Lys Met Leu Ala Val
        515                 520

<210> SEQ ID NO 65
<211> LENGTH: 511
<212> TYPE: PRT
<213> ORGANISM: Magnaporthe grisea
<220> FEATURE:
<221> NAME/KEY: MISC_FEATURE
<222> LOCATION: (1)..(511)
<223> OTHER INFORMATION: N- and C-terminal deleted Magnaporthe ACCase
      BC domain (AAs 72-582)

<400> SEQUENCE: 65

Thr Asn Val Leu Ile Ala Asn Asn Gly Ile Ala Ala Val Lys Glu Ile
1               5                   10                  15
Arg Ser Val Arg Lys Trp Ala Tyr Glu Thr Phe Gly Asp Glu Arg Ala
            20                  25                  30
Ile Gln Phe Thr Val Met Ala Thr Pro Glu Asp Leu Gln Ala Asn Ala
        35                  40                  45
Asp Tyr Ile Arg Met Ala Asp His Tyr Val Glu Val Pro Gly Gly Thr
    50                  55                  60
Asn Asn Asn Asn

-continued

```
Asn Pro Arg Leu Gln Val Glu His Pro Thr Thr Glu Gly Val Ser Gly
                325                 330                 335

Val Asn Leu Pro Ala Ser Gln Leu Gln Ile Ala Met Gly Ile Pro Leu
            340                 345                 350

His Arg Ile Ser Asp Ile Arg Leu Leu Tyr Gly Val Asp Pro Lys Leu
        355                 360                 365

Ser Thr Glu Ile Asp Phe Asp Phe Lys Asn Pro Asp Ser Glu Lys Thr
    370                 375                 380

Gln Arg Arg Pro Ser Pro Lys Gly His Leu Thr Ala Cys Arg Ile Thr
385                 390                 395                 400

Ser Glu Asp Pro Gly Glu Gly Phe Lys Pro Ser Asn Gly Val Met His
                405                 410                 415

Glu Leu Asn Phe Arg Ser Ser Ser Asn Val Trp Gly Tyr Phe Ser Val
            420                 425                 430

Gly Thr Gln Gly Gly Ile His Ser Phe Ser Asp Ser Gln Phe Gly His
        435                 440                 445

Ile Phe Ala Tyr Gly Glu Asn Arg Ser Ala Ser Arg Lys His Met Val
    450                 455                 460

Ile Ala Leu Lys Glu Leu Ser Ile Arg Gly Asp Phe Arg Thr Thr Val
465                 470                 475                 480

Glu Tyr Leu Ile Lys Leu Leu Glu Thr Glu Ala Phe Glu Glu Asn Thr
                485                 490                 495

Ile Thr Thr Gly Trp Leu Asp Glu Leu Ile Ser Lys Lys Leu Thr
            500                 505                 510

<210> SEQ ID NO 66
<211> LENGTH: 501
<212> TYPE: PRT
<213> ORGANISM: Magnaporthe grisea
<220> FEATURE:
<221> NAME/KEY: misc_feature
<223> OTHER INFORMATION: N- and C-terminal deleted Magnaporthe ACCase BC
      domain (AAs 72-572)

<400> SEQUENCE: 66

Thr Asn Val Leu Ile Ala Asn Asn Gly Ile Ala Ala Val Lys Glu Ile
1               5                   10                  15

Arg Ser Val Arg Lys Trp Ala Tyr Glu Thr Phe Gly Asp Glu Arg Ala
            20                  25                  30

Ile Gln Phe Thr Val Met Ala Thr Pro Glu Asp Leu Gln Ala Asn Ala
        35                  40                  45

Asp Tyr Ile Arg Met Ala Asp His Tyr Val Glu Val Pro Gly Gly Thr
    50                  55                  60

Asn Asn Asn Asn Tyr Ala Asn Val Glu Leu Ile Val Asp Val Ala Glu
65                  70                  75                  80

Arg Met Asn Val His Ala Val Trp Ala Gly Trp Gly His Ala Ser Glu
                85                  90                  95

Asn Pro Lys Leu Pro Glu Ser Leu Ala Ala Ser Pro Lys Lys Ile Ile
            100                 105                 110

Phe Ile Gly Pro Pro Gly Ser Ala Met Arg Ser Leu Gly Asp Lys Ile
        115                 120                 125

Ser Ser Thr Ile Val Ala Gln His Ala Gln Val Pro Cys Ile Pro Trp
    130                 135                 140

Ser Gly Thr Gly Val Asp Ala Val Gln Ile Asp Lys Lys Gly Ile Val
145                 150                 155                 160
```

```
Thr Val Asp Asp Asp Thr Tyr Ala Lys Gly Cys Val Thr Ser Trp Gln
                165                 170                 175

Glu Gly Leu Glu Lys Ala Arg Gln Ile Gly Phe Pro Val Met Ile Lys
            180                 185                 190

Ala Ser Glu Gly Gly Gly Lys Gly Ile Arg Lys Ala Val Ser Glu
        195                 200                 205

Glu Gly Phe Glu Glu Leu Tyr Lys Ala Ala Ser Glu Ile Pro Gly
    210                 215                 220

Ser Pro Ile Phe Ile Met Lys Leu Ala Gly Asn Ala Arg His Leu Glu
225                 230                 235                 240

Val Gln Leu Leu Ala Asp Gln Tyr Gly Asn Asn Ile Ser Leu Phe Gly
                245                 250                 255

Arg Asp Cys Ser Val Gln Arg His Gln Lys Ile Ile Glu Glu Ala
            260                 265                 270

Pro Val Thr Ile Ala Lys Pro Asp Thr Phe Lys Ala Met Glu Glu Ala
                275                 280                 285

Ala Val Arg Leu Gly Arg Leu Val Gly Tyr Val Ser Ala Gly Thr Val
        290                 295                 300

Glu Tyr Leu Tyr Ser His Ala Asp Asp Lys Phe Tyr Phe Leu Glu Leu
305                 310                 315                 320

Asn Pro Arg Leu Gln Val Glu His Pro Thr Thr Glu Gly Val Ser Gly
                325                 330                 335

Val Asn Leu Pro Ala Ser Gln Leu Gln Ile Ala Met Gly Ile Pro Leu
                340                 345                 350

His Arg Ile Ser Asp Ile Arg Leu Leu Tyr Gly Val Asp Pro Lys Leu
            355                 360                 365

Ser Thr Glu Ile Asp Phe Asp Phe Lys Asn Pro Asp Ser Glu Lys Thr
            370                 375                 380

Gln Arg Arg Pro Ser Pro Lys Gly His Leu Thr Ala Cys Arg Ile Thr
385                 390                 395                 400

Ser Glu Asp Pro Gly Glu Gly Phe Lys Pro Ser Asn Gly Val Met His
                405                 410                 415

Glu Leu Asn Phe Arg Ser Ser Ser Asn Val Trp Gly Tyr Phe Ser Val
            420                 425                 430

Gly Thr Gln Gly Gly Ile His Ser Phe Ser Asp Ser Gln Phe Gly His
        435                 440                 445

Ile Phe Ala Tyr Gly Glu Asn Arg Ser Ala Ser Arg Lys His Met Val
    450                 455                 460

Ile Ala Leu Lys Glu Leu Ser Ile Arg Gly Asp Phe Arg Thr Thr Val
465                 470                 475                 480

Glu Tyr Leu Ile Lys Leu Leu Glu Thr Glu Ala Phe Glu Glu Asn Thr
                485                 490                 495

Ile Thr Thr Gly Trp
            500

<210> SEQ ID NO 67
<211> LENGTH: 491
<212> TYPE: PRT
<213> ORGANISM: Magnaporthe grisea
<220> FEATURE:
<221> NAME/KEY: MISC_FEATURE
<222> LOCATION: (1)..(491)
<223> OTHER INFORMATION: N- and C-terminal deleted ACCase BC domain
      (AAs 72-562)

<400> SEQUENCE: 67
```

-continued

```
Thr Asn Val Leu Ile Ala Asn Asn Gly Ile Ala Ala Val Lys Glu Ile
1               5                   10                  15

Arg Ser Val Arg Lys Trp Ala Tyr Glu Thr Phe Gly Asp Glu Arg Ala
                20                  25                  30

Ile Gln Phe Thr Val Met Ala Thr Pro Glu Asp Leu Gln Ala Asn Ala
            35                  40                  45

Asp Tyr Ile Arg Met Ala Asp His Tyr Val Glu Val Pro Gly Gly Thr
        50                  55                  60

Asn Asn Asn Asn Tyr Ala Asn Val Glu Leu Ile Val Asp Val Ala Glu
65                  70                  75                  80

Arg Met Asn Val His Ala Val Trp Ala Gly Trp Gly His Ala Ser Glu
                85                  90                  95

Asn Pro Lys Leu Pro Glu Ser Leu Ala Ala Ser Pro Lys Lys Ile Ile
                100                 105                 110

Phe Ile Gly Pro Pro Gly Ser Ala Met Arg Ser Leu Gly Asp Lys Ile
            115                 120                 125

Ser Ser Thr Ile Val Ala Gln His Ala Gln Val Pro Cys Ile Pro Trp
        130                 135                 140

Ser Gly Thr Gly Val Asp Ala Val Gln Ile Asp Lys Lys Gly Ile Val
145                 150                 155                 160

Thr Val Asp Asp Asp Thr Tyr Ala Lys Gly Cys Val Thr Ser Trp Gln
                165                 170                 175

Glu Gly Leu Glu Lys Ala Arg Gln Ile Gly Phe Pro Val Met Ile Lys
            180                 185                 190

Ala Ser Glu Gly Gly Gly Gly Lys Gly Ile Arg Lys Ala Val Ser Glu
        195                 200                 205

Glu Gly Phe Glu Glu Leu Tyr Lys Ala Ala Ser Glu Ile Pro Gly
    210                 215                 220

Ser Pro Ile Phe Ile Met Lys Leu Ala Gly Asn Ala Arg His Leu Glu
225                 230                 235                 240

Val Gln Leu Leu Ala Asp Gln Tyr Gly Asn Asn Ile Ser Leu Phe Gly
                245                 250                 255

Arg Asp Cys Ser Val Gln Arg Arg His Gln Lys Ile Ile Glu Glu Ala
            260                 265                 270

Pro Val Thr Ile Ala Lys Pro Asp Thr Phe Lys Ala Met Glu Glu Ala
        275                 280                 285

Ala Val Arg Leu Gly Arg Leu Val Gly Tyr Val Ser Ala Gly Thr Val
    290                 295                 300

Glu Tyr Leu Tyr Ser His Ala Asp Asp Lys Phe Tyr Phe Leu Glu Leu
305                 310                 315                 320

Asn Pro Arg Leu Gln Val Glu His Pro Thr Thr Glu Gly Val Ser Gly
                325                 330                 335

Val Asn Leu Pro Ala Ser Gln Leu Gln Ile Ala Met Gly Ile Pro Leu
            340                 345                 350

His Arg Ile Ser Asp Ile Arg Leu Leu Tyr Gly Val Asp Pro Lys Leu
        355                 360                 365

Ser Thr Glu Ile Asp Phe Asp Phe Lys Asn Pro Asp Ser Glu Lys Thr
    370                 375                 380

Gln Arg Arg Pro Ser Pro Lys Gly His Leu Thr Ala Cys Arg Ile Thr
385                 390                 395                 400

Ser Glu Asp Pro Gly Glu Gly Phe Lys Pro Ser Asn Gly Val Met His
                405                 410                 415

Glu Leu Asn Phe Arg Ser Ser Ser Asn Val Trp Gly Tyr Phe Ser Val
```

-continued

```
              420                 425                 430
Gly Thr Gln Gly Gly Ile His Ser Phe Ser Asp Ser Gln Phe Gly His
            435                 440                 445

Ile Phe Ala Tyr Gly Glu Asn Arg Ser Ala Ser Arg Lys His Met Val
450                 455                 460

Ile Ala Leu Lys Glu Leu Ser Ile Arg Gly Asp Phe Arg Thr Thr Val
465                 470                 475                 480

Glu Tyr Leu Ile Lys Leu Leu Glu Thr Glu Ala
                485                 490

<210> SEQ ID NO 68
<211> LENGTH: 525
<212> TYPE: PRT
<213> ORGANISM: Saccharomyces cerevisiae
<220> FEATURE:
<221> NAME/KEY: MISC_FEATURE
<222> LOCATION: (1)..(525)
<223> OTHER INFORMATION: N-terminal deleted Yeast ACCase BC domain
      (AAs--57-581)

<400> SEQUENCE: 68

Thr Val Ile Ser Lys Ile Leu Ile Ala Asn Asn Gly Ile Ala Ala Val
1               5                   10                  15

Lys Glu Ile Arg Ser Val Arg Lys Trp Ala Tyr Glu Thr Phe Gly Asp
            20                  25                  30

Asp Arg Thr Val Gln Phe Val Ala Met Ala Thr Pro Glu Asp Leu Glu
        35                  40                  45

Ala Asn Ala Glu Tyr Ile Arg Met Ala Asp Gln Tyr Ile Glu Val Pro
    50                  55                  60

Gly Gly Thr Asn Asn Asn Tyr Ala Asn Val Asp Leu Ile Val Asp
65                  70                  75                  80

Ile Ala Glu Arg Ala Asp Val Asp Ala Val Trp Ala Gly Trp Gly His
                85                  90                  95

Ala Ser Glu Asn Pro Leu Leu Pro Glu Lys Leu Ser Gln Ser Lys Arg
            100                 105                 110

Lys Val Ile Phe Ile Gly Pro Pro Gly Asn Ala Met Arg Ser Leu Gly
        115                 120                 125

Asp Lys Ile Ser Ser Thr Ile Val Ala Gln Ser Ala Lys Val Pro Cys
    130                 135                 140

Ile Pro Trp Ser Gly Thr Gly Val Asp Thr Val His Val Asp Glu Lys
145                 150                 155                 160

Thr Gly Leu Val Ser Val Asp Asp Ile Tyr Gln Lys Gly Cys Cys
                165                 170                 175

Thr Ser Pro Glu Asp Gly Leu Gln Lys Ala Lys Arg Ile Gly Phe Pro
            180                 185                 190

Val Met Ile Lys Ala Ser Glu Gly Gly Gly Lys Gly Ile Arg Gln
        195                 200                 205

Val Glu Arg Glu Glu Asp Phe Ile Ala Leu Tyr His Gln Ala Ala Asn
    210                 215                 220

Glu Ile Pro Gly Ser Pro Ile Phe Ile Met Lys Leu Ala Gly Arg Ala
225                 230                 235                 240

Arg His Leu Glu Val Gln Leu Leu Ala Asp Gln Tyr Gly Thr Asn Ile
                245                 250                 255

Ser Leu Phe Gly Arg Asp Cys Ser Val Gln Arg Arg His Gln Lys Ile
            260                 265                 270

Ile Glu Glu Ala Pro Val Thr Ile Ala Lys Ala Glu Thr Phe His Glu
```

```
                275                 280                 285
Met Glu Lys Ala Ala Val Arg Leu Gly Lys Leu Val Gly Tyr Val Ser
            290                 295                 300
Ala Gly Thr Val Glu Tyr Leu Tyr Ser His Asp Asp Gly Lys Phe Tyr
305                 310                 315                 320
Phe Leu Glu Leu Asn Pro Arg Leu Gln Val Glu His Pro Thr Thr Glu
                325                 330                 335
Met Val Ser Gly Val Asn Leu Pro Ala Ala Gln Leu Gln Ile Ala Met
                340                 345                 350
Gly Ile Pro Met His Arg Ile Ser Asp Ile Arg Thr Leu Tyr Gly Met
                355                 360                 365
Asn Pro His Ser Ala Ser Glu Ile Asp Phe Glu Phe Lys Thr Gln Asp
                370                 375                 380
Ala Thr Lys Lys Gln Arg Arg Pro Ile Pro Lys Gly His Cys Thr Ala
385                 390                 395                 400
Cys Arg Ile Thr Ser Glu Asp Pro Asn Asp Gly Phe Lys Pro Ser Gly
                405                 410                 415
Gly Thr Leu His Glu Leu Asn Phe Arg Ser Ser Ser Asn Val Trp Gly
                420                 425                 430
Tyr Phe Ser Val Gly Asn Asn Gly Asn Ile His Ser Phe Ser Asp Ser
                435                 440                 445
Gln Phe Gly His Ile Phe Ala Phe Gly Glu Asn Arg Gln Ala Ser Arg
                450                 455                 460
Lys His Met Val Val Ala Leu Lys Glu Leu Ser Ile Arg Gly Asp Phe
465                 470                 475                 480
Arg Thr Thr Val Glu Tyr Leu Ile Lys Leu Leu Glu Thr Glu Asp Phe
                485                 490                 495
Glu Asp Asn Thr Ile Thr Thr Gly Trp Leu Asp Asp Leu Ile Thr His
                500                 505                 510
Lys Met Thr Ala Glu Lys Pro Asp Pro Thr Leu Ala Val
                515                 520                 525

<210> SEQ ID NO 69
<211> LENGTH: 515
<212> TYPE: PRT
<213> ORGANISM: Saccharomyces cerevisiae
<220> FEATURE:
<221> NAME/KEY: MISC_FEATURE
<222> LOCATION: (1)..(515)
<223> OTHER INFORMATION: N- and C-terminal deleted Yeast ACCase BC
      domain (AAs 57-571)

<400> SEQUENCE: 69

Thr Val Ile Ser Lys Ile Leu Ile Ala Asn Asn Gly Ile Ala Ala Val
1               5                   10                  15
Lys Glu Ile Arg Ser Val Arg Lys Trp Ala Tyr Glu Thr Phe Gly Asp
                20                  25                  30
Asp Arg Thr Val Gln Phe Val Ala Met Ala Thr Pro Glu Asp Leu Glu
            35                  40                  45
Ala Asn Ala Glu Tyr Ile Arg Met Ala Asp Gln Tyr Ile Glu Val Pro
        50                  55                  60
Gly Gly Thr Asn Asn Asn Tyr Ala Asn Val Asp Leu Ile Val Asp
65                  70                  75                  80
Ile Ala Glu Arg Ala Asp Val Asp Ala Val Trp Ala Gly Trp Gly His
                85                  90                  95
Ala Ser Glu Asn Pro Leu Leu Pro Glu Lys Leu Ser Gln Ser Lys Arg
```

-continued

```
                    100                 105                 110
Lys Val Ile Phe Ile Gly Pro Pro Gly Asn Ala Met Arg Ser Leu Gly
                115                 120                 125

Asp Lys Ile Ser Ser Thr Ile Val Ala Gln Ser Ala Lys Val Pro Cys
            130                 135                 140

Ile Pro Trp Ser Gly Thr Gly Val Asp Thr Val His Val Asp Glu Lys
145                 150                 155                 160

Thr Gly Leu Val Ser Val Asp Asp Ile Tyr Gln Lys Gly Cys Cys
                165                 170                 175

Thr Ser Pro Glu Asp Gly Leu Gln Lys Ala Lys Arg Ile Gly Phe Pro
            180                 185                 190

Val Met Ile Lys Ala Ser Glu Gly Gly Gly Lys Gly Ile Arg Gln
            195                 200                 205

Val Glu Arg Glu Glu Asp Phe Ile Ala Leu Tyr His Gln Ala Ala Asn
        210                 215                 220

Glu Ile Pro Gly Ser Pro Ile Phe Ile Met Lys Leu Ala Gly Arg Ala
225                 230                 235                 240

Arg His Leu Glu Val Gln Leu Leu Ala Asp Gln Tyr Gly Thr Asn Ile
                245                 250                 255

Ser Leu Phe Gly Arg Asp Cys Ser Val Gln Arg Arg His Gln Lys Ile
            260                 265                 270

Ile Glu Glu Ala Pro Val Thr Ile Ala Lys Ala Glu Thr Phe His Glu
        275                 280                 285

Met Glu Lys Ala Ala Val Arg Leu Gly Lys Leu Val Gly Tyr Val Ser
    290                 295                 300

Ala Gly Thr Val Glu Tyr Leu Tyr Ser His Asp Asp Gly Lys Phe Tyr
305                 310                 315                 320

Phe Leu Glu Leu Asn Pro Arg Leu Gln Val Glu His Pro Thr Thr Glu
                325                 330                 335

Met Val Ser Gly Val Asn Leu Pro Ala Ala Gln Leu Gln Ile Ala Met
            340                 345                 350

Gly Ile Pro Met His Arg Ile Ser Asp Ile Arg Thr Leu Tyr Gly Met
        355                 360                 365

Asn Pro His Ser Ala Ser Glu Ile Asp Phe Glu Phe Lys Thr Gln Asp
    370                 375                 380

Ala Thr Lys Lys Gln Arg Arg Pro Ile Pro Lys Gly His Cys Thr Ala
385                 390                 395                 400

Cys Arg Ile Thr Ser Glu Asp Pro Asn Asp Gly Phe Lys Pro Ser Gly
                405                 410                 415

Gly Thr Leu His Glu Leu Asn Phe Arg Ser Ser Asn Val Trp Gly
            420                 425                 430

Tyr Phe Ser Val Gly Asn Asn Gly Asn Ile His Ser Phe Ser Asp Ser
        435                 440                 445

Gln Phe Gly His Ile Phe Ala Phe Gly Glu Asn Arg Gln Ala Ser Arg
    450                 455                 460

Lys His Met Val Val Ala Leu Lys Glu Leu Ser Ile Arg Gly Asp Phe
465                 470                 475                 480

Arg Thr Thr Val Glu Tyr Leu Ile Lys Leu Leu Glu Thr Glu Asp Phe
                485                 490                 495

Glu Asp Asn Thr Ile Thr Thr Gly Trp Leu Asp Asp Leu Ile Thr His
            500                 505                 510

Lys Met Thr
        515
```

<210> SEQ ID NO 70
<211> LENGTH: 505
<212> TYPE: PRT
<213> ORGANISM: Saccharomyces cerevisiae
<220> FEATURE:
<221> NAME/KEY: MISC_FEATURE
<222> LOCATION: (1)..(505)
<223> OTHER INFORMATION: N- and C-terminal deleted Yeast ACCase BC
      domain (AAs 57-561)

<400> SEQUENCE: 70

Thr Val Ile Ser Lys Ile Leu Ile Ala Asn Asn Gly Ile Ala Ala Val
1               5                   10                  15

Lys Glu Ile Arg Ser Val Arg Lys Trp Ala Tyr Glu Thr Phe Gly Asp
            20                  25                  30

Asp Arg Thr Val Gln Phe Val Ala Met Ala Thr Pro Glu Asp Leu Glu
        35                  40                  45

Ala Asn Ala Glu Tyr Ile Arg Met Ala Asp Gln Tyr Ile Glu Val Pro
    50                  55                  60

Gly Gly Thr Asn Asn Asn Tyr Ala Asn Val Asp Leu Ile Val Asp
65                  70                  75                  80

Ile Ala Glu Arg Ala Asp Val Asp Ala Val Trp Ala Gly Trp Gly His
                85                  90                  95

Ala Ser Glu Asn Pro Leu Leu Pro Glu Lys Leu Ser Gln Ser Lys Arg
            100                 105                 110

Lys Val Ile Phe Ile Gly Pro Pro Gly Asn Ala Met Arg Ser Leu Gly
        115                 120                 125

Asp Lys Ile Ser Ser Thr Ile Val Ala Gln Ser Ala Lys Val Pro Cys
    130                 135                 140

Ile Pro Trp Ser Gly Thr Gly Val Asp Thr Val His Val Asp Glu Lys
145                 150                 155                 160

Thr Gly Leu Val Ser Val Asp Asp Ile Tyr Gln Lys Gly Cys Cys
                165                 170                 175

Thr Ser Pro Glu Asp Gly Leu Gln Lys Ala Lys Arg Ile Gly Phe Pro
            180                 185                 190

Val Met Ile Lys Ala Ser Glu Gly Gly Gly Gly Lys Gly Ile Arg Gln
        195                 200                 205

Val Glu Arg Glu Glu Asp Phe Ile Ala Leu Tyr His Gln Ala Ala Asn
    210                 215                 220

Glu Ile Pro Gly Ser Pro Ile Phe Ile Met Lys Leu Ala Gly Arg Ala
225                 230                 235                 240

Arg His Leu Glu Val Gln Leu Leu Ala Asp Gln Tyr Gly Thr Asn Ile
                245                 250                 255

Ser Leu Phe Gly Arg Asp Cys Ser Val Gln Arg Arg His Gln Lys Ile
            260                 265                 270

Ile Glu Glu Ala Pro Val Thr Ile Ala Lys Ala Glu Thr Phe His Glu
        275                 280                 285

Met Glu Lys Ala Ala Val Arg Leu Gly Lys Leu Val Gly Tyr Val Ser
    290                 295                 300

Ala Gly Thr Val Glu Tyr Leu Tyr Ser His Asp Asp Gly Lys Phe Tyr
305                 310                 315                 320

Phe Leu Glu Leu Asn Pro Arg Leu Gln Val Glu His Pro Thr Thr Glu
                325                 330                 335

Met Val Ser Gly Val Asn Leu Pro Ala Ala Gln Leu Gln Ile Ala Met
            340                 345                 350

```
Gly Ile Pro Met His Arg Ile Ser Asp Ile Arg Thr Leu Tyr Gly Met
            355                 360                 365

Asn Pro His Ser Ala Ser Glu Ile Asp Phe Glu Phe Lys Thr Gln Asp
        370                 375                 380

Ala Thr Lys Lys Gln Arg Arg Pro Ile Pro Lys Gly His Cys Thr Ala
385                 390                 395                 400

Cys Arg Ile Thr Ser Glu Asp Pro Asn Asp Gly Phe Lys Pro Ser Gly
                405                 410                 415

Gly Thr Leu His Glu Leu Asn Phe Arg Ser Ser Asn Val Trp Gly
            420                 425                 430

Tyr Phe Ser Val Gly Asn Asn Gly Asn Ile His Ser Phe Ser Asp Ser
        435                 440                 445

Gln Phe Gly His Ile Phe Ala Phe Gly Glu Asn Arg Gln Ala Ser Arg
    450                 455                 460

Lys His Met Val Val Ala Leu Lys Glu Leu Ser Ile Arg Gly Asp Phe
465                 470                 475                 480

Arg Thr Thr Val Glu Tyr Leu Ile Lys Leu Leu Glu Thr Glu Asp Phe
                485                 490                 495

Glu Asp Asn Thr Ile Thr Thr Gly Trp
            500                 505

<210> SEQ ID NO 71
<211> LENGTH: 495
<212> TYPE: PRT
<213> ORGANISM: Saccharomyces cerevisiae
<220> FEATURE:
<221> NAME/KEY: MISC_FEATURE
<222> LOCATION: (1)..(495)
<223> OTHER INFORMATION: N- and C-terminal deleted Yeast ACCase BC
      domain (AAs 57-551)

<400> SEQUENCE: 71

Thr Val Ile Ser Lys Ile Leu Ile Ala Asn Asn Gly Ile Ala Ala Val
1               5                   10                  15

Lys Glu Ile Arg Ser Val Arg Lys Trp Ala Tyr Glu Thr Phe Gly Asp
            20                  25                  30

Asp Arg Thr Val Gln Phe Val Ala Met Ala Thr Pro Glu Asp Leu Glu
        35                  40                  45

Ala Asn Ala Glu Tyr Ile Arg Met Ala Asp Gln Tyr Ile Glu Val Pro
    50                  55                  60

Gly Gly Thr Asn Asn Asn Tyr Ala Asn Val Asp Leu Ile Val Asp
65                  70                  75                  80

Ile Ala Glu Arg Ala Asp Val Asp Ala Val Trp Ala Gly Trp Gly His
                85                  90                  95

Ala Ser Glu Asn Pro Leu Leu Pro Glu Lys Leu Ser Gln Ser Lys Arg
            100                 105                 110

Lys Val Ile Phe Ile Gly Pro Pro Gly Asn Ala Met Arg Ser Leu Gly
        115                 120                 125

Asp Lys Ile Ser Ser Thr Ile Val Ala Gln Ser Ala Lys Val Pro Cys
    130                 135                 140

Ile Pro Trp Ser Gly Thr Gly Val Asp Thr Val His Val Asp Glu Lys
145                 150                 155                 160

Thr Gly Leu Val Ser Val Asp Asp Ile Tyr Gln Lys Gly Cys Cys
                165                 170                 175

Thr Ser Pro Glu Asp Gly Leu Gln Lys Ala Lys Arg Ile Gly Phe Pro
            180                 185                 190
```

-continued

```
Val Met Ile Lys Ala Ser Glu Gly Gly Gly Lys Gly Ile Arg Gln
        195                 200                 205

Val Glu Arg Glu Glu Asp Phe Ile Ala Leu Tyr His Gln Ala Ala Asn
        210                 215                 220

Glu Ile Pro Gly Ser Pro Ile Phe Ile Met Lys Leu Ala Gly Arg Ala
225                 230                 235                 240

Arg His Leu Glu Val Gln Leu Leu Ala Asp Gln Tyr Gly Thr Asn Ile
                245                 250                 255

Ser Leu Phe Gly Arg Asp Cys Ser Val Gln Arg Arg His Gln Lys Ile
                260                 265                 270

Ile Glu Glu Ala Pro Val Thr Ile Ala Lys Ala Glu Thr Phe His Glu
        275                 280                 285

Met Glu Lys Ala Ala Val Arg Leu Gly Lys Leu Val Gly Tyr Val Ser
        290                 295                 300

Ala Gly Thr Val Glu Tyr Leu Tyr Ser His Asp Asp Gly Lys Phe Tyr
305                 310                 315                 320

Phe Leu Glu Leu Asn Pro Arg Leu Gln Val Glu His Pro Thr Thr Glu
                325                 330                 335

Met Val Ser Gly Val Asn Leu Pro Ala Ala Gln Leu Gln Ile Ala Met
                340                 345                 350

Gly Ile Pro Met His Arg Ile Ser Asp Ile Arg Thr Leu Tyr Gly Met
        355                 360                 365

Asn Pro His Ser Ala Ser Glu Ile Asp Phe Glu Phe Lys Thr Gln Asp
        370                 375                 380

Ala Thr Lys Lys Gln Arg Arg Pro Ile Pro Lys Gly His Cys Thr Ala
385                 390                 395                 400

Cys Arg Ile Thr Ser Glu Asp Pro Asn Asp Gly Phe Lys Pro Ser Gly
                405                 410                 415

Gly Thr Leu His Glu Leu Asn Phe Arg Ser Ser Ser Asn Val Trp Gly
                420                 425                 430

Tyr Phe Ser Val Gly Asn Asn Gly Asn Ile His Ser Phe Ser Asp Ser
        435                 440                 445

Gln Phe Gly His Ile Phe Ala Phe Gly Glu Asn Arg Gln Ala Ser Arg
        450                 455                 460

Lys His Met Val Val Ala Leu Lys Glu Leu Ser Ile Arg Gly Asp Phe
465                 470                 475                 480

Arg Thr Thr Val Glu Tyr Leu Ile Lys Leu Leu Glu Thr Glu Asp
                485                 490                 495
```

RECOMBINANT BIOTIN CARBOXYLASE DOMAINS FOR IDENTIFICATION OF ACETYLE COA CARBOXYLASE INHIBITORS

RELATED APPLICATIONS

This application claims priority under 35 U.S.C. 119(e) from United States Provisional Patent Application 60/401, 170, filed Aug. 5, 2002, the disclosure of which is incorporated by reference herein in its entirety.

FIELD OF THE INVENTION

The present invention relates to a peptide comprising a biotin carboxylase domain and fragments thereof useful for the identification of Acetyl CoA carboxylase inhibitors, which in turn are useful among other things as fungicides, insecticides, nematicides, herbicides and pharmaceuticals.

BACKGROUND OF THE INVENTION

Acetyl CoA carboxylase (ACCase) catalyzes the first committed step in fatty acid biosynthesis and has also been chemically validated as an herbicide and fungicide target. Structurally, ACCases are biotinylated, multifunctional enzymes comprised of three domains: a biotin carboxylase domain, a biotin binding site, and a carboxytransferase domain. In prokaryotic ACCases, as well as in the plastidic isoforms of most plant ACCases, the three domains reside on three distinct, dissociable proteins. In contrast, in most eukaryotic ACCases the three domains reside on a single polypeptide of 160 kD to 280 kD. In their native state, the eukaryotic enzymes are typically dimers or tetramers ranging in size from approximately 400-800 kD.

The ACCase reaction takes place at two catalytic sites via two partial reactions: the ATP dependent carboxylation of the enzyme-bound biotin prosthetic group, and the subsequent transfer of the carboxyl group from biotin to acetyl CoA to form malonyl CoA. The natural product soraphen has been demonstrated to be a broad-spectrum fungicide that acts by inhibiting the biotin carboxylase reaction of ACCase. ACCase's are known to be low abundant and labile proteins. These properties impede the identification of new ACCase inhibitors.

The present invention provides a peptide comprising a biotin carboxylase domain and fragments thereof useful for the identification of Acetyl CoA carboxylase inhibitors, which in turn are useful among other things as fungicides, insecticides, nematicides, herbicides and pharmaceuticals.

SUMMARY OF THE INVENTION

According to embodiments of the present invention, the present invention relates to a peptide comprising an Acetyl CoA carboxylase (ACCase) having a deleted biotin binding domain, having a deleted carboxy transferase domain, and having a functional biotin carboxylase (BC) domain (e.g., capable of binding soraphen). In some embodiments of the invention where such BC domains are used as counterselection agents in conjunction with peptides or BC domains as described above, the peptide or BC domain is non-functional.

"Functional" as used herein refers to a BC domain that binds soraphen with similar affinity as enzymatically active, full length ACCase protein. Thus, "non-functional" as used herein refers to a BC domain that does not bind soraphen. These non-functional BC domains would be functional with respect to enzyme activity/catalytic function when incorporated into an intact ACCase.

The carboxylase (and corresponding peptide) may be from any suitable source, including plant, animal (e.g., mammalian), insect, yeast, and fungal carboxylases/peptides.

According to other embodiments of the present invention, the carboxylase (and corresponding peptide) is from *Ustilago maydis* carboxylase.

According to still other embodiments of the present invention, the carboxylase (and corresponding peptide) are from *Phytophthora infestans* carboxylase.

According to still other embodiments of the present invention, the carboxylase (and corresponding peptide) are from *Magnaporthe grisea, Saccharomyces cerevisiae* and *Homo sapiens*.

According to other embodiments of the present invention, the present invention relates to the molecules described above wherein the respective peptides are each an Acetyl CoA carboxylase (ACCase) having a deleted biotin binding domain, selecting a compound identified in step (c) that inhibits Acetyl CoA carboxylase activity.

According to still other embodiments of the present invention, the present invention relates to a method of identifying fungicides, comprising a) combining a peptide as described above and a compound to be tested for the ability to bind to said biotin carboxylase domain, under conditions that permit binding to said biotin carboxylase domain, b) determining whether or not said compound binds to said biotin carboxylase domain, the presence of binding indicating said compound is or may be a fungicide, c) employing a compound identified as binding in step (b) in an assay to detect inhibition of Acetyl CoA carboxylase activity, and d) selecting a compound identified in step (c) that inhibits Acetyl CoA carboxylase activity.

According to still other embodiments of the present invention, the present invention relates to the use of a peptide or compound as described above for carrying out a method as described above.

BRIEF DESCRIPTION OF THE DRAWINGS

FIG. 1 illustrates full-length ACCase protein from *Ustilago maydis* (pCS 11) with the three functional domains detailed.

FIG. 2 illustrates soraphen binding to and inhibition of the full-length pCS11 protein.

FIG. 3 illustrates soraphen binding to the *Ustilago* BC domain (pCS8) with comparable affinity to full length ACCase (pCS11).

FIG. 4 illustrates soraphen binding to *Phytopthora infestans* BC domain.

FIG. 6 illustrates the amino acid sequence of *Ustilago maydis* ACCase BC domain, amino acids 2-560 (pCS8, SEQ ID NO: 2)(Taken from Full Length Amino Acid Sequence for *Ustilago maydis* ACCase, Accession Number: Z46886;A. Bailey, J. Keon, J. Owen, and J. Hargreaves, ACC1 gene, encoding acetyl-CoA carboxylase, is essential for growth in *Ustilago maydis, Mol. Gen. Genet.* 249 (2), 191-201 (1995)).

FIG. 7 illustrates the amino acid sequence of *Phytopthora infestans* ACCase BC domain, amino acids 1-555 (pCS 15, SEQ ID NO: 4).

FIG. 8 illustrates anion Exchange Chromatography of pCS8 peptide.

FIG. 9B shows (i) spectrophotometric and (ii) 14C isotope exchange activity assays on pCS11 protein.

FIG. 10 illustrates the alignment of *Ustilago* (SEQ ID NO: 2), *Phytophthora* (SEQ ID NO: 4), *Magnaporthe* (SEQ ID NO: 6) and yeast (SEQ ID NO: 8) ACCase BC domains.

FIG. 13 illustrates the alignment of the human ACC1 BC (SEQ ID NO: 10) and ACC2 BC (SEQ ID NO: 12) domains with the *Ustilago* ACCase BC (SEQ ID NO: 2) domain.

FIG. 15 illustrates the binding of [$^3$H]-soraphen A and soraphen C conjugates to (A) the *Ustilago* ACCase BC domain and (B) the full-length *Ustilago* ACCase protein.

DETAILED DESCRIPTION OF THE PREFERRED EMBODIMENTS

Figure 5:
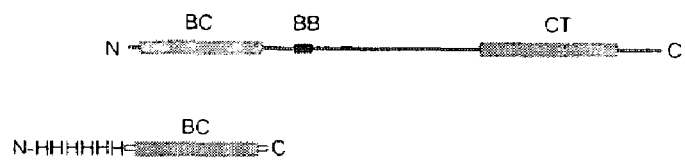
FIG. 5 illustrates the biotin carboxylase domain of *Ustilago* peptide (pCS8) compared to full-length *Ustilago* ACCase.

The present invention will now be described more fully hereinafter with reference to the accompanying figures, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art. The disclosures of all United States patent references cited herein are to be incorporated by reference herein in their entirety.

Described herein is the use of recombinant, isolated, biotin carboxylase domains for the discovery of new Acetyl CoA carboxylase (ACCase) inhibitors. A biotin carboxylase (BC) domain from the ACCase gene of the basidiomycete *Ustilago maydis* was isolated, cloned, expressed, and characterized. The isolated BC domain was shown to have similar high-affinity, soraphen-binding properties as the full-length protein. In contrast to the full-length protein (FIG. 1), however, the BC domain is significantly smaller and can be expressed at higher levels, is more stable, and exists as a monomer. The isolated BC domain is useful for screening new ACCase inhibitors. The BC domain from the oomycete *Phytophthora infestans* was also cloned. A full-length ACCase sequence from this organism has not been published. The appropriate fragment was cloned utilizing PCR using primers derived from published EST's that showed homology to sequences flanking the soraphen-binding domain that was identified in the *Ustilago* gene. The recombinantly expressed *Phytopthora* BC domain exhibited high-affinity soraphen-binding. BC domains from *M. grisea*, *S. cerevisiae*, and *H. sapiens* were also similarly cloned and determined to exhibit high-affinity soraphen-binding, thus demonstrating the applicability of this approach to distantly related organisms.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

As used herein, an "isolated" nucleic acid (e.g., an "isolated DNA" or an "isolated genomic RNA") means a nucleic acid separated or substantially free from at least some of the other components of the naturally occurring organism or virus, for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide. As used herein, the terms "polypeptide" and "peptide" have the same meaning.

As used herein, the terms "deleted" or "deletion" mean either total deletion of the specified segment or the deletion of a sufficient portion of the specified segment to render the segment inoperative or nonfunctional (e.g., does not encode a functional peptide, wherein functional is defined as the ability to bind soraphen), in accordance with common usage. See, e.g. U.S. Pat. No. 6,180,362; U.S. Pat. No. 5,689,039.

As used herein, the term modulation of Acetyl CoA carboxylase activity refers to the ability of a compound to alter the activity of the enzyme. The alteration may be by enhancing or decreasing the activity of the enzyme, or by causing the enzyme to function in a manner other than that observed in the absence of the compound.

Also as used herein, the term activator refers to the ability of a compound to initiate and/or enhance Acetyl CoA carboxylase activity (e.g., an agonist).

The term inhibitor as used herein refers to the ability of a compound to decrease and/or terminate Acetyl CoA carboxylase activity (e.g., an antagonist).

As used herein, test compounds refer to compounds that may bind the biotin carboxylase domain, under conditions that permit binding to the biotin carboxylase domain. The presence of binding indicating the compound is or may be an Acetyl CoA carboxylase inhibitor. Moreover, binding of the compound to the biotin carboxylase domain may indicate that the compound may be a fungicide, insecticide, nematicide, or herbicide or may be a pharmaceutical (e.g., a compound that reduces, controls, inhibits or otherwise regulates weight gain in a human or animal subject, particularly compounds that are inhibitors of human or mammalian ACC2, and more particularly compounds that preferentially inhibit or antagonize human or mammalian ACC2 and not human or mammalian ACC1, see, e.g., L. Abu-Elheiga et al., *Science* 291, 2613 (30 Mar. 2001)). Additionally, binding of the test compound refers to specific binding wherein the binding interaction between the BC domain and test compounds is high. The dissociation constant of the BC domain complexes is from about $10^{-4}$ M to about $10^{-14}$ M, more preferably $10^{-7}$ to $10^{-14}$, and still more preferably $10^{-8}$ to $10^{-14}$ and most preferably lower than $2\times10^{-9}$ M. The test compound may be identified by any available means, including but not limited to the Evolutionary Chemistry process described herein below.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three-letter code, in accordance with 37

C.F.R §1.822 and established usage. See, e.g., Patent In User Manual, 99-102 (November 1990) (U.S. Patent and Trademark Office).

In general, the term "peptide" refers to a molecular chain of amino acids with a biological activity (e.g., capacity to bind soraphen). If required, it can be modified in vivo and/or in vitro, for example by glycosylation, myristoylation, amidation, carboxylation or phosphorylation; thus inter alia oligopeptides and polypeptides are included. It is understood however that the peptides of the present invention do not extend to native proteins which may contain the disclosed peptides. The peptides disclosed herein may be obtained, for example, by synthetic or recombinant techniques known in the art. It will also be understood that amino acid and nucleic acid sequences may include or exclude additional residues, Such as additions or deletions of N- or C-terminal amino acids or 5' or 3' sequences, and yet still be essentially as set forth as disclosed herein, so long as the sequence meets the criteria set forth above, including the maintenance of biological activity (e.g., capacity to bind soraphen). Thus, Up to about 10, 20, 30, or about 40 amino acids may be deleted from either, or both, the N- and/or C-terminus of the peptide, so long as a functional biotin carboxylase domain (e.g., soraphen binding) is retained. Examples of such peptides are peptides having the amino acid sequence given in SEQ ID NO: 14, 16 and 17 through 71 herein. Note that, for BC domains of human ACC1 and ACC2, Up to 102 and 244 amino acids, respectively may be deleted from the N-terminal end, alone or in combination with the above listed C-terminal deletions, so long as a function biotin carboxylase domain (e.g., soraphen binding) is retained.

"Nucleic acid sequence" as used herein refers to an oligonucleotide, nucleotide, or polynucleotide, and to DNA or RNA of genomic or synthetic origin which may be single- or double-stranded, and represent the sense or antisense strand. Suitable nucleic acid sequences encoding an ACCase biotin carboxylase (BC) domain (that is, an ACCase having a deleted biotin binding domain and a deleted carboxy transferase domain) include, for example, a nucleic acid encoding a *Ustilago maydis* BC domain. Examples of such are given as SEQ ID NOS: 1, 3, 5, 7, 9, 11, 13, and 15 herein.

Polynucleotides of the present invention include those coding for peptides homologous to, and having essentially the same biological properties as, the peptides disclosed herein. For example, the DNA sequences disclosed herein as SEQ ID NOS:1, 3, 5, 7, 9, 11, 13, and 15. This definition is intended to encompass natural allelic sequences thereof. Thus, isolated DNA or cloned genes of the present invention can be of any species of origin. Thus, polynucleotides that hybridize to any one or more of the DNA sequences disclosed herein as SEQ ID NOS: 1, 3, 5, 7, 9, 11, 13, and 15 and which code on expression for an ACCase BC domain, are also an aspect of the invention. Conditions which will permit other polynucleotides that code on expression for a protein or peptide of the present invention to hybridize to the DNA of SEQ ID NOS:1, 3, 5, 7, 9, 11, 13, and 15 herein can be determined in accordance with known techniques.

For example, hybridization of such sequences may be carried out under conditions of reduced stringency, medium stringency or even stringent conditions (e.g., conditions represented by a wash stringency of 35-40% Formamide with 5× Denhardt's solution, 0.5% SDS and 1×SSPE at 37° C.; conditions represented by a wash stringency of 40-45% Formamide with 5× Denhardt's solutions 0.5% SDS and 1×SSPE at 42° C.; and conditions represented by a wash stringency of 50% Formamide with 5× Denhardt's solution, 0.5% SDS and 1×SSPE at 42° C. respectively) to DNA of SEQ ID NOS:1, 3, 5, 7, 9, 11, 13, and 15 herein in a standard hybridization assay. See, e.g., J. Sambrook et al., *Molecular Cloning, A Laboratory Manual* (2d Ed. 1989) (Cold Spring Harbor Laboratory). In general, sequences which code for proteins or peptides of the present invention and which hybridize to the DNA of SEQ ID NOS:1, 3, 5, 7, 9, 11, 13, and 15, for example, will be at least 60% or 75% identical or homologous, 85% identical or homologous, 90% identical or homologous and even 95% identical or homologous, or more with one or more of SEQ ID NOS:1, 3, 5, 7, 9, 11, 13, and 15.

Mathematical algorithms can be used to determine the percent identity of two sequences. Non-limiting examples of mathematical algorithms are the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877; the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; and the search-for-similarity-method of Pearson and Lipman (1988) *Proc. Natl. Acad. Sci. USA* 85:2444-2448.

Various computer implementations based on these mathematical algorithms have been designed to enable the determination of sequence identity. The BLAST programs of Altschul et al. (1990) *J. Mol. Biol.* 215:403 are based on the algorithm of Karlin and Altschul (1990) supra. Searches to obtain nucleotide sequences that are homologous to nucleotide sequences of the present invention can be performed with the BLASTN program, score=100, wordlength=12. To obtain amino acid sequences homologous to sequences encoding a protein or polypeptide of the current invention, the BLASTX program may be used, score=50, wordlength=3. Gapped alignments may be obtained by using Gapped BLAST as described in Altschul et al. (1997) *Nucleic Acids Res.* 25:3389. To detect distant relationships between molecules, PSI-BLAST can be used. See Altschul et al. (1997) supra. For all of the BLAST programs, the default parameters of the respective programs can be used.

Further, polynucleotides that code for proteins or peptides of the present invention, or polynucleotides that hybridize to that as SEQ ID NO:1, 3, 5, 7, 9, 11, 13, and 15, or polynucleotides having sequence identity or homology thereto as described above, for example, but which differ in codon sequence therefrom due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

PCR is the polymerase chain reaction—a technique for copying the complementary strands of a target DNA molecule simultaneously for a series of cycles until the desired amount is obtained. First, primers are synthesized that have nucleotide sequences complementary to the DNA that flanks the target region. The DNA is heated to separate the complementary strands and then cooled to let the primers bind to the flanking sequences. A heat-stable DNA polymerase is added, and the reaction is allowed to proceed for a series of replication cycles. Twenty will yield a millionfold amplification; thirty cycles will yield an amplification factor of one billion.

A vector is a replicable DNA construct. Vectors are used herein either to amplify DNA encoding the proteins or peptides of the present invention or to express the proteins or peptides of the present invention. An expression vector is a replicable DNA construct in which a DNA sequence encoding the proteins of the present invention is operably linked to suitable control sequences capable of effecting the expression of proteins or peptides of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells are cells which have been transformed or transfected with vectors containing DNA coding for proteins or peptides of the present invention and need not express protein or peptide. However, in the present invention, the cells preferably express the protein or peptide.

Suitable host cells include prokaryotes, yeast cells, or higher eukaryotic organism cells. Prokaryote host cells include grain negative or gram positive organisms, for example *Escherichia coli* (*E. coli*) or *Bacilli*. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. See Bolivar et al., *Gene* 2, 95 (1977). Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983). The promoter and Shine-Dalgarno sequence (for prokaryotic host expression) are operably linked to the DNA of the present invention, i.e., they are positioned so as to promote transcription of the messenger RNA from the DNA.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980). The promoter and Shine-Dalgarno sequence (for prokaryotic host expression) are operably linked to the DNA encoding the desired protein, i.e., they are positioned so as to promote transcription of the protein messenger RNA from the DNA.

Eukaryotic microbes such as yeast cultures may be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977). The presence of the trp1 lesion in the yeast host cell genome then provides an effective environment for detecting transformation by growth in the absence of tryptophan.

Suitable promoting sequences in yeast vectors include the promoters for metallothionein, 3-phospho-glycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., Nature 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculorivus expression vector (e.g., vectors derived from *Autographa californica* MNPV, *Trichoplusia ni* MNPV, *Rachiplusia ou* MNPV, or *Galleria ou* MNPV) may be employed to make proteins useful in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Host cells transformed with nucleotide sequences encoding a protein or peptide of the invention may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode a protein or peptide of the invention may be designed to contain signal sequences which direct secretion of the protein or peptide through a prokaryotic or eukaryotic cell membrane. Other constructions may be used to join sequences encoding the protein or peptide to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the protein or peptide of the invention may be used to facilitate purification. One such expression vector provides for expression of a fusion protein containing a protein or peptide of the invention and a nucleic acid encoding 6 histidine residues preceding a thioredoxin or an enterokinase cleavage site. The histidine residues facilitate purification on IMAC (immobilized metal ion affinity chromatography) as described in Porath, J. et al. (1992, Prot. Exp. Purif. 3: 263-281) while the enterokinase cleavage site provides a means for purifying the protein or peptide of the invention from the fusion protein. A discussion of vectors which contain fusion proteins is provided in Kroll, D. J. et al. (1993; DNA Cell Biol. 12:441-453).

ACCase activity can be measured spectrophotometrically and also through the isotope exchange technique. ACCase activity was measured spectrophotometrically by coupling the production of ADP to the oxidation of NADH using pyruvate kinase and lactate dehydrogenase. This assay was used to measure overall ACCase activity by supplying acetyl CoA as a substrate. Activity of the full length Ustilago ACCase is detailed in FIG. 2. ACCase activity was measured by way of isotope exchange based upon the fact that ACCase catalyzes the formation of malonyl CoA from acetyl-CoA and bicarbonate. The isotope exchange assay is designed to monitor the incorporation of $^{14}C$ from bicarbonate into the malonyl CoA product.

Binding assays were conducted to detect binding to the BC domain, and thus, enabled identification of test compounds. Methods of conducting binding assays are well known in the art. Direct measurement of the binding of radiolabeled ligands is typically performed by incubating numerous concentrations of radioligand with a constant amount of target peptide under equilibrium binding conditions followed by determining the amount of labeled probe specifically bound. "Specifically bound" is defined as total binding minus non-specific binding, where non-specific binding is determined in the presence of excess unlabled ligand. The strength of the binding interaction between the BC domain and soraphen is high and comparable to binding of soraphen to the full length ACCase (FIGS. 2, 3 and 4). The dissociation constant of the BC domain complexes, for example for soraphen, is from about $10^{-4}$ to about $10^{-14}$ M, and preferably at $10^{-7}$ M to $10^{-14}$ M, and more preferably at least $10^{-8}$ M to $10^{-14}$ M, and still more preferably lower than $2\times10^{-9}$ M. Complexes can be formed by covalent or noncovalent interactions. Once one possesses a radiolabeled ligand that binds to a target protein, any additional compound that is not radiolabeled can be assayed for binding to the same site using a competition binding assay. A competition binding assay is performed by incubating a constant concentration of target protein and radiolabled ligand with numerous concentrations of test compounds under equilibrium conditions followed by determining the amount of radiolabeled ligand that is specifically bound.

Thus, a further aspect of the present invention is a composition comprising: (a) an aqueous carrier solution; and (b) the peptide (or ACCase BC domain described herein) solubilized in said aqueous carrier solution. The composition is useful for, among other things, the binding or screening assays described herein. In general, "solubilized" means that the peptide is homogeneously or uniformly dissolved or dispersed in the carrier solution in a manner that makes the peptide in the composition available for participation in the binding events (e.g., soraphen binding) described herein. The carrier solution may be any suitable aqueous solution that comprises, consists of or consists essentially of water, along with other typical optional ingredients such as buffers, agents for adjusting pH, preservatives, etc. In general, the peptide is included in the composition in any suitable amount, for example from 0.001, 0.01 or 0.1 nanograms up to 0.1, 1, 10, or 20 milligrams per milliliter of aqueous carrier solution. The peptide is in a physical form in the composition that renders it suitable for a binding assay and thus has a soraphen dissociation constant in said composition of, for example, from $10^{-4}$ up to $10^{-14}$ M. The pH of the composition may be at, or adjusted to be at, a pH suitable for binding studies, such as a pH of 5 through 9. Preferably, the Evolutionary Chemistry process as referenced herein could be utilized to identify test compounds that bind to the BC domain. In such instance, the composition should be comprised of an aqueous carrier solution containing a BC domain peptide, possessing a soraphen dissociation constant of $10^{-8}$ to $10^{-9}$ M. The BC domain would be utilized at a concentration of 0.02 to 20 milligrams per milliliter at pH 7 incubated in combination with one or more RNA-tethered test compounds for 1 hour to enable equilibrium binding to occur. Depending upon the level of stringency applied, low affinity test compounds would be washed away from the BC domain peptide and high affinity binding compounds would be retained. The retained compounds are potential ACCase inhibitors.

Alternatively, ACCase inhibitors could be identified in a screen based on the principle of competition binding with soraphen. As mentioned previously, one way to detect competitive binding is by use of radiolabeled soraphen. In such instance, the composition should be comprised of an aqueous carrier solution containing a BC domain peptide, possessing a soraphen dissociation constant of $10^{-8}$ to $10^{-9}$ M. The BC domain would be utilized at a concentration of 5 nM to 10 nM at pH 7 incubated in combination with $^3$H-soraphen (with a specific activity greater than 500 cpm per picomole) at a concentration 10% to 90% that of the BC domain, and with one or more test compounds at a concentration of $10^{-4}$ M to $10^{-10}$ M for 1 hour or more to enable equilibrium binding. The amount of $^3$H-soraphen that remains bound to the BC domain would then be determined. A reduction in the amount of bound soraphen indicates that the test compound or compounds can bind to the same site on the BC domain and thus represent potential ACCase inhibitors.

Another preferred method to screen for ACCase inhibitors based on the principle of competitive binding with soraphen is by a fluorescence polarization assay. In this method, a fluorescent soraphen derivative that retained high affinity for BC domains would need to be acquired or prepared through standard synthetic procedures. In such instance, the composition should be comprised of an aqueous carrier solution containing a BC domain peptide, possessing a fluorescent-soraphen derivative dissociation constant of $10^{-6}$ M to $10^{-9}$ M. The BC domain would be utilized at a concentration approximately equal to the dissociation constant of the fluorescent probe, and incubated in the presence of one or more test compounds at a concentration of $10^{-4}$ M to $10^{-10}$ M for 1 hour or more to enable equilibrium binding. The fluorescence polarization would then be measured. Since the fluorescence polarization is directly related to the amount of fluorescent-soraphen derivative bound, a reduction in fluorescence polarization indicates that the test compound or compounds can bind to the same site on the BC domain and thus represent potential ACCase inhibitors.

Evolutionary chemistry (EC) as described herein relates to the process wherein product libraries are formed by combining a pool of first chemical reactants coupled to a nucleic acid with a pool of free chemical reactants. The coupled nucleic acid is capable of mediating the chemical reaction which leads to the product library and further the nucleic acid is amplifiable so a product which has a predetermined desirable characteristic can be enriched for and identified from the product library. In its most general form, a nucleic acid-reactant test mixture is formed by attaching a first reactant (R) to each of the nucleic acids in a test mixture (containing $10^2$ to $10^{18}$, nucleic acids with randomized sequences). The nucleic acid-reactant test mixture is treated with other free reactants that will combine with the first reactant (R) to form different products. It is important to note that from the nucleic acid test mixture (NA), discrete nucleic acid sequences will be associated with facilitating the formation of the different shaped products and are denoted, for example, by sequence-A, sequence-B and sequence-C. The products may differ in shape, reactivity or both shape and reactivity. Partitioning of the desirable product shape or reactivity is accomplished by binding to or reaction with a target. Proteins, small molecules, lipids, saccharides, etc., are all examples of targets (T). After binding to or reacting with the target the non-interacting products, which are attached to sequence-B and sequence-C are separated from sequence-A and discarded. The nucleic acid sequence-A is then amplified by a variety of methods known to those experienced in the art. Sequence-A is then used to facilitate the assembly of the desirable product by facilitating the specific reaction to form the selected product on treatment with the mixture of starting reactants. In a typical reaction, Sequence-A can be reattached to the first reactant, however, said reattachment is not always required. This is an idealized case and in many examples the nucleic acid facilitator may assemble more than one product from the starting mixture, but all of the products selected will have the desired properties of binding to or chemical reaction with the target. EC is more fully described in U.S. Pat. Nos. 6,048,698; 6,030,776; 5,858,660; 5,789,160; 5723,592; and 5,723,289.

In sum, BC peptide domains, as exemplified by Ustilago pCS8, are expressed at high levels, can be purified to homogeneity, are stable under typical laboratory conditions, and exhibit high affinity soraphen binding comparable to that of full length ACCase (FIG. 5). Therefore, it is an excellent agent for use in target based affinity binding screens and selections, including but not limited to evolutionary chemistry selections, for the identification of ACCase inhibitors.

In some assays it may be desirable to use a first peptide of the present invention in conjunction (e.g., sequentially or simultaneously) with a second peptide that serves as a counterselection agent. For one embodiment, the counterselection agent may be a peptide of the same species as the first peptide (that is, with substantially the same amino acid sequence as the first peptide), but with a nonfunctional BC domain (for example, by introduction of a deletion or substitution mutation therein), to select against agents that bind non-specifically (e.g., not at the soraphen binding site) to the first peptide. An example would be an *S. cerevisiae* first peptide and a corresponding *S. cerevisiae* second peptide in which the second peptide contains a mutation that disrupts soraphen binding (e.g., S77->Y). In another embodiment, the second peptide counterselection agent may be a peptide of a different species as the first peptide, but with a functional BC domain, to detect agents that bind to and act on the first species but not the second species. For example, the first peptide may be non-mammalian, and the second peptide may be ammalian or human (e.g., to select against agents that are active on the mammalian or human ACCase). Where a species contains two different ACCases such as does human, the first and second peptide may be of the same species but a different ACCase (e.g., human ACC1 and human ACC2). In either embodiment, the first and second peptides can be provided together as kits or sets, either per se or as compositions/formulations as described above, which may be stored, utilized and/or packaged together, optionally including instructions for their use in assays as described herein.

While the present invention has been described primarily with reference to a ACCase BC domains isolated from *Ustilago maydis* (FIG. 6; SEQ ID NO: 2), *Phytophthora infestans* (FIG. 7; SEQ ID NO: 4), *Magnaporthe grisea* (SEQ ID NO: 6), *Saccharomyces cerevisiae* (SEQ ID NO: 8), and *Homo sapiens* (SEQ ID NOS: 10, 12, 14, 16), it will be appreciated that distantly related organisms may be substituted for the organisms described herein. For example, peptides of the present invention may be isolated from other fungal, insect, or plant species, such as set forth in Tables 1-3 below, including any other members of the kingdoms, divisions, classes, orders or families set forth therein, as well as nematodes and mammals.

TABLE 1

Fungal Pests (Kingdom = Fungi if Division is not Oomycota;
If Division = Oomycota, then Kingdom = Chromista)

| Genus | Species | Common Name | Family | Order | Class | Division | Major Crop |
|---|---|---|---|---|---|---|---|
| Magnaporthe | grisea | rice blast | Magnaporthaceae | Diaporthales | Ascomycetes | Ascomycota | rice |
| Erysiphe | graminis tritici | powdery mildew | Erysiphaceae | Erysiphales | Ascomycetes | Ascomycota | wheat |
| Septoria (Leptosphaeria) | nodorum and tritici | septoria | Leptosphaeriaceae | Pleosporales | Ascomycetes | Ascomycota | wheat |
| Gaeumannomyces | graminis | take-all | Pythiaceae | Pythiales | Oomycetes | Oomycota | wheat |
| Pythium spp | | | Pythiaceae | Pythiales | Oomycetes | Oomycota | turf |
| Puccinia | sorghi | stalk rot/rust | Pucciniaceae | Uredinales | Urediniomycetes | Basidiomycota | maize |
| Aspergillus | flavus | | Trichocomaceae | Eurotiales | Ascomycetes | Ascomycota | maize |
| Phytophthora | Infestans | late blight | Pythiaceae | Pythiales | Oomycetes | Oomycota | potatoes |
| Fusarium spp | | wilt | Nectriaceae | Hypocreales | Ascomycetes | Ascomycota | potatoes |
| Botrytis spp | | | Clavicipitaceae | Hypocreales | Ascomycetes | Ascomycota | tree/vines |
| Alternaria spp | | | Pleosporaceae | Pleosporales | Ascomycetes | Ascomycota | |
| Cercospora spp | | | Mycosphaerellaceae | Mycosphaerellales | Ascomycetes | Ascomycota | |
| Rhizoctonia spp | | | Platygloeaceae Ceratobasidiaceae | Platygloeales Ceratobasidiales | Ustilaginomycetes Basidiomycetes | Basidiomycota Basidiomycota | |
| Peronospora spp | | Downy mildew | Peronosporaceae | Peronosporales | Oomycetes | Oomycota | |
| Colletotrichum spp | | | Glomerella | Glomerellaceae | Ascomycetes | Ascomycota | |
| Bremia spp | | Downy mildew | Peronosporaceae | Peronosporales | Oomycetes | Oomycota | |

TABLE 2

Insect Pests (Kingdom = Animalia; Phylum = Arthropoda)

| Genus | Species | Common Name | Family | Order | Class | Major Crop |
|---|---|---|---|---|---|---|
| Nilaparvata | lugens | Brown planthopper | Delphacidae | Hemiptera | Insecta | rice |
| Mayetiola | destructor | Hessian fly | Cecidomyiidae | Diptera | Insecta | wheat |
| Heliothis | zea | Corn earworm/bollworm | Noctuidae | Lepidoptera | Insecta | maize |
| Ostrinia | nubilalis | European cornborer | Pyralidae/Crambidae | Lepidoptera | Insecta | maize |
| Diabrotica spp | | Corn rootworm | Chrysomelidae | Coleoptera | Insecta | maize |
| Myzus spp | | aphid | Aphididae | Homoptera | Insecta | potato |
| Leptinotarsa | decemlineata | Colorado beetle | Chrysomelidae | Coleoptera | Insecta | potato |
| Pectinophora | gossypiella | Pink bollworm | Gelechiidae | Lepidoptera | Insecta | cotton |
| Heliothis spp | | | Noctuidae | Lepidoptera | Insecta | cotton |
| | | whiteflies | Aleyrodidae | Homoptera | Insecta | |
| | | Potato leafhopper | Cicadellidae | Hemiptera | Insecta | |
| Plutella | xylostella | Diamondback moth | Plutellidae | Lepidoptera | Insecta | |
| Chaetocnema spp | | Flea beetles | Chrysomelidae | Coleoptera | Insecta | |

TABLE 3

Weedy Pests (Kingdom = Plantae; Division = Magnoliophyta)

| Genus | Species | Common Name | Family | Order | Class | Major Crop |
|---|---|---|---|---|---|---|
| Echinochloa | crus-galli | Barnyard grass | Poaceae | Cyperales | Liliopsida | rice, cotton |
| Echinochloa | colonum | | Poaceae | Cyperales | Liliopsida | maize |
| Avena | fatua | Wild oats | Poaceae | Cyperales | Liliopsida | wheat |
| Polygonum | convolvulus | black bindweed | Polygonaceae | Polygonales | Magnoliopsida | wheat |
| Cyperus | rotundus | sedge | Cyperaceae | Cyperales | Liliopsida | maize, cotton |
| Chenopodium | album | lambsquarters | Chenopodiaceae | Caryophyllales | Magnoliopsida | potato |
| Galium spp | | bedstraw | Rubiaceae | | | |
| Ipomoea spp | | morningglory | Convolvulaceae | Solanales | Magnoliopsida | |
| Amaranthus spp | | pigweed | Amaranthaceae | Caryophyllales | Magnoliopsida | |
| Digitaria spp | | Crabgrass | Poaceae | Cyperales | Liliopsida | |
| Lolium spp | | ryegrass | Poaceae | Cyperales | Liliopsida | |
| Sorghum | halepense | Johnson grass | Poaceae | Cyperales | Liliopsida | |
| Panicum | miliaceum | Wild proso millet | Poaceae | Cyperales | Liliopsida | |
| Senna spp | | Velvet leaf | Fabaceae | Fabales | Magnoliopsida | |

The present invention is explained in greater detail in the following non-limiting Examples and the Figures herein, in which the following abbreviations are used: pCS8—*Ustilago maydis*, basidomycete, N-terminal His-tag BC domain, 64.6 kDa protein; pCS11—*Ustilago maydis*, basidomycete, full length ACCase with C-terminal His-tag, 241.4 kDa protein; pCS15—*Phytophthora infestans*, oomycete C-terminal His-tag BC domain, 63.3 kDa protein; pCS16—*Saccharomyces cerevisiae*, wild type N-terminal His-tag BC domain, 68.0 kDa protein; pCS16M—*Saccharomyces cerevisiae*, S77Y mutant, N-terminal His-tag BC domain, 68.0 kDa protein; pCS 17—*Magnaporthe grisea*, ascomycete, N-terminal His-tag BC domain, 68.2 IcDa protein; pCS19—*Homo sapiens*, C-term His-tag ACC1 BC domain, 71.2 kDa protein; pCS20—*Homo sapiens*, C-term His-tag ACC2 BC domain, 86.7 kDa protein; pCS201—*Escherichia coli*, N-terminal His-tag BC protein, 51.6 kDa protein; pCS204—*Saccharomyces cerevisiae*, C-terminal His-tag wild type full length ACCase protein, 254.3 kDa protein; and pCS204M—*Saccharomyces cerevisiae*, C-terminal His-tag S77Y mutant full length ACCase protein, 254.3 kDa protein.

EXAMPLE 1

A. Preparation of BC Domain Peptide. *E. coli* cultures transformed with protein expression constructs for BC domains with either N or C terminal his-tags (as illustrated in FIG. 5 for pCS8) were induced by the addition of IPTG (0.2 mM) at an $OD_{600}$=0.5. The cultures were grown overnight at 18° C., harvested and stored at −80° C. The bacterial pellet was resuspended in a buffer containing 50 mM $NaH_2PO_4$ (pH8), 300 mM NaCl, 10 mM imidazole, protease inhibitor and 1 mg/mL lysozyme. The lysate was sonicated and nuclease was added. The lysate was then incubated with Ni-NTA resin (Novagen) for 1 hour at 4° C. pCS8 was eluted with a buffer containing 50 mM $NaH_2PO_4$ (pH8), 300 mM NaCl, and 250 mM imidazole. Fractions containing pCS8 were combined and ammonium sulfate precipitated (40% ammonium sulfate). The pellet from the ammonium sulfate precipitation was resuspended in SB (SB=200 mM $NaH_2PO_4$ pH 7.0, 10% glycerol). Protein concentrations were determined by Bradford analysis. The purified protein was stored at −80° C.

B. Purification of BC Domain Peptide. A one-step purification of his-tagged BC domain peptides, as exemplified for pCS8, on Ni-NTA-agarose yields protein that is approximately 90-95% pure as judged by SDS-PAGE was utilized. This method is similar to the purification performed with a histidine-tag attached to the amino terminus of a mutant form of the enzyme and nickel affinity chromatography as described in C. Blanchard et al., "Mutations at Four Active Site Residues of Biotin Carboxylase Abolish Substrate-Induced Synergism by Biotin," Biochemistry, vol. 38, pp. 3393-3400 (1999). After elution from the Ni-NTA agarose column, the pCS8 protein was precipitated by adding an equal volume of saturated ammonium sulfate. The precipitated protein was then resuspended in SB to a concentration of 10 to 20 milligrams per milliliter and stored at −80° C. until used. This method is utilized for purification of all BC domains described herein. Because purer preparations may be required for some purposes, an additional polishing step was investigated. For this purpose, a single UNO-Q (Bio-Rad) anion exchange step subsequent to the Ni-NTA-agarose chromatography purified pCS8 to apparent homogeneity with good yield. UNO-Q is a fast flow matrix that is readily amenable to scale-up. See also FIG. 8.

EXAMPLE 2

ACCase Activity Assays. The following methods were employed to detect ACCase activity. See also FIGS. 9A and 9B.

Method 1: Assay-Spectrophotometric. ACCase activity was measured spectrophotometrically by coupling the production of ADP to the oxidation of NADH using pyruvate kinase and lactate dehydrogenase. This assay was used to measure either overall ACCase activity by supplying acetyl CoA as a substrate, or BC activity by supplying free biotin as a substrate (note, however, that this has only been demonstrated with "prokaryotic type" BC's). This assay is best suited for purified protein. This assay would be used to test for enzymatic activity of compounds identified by virtue of their binding to isolated BC domains, including but not limited to the EC process.

Figure 9A:
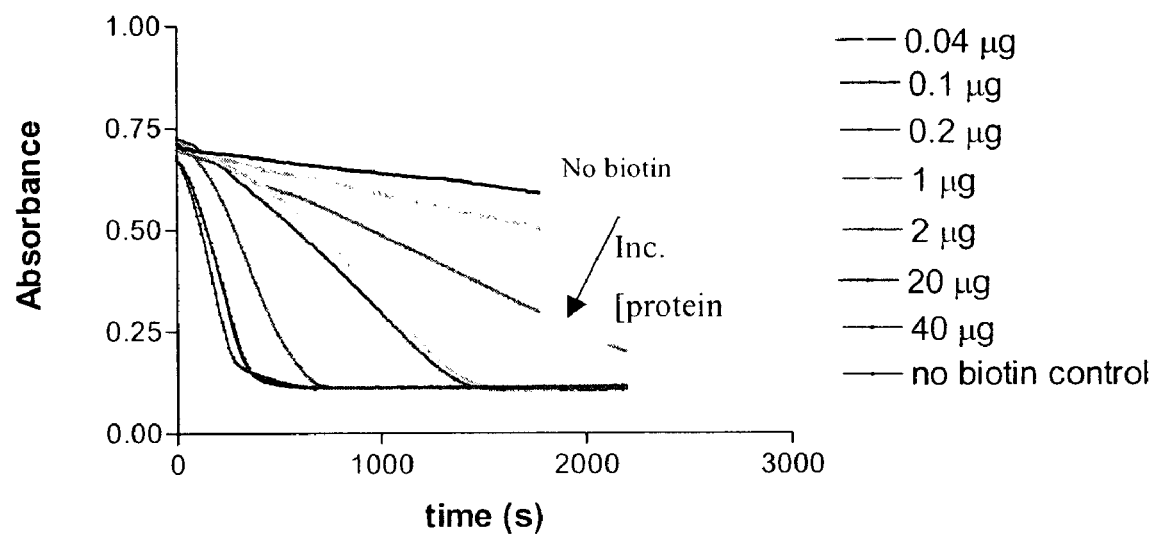
FIG. 9A illustrates spectrophotometric assay absorbance traces for *E. coli* BC

To establish this assay, *E. coli* biotin carboxylase was first cloned and expressed according to the literature (Biochemistry 38:3393-3400, 1999). As seen in FIG. 9A, the activity of *E coli* BC towards a free biotin substrate was readily detectable. Under the conditions of the assay, activity was detected with as little as 40 ng protein, and a maximal velocity was reached between 2 and 20 µg pCS201. In repeated attempts with multiple pCS8 preparations, however, no activity was detected using up to 7 µg protein. We conclude that pCS8 is unable to carboxylate free biotin, as would be expected since such activity has not been detected utilizing eukaryotic BC domains.

To measure overall ACCase activity, a full-length *Ustilago maydis* ACCase was cloned, expressed in *E. coli* with a C-terminal His-tag (pCS11), and purified. As seen in FIG. 9B(i), the time dependent oxidation of NADH, detected by a decrease in absorbance at 340 nm, was dependent on both pCS11 protein as well as acetyl CoA substrate.

Method 2: Assay-$^4C$ Isotope Exchange. ACCase catalyzes the formation of malonyl CoA from acetyl-CoA and bicarbonate. The isotope exchange assay is designed to monitor the incorporation of $^{14}C$ from bicarbonate into the malonyl CoA product. Malonyl CoA is acid and heat stable so the unreacted $H^{14}CO_3^-$ can be removed by acidification followed by evaporation. As can be seen in FIG. 9B(ii) and consistent with the spectrophotometric assay, activity (measured as the incorporation of $^{14}C$ into malonyl CoA) was dependent on both pCS11 protein and acetyl CoA substrate. Because this an endpoint assay, it is less suitable than the spectrophotometric assay for kinetic measurements; however, it is superior for detecting activity in crude preparations. It will also be used to test for enzymatic activity of compounds identified by virtue of their binding to isolated BC domains, including but not limited to the EC process.

EXAMPLE 3

Soraphen binding assay. Affinity based screens and selection assays, including but not limited to EC selections, rely on binding of small molecules and not inhibition of enzymatic activity. Therefore, despite the lack of enzymatic activity, pCS8 would be a suitable affinity based screening or selection agent if it retained the high affinity soraphen binding activity of the full-length *Ustilago* ACCase. Soraphen A was tritium labeled by Sibtech, Inc. (Newington, Conn.) and used for binding experiments with pCS8 protein. Briefly, 6.7 nM purified pCS8 protein was incubated with various concentrations (approximately 0.5-20 nM) of $^3$H-soraphen in PNT buffer (100 mM $NaH_2PO_4$, 150 mM NaCl, 0.01% Triton X-100, pH 7.0) for 45 min at room temperature. pCS8 protein (with bound ligand) was separated from free ligand oil NAP-5 desalting columns (Amersham Biosciences) and the amount of bound $^3$H-soraphen determined by liquid scintillation counting. Non-specific binding was determined with duplicate samples containing 2 µM cold soraphen. The data were fit by non-linear regression to a one site ligand binding equation: $Y=B_{max}*X/(K_D+X)$ where Y=bound ligand and X=free ligand.

pCS8 exhibited saturable binding of $^3$H-Soraphen consistent with a single high affinity binding site (FIG. 3). The data shown for pCS8 are combined from two experiments with independent protein preps demonstrating little prep-to-prep variability. A negative control was provided by pCS201. pCS201 encodes an N-terminal His-tagged enzymatically active *E. coli* BC that is not inhibited by soraphen. As expected, pCS201 did not exhibit high affinity soraphen binding.

Non-linear regression fits of the data gave an estimate of 1.5 nM for the $K_D$ of the soraphen-pCS8 interaction (FIG. 4). This is in good agreement with the $K_D$ estimate of the soraphen-pCS11 full length ACCase of 1.6 nM (FIG. 2) and is in good agreement with the published value of a 1.4 nM $K_i$ for soraphen inhibition of *Ustilago* ACCase activity (Heike Behrbohm Ph.D. thesis, Braunschweig Techn. Univ., 1996). As such, the pCS8 is a suitable affinity-based screening and selection agent as it retains high-affinity soraphen binding comparable to full-length *Ustilago* ACCase.

EXAMPLE 4

Additional characterization of pCS8. No protein degradation or loss of soraphen binding was seen after incubation of SB solubilized pCS8 peptide for 24 h at room temperature. No protein degradation or loss of soraphen binding was seen after storage of SB solubilized pCS8 peptide for 5 weeks at −80° C., including multiple freeze thaws.

EXAMPLE 5

Partial summary of BC domains generated. A number of biotin carboxylase (BC) domains that have been characterized herein and can be purified in sufficient quantities for use in affinity based screens or selections, including but not limited to selections using Evolutionary Chemistry, and five BC domains are as follows: wild type versions from *Ustilago maydis*, *Phytophthora infestans*, *Magnaporthe grisea*, and *Saccharomyces cerevisiae*; and the mutated version from *Saccharomyces cerevisiae*. Amino acid sequence alignments of the expressed domains are shown in FIG. 10. Identical residues are indicated with an asterisk, and the S to Y mutation in *S. ceravisiae* that abolishes soraphen binding is indicated in bold.

EXAMPLE 6

Figure 11:
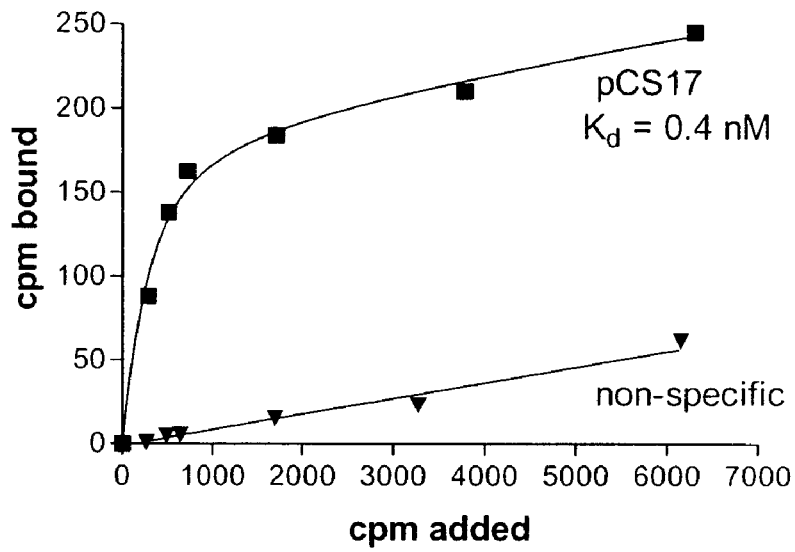
FIG. 11 illustrates soraphen binding to the *Magnaporthe* BC domain.

Generation of the *Magnaporthe grisea* BC domain. A preliminary sequence of the entire genome of *Magnaporthe grisea* (ascomycete, causal agent of rice blast) was recently released into the public domain by the Whitehead Institute in collaboration with Ralph Dean's lab at North Carolina State University. The full-length *M. grisea* ACCase gene was PCR amplified from genomic DNA, cloned, and sequenced. One small predicted intron was removed to create a full-length cDNA. The biotin carboxylase domain was subcloned (based on alignment with our pCS8 *U. maydis* BC domain) and inserted into a pET vector (5'His tag) to make pCS17. pCS17 was expressed in *E. coli* and the His-tagged BC domain was purified and assayed for soraphen binding. As expected, the Magnaporthe BC domain exhibited high affinity soraphen binding, as demonstrated in FIG. 11.

EXAMPLE 7

Cloning and expression of human ACCase genes. There are at least two forms of the acetyl-CoA carboxylase enzyme in humans. ACC1 is a cytosolic enzyme present at high levels in liver and lipogenic tissues, and is the primary species responsible for fatty acid synthesis. ACC2 is a mitochondrial enzyme found primarily in heart and muscle tissue, and is thought to regulate fatty acid oxidation. Biotin carboxylase domains from human ACCases could potentially be useful as counterselection agents with potential to select against mammalian toxicity. Additionally, agonists and inhibitors of human ACCase that can distinguish between ACC1 and ACC2 BC domains may have potential pharmaceutical applications.

Figure 12:
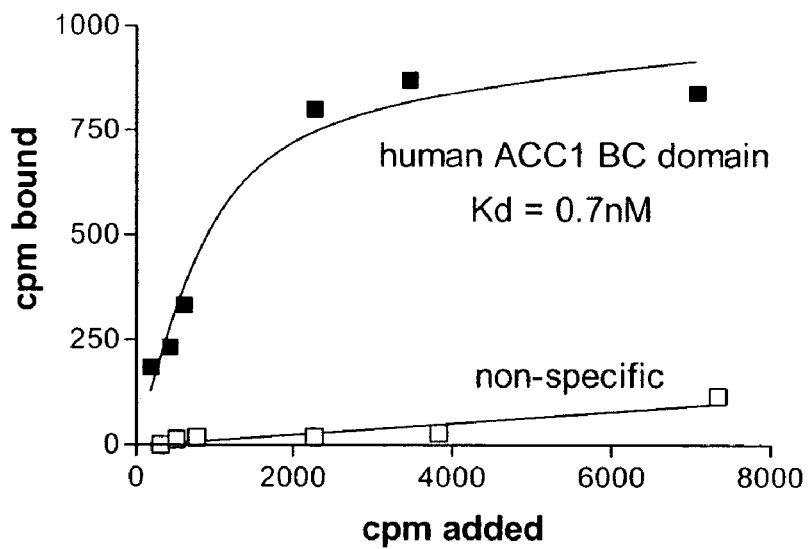
FIG. 12 illustrates soraphen binding to the human ACC1 BC domain.

Complete genomic DNA sequences are available for both genes. Their BC domains (based on homology with our pCS8 ustilago clone) were successfully cloned by amplifying small exons from genomic DNA and using PCR to splice them together. The ACC1 BC domain consists of 14 exons, 104 bp to 237 bp in length, which were assembled to make an 1896 bp (SEQ ID NO: 9) BC domain cDNA. The ACC2 BC domain consists of 14 exons, 108-661 bp in length, assembled to make a 2322 bp (SEQ ID NO: 11) BC domain cDNA. Both BC domains were cloned into pET30 to make 3' His-tagged fusion proteins. The ACC1 clone is designated pCS19 and should produce a fusion protein of 71.2 kD. The ACC2 clone is designated pCS20 and should produce a fusion protein of 86.7 kD. Expression analysis showed that the ACC1 fusion protein is expressed at low levels in *E. coli* and can be purified from the soluble fraction. The purified pCS19 protein exhibited high affinity soraphen binding (see FIG. 12). Alignments of the Ustilago and human ACCase domains are depicted in FIG. 13. Besides being useful in identifying selective agrochemicals, a particularly intriguing use of the human BC domains is to identify specific inhibitors that preferentially target the ACC2 domain, but not the ACC1 domain, since such inhibitors could prove useful in controlling body weight.

EXAMPLE 8

This example demonstrates that pCS8 has binding characteristics amenable for use in affinity based screening or selection procedures.

Figure 14:
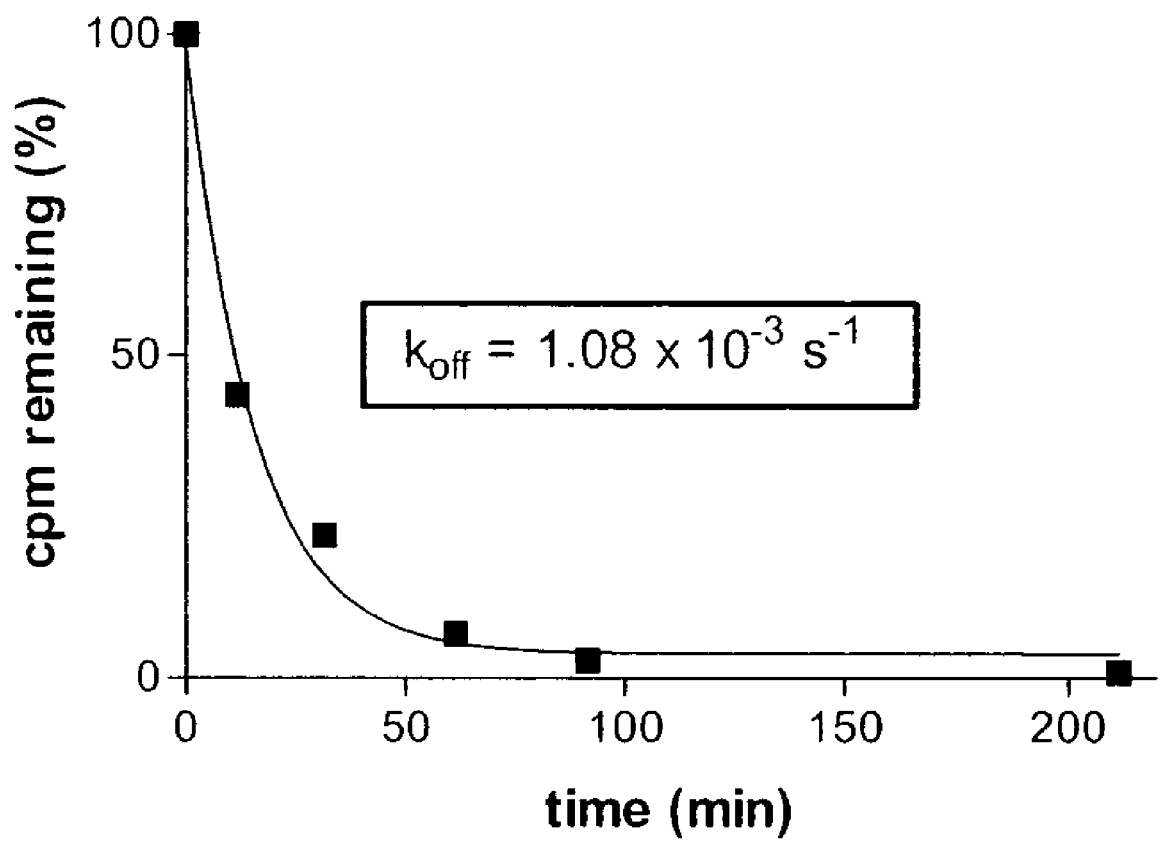
FIG. 14 illustrates dissociation experiments using [$^3$H]-soraphen to determine the soraphen off rate for *Ustilago* ACCase BC domain.

Soraphen off-rate determination. Kinetic aspects of binding interactions are an important parameter in designing optimal conditions for affinity-based screening and selection assays, including but not limited to EC. Therefore, soraphen dissociation experiments were performed to determine the off-rate for the binding interaction using the *Ustilago* BC domain (pCS8). 53.6 pmol pCS8 protein was incubated with 30 pmol $^3$H-soraphen in a volume of 2 ml for 15 min. The protein with bound soraphen was separated from free soraphen on NAP5 columns and eluted in a total of 4 ml. Cold soraphen was added to 2 µM and dissociation of the bound soraphen was followed by removing 0.5 ml aliquots at various times and applying them to NAP 5 columns to again separate bound from free radiolabel. The $^3$H-soraphen in the eluted fractions was quantified by liquid scintillation counting and the data were fit to the following equation: $Y=Y_{max}*e^{-k1}+NS$ (FIG. 14).

This off rate corresponds to 10.7 min half-life. Note that the on-rate can be calculated from this data since $K_d=k_{off}/k_{on}$; so $k_{on}$=9.31×10⁵ M⁻¹ s⁻¹. At 10 μM protein, even with very low ligand concentrations, such a binding interaction would approach equilibrium very rapidly.

EXAMPLE 9

Competitive Binding Assay. Isolated biotin carboxylase domains and radiolabeled soraphen can be employed in a competitive binding assay to test the ability of any compound to bind to the soraphen binding site. Like soraphen, such compounds are likely to inhibit ACCase activity. To exemplify this assay, we prepared two soraphen derivatives with modifications at the 5-position (soraphen A-conjugate) or 11-position (soraphen C-conjugate). Both derivatives were then tested in competition binding assays with both pCS8 and pCS11 proteins. The proteins were incubated with ³H-soraphen and various concentrations of the 2 conjugates for 1 hr. Bound ³H-soraphen was then separated from unbound on NAP 5 columns and quantified by scintillation counting. To estimate the conjugates $K_i$'s, the resulting data was fit to an equation for heterologous competitive binding with ligand depletion (H. J. Motulsky, Analyzing Data with GraphPad Prism, 1999, GraphPad Software Inc., San Diego Calif., www.graphpad.com):

$$Y = \frac{[\text{free}] * B\text{max}}{[\text{free}] + Kd(1 + [\text{cold}]/Ki)} + NS$$

Representative data are shown in FIG. 15, in which the soraphen A-conjugate is labeled A-conj and the soraphen C-conjugate is labeled C-conj. As expected, there was no significant difference between the affinities of the conjugates for the BC domain (pCS8) (FIG. 15A) and the full-length protein (pCS11) (FIG. 15B). As a positive control for this assay, an experiment using cold soraphen A as the competitor was performed and yielded a $K_i$ estimate of 1.1 nM (data not shown), consistent with direct saturation binding experiments.

EXAMPLE 10

Soraphen resistant *Saccharomyces cerevisiae* ACCase and ACCase BC domain mutants—Counterselection Agents. Mutation of Serine 77 to Tyrosine in the *S. cerevisiae* ACCase protein has been shown to confer soraphen resistance (European Patent Application 94810710, 1994; and U.S. Pat. No. 5,641,666, 1997).

Figure 16:
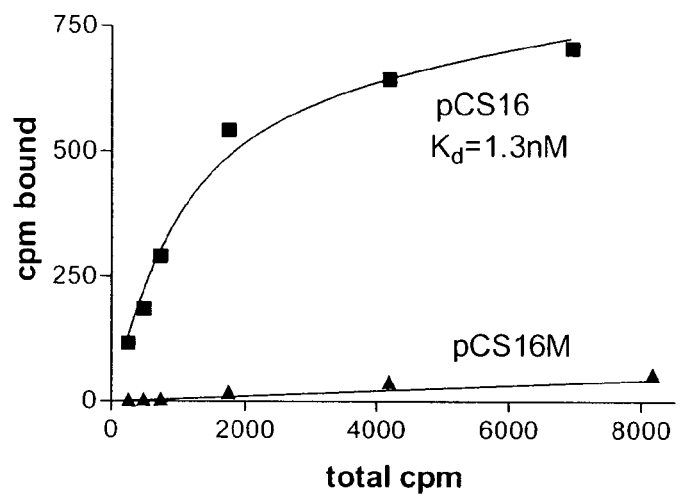
FIG. 16 depicts soraphen binding to wild type and mutant *S. cerevisiae* ACCase BC domain peptides.

This soraphen resistance mutation was introduced into pCS204, a yeast expression vector containing the full-length *S. cerevisiae* ACCase gene constructed by cloning a PCR-amplified full-length *S. cerevisiae* ACCase gene into the expression vector pYES2 for inducible overexpression of His-tagged ACCase in *S. cerevisiae*. The resulting construct was designated pCS204M. The *S. cerevisiae* biotin carboxylase domains from pCS204 and pCS204M were then subcloned into an *E. coli* pET expression vector to form pCS16 and pCS16M, respectively. Like pCS8, both of these constructs express their respective BC domains as N-terminal-His-tagged fusion proteins to facilitate purification. Expression analysis demonstrated that both pCS16 and pCS16M yielded comparable amounts of purified, soluble protein. The products were then analyzed by size exclusion chromatography and, like pCS8 protein, both were found to exist primarily as monomers (>90%). The proteins were then tested for soraphen binding and the results are shown in FIG. 16. pCS16 protein exhibited high-affinity soraphen binding comparable to pCS8 protein. In contrast, soraphen binding by pCS16M was similar to the non-specific control (Data not shown) confirming that introduction of this single amino acid mutation into a BC domain abolishes soraphen binding. Therefore, pCS16M protein would be an excellent counter-selection agent to eliminate non-soraphen-binding-site interactions.

The effect of the mutation on full-length ACCase was also assessed. pCS204 and pCS204M were overexpressed in *S. cerevisiae* and purified by Ni-NTA chromatography. Both proteins appeared identical on SDS-PAGE (Data not shown).

The proteins were then assayed for ACCase activity using the ¹⁴C isotope exchange assay. The resulting data were similar to those from a published report (*Curr. Genet.* 25:95-100 (1994)) comparing the activity of the endogenous protein from wild type and mutant yeast, and demonstrate that pCS204M protein activity is insensitive to soraphen but still sensitive to avidin inhibition (Table 4).

TABLE 4

| | Relative Enzymatic Activity (%) | | | |
|---|---|---|---|---|
| Treatment | WT enzyme* | Mutant enzyme* | pCS204 | pCS204M |
| Control | 100.0 | 100.0 | 100.0 | 100.0 |
| +150 μg/mL soraphen A | 0.8 | 74.7 | 7.5 | 105 |
| +1.5 μg/mL soraphen A | 1.0 | 74.9 | 11.6 | 101 |
| +1.5 ng/mL soraphen A | 71.8 | 79.4 | 92.0 | 103 |
| +250 μg/ml avidin | 0.4 | 0.1 | 2.1 | 2.5 |
| −acetyl CoA | 0.6 | 0.2 | 2.0 | 2.8 |

*Data from Curr. Genet. 25: 95-100 (1994).

Figure 17:
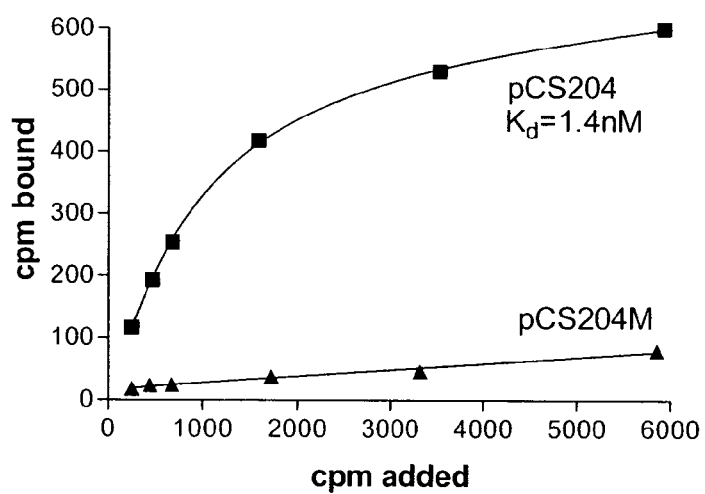
FIG. 17 illustrates soraphen A binding to wild-type and mutant full-length *S. cerevisiae* ACCase.

Finally, pCS204 and pCS204M were assayed for soraphen A binding and the results are shown in FIG. 17. Full-length pCS204 protein bound soraphen with similar high affinity as the BC domain expressed by pCS16. Soraphen binding by pCS204M, like that of pCS16M, was comparable to the non-specific control.

The foregoing is illustrative of the present invention, and is not to be construed as limiting thereof. The invention is defined by the following claims, with equivalents of the claims to be included therein.

That which is claimed is:

1. An isolated peptide comprising an Acetyl CoA carboxylase (ACCase) having a nonfunctional biotin binding domain, having a nonfunctional carboxy transferase domain, and having a functional biotin carboxylase domain, wherein said peptide is a monomer and binds to soraphen, and wherein said ACCase is selected from the group consisting of mammal, insect, yeast, Ascomycota, Basidiomycota. and Oomycota ACCase.

2. The peptide according to claim 1, wherein said carboxylase is *Ustilago maydis* carboxylase.

3. The peptide according to claim 1 having the amino acid sequence given in SEQ ID NO: 2.

4. The peptide according to claim 1, wherein said peptide has a soraphen dissociation constant of from $10^{-7}$ to $10^{-14}$ M.

5. A composition comprising:

(a) an aqueous carrier solution; and (b) the peptide of claim 1 solubilized in said aqueous carrier solution; with said peptide included in said composition in an amount of from 0.001 nanograms to 20 milligrams per milliliter of aqueous carrier solution;

said peptide having a soraphen dissociation constant in said composition of from $10^{-7}$ to $10^{-14}$ M; and said composition having a pH of from 5 through 9.

6. An isolated peptide consisting essentially of a functional Acetyl CoA carboxylase (ACCase) biotin carboxylase domain, wherein said functional biotin carboxylase domain is a monomer and binds to soraphen and wherein said functional ACCase biotin carboxylase domain is selected from the group consisting of: mammal, insect, yeast, Ascomycota, Basidiomycota, and Oomycota ACCase.

7. The peptide of claim 6, wherein said carboxylase is *Ustilago maydis* carboxylase.

8. The peptide of claim 1, wherein said nonfunctional biotin binding domain, and said nonfunctional carboxy transferase domain are deleted.

* * * * *

UNITED STATES PATENT AND TRADEMARK OFFICE
CERTIFICATE OF CORRECTION

| | |
|---|---|
| PATENT NO. | : 7,432,350 B2 |
| APPLICATION NO. | : 10/633835 |
| DATED | : October 7, 2008 |
| INVENTOR(S) | : Elich et al. |

It is certified that error appears in the above-identified patent and that said Letters Patent is hereby corrected as shown below:

<u>On the Title Page, Item 54 and Column 1, Lines 1-4</u>:
    Please correct the title to read as:
        -- RECOMBINANT BIOTIN CARBOXYLASE DOMAINS FOR IDENTIFICATION OF ACETYL COA CARBOXYLASE INHIBITORS --

On column 2, lines 20-21, please insert missing page from specification:
    Please correct "biotin binding domain, selecting a compound"
        To read -- biotin binding domain, having a deleted carboxy transferase domain, and having a functional biotin carboxylase domain comprising amino acids as detailed in SEQ ID NOS: 2, 4, 6, 8, 10, 12, 14, or 16, and functional fragments thereof.

According to other embodiments of the present invention, the molecules described above are each a monomer.

According to still other embodiments of the present invention, the present invention relates to the molecules described above wherein the respective carboxylase domains bind to compounds that modulate Acetyl CoA carboxylase activity.

According to other embodiments of the present invention, the carboxylase domains bind to competitive inhibitors, noncompetitive inhibitors, and also binds to soraphen.

According to other embodiments of the present invention, the present invention relates to a nucleic acid that encodes a peptide comprising an Acetyl CoA carboxylase (ACCase) having a deleted biotin binding domain, having a deleted carboxy transferase domain, and having a functional biotin carboxylase domain, such as described above and further herein below.

UNITED STATES PATENT AND TRADEMARK OFFICE
CERTIFICATE OF CORRECTION

PATENT NO. : 7,432,350 B2
APPLICATION NO. : 10/633835
DATED : October 7, 2008
INVENTOR(S) : Elich et al.

It is certified that error appears in the above-identified patent and that said Letters Patent is hereby corrected as shown below:

According to other embodiments of the present invention, the present invention relates to a recombinant host cell that contains a nucleic acid as described above and expresses the encoded peptide.

According to other embodiments of the present invention, the present invention relates to a method of identifying Acetyl CoA carboxylase inhibitors, or activators, comprising a) combining a peptide as described above and a compound to be tested for the ability to bind to said biotin carboxylase domain, under conditions that permit binding to said biotin carboxylase domain, and b) determining whether or not said compound binds to said biotin carboxylase domain, the presence of binding indicating said compound is or may be an Acetyl CoA carboxylase inhibitor. Such compounds are candidates for and useful as pesticides, including but not limited to insecticides, nematocides, fungicides, and/or herbicides, and/or also pharmaceuticals, including but not limited to antifungals.

UNITED STATES PATENT AND TRADEMARK OFFICE
CERTIFICATE OF CORRECTION

PATENT NO. : 7,432,350 B2
APPLICATION NO. : 10/633835
DATED : October 7, 2008
INVENTOR(S) : Elich et al.

It is certified that error appears in the above-identified patent and that said Letters Patent is hereby corrected as shown below:

According to other embodiments of the present invention, the present invention relates to a method of identifying Acetyl CoA carboxylase inhibitors, further comprising the steps of c) employing a compound identified as binding in step (b) in an assay to detect inhibition of Acetyl CoA carboxylase activity; and d) selecting a compound --

On column 16, line 36:
Please correct "Assay-$^4$C"
To read -- Assay-$^{14}$C --

On column 17, line 51:
Please correct "*S. ceravisiae*"
To read -- *S. cerevisiae* --

On column 18, line 64:
Please correct "$Y=Y_{max}*e^{-kl}+NS$"
To read -- $Y=Y_{max}*e^{-kt}+NS$ --

Signed and Sealed this

Thirty-first Day of March, 2009

JOHN DOLL
*Acting Director of the United States Patent and Trademark Office*